(12) United States Patent
Jorgensen et al.

(10) Patent No.: US 7,727,715 B2
(45) Date of Patent: Jun. 1, 2010

(54) GLOBAL GENE EXPRESSION ANALYSIS OF HUMAN BRONCHIAL EPITHELIAL CELLS EXPOSED TO CIGARETTE SMOKE, SMOKE CONDENSATES, OR COMPONENTS THEREOF

(75) Inventors: Ellen D. Jorgensen, South Salem, NY (US); Anthony P. Albino, New York, NY (US); Wendy Jin, Chapel Hill, NC (US)

(73) Assignee: Vector Tobacco, Inc., Morrisville, NC (US)

(*) Notice: Subject to any disclaimer, the term of this patent is extended or adjusted under 35 U.S.C. 154(b) by 496 days.

(21) Appl. No.: 10/593,596

(22) PCT Filed: Mar. 29, 2005

(86) PCT No.: PCT/US2005/010733

§ 371 (c)(1),
(2), (4) Date: Jul. 27, 2007

(87) PCT Pub. No.: WO2005/103296

PCT Pub. Date: Nov. 3, 2005

(65) Prior Publication Data

US 2008/0052789 A1      Feb. 28, 2008

Related U.S. Application Data

(60) Provisional application No. 60/557,929, filed on Mar. 30, 2004.

(51) Int. Cl.
C12Q 1/68         (2006.01)
C07H 21/04       (2006.01)
C12P 19/34       (2006.01)

(52) U.S. Cl. .................. 435/6; 536/24.3; 435/91.2

(58) Field of Classification Search ............. None
See application file for complete search history.

(56) References Cited

U.S. PATENT DOCUMENTS 3,586,005 A    6/1971   Lippman et al.
3,812,865 A    5/1974   Anderson
2006/0157072 A1   7/2006   Albino et al.
2008/0227088 A1   9/2008   Albino et al.

FOREIGN PATENT DOCUMENTS

| WO | WO 01/34834 A2 | 5/2001 |
|---|---|---|
| WO | WO 2005/047451 A2 | 5/2005 |
| WO | WO 2005/081867 A2 | 9/2005 |
| WO | WO 2007/005879 A2 | 1/2007 |
| WO | WO 2009/045860 | 4/2009 |

OTHER PUBLICATIONS

Benner et al (Trends in Genetics (2001) vol. 17, pp. 414-418).*
Cheung et al (Nature Genetics, 2003, vol. 33, pp. 422-425).*
Hibi et al., Gene expression in tobacco low-niccotine mutants, The Plant Cell, 1994, 6:723-735.
Office Action for U.S. Appl. No. 11/285,537 dated Feb. 14, 2008.
Yoneda, Ken et al., "Application of High-Density DNA Microarray to Study Smoke- and Hydrogen Peroxide-Induced Injury and Repair in Human Bronchial Epithelial Cells" J Am Soc Nephrol, 2003, pp. S284-S289, vol. 14.
Rangasamy, Tirumalai et al., "Genetic ablation of Nrf2 enhances susceptibility to cigarette smoke-induced emphysema in mice" The Journal of Clinical Investigation, Nov. 2004, pp. 1248-1259. vol. 114, No. 9.
U.S. Appl. No. 11/913,870, filed Nov. 8, 2007, Anthony Albino et al.

* cited by examiner

*Primary Examiner*—Steven C Pohnert
(74) *Attorney, Agent, or Firm*—Knobbe Martens Olson & Bear LLP

(57) ABSTRACT

Aspects of the present invention concern the identification of several methods to analyze the genes that are modulated in normal human bronchial epithelial (NHBE) cells after exposure to cigarette smoke condensates (CSC) or cigarette smoke (CS). Embodiments described herein include methods to identify a gene that is modulated in response to exposure to CSC or CS, methods to identify tobacco products that have a reduced potential to contribute to tobacco-related disease, methods to make tobacco products that have a reduced potential to contribute to a tobacco-related disease, methods to identify a subject's predilection to acquire a tobacco related disease, the use of particular genes as biomarkers for tobacco-related disease, and patterns of gene expression or genetic signatures that are unique to each particular tobacco product.

12 Claims, 13 Drawing Sheets

US 7,727,715 B2

SEQUENCE LISTING

```
<160> NUMBER OF SEQ ID NOS: 5

<210> SEQ ID NO 1
<211> LENGTH: 5688
<212> TYPE: DNA
<213> ORGANISM: Artificial Sequence
<220> FEATURE:
<223> OTHER INFORMATION: Full-length QTPase RNAi construct

<400> SEQUENCE: 1
ctcgaggatc taaattgtga gttcaatctc ttccctattg gattgattat cctttctttt      60
cttccaattt gtgtttcttt ttgcctaatt tattgtgtta tccctttat cctattttgt     120 ttctttactt atttatttgc ttctatgtct ttgtacaaag atttaaactc tatggcacat     180
attttaaagt tgttagaaaa taaattcttt caagattgat gaaagaactt tttaattgta     240
gatatttcgt agattttatt ctcttactac caatataacg cttgaattga cgaaaatttg     300
tgtccaaata tctagcaaaa aggtatccaa tgaaaatata tcatatgtga tcttcaaatc     360
ttgtgtctta tgcaagattg atactttgtt caatggaaga gattgtgtgc atatttaa      420 aattttatt agtaataaag attctatata gctgttatag agggataatt ttacaaagaa     480
cactataaat atgattgttg ttgttagggt gtcaatggtt cggttcgact ggttatttta     540
taaaatttgt accataccat ttttttcgat attctatttt gtataaccaa aattagactt     600
ttcgaaatcg tcccaatcat gtcggtttca cttcggtatc ggtaccgttc ggttaatttt     660
catttttttt taaatgtcat taaaattcac tagtaaaaat agaatgcaat aacatacgtt     720
```

```
cttttatagg acttagcaaa agctctctag acatttttac tgtttaaagg ataatgaatt      780
aaaaaacatg aaagatggct agagtataga tacacaacta ttcgacagca acgtaaaaga      840
aaccaagtaa aagcaagaa aatataaatc acacgagtgg aaagatatta accaagttgg       900
gattcaagaa taaagtctat attaaatatt caaaaagata aatttaaata atatgaaagg      960
aaacatattc aatacattgt agtttgctac tcataatcgc tagaatactt tgtgccttgc     1020
taataaagat acttgaaata gcttagttta aatataaata gcataataga ttttaggaat     1080
tagtattttg agtttaatta cttattgact tgtaacagtt tttataattc caaggcccat     1140
gaaaatttta atgctttatt agtttaaac ttactatata aattttttcat atgtaaaatt     1200 taatcggtat agttcgatat ttttcaatt tattttttata aataaaaaaa cttaccctaa     1260
ttatcggtac agttatagat ttatataaaa atctacggtt cttcagaaga aacctaaaaa     1320
tcggttcggt gcggacggtt cgatcggttt agtcgatttt caaatattca ttgacactcc     1380
tagttgttgt tataggtaaa aagcagttac agagaggtaa aatataactt aaaaaatcag     1440
ttctaaggaa aaattgactt ttatagtaaa tgactgttat ataaggatgt tgttacagag     1500
aggtatgagt gtagttggta aattatgttc ttgacggtgt atgtcacata ttatttatta     1560
aaactagaaa aaacagcgtc aaaactagca aaaatccaac ggacaaaaaa atcggctgaa     1620
tttgatttgg ttccaacatt taaaaaagtt tcagtgagaa agaatcggtg actgttgatg     1680
atataaacaa agggcacatt ggtcaataac cataaaaaat tatatgacag ctacagttgg     1740
tagcatgtgc tcagctattg aacaaatcta aagaaggtac atctgtaacc ggaacaccac     1800
ttaaatgact aaattaccct catcagaaag cagatggagt gctacaaata acacactatt     1860
caacaaccat aaataaaacg tgttcagcta ctaaaacaaa tataaataaa tctatgtttg     1920
taagcactcc agccatgtta atggagtgct attgcctgtt aactctcact tataaaatag     1980
tagtagaaaa aatatgaacc aaaacacaac aacatctcaa aatatttgaa gtaacacaga     2040
attttacata caccaaactt ataaatcaag tattttcatt gtaacaaatt ccatgaaaca     2100
tgaaaacaaa gctataatga aattaccaac tcaagcaata aggttggaaa agagccatct     2160
gagatattcc agcaatttac atcttttttgt ttgattacac agtgaaggat cttttgtttg     2220
acaactagta aaatgattct tatttgcacc tttcagctat tcagctgctt ttactccaac     2280
cctatagcag aagtaatggc gctcatgctc gttttgtacg ccttccaact tcaagggcga     2340
gctctgtatc gatcttcagg gaaatgtcaa gtgcttttcac ggaatgcgtc agggcaccac     2400
tagaaatgta ggtaacacca gtttgtccaa tcttgtgtac tgtttcaagg gtaacatttc     2460
ctgaagcctc cgtatcaaac ctcccattga tcaattctac agcctcctta agcatggata     2520
catcaatatc tccgttagat aatggaacaa ccatattgtc cagcattatc ctagtcaacg     2580
aagtctttgt ttgagatgca tagtctagaa cctcacgtac ttcttcaatt gtcctggttt     2640
caacctcaac ccctatttga agtttatttt gctccaaata ctgatccaca gattttagag     2700
ctttgccgac acctccagca gcagatatgt gattgtcttt tatcattacc atatcaaata     2760
agcccattct gtgattcttc cccccaccga tcaataccgc ccatttatcc accaaacgta     2820
atccaggagc agttttccta gtctccaaga tgtaagcagg gtgtgcagca tctgccatt       2880 ccttagttag tgtagctatt ccactcattc tttgcataaa attgagaaca accctctcag     2940
ctataacaat gttgtaagcg tttccttgta ctttgccaaa tttcaagcct ttatgaactt     3000
tatcgccatc atttacatac cactccacct ttaatgaagg atcaacttcc gcgaatatca     3060
tctcagcaag tgcaattcct gctatgatcc cgtcttcctt tgctagaaaa tgagcatcgg     3120
```

```
attccatatc aagaggaatt gtcgccttac aagtcacatc tcctaaattc ccagcatctt    3180
cagagagtgc aagtttcata acttccttta aatcataagt tgggtgtgct ggtggtttca    3240
cctctaatga ctccactctt gtattcttgg tggctattgc tgacattttc accaccaacc    3300
ttggagctgt aattgcataa ggatgcactg tagcagtgaa aggaatagct ctaaacatgg    3360
tttttttttg gggggggttgt gaaatgaatt ttgtggaaaa tagttttgg ggcacatcaa    3420
tcctgcggtg acattcggaa tgtttctaac aagaaagata tcgttggtcc gagccttgct    3480
ctacatcata gctcagtgca tagggggccct gtgcgggtgc gccttagtca agacattgca    3540
gcgagatcat tacaaccact atggcggtgg cgctaaccag ctcgttgatg gttatagccg    3600
aggcactggc cttgctgttg agattatggg cacctttatt cttctgtata ctgtcttctc    3660
cgccactgat cccaaacgca atgctagaga ttcccatgtt cctgtcttgg ctccactccc    3720
cattggcttt gctgtcttca ttgttcacct cgccaccatt cccgtcaccg gcactggcat    3780
caacccagcg agcaaaaact attttccaca aaattcattt cacaaccccc ccaaaaaaaa    3840
accatgttta gagctattcc tttcactgct acagtgcatc cttatgcaat tacagctcca    3900
aggttggtgg tgaaaatgtc agcaatagcc accaagaata caagagtgga gtcattagag    3960
gtgaaaccac cagcacaccc aacttatgat ttaaaggaag ttatgaaact tgcactctct    4020
gaagatgctg ggaatttagg agatgtgact tgtaaggcga caattcctct tgatatggaa    4080
tccgatgctc atttctagc aaggaagac gggatcatag caggaattgc acttgctgag    4140
atgatattcg cggaagttga tccttcatta aaggtggagt ggtatgtaaa tgatggcgat    4200
aaagttcata aaggcttgaa atttggcaaa gtacaaggaa acgcttacaa cattgttata    4260
gctgagaggg ttgttctcaa ttttatgcaa agaatgagtg gaatagctac actaactaag    4320
gaaatggcag atgctgcaca ccctgcttac atcttggaga ctaggaaaac tgctcctgga    4380
ttacgtttgg tggataaatg ggcggtattg atcggtgggg ggaagaatca cagaatgggc    4440
ttatttgata tggtaatgat aaaagacaat cacatatctg ctgctggagg tgtcggcaaa    4500
gctctaaaat ctgtggatca gtatttggag caaaataaac ttcaaatagg ggttgaggtt    4560
gaaaccagga caattgaaga agtacgtgag gttctagact atgcatctca aacaaagact    4620
tcgttgacta ggataatgct ggacaatatg gttgttccat tatctaacgg agatattgat    4680
gtatccatgc ttaaggaggc tgtagaattg atcaatggga ggtttgatac ggaggcttca    4740
ggaaatgtta cccttgaaac agtacacaag attggacaaa ctggtgttac ctacatttct    4800
agtggtgccc tgacgcattc cgtgaaagca cttgacattt ccctgaagat cgatacagag    4860
ctcgcccttg aagttggaag gcgtacaaaa cgagcatgag cgccattact tctgctatag    4920
ggttggagta aaagcagctg aatagctgaa aggtgcaaat aagaatcatt ttactagttg    4980
tcaaacaaaa gatccttcac tgtgtaatca aacaaaaga tgtaaattgc tggaatatct    5040
cagatggctc ttttccaacc ttattgcttg agttggtaat ttcattatag ctttgttttc    5100
atgtttcatg gaatttgtta caatgaaaat acttgattta aagtttggt gtatgtaaaa    5160
ttctgtgtta cttcaaatat tttgagatgt tgagctcgtg aaatggcctc tttagttttt    5220
gattgaatca tagggtatt agttttctat ggccgggagt ggtcttcttg cttaattgta    5280
atggaataac cagagaggaa ctactgtgtt atctttgagg aatgttgggc tttttttcgtt    5340
tgaattatca tgaatgaaat tttacttttt cccaatacaa gtttgttttc gtttcttggt    5400
ttttgttatc ccttggttta tgtcttggtt tggcttaaat gattgaagat tacactacct    5460
```

```
atgtttctgc tattcctgtt gaagatcaca tttgataata atgcatcgaa tgcattaaag    5520
tttcttattg gctctgtcaa aagtattgaa ggtggatttt tctaattggc aagagaaagt    5580
attaaagagg tgatttatta gtacttatat ttttctcagc atctctcttt cagtgttgga    5640
gcttcataaa attagcactt cagagtttca gtcgggagct gaattcga                 5688

<210> SEQ ID NO 2
<211> LENGTH: 3600
<212> TYPE: DNA
<213> ORGANISM: Artificial Sequence
<220> FEATURE:
<223> OTHER INFORMATION: Selection cassette for full-length QTPase RNAi
      construct

<400> SEQUENCE: 2
tctagaatgt tcgtgcgtca aatggataaa caaaaaaata gcataagtta gttttgttac      60
tcgagagtta tgtattataa ggtataggga aatgactcaa acataccact gaacttaacg     120
aaacgacgca tatatatact acttaactta acgaaaaagg ggtgagagtg gatgggtgct     180
ggtaaataat gaagggttta tataacgtca cgtgtcaaaa ttcgatagta gtagtttcgt     240
tagttgtaat agcatatatg gcccaaagtt ataatataga taatatgttt atgtccaact     300
attaacgagt gacatagaca gttcattttg tgaagttcaa tgacatattt gagccctttc     360
ccttttatta tctccttta ttgttctaa taaagaatg gcatttatta tgtacataga      420
caaataacta ttttctttgg aatataattt gtttatatat tttaaaatca tgtctcaatt     480
tagtttgttt tgtgcatatt tcaactattc aattttgtcc atatatttat taccttcccc     540
catttacaag cattgaaccg ctttgctcac caaaacttat gcacattgca aaaatatcat     600
gtaaaggttt tatgtatgct gtaattaagg tctgaactca tcgtgatttt attttaggc      660 ttcattgacc actaccaaac tctttgatgc tacattttct aattatattg gagttcgatt     720
atatccgaat tcgcgttgcg tagggcccat tcgaggaaaa acactcccta tcaaggattt     780
tttcataccc agagctcgaa ctcaagacat ctggttaagg gaagaacagt ctcatccact     840
gcaccatatc ctttttgtggt caacaagtaa attttatgta gaaccaaaaa ctatactcga     900
attgataaaa taaatggtgt aaaatattgt tttctttctt acattttgga cagtaaatat     960
gtaggacaat aataattagc gtggggtctt aagaaaatta gcatagattt ccagaaattc    1020
caaatcaacc ggcagttcca ggtttgaaaa ctacaactca ttccgacggt tcaaacttca    1080
aaccatgctt gctgactcgg cttcttcttt cttttcacc aagacagagc agtagtcacg    1140
tgacacccct cacgtgcctc cccctttat atttcagact gcaaccctac actttcgcta    1200
cattcactac catattcttt tcactaagca attttctctc ctacttttct ttaaaccct     1260 ttttctccc ctaagccatg gcatctagat catgttacgt cctgtagaaa ccccaacccg    1320
tgaaatcaaa aaactcgacg gcctgtgggc attcagtctg gatcgcgaaa actgtggaat    1380
tgatcagcgt tggtgggaaa gcgcgttaca agaaagccgg gcaattgctg tgccaggcag    1440
ttttaacgat cagttcgccg atgcagatat tcgtaattat gcgggcaacg tctggtatca    1500
gcgcgaagtc tttataccga aaggttgggc aggccagcgt atcgtgctgc gtttcgatgc    1560
ggtcactcat tacggcaaag tgtgggtcaa taatcaggaa gtgatggagc atcagggcgg    1620
ctatacgcca tttgaagccg atgtcacgcc gtatgttatt gccggaaaa gtgtacgtat    1680 caccgtttgt gtgaacaacg aactgaactg gcagactatc ccgccgggaa tggtgattac    1740
cgacgaaaac ggcaagaaaa agcagtctta cttccatgat ttctttaact atgccggaat    1800
```

```
ccatcgcagc gtaatgctct acaccacgcc gaacacctgg gtggacgata tcaccgtggt   1860
gacgcatgtc gcgcaagact gtaaccacgc gtctgttgac tggcaggtgg tggccaatgg   1920
tgatgtcagc gttgaactgc gtgatgcgga tcaacaggtg gttgcaactg gacaaggcac   1980
tagcgggact ttgcaagtgg tgaatccgca cctctggcaa ccgggtgaag gttatctcta   2040
tgaactgtgc gtcacagcca aaagccagac agagtgtgat atctaccgc ttcgcgtcgg    2100 catccggtca gtggcagtga agggcgaaca gttcctgatt aaccacaaac cgttctactt   2160
tactggcttt ggtcgtcatg aagatgcgga cttgcgtggc aaaggattcg ataacgtgct   2220
gatggtgcac gaccacgcat taatggactg gattggggcc aactcctacc gtacctcgca   2280
ttacccttac gctgaagaga tgctcgactg gcagatgaa catggcatcg tggtgattga    2340
tgaaactgct gctgtcggct ttaacctctc tttaggcatt ggtttcgaag cgggcaacaa   2400
gccgaaagaa ctgtacagcg aagaggcagt caacggggaa actcagcaag cgcacttaca   2460
ggcgattaaa gagctgatag cgcgtgacaa aaaccaccca agcgtggtga tgtggagtat   2520
tgccaacgaa ccggataccc gtccgcaagg tgcacgggaa tatttcgcgc cactggcgga   2580
agcaacgcgt aaactcgacc cgacgcgtcc gatcacctgc gtcaatgtaa tgttctgcga   2640
cgctcacacc gataccatca gcgatctctt tgatgtgctg tgcctgaacc gttattacgg   2700
atggtatgtc caaagcggcg atttggaaac ggcagagaag gtactggaaa aagaacttct   2760
ggcctggcag gagaaactgc atcagccgat tatcatcacc gaatacggcg tggatacgtt   2820
agccgggctg cactcaatgt acaccgacat gtggagtgaa gagtatcagt gtgcatggct   2880
ggatatgtat caccgcgtct ttgatcgcgt cagcgccgtc gtcggtgaac aggtatggaa   2940
tttcgccgat tttgcgacct cgcaaggcat attgcgcgtt ggcggtaaca agaaagggat   3000
cttcactcgc gaccgcaaac cgaagtcggc ggcttttctg ctgcaaaaac gctggactgg   3060
catgaacttc ggtgaaaaac cgcagcaggg aggcaaacaa tgagagctcg tgaaatggcc   3120
tctttagttt ttgattgaat catagggta ttagttttct atggccggga gtggtcttct    3180
tgcttaattg taatggaata accagagagg aactactgtg ttatctttga ggaatgttgg   3240
gcttttttcg tttgaattat catgaatgaa attttacttt ttcccaatac aagtttgttt   3300
tcgtttcttg gttttttgtta tcccttggtt tatgtcttgg tttggcttaa atgattgaag   3360
attacactac ctatgtttct gctattcctg ttgaagatca catttgataa taatgcatcg   3420
aatgcattaa agtttcttat tggctctgtc aaaagtattg aaggtggatt tttctaattg   3480
gcaagagaaa gtattaaaga ggtgatttat tagtacttat attttctca gcatctctct     3540 ttcagtgttg gagcttcata aaattagcac ttcagagttt cagtcgggag ctgaattcga    3600
```

<210> SEQ ID NO 3
<211> LENGTH: 4134
<212> TYPE: DNA
<213> ORGANISM: Artificial Sequence
<220> FEATURE:
<223> OTHER INFORMATION: Partial QTPase RNAi construct

<400> SEQUENCE: 3

```
ctcgaggatc taaattgtga gttcaatctc ttccctattg gattgattat cctttctttt    60
cttccaattt gtgtttcttt ttgcctaatt tattgtgtta tccccttttat cctattttgt   120 ttctttactt atttatttgc ttctatgtct ttgtacaaag atttaaactc tatggcacat    180
attttaaagt tgttagaaaa taaattcttt caagattgat gaaagaactt tttaattgta    240
gatatttcgt agattttat tctcttactac caatataacg cttgaattga cgaaaatttg    300
```

-continued

```
tgtccaaata tctagcaaaa aggtatccaa tgaaaatata tcatatgtga tcttcaaatc    360
ttgtgtctta tgcaagattg atactttgtt caatggaaga gattgtgtgc atattttaa     420 aattttatt  agtaataaag attctatata gctgttatag agggataatt ttacaaagaa    480
cactataaat atgattgttg ttgttagggt gtcaatggtt cggttcgact ggttatttta   540
taaaatttgt accataccat ttttttcgat attctatttt gtataaccaa aattagactt    600
ttcgaaatcg tcccaatcat gtcggtttca cttcggtatc ggtaccgttc ggttaatttt   660 cattttttt  taaatgtcat taaaattcac tagtaaaaat agaatgcaat aacatacgtt    720
cttttatagg acttagcaaa agctctctag acattttac  tgtttaaagg ataatgaatt    780
aaaaaacatg aaagatggct agagtataga tacacaacta ttcgacagca acgtaaaaga   840
aaccaagtaa aagcaaagaa aatataaatc acacgagtgg aaagatatta accaagttgg   900
gattcaagaa taaagtctat attaaatatt caaaaagata aatttaaata atatgaaagg   960
aaacatattc aatacattgt agtttgctac tcataatcgc tagaatactt tgtgccttgc  1020
taataaagat acttgaaata gcttagttta aatataaata gcataataga ttttaggaat  1080
tagtattttg agtttaatta cttattgact tgtaacagtt tttataattc caaggcccat  1140
gaaaaattta atgctttatt agttttaaac ttactatata aattttcat  atgtaaaatt  1200 taatcggtat agttcgatat ttttcaatt  tattttata aaataaaaaa cttaccctaa   1260
ttatcggtac agttatagat ttatataaaa atctacggtt cttcagaaga aacctaaaaa  1320
tcggttcggt gcggacggtt cgatcggttt agtcgatttt caaatattca ttgacactcc  1380
tagttgttgt tataggtaaa aagcagttac agagaggtaa aatataactt aaaaaatcag  1440
ttctaaggaa aaattgactt ttatagtaaa tgactgttat ataaggatgt tgttacagag  1500
aggtatgagt gtagttggta aattatgttc ttgacggtgt atgtcacata ttatttatta  1560
aaactagaaa aaacagcgtc aaaactagca aaaatccaac ggacaaaaaa atcggctgaa  1620
tttgatttgg ttccaacatt taaaaagtt  tcagtgagaa agaatcggtg actgttgatg  1680
atataaacaa agggcacatt ggtcaataac cataaaaaat tatatgacag ctacagttgg  1740
tagcatgtgc tcagctattg aacaaatcta agaaggtac  atctgtaacc ggaacaccac  1800
ttaaatgact aaaattaccct catcagaaag cagatggagt gctacaaata acacactatt  1860
caacaaccat aaataaaacg tgttcagcta ctaaaacaaa tataaataaa tctatgtttg  1920
taagcactcc agccatgtta atggagtgct attgcctgtt aactctcact tataaaatag  1980
tagtagaaaa aatatgaacc aaaacacaac tttatcgcca tcatttacat accactccac  2040
ctttaatgaa ggatcaactt ccgcgaatat catctcagca agtgcaattc ctgctatgat  2100
cccgtcttcc tttgctagaa aatgagcatc ggattccata tcaagaggaa ttgtcgcctt  2160
acaagtcaca tctcctaaat tcccagcatc ttcagagagt gcaagtttca taacttcctt  2220
taaatcataa gttgggtgtg ctggtggttt cacctctaat gactccactc ttgtattctt  2280
ggtggctatt gctgacattt tcaccaccaa ccttggagct gtaattgcat aaggatgcac  2340
tgtagcagtg aaaggaatag ctctaaacat gtccgtcgct tctcttccat ttcttctcat  2400
tttcgatttt gattcttatt tctttccagt agctcctgct ctgtgaattt ctccgctcac  2460
gatagatctg cttatactcc ttacattcaa ccttagatct ggtctcgatt ctctgtttct  2520 ctgtttttt  cttttggtcg agaatctgat gtttgtttat gttctgtcac cattaataat  2580
aatgaactct ctcattcata caatgattag tttctctcgt ctacaaaacg atatgttgca  2640
```

```
ttttcacttt tcttcttttt ttctaagatg atttgctttg accaatttgt ttagatcttt    2700
attttatttt atttttctggt gggttggtgg aaattgaaaa aaaaaaaaac agcataaatt    2760
gttatttgtt aatgtattca ttttttggct atttgttctg ggtaaaaatc tgcttctact    2820
attgaatctt tcctggattt tttactccta ttgggttttt atagtaaaaa tacataataa    2880
aaggaaaaca aaagttttat agattctctt aaacccctta cgataaaagt tggaatcaaa    2940
ataattcagg atcagatgct ctttgattga ttcagatgcg attacagttg catggcaaat    3000
tttctagatc cgtcgtcaca ttttattttc tgtttaaata tctaaatctg atatatgatg    3060
tcgacaaatt ctggtggctt atacatcact tcaactgttt tcttttggct ttgtttgtca    3120
acttggtttt caatacgatt tgtgatttcg atcgctgaat ttttaataca agcaaactga    3180
tgttaaccac aagcaagaga tgtgacctgc cttattaaca tcgtattact tactactagt    3240
cgtattctca acgcaatcgt ttttgtattt ctcacattat gccgcttctc tactctttat    3300
tccttttggt ccacgcattt tctatttgtg gcaatccctt tcacaacctg atttcccact    3360
ttggatcatt tgtctgaaga ctctcttgaa tcgttaccac ttgtttcttg tgcatgctct    3420 gtttttaga attaatgata aaactattcc atagtcttga gttttcagct tgttgattct    3480
tttgcttttg gttttctgca gatgtttaga gctattcctt tcactgctac agtgcatcct    3540
tatgcaatta cagctccaag gttggtggtg aaaatgtcag caatagccac caagaataca    3600
agagtggagt cattagaggt gaaaccacca gcacacccaa cttatgATTT aaaggaagtt    3660
```
agagtggagt cattagaggt gaaaccacca gcacacccaa cttatgattt aaaggaagtt    3660
atgaaacttg cactctctga agatgctggg aatttaggag atgtgacttg taaggcgaca    3720
attcctcttg atatggaatc cgatgctcat tttctagcaa aggaagacgg gatcatagca    3780
ggaattgcac ttgctgagat gatattcgcg gaagttgatc cttcattaaa ggtggagtgg    3840
tatgtaaatg atggcgataa agcaagtgtg ttgcctttgt gtggaaatga agaggtactt    3900
gcgaggactt tgcgtttatc agtttatgtg tttgtatatc tatttgatcc agttattatg    3960
gattatatac gcttgaaact catttttaagc cattgttatt gaacgtttat caaatacttt    4020
attatgccaa gcaagtcaaa cacatgcttg ttgattgaaa tcaagctata gaaatctctt    4080
cttcacatac agcagtttag attcacaata caacaagcga aacgataaag tttc          4134

<210> SEQ ID NO 4
<211> LENGTH: 3387
<212> TYPE: DNA
<213> ORGANISM: Artificial Sequence
<220> FEATURE:
<223> OTHER INFORMATION: Selection cassette for partial length QTPase
      RNAi construct

<400> SEQUENCE: 4
cgttttgacg agttcggatg tagtagtagc cattatttaa tgtacatact aatcgtgaat     60
agtgaatatg atgaaacatt gtatcttatt gtataaatat ccataaacac atcatgaaag    120
acactttctt tcacggtctg aattaattat gatacaattc taatagaaaa cgaattaaat    180
tacgttgaat tgtatgaaat ctaattgaac aagccaacca cgacgacgac taacgttgcc    240
tggattgact cggtttaagt taaccactaa aaaacggag ctgtcatgta acacgcggat    300
cgagcaggtc acagtcatga agccatcaaa gcaaagaaac taatccaagg gctgagatga    360
ttaattagtt taaaaattag ttaacacgag ggaaaaggct gtctgacagc caggtcacgt    420
tatctttacc tgtggtcgaa atgattcgtg tctgtcgatt ttaattattt ttttgaaagg    480
ccgaaaataa agttgtaaga gataaacccg cctatataaa ttcatatatt ttctctccgc    540
```

```
tttgaattgt ctcgttgtcc tcctcacttt catcggccgt ttttgaatct ccggcgactt    600
gacagagaag aacaaggaag aagactaaga gagaaagtaa gagataatcc aggagattca    660
ttctccgttt tgaatcttcc tcaatctcat cttcttccgc tctttctttc caaggtaata    720
ggaactttct ggatctactt tatttgctgg atctcgatct tgttttctca atttccttga    780
gatctggaat tcgtttaatt tggatctgtg aacctccact aaatcttttg gttttactag    840
aatcgatcta agttgaccga tcagttagct cgattatagc taccagaatt tggcttgacc    900
ttgatggaga gatccatgtt catgttacct gggaatgat ttgtatatgt gaattgaaat     960
ctgaactgtt gaagttagat tgaatctgaa cactgtcaat gttagattga atctgaacac   1020
tgtttaagtt agatgaagtt tgtgtataga ttcttcgaaa ctttaggatt tgtagtgtcg   1080
tacgttgaac agaaagctat ttctgattca atcagggttt atttgactgt attgaactct   1140
ttttgtgtgt ttgcagctca tatggttgtg tttgggaatg tttctgcggc gaatttgcct   1200
tatcaaaacg ggttttttgga ggcactttca tctggaggtt gtgaactaat gggacatagc   1260
tttagggttc ccacttctca agcgcttaag acaagaacaa ggaggaggag tactgctggt   1320
cctttgcagg tagtttgtgt ggatattcca aggccagagc tagagaacac tgtcaatttc   1380
ttggaagctg ctagtttatc tgcatccttc cgtagtgctc ctcgtcctgc taagcctttg   1440
aaagttgtaa ttgctggtgc tggattggct ggattgtcaa ctgcaaagta cctggctgat   1500
gcaggccaca aacctctgtt gcttgaagca agagatgttc ttggtggaaa gatagctgca   1560 tggaaggat aagatgggga ctggtatgag actggtttac atattttctt cggtgcttat    1620
ccgaatgtgc agaatttatt tggagaactt gggatcaatg atcggttgca gtggaaggaa   1680
cactccatga ttttgctat gccaagtaaa cctggagaat ttagtagatt tgacttccca    1740
gatgtcctac cagcacccct aaatggtatt tgggctattt tgcggaacaa cgagatgctg   1800
acatggccag agaaaataaa gtttgctatt ggacttttgc cagccatggt cggcggtcag   1860
gcttatgttg aggcccaaga tggtttatca gtcaaagaat ggatggaaaa gcagggagta   1920
cctgagcgcg tgaccgacga ggtgtttatt gccatgtcaa aggcgctaaa ctttataaac   1980
cctgatgaac tgtcaatgca atgcattttg atagctttga accggtttct tcaggaaaaa   2040
catggttcca agatggcatt cttggatggt aatcctccgg aaaggctttg tatgccagta   2100
gtggatcata ttcgatcact aggtggggaa gtgcaactta attctaggat aaagaaaatt   2160
gagctcaatg acgatggcac ggttaagagt ttcttactca ctaatggaag cactgtcgaa   2220
ggagacgctt atgtgtttgc cgctccagtc gatatcctga agctccttt accagatccc    2280 tggaaagaaa taccgtactt caagaaattg gataaattag ttggagtacc agttattaat   2340
gttcatatat ggtttgatcg aaaactgaag aacacatatg atcacctact ctttagcaga   2400
agtaaccttc tgagcgtgta tgccgacatg tccttaactt gtaaggaata ttacgatcct   2460
aaccggtcaa tgctggagct agtatttgca ccagcagagg aatggatatc acggactgat   2520
tctgacatca tagatgcaac aatgaaagaa cttgagaaac tcttccctga tgaaatctca   2580
gctgaccaaa gcaaagctaa aattctgaag taccatgtcg ttaagactcc aagatctggg   2640
tacaagacca tcccaaactg tgaaccatgt cgtcctctac aaagatcacc tattgaagga   2700
ttctacttag ctggagatta cacaaaacag aagtacttag cttccatgga aggcgctgtc   2760
ctctctggca aattctgctc tcagtctatt gttcaggatt acgagctact ggctgcgtct   2820
ggaccaagaa agttgtcgga ggcaacagta tcatcatcat gagaaaaggg cgaattcgtt   2880
aaccgcagac gagctcgtga aatggcctct ttagtttttg attgaatcat aggggtatta   2940
```

-continued

| | |
|---|---|
| gttttctatg gccgggagtg gtcttcttgc ttaattgtaa tggaataacc agagaggaac | 3000 |
| tactgtgtta tctttgagga atgttgggct tttttcgttt gaattatcat gaatgaaatt | 3060 |
| ttacttttc ccaatacaag tttgttttcg ttcttggtt tttgttatcc cttggtttat | 3120 |
| gtcttggttt ggcttaaatg attgaagatt acactaccta tgtttctgct attcctgttg | 3180 |
| aagatcacat ttgataataa tgcatcgaat gcattaaagt ttcttattgg ctctgtcaaa | 3240 |
| agtattgaag gtggattttt ctaattggca agagaaagta ttaaagaggt gatttattag | 3300 |
| tacttatatt tttctcagca tctctctttc agtgttggag cttcataaaa ttagcacttc | 3360 |
| agagtttcag tcgggagctg aattcga | 3387 |

<210> SEQ ID NO 5
<211> LENGTH: 3458
<212> TYPE: DNA
<213> ORGANISM: Arabidopsis thaliana

<400> SEQUENCE: 5

| | |
|---|---|
| atggttgtgt ttgggaatgt ttctgcggcg aatttgcctt atcaaaacgg gttttggag | 60 |
| gcactttcat ctggaggttg tgaactaatg ggacatagct ttagggttcc cacttctcaa | 120 |
| gcgcttaaga caagaacaag gaggaggagt actgctggtc ctttgcaggt agtttgtgtg | 180 |
| gatattccaa ggccagagct agagaacact gtcaatttct tggaagctgc tagtttatct | 240 |
| gcatccttcc gtagtgctcc tcgtcctgct aagcctttga agttgtaat tgctggtgct | 300 |
| ggattggctg gattgtcaac tgcaaagtac ctggctgatg caggccacaa acctctgttg | 360 |
| cttgaagcaa gagatgttct tggtggaaag atagctgcat ggaaggatga agatggggac | 420 |
| tggtatgaga ctggtttaca tattttcttc ggtgcttatc gaatgtgca gaatttattt | 480 |
| ggagaacttg ggatcaatga tcggttgcag tggaaggaac actccatgat ttttgctatg | 540 |
| ccaagtaaac ctggagaatt tagtagattt gacttcccag atgtcctacc agcacccta | 600 |
| aatggtattt gggctatttt gcggaacaac gagatgctga catggccaga gaaaataaag | 660 |
| tttgctattg acttttgcc agccatggtc ggcggtcagg cttatgttga gcccaagat | 720 |
| ggtttatcag tcaaagaatg gatggaaaag caggagtac ctgagcgcgt gaccgacgag | 780 |
| gtgtttattg ccatgtcaaa ggcgctaaac tttataaacc ctgatgaact gtcaatgcaa | 840 |
| tgcattttga tagctttgaa ccggtttctt caggaaaaac atggttccaa gatggcattc | 900 |
| ttggatggta atcctccgga aaggctttgt atgccagtag tggatcatat tcgatcacta | 960 |
| ggtggggaag tgcaacttaa ttctaggata aagaaattg agctcaatga cgatggcacg | 1020 |
| gttaagagtt tcttactcac taatggaagc actgtcgaag gagacgctta tgtgtttgcc | 1080 |
| gctccagtcg atatcctgaa gctccttta ccagatccct ggaagaaaat accgtacttc | 1140 |
| aagaaattgg ataaattagt tggagtacca gttattaatg ttcatatatg gtttgatcga | 1200 |
| aaactgaaga acacatatga tcacctactc tttagcagaa gtaaccttct gagcgtgtat | 1260 |
| gccgacatgt ccttaacttg taaggaatat tacgatccta accggtcaat gctgagcta | 1320 |
| gtatttgcac cagcagatgg ttgtgtttgg aatgtttct gcggcgaatt tgccttatca | 1380 |
| aaacgggttt ttggaggcac tttcatctgg aggttgtgaa ctaatgggac atagctttag | 1440 |
| ggttcccact tctcaagcgc ttaagacaag aacaaggagg aggagtactg ctggtccttt | 1500 |
| gcaggtagtt tgtgtggata ttccaaggcc agagctagaa acactgtca atttcttgga | 1560 |
| agctgctagt ttatctgcat ccttccgtag tgctcctcgt cctgctaagc ctttgaaagt | 1620 |

```
-continued tgtaattgct ggtgctggat tggctggatt gtcaactgca aagtacctgg ctgatgcagg    1680
ccacaaacct ctgttgcttg aagcaagaga tgttcttggt ggaaagatag ctgcatggaa    1740
ggatgaagat ggggactggt atgagactgg tttacatatt ttcttcggtg cttatccgaa    1800
tgtgcagaat ttatttggag aacttgggat caatgatcgg ttgcagtgga aggaacactc    1860
catgattttt gctatgccaa gtaaacctgg agaatttagt agatttgact tcccagatgt    1920
cctaccagca cccttaaatg gtatttgggc tattttgcgg aacaacgaga tgctgacatg    1980
gccagagaaa ataaagtttg ctattggact tttgccagcc atggtcggcg gtcaggctta    2040
tgttgaggcc caagatggtt tatcagtcaa agaatggatg gaaaagcagg gagtacctga    2100
gcgcgtgacc gacgaggtgt ttattgccat gtcaaaggcg ctaaacttta taaaccctga    2160
tgaactgtca atgcaatgca ttttgatagc tttgaaccgg tttcttcagg aaaaacatgg    2220
ttccaagatg gcattcttgg atggtaatcc tccggaaagg ctttgtatgc cagtagtgga    2280
tcatattcga tcactaggtg gggaagtgca acttaattct aggataaaga aaattgagct    2340
caatgacgat ggcacggtta agagtttctt actcactaat ggaagcactg tcgaaggaga    2400
cgcttatgtg tttgccgctc cagtcgatat cctgaagctc cttttaccag atccctggaa    2460
agaaataccg tacttcaaga aattggataa attagttgga gtaccagtta ttaatgttca    2520
tatatggttt gatcgaaaac tgaagaacac atatgatcac ctactcttta gcagaagtaa    2580
ccttctgagc gtgtatgccg acatgtcctt aacttgtaag gaatattacg atcctaaccg    2640
gtcaatgctg gagctagtat ttgcaccagc agaggaatgg atatcacgga ctgattctga    2700
catcatagat gcaacaatga aagaacttga gaaactcttc cctgatgaaa tctcagctga    2760
ccaaagcaaa gctaaaattc tgaagtacca tgtcgttaag actccaagat ctgggtacaa    2820
gaccatccca aactgtgaac catgtcgtcc tctacaaaga tcacctattg aaggattcta    2880
cttagctgga gattacacaa aacagaagta cttagcttcc atggaaggcg ctgtcctctc    2940
tggcaaattc tgctctcagt ctattgttca ggattacgag ctactggctg cgtctggacc    3000
aagaaagttg tcggaggcaa cagtatcatc atcatgagaa aagggcgaat tcgttaaccg    3060
cagacaggaa tggatatcac ggactgattc tgacatcata gatgcaacaa tgaaagaact    3120
tgagaaactc ttccctgatg aaatctcagc tgaccaaagc aaagctaaaa ttctgaagta    3180
ccatgtcgtt aagactccaa gatctgggta caagaccatc ccaaactgtg aaccatgtcg    3240
tcctctacaa agatcaccta ttgaaggatt ctacttagct ggagattaca caaaacagaa    3300
gtacttagct tccatggaag gcgctgtcct ctctggcaaa ttctgctctc agtctattgt    3360
tcaggattac gagctactgg ctgcgtctgg accaagaaag ttgtcggagg caacagtatc    3420
atcatcatga gaaagggcg aattcgttaa ccgcagac    3458
```

GLOBAL GENE EXPRESSION ANALYSIS OF HUMAN BRONCHIAL EPITHELIAL CELLS EXPOSED TO CIGARETTE SMOKE, SMOKE CONDENSATES, OR COMPONENTS THEREOF

This application is the U.S. National Phase under 35 U.S.C. 371 of International Application No. PCT/US2005/010733, filed Mar. 29, 2005, which claims priority to the U.S. Provisional Patent Application No. 60/557,929, filed Mar. 30, 2004. The International Application was published in English under PCT Article 21(2) on Nov. 3, 2005. The above-referenced applications are hereby expressly incorporated by reference in their entireties.

FIELD OF THE INVENTION

Aspects of the invention relate generally to methods of identifying a gene or a plurality of genes that are modulated in response to contact with cigarette smoke (CS), cigarette smoke condensate (CSC), or a component thereof. Embodiments include methods to identify a gene or a plurality of genes of normal human bronchial epithelial cells (NHBE) cells that are modulated in response to contact with CS, CSC, or a component thereof. By using the techniques described herein, one can identify markers for a tobacco-related disease, identify and develop tobacco products that have a reduced potential to contribute to a tobacco-related disease, and detect exposure to tobacco products.

BACKGROUND OF THE INVENTION

The leading preventable cause of death and disability in the United States is the chronic use of tobacco products, in particular, cigarettes. In addition to lung cancers, tobacco use plays important direct and indirect roles in the etiology of a wide range of other cancers, including those of the upper aerodigestive tract (e.g., oral cavity, pharynx, larynx, and esophagus), kidney, stomach, bladder, pancreas, uterine cervix, and blood (e.g., certain leukemias). Exposure to tobacco carcinogens and toxins is also a major cause of other diseases of the pulmonary system (e.g., bronchitis, emphysema, chronic obstructive pulmonary disease), the cardiovascular system (e.g., stroke, atherosclerosis, and myocardial infarction), and the female reproductive system (e.g., increased risk of miscarriage, premature delivery, low birth weight, stillbirth, and infant death). While numerous studies have elucidated some of the chemical and biological properties of cigarette smoke that result in its ability to induce this range of pathologies in the smoker, little is known about the nature and temporal association of molecular events that drive specific stages in the multi-step processes that result in clinically evident disease. This is due, in part, to the limited number of individual tobacco constituents such as benzo[a]pyrene that have been assessed for genetic impact, and the fact that few studies have attempted to address the synergistic relationships between the thousands of individual compounds that constitute the various classes of carcinogens in the vapor and particulate phases of tobacco smoke on gene expression.

Cigarette smoke is primarily a mixture of gases (e.g., nitrogen, oxygen, and carbon dioxide) and suspended particulate material that consists of a wide variety of condensed organic compounds (e.g., 'tar'). This particulate phase contains the majority of compounds [at least 60] for which there is sufficient evidence of carcinogenic potential in animals or human. Presumably, the inherent chemical complexity of cigarette smoke results in an equally complex biological response involving a number of signaling pathways and checkpoints that respond to the direct and indirect stress on the genome in exposed tissues.

There are many available approaches to analyze gene expression after cells are exposed to toxicants. Analysis of gene expression after exposure to cigarette smoke is non-trivial, however, due to the complexity and size of data sets and the fact that technical variation can be introduced at different stages of analysis. Establishing well-specified and carefully validated procedures for standardization and normalization of the data from individual specimens is very important. Selection criteria based on the ratio of measured expression levels fails to account for intra-group variations (e.g., normal biologic variance) and can result in false positive selections, for example. (See Dozmorov et al., *J Gerontol A Biol Sci Med Sci* 57: B99-108, 2002; Kerr et al., *J Comput Biol* 7: 819-837, 2000, each of which are expressly incorporated by reference in their entirety).

Many available statistical methods also do not adequately address the mutually exclusive characteristics of sensitivity and specificity. The common practice of using low thresholds for selection of significance ($p<0.05$) can result in a large number of false positive selections, for example. This is especially problematic for high-density array analysis as the number of false positive selections expected to occur by chance may limit the ability to perform higher order analyses, such as that required to identify molecular pathways that contribute to disease or disease sub-phenotyping, which require the accurate prediction of groups of differentially expressed genes. Attempts to increase stringency by raising the threshold of significance above this value can also be problematic, as it will cause a compensatory decrease in sensitivity and a resultant increase in false negative selections. The use of large numbers of replicates is able improve the analysis, however, this approach is expensive and labor intensive.

Hypervariable analysis (HV), which uses statistical robust delimiters for defining biologically-relevant changes in gene expression, can also be used to analyze cells after exposure to a toxicant. (See Dozmorov et al., *Physiol Genomics* 12: 239-250, 2003; and Glynne et al., *Curr Opin Immunol* 12: 210-214, 2000, each of which are expressly incorporated by reference in their entirety). Hypervariable analysis is predicated on the observation that a biologically relevant stimulus will alter gene expression such that homeostasis of the transcriptome is disrupted. Accordingly, these stimuli will modulate the levels of mRNAs of affected genes such that their expression variance over time exceeds the variance observed in the majority of genes in an unstimulated state. Using HV analysis, relatively small biologically relevant changes in gene expression can be identified. Despite current advances in gene expression analysis, there remains a need to identify the genetic events and molecular pathways induced by exposure to tobacco (e.g., cigarette) smoke and tobacco (e.g., cigarette) smoke condensates.

SUMMARY OF THE INVENTION

Several approaches to evaluate tobacco products for the potential to contribute to a tobacco-related disease have been developed. Many embodiments concern obtaining smoke or a smoke condensate from a tobacco or a tobacco product, contacting cells, preferably human cells that typically come in contact with a tobacco product, such as cells of the mouth, lips, tongue, gums, larynx, pharynx, trachea, bronchial cells and lung cells, and analyzing the modulation of expression (e.g., up-regulation or down-regulation) of one or more genes in said cells after contact with said smoke or smoke condensate. The analysis of the modulation of expression of a gene can be accomplished by oligonucleotide array, microarray, hybridization, amplification, protein detection, antibody detection, detection of a modified gene product (e.g., phosphorylation), or detection of a metabolite. The gene expression information obtained can be further analyzed so as to determine whether a particular gene contributes to a tobacco-related disease. Commercially available software allows one to rapidly make this determination.

In some embodiments, a second population of cells, preferably the same type as that, which are contacted with said smoke or smoke condensate above, are also analyzed so as to obtain a baseline of expression of one or more genes. By comparing the baseline of expression of one or more genes with the modulation of expression seen after cells are contacted with a smoke or smoke condensate, one can determine whether the modulation of expression of the analyzed gene is significantly above a baseline value for expression of the particular gene. Quantitative PCR or hybridization or protein detection methods can be employed.

In more embodiments, a first tobacco product is compared to a second tobacco product using the methodologies described above. That is, a first population of cells are contacted with smoke or smoke condensate obtained from a first tobacco (e.g., cigarette) and the modulation of gene expression is analyzed, as above. Next, a second population of cells are contacted with smoke or smoke condensate obtained from said second tobacco (e.g., a cigarette) and the modulation of gene expression is analyzed, as above. By comparing the expression of genes that are modulated in response to exposure to the first tobacco's smoke or smoke condensate with the expression of genes that are modulated in response to exposure to the second tobacco, one can identify differences in the genes that are modulated between the two tobaccos, as well as, the levels of expression of genes that are common to both tobaccos. By analyzing the genes that are modulated in one or both tobaccos using commercially available software or the available literature, one can determine whether a particular gene contributes to a tobacco-related disease, such as cancer, pulmonary, or cardiovascular disease. In this manner, one can identify whether one tobacco product is less likely to contribute to a tobacco-related disease, as compared to a second tobacco product. Although the description herein provides several methods in the context of comparing tobacco products that undergo pyrolysis (e.g., cigarettes, pipe tobacco, and cigars), similar approaches can be applied to the evaluate snuff, chew, and other tobacco products that do not undergo pyrolysis. The preparation and analysis of condensates from such non-pyrolysis tobacco products is straightforward given the teachings provided herein.

In still more embodiments, components that are present in conventional tobacco products can be identified as contributing to a tobacco-related disease using the approaches described herein. Further, the identification and development of tobacco products that have a reduced potential to contribute to a tobacco-related disease are embodiments. For example, as above, smoke or a smoke condensate is obtained from a first tobacco product, a conventional tobacco, which comprises a component that contributes to a tobacco-related disease and this smoke or smoke condensate is contacted with human cells (e.g., normal human bronchial epitheilial cells or NHBE cells) and a modulation of at least one human gene in response to contact with the smoke or smoke condensate is identified. The human gene(s) that are modulated in response to contact with the smoke or smoke condensate obtained form the conventional tobacco can be identified as contributing to a tobacco-related disease using available literature or commercially available software, as described above. Next, smoke or a smoke condensate is obtained from a second tobacco, which is a modified tobacco, (e.g., genetically modified or chemically modified) having a reduced amount of expression of a tobacco gene that is involved in the production of a component that contributes to a tobacco-related disease (e.g., a nicotine synthesis gene, such as quinolate phosphoribosyl transferase), and this smoke or smoke condensate is contacted with human cells (e.g., NHBE cells) and a modulation of expression of at least one human gene that is different than the modulation of expression of the human gene(s) that resulted from exposure to the conventional first tobacco will be observed. Typically, the modified second tobacco will induce expression of fewer genes (or have lower levels of expression of a gene(s)) that are associated with a tobacco-related disease than the conventional tobacco or the modified second tobacco will induce expression of genes or increase expression of genes, as compared to the first conventional tobacco, which are involved in preventing a tobacco-related disease. In this manner, the gene expression events that are directly correlated with the presence or absence of a component can be identified. Further, by selectively removing certain components in tobacco and analyzing the modified tobacco using the approaches described herein, one can determine whether the modified tobacco is less likely to contribute to a tobacco-related disease, as compared to the parental strain of tobacco that was used to generate the modified tobacco. That is, by using the approaches described herein, a tobacco product that has a reduced potential to contribute to a tobacco related disease, a "reduced risk" tobacco product can be made. Accordingly, tobacco products made by the processes described herein are embodiments of the invention.

Additionally, some embodiments described herein concern the use of the genes that are modulated in response to contact with smoke or a smoke condensate from various tobaccos as biomarkers for a tobacco-related disease. That is, aspects of the invention concern the use of the biomarkers identified using the approaches herein to predict the likelihood, diagnose or provide a prognosis of a subject's predilection to acquire a tobacco-related disease.

Aspects of the invention also concern particular approaches that were used to reduce expression of a component in tobacco that contributes to a tobacco related disease. Preferred embodiments, in this regard, concern RNAi constructs that are designed to inhibit nicotine synthesis. Additionally, a novel gene that confers resistance to the herbicide norflurazone was also created using site directed mutagenesis (SEQ. ID. No. 5). Although a selection cassette comprising this norflurazone resistance gene was used to isolate tobacco transformants, this gene can be introduced into most any plant and used to confer resistance to the herbicide either for selection purposes or to confer herbicide resistance in the field, so as to rid the field of weeds and non-transformed plants. Accordingly, aspects of the invention include nucleic acids that comprise (SEQ. ID. No. 5), and fragments of these nucleic acids that contain at least, equal to, or more than 5, 10, 15, 20, 25, 30, 35, 40, 45, 50, 55, 60, 65, 70, 75, 80, 85, 90, 95, 100, 105, 110, 120, 130, 140, 15, 200, 300, 400, 500, 600, 700, 800, 900, or 1,000 consecutive nucleotides of SEQ. ID. No. 5) that include the point mutation of a T to G at nucleotide position 1478, which results in a valine to glycine change at amino acid residue 493, and peptides that encode these nucleic acids, as well as, methods of using these nucleic acids to confer resistance to norflurazone, norflurazone analogs, or other herbicides.

Particularly preferred embodiments include a method of making a tobacco product that has a reduced potential to contribute to a tobacco-related disease comprising providing a first tobacco that comprises a compound that contributes to a tobacco-related disease; obtaining smoke or a smoke condensate from said first tobacco; contacting a first isolated population of cells with said smoke or smoke condensate from said first tobacco; identifying a first gene that is expressed in said first population of cells in response to said contact with said smoke or smoke condensate from said first tobacco, wherein expression of said first gene contributes to a tobacco-related disease; providing a second tobacco that has been modified to reduce expression of a second gene; obtaining smoke or a smoke condensate from said second tobacco; contacting a second isolated population of cells with said smoke or smoke condensate from said second tobacco; identifying a reduction in expression of said first gene that contributes to a tobacco-related disease in said second population of cells, which are contacted with said smoke or smoke condensate from said second tobacco; and making said tobacco product from said second tobacco, wherein said tobacco product comprising said second tobacco has a reduced potential to contribute to a tobacco-related disease as compared to a tobacco product comprising said first tobacco.

In some embodiments, first tobacco is a burley tobacco, a flue tobacco, or an oriental tobacco. In some embodiments, the first and second populations of cells are contacted with smoke and, in other embodiments, the first and second populations of cells are the same cell type. In some embodiments, the first and second populations of cells are immortal cells and, in other embodiments, the first and second populations of cells are normal human cells of the lung, mouth, or tongue. Preferably, the first and second populations of cells are normal human bronchial epithelial (NHBE) cells. In some embodiments, the second gene that has been modified in said second tobacco is a gene in a pathway of nicotine synthesis and the second gene can be selected from the group consisting of putrescine N-methyltransferase, N-methylputrescine oxidase, ornithine decarboxylase, S-adenosylmethionine synthetase, NADH dehydrogenase, phosphoribosylanthranilate isomerase, and quinolate phosphoribosyl transferase (QPTase). Preferably, the second gene is quinolate phosphoribosyl transferase (QPTase) or putrescine methyltransferase (PMTase). In some embodiments, said modification of said second gene in said second tobacco is a genetic modification and in other embodiments, said modification of said second tobacco is a chemical treatment. In some embodiments, said tobacco-related disease is selected from the group consisting of pulmonary disease, cardiovascular disease, and cancer and, preferably, said tobacco related disease is cancer.

In some embodiments, said first gene has a sequence selected from the group consisting of NM_004261, NM_000859, AK025736, NM_002526, NM_001109, NM_005891, NM_006409, NM_018445, NM_001284, NM_000485, NM_007002, NM_006829, NM_001667, NM_000693, NM_001635, NM_001657, NM_001145, NM_000700, NM_005139, NM_001154, NM_004034, NM_016476, NM_016085, NM_005721, NM_017900, M90355, NM_004281, NM_001196, NM_003860, NM_014567, NM_021096, NM_005186, NM_001750, NM_013376, NM_015965, NM_016041, NM_016038, BC002971, NM_006429, NM_000647, NM_012111, AK026450, NM_007096, BC010039, NM_016451, NM_007263, NM_004645, AL162070, NM_000389, NM_000099, NM_001554, NM_007274, NM_020193, NM_004396, NM_001357, AB040961, NM_007326, NM_020548, NM_013253, NM_004405, AL080156, NM_014045, NM_001539, NM_006145, NM_004419, NM_001946, NM_014390, NM_005451, NM_004092, NM_004431, NM_016357, BF541376, NM_003757, NM_003755, NM_001417, NM_004095, NM_005243, NM_005245, NM_004104, AK054816, NM_001457, NM_014164, AL365404, NM_007278, NM_001520, AK024486, NM_001498, NM_002061, NM_004446, NM_002064, NM_002083, NM_000637, NM_002087, L24498, NM_006644, NM_002157, NM_005345, NM_006597, NM_004134, NM_016292, NM_002133, NM_004712, NM_001533, AK057120, AF130111, NM_001536, AK023395, AK054711, AK055071, AK056736, AK024927, AK055564, AK026181, AK026902, AL512727, AL117595, AL050378, AF041429, AF118072, AF065241, BC010009, BC011880, BC017001, BC007307, NM_014029, NM_014047, AF161415, NM_016099, NM_014168, NM_014182, AL139112, AL354915, NM_000182, NM_016404, NM_016623, NM_015932, NM_015343, AF103803, NM_014886, NM_018437, NM_018306, NM_032813, NM_022842, NM_031207, NM_024508, AK027859, NM_032771, BC014850, NM_032899, NM_024040, NM_024038, NM_031943, NM_052815, NM_016545, NM_005542, NM_021999, NM_006147, NM_000576, Z17227, NM_004508, NM_005354, NM_006854, NM_000421, NM_000224, NM_005555, NM_014815, NM_000899, NM_001730, NM_003937, NM_005558, NM_016201, NM_015925, NM_014463, NM_004995, NM_005916, NM_006428, NM_006636, NM_004528, NM_022818, NM_014341, NM_014161, NM_021134, NM_017446, NM_021210, NM_004529, NM_033546, AB032945, NM_017534, NM_002473, NM_002356, NM_000903, NM_004541, NM_004548, NM_004547, NM_002494, NM_014328, BC010285, NM_000271, NM_006096, NM_006164, NM_003489, NM_017838, NM_002820, NM_020992, NM_002574, NM_003713, NM_002631, NM_002632, NM_002658, NM_014287, NM_003819, NM_000937, NM_001198, NM_002583, NM_000917, NM_053024, AB051437, NM_002778, NM_000963, BC013908, NM_002806, NM_002815, NM_002812, NM_002797, NM_002799, NM_014330, NM_004156, NM_006808, NM_015714, BC012513, NM_003979, NM_001666, NM_001033, NM_002950. NM_001029, NM_002953, AB037819, NM_014248, NM_006743, NM_004902, NM_000687, AB051532, NM_003900, NM_001085, NM_030666, NM_000602, NM_015966, NM_006622, AB000462, NM_003134, NM_003145, NM_007107, AF395440, NM_005870, NM_006109, NM_015523, NM_030981, NM_006518, NM_005628, NM_004207, NM_018976, NM_014331, NM_003130, NM_004599, NM_006745, NM_006918, NM_006819, NM_006704, NM_002999, NM_006289, NM_015641, NM_003217, NM_003314, NM_003329, NM_003330, NM_004238, NM_006755, NM_003234, NM_001064, NM_012459, NM_006470, NM_003449, NM_003289, NM_003404, NM_012321, M26880, NM_014501, NM_003334, AL110132, BC007657, NM_003364, NM_003574, NM_012323, NM_002359, NM_002467, NM_006007, NM_013360, and NM_004234.

In some embodiments, said first gene has a sequence selected from the group consisting of: NM_00359, NM_00405, NM_00521, NM_00626, NM_01225, NM_00482, NM_00284, AF308602, NM_01438, NM_00371, NM_00164, NM_01633, NM_01865, NM_01242, AF156165, NM_00205, AF163473, NM_03328 AK024486, NM_00343, U18018, NM_00523, BC013971, AJ420488, NM_00548, NM_00578, NM_00094, NM_00675, NM_00228, AL110274, NM_01428, NM_01787, and NM_00437.

In some embodiments, said first gene is selected from the group consisting of Cullin 4A, C-jun, Hoxa10, and PPP2R1B. Preferably, said tobacco product is a cigarette and aspects of the invention include the tobacco products made by the methods described herein.

More embodiments concern a method of reducing the potential of a tobacco consumer to acquire a tobacco-related disease comprising providing the tobacco product made by the method of Claim 1 to said tobacco consumer. Additionally, the use of the methods described herein to prepare a tobacco product that has a reduced potential to contribute to a tobacco-related disease are also embodiments.

Still more embodiments concern a method of making a tobacco product that has a reduced potential to contribute to a tobacco-related disease comprising providing a first tobacco that comprises a compound that contributes to a tobacco-related disease; obtaining smoke or a smoke condensate from said first tobacco; contacting a first isolated population of cells with said smoke or smoke condensate from said first tobacco; identifying a first gene that has reduced expression in said first population of cells in response to said contact with said smoke or smoke condensate from said first tobacco, wherein said reduced expression of said first gene contributes to a tobacco-related disease; providing a second tobacco that is the same variety and grown under the same conditions as said first tobacco, wherein said second tobacco has been modified to reduce expression of a second gene; obtaining smoke or a smoke condensate from said second tobacco; contacting a second isolated population of cells with said smoke or smoke condensate from said second tobacco; identifying an up-regulation in expression of said first gene in said second population of cells, which are contacted with said smoke or smoke condensate from said second tobacco; and making said tobacco product from said second tobacco, wherein said tobacco product comprising said second tobacco has a reduced potential to contribute to a tobacco-related disease as compared to a tobacco product comprising said first tobacco.

As above, in these methods, said first tobacco can be a burley tobacco, a flue tobacco, or an oriental tobacco. In some embodiments, said first and second populations of cells are contacted with smoke and in others said first and second populations of cells are the same cell type. The first and second populations of cells can be immortal cells and the first and second populations of cells can be normal human cells of the lung, mouth, or tongue. Preferably, said first and second populations of cells are normal human bronchial epithelial (NHBE) cells.

In some embodiments, said second gene that has been modified in said second tobacco is a gene in a pathway of nicotine synthesis, which can be selected from the group consisting of putrescine N-methyltransferase, N-methylputrescine oxidase, ornithine decarboxylase, S-adenosylmethionine synthetase, NADH dehydrogenase, phosphoribosylanthranilate isomerase, and quinolate phosphoribosyl transferase (QPTase). Preferably, said second gene is quinolate phosphoribosyl transferase (QPTase) or putrescine methyltransferase (PMTase). The modification of said second gene in said second tobacco can be a genetic modification or a chemical treatment. In some embodiments, said tobacco-related disease is selected from the group consisting of pulmonary disease, cardiovascular disease, and cancer. Preferably, said tobacco related disease is cancer.

In some embodiments, said first gene has a sequence selected from the group consisting of NM_006856, NM_001143, NM_001657, AB053314, AK023086, BI820294, AK025253, NM_001271, NM_006589, AK000796, NM_001934, NM_005509, NM_004419, NM_003494, NM_000145, NM_005708, NM_002053, AB033063, NM_002129, NM_003542, NM_024598, NM_017933, NM_024037, BC016840, AK027858, NM_006903, NM_000526, NM_000424, NM_005554, NM_005556, AK024583 NM_005583, AL137524, AL117623, NM_012334, AB007959, NM_002520, NM_033014, NM_024594, AB029015, NM_018049, BC015542, NM_018936 NM_000320, NM_000456, NM_007273, NM_005978, NM_016372, NM_006456 NM_024624, AL353933, AK027663, AK024451, NM_005480, NM_002466, NM_006385, NM_005096, NM_003430, AC006033, AF111848, AK025272, AL137077 L24498, NM_003590, NM_005774, and NM_014111.

In some embodiments, said tobacco product is a cigarette and tobacco products made by the methods above are also embodiments. More embodiments concern a method of reducing the potential of a tobacco consumer to acquire a tobacco-related disease comprising providing the tobacco product made by the approaches described herein to said tobacco consumer and the use of the methods described herein to prepare a tobacco product that has a reduced potential to contribute to a tobacco-related disease.

Still more embodiments concern a method to identify a gene that is modulated by exposure to tobacco smoke or a tobacco smoke condensate comprising providing a first isolated population of human bronchial epithelial cells (NHBE cells); contacting said NHBE cells with tobacco smoke or a tobacco smoke condensate; and identifying a gene that is modulated in response to contact with said tobacco smoke or said tobacco smoke condensate. In some embodiments, the expression of said gene is up-regulated. In some embodiments, the expression of said gene is down-regulated. In some embodiments, an oligonucleotide array is used to identify said gene that is modulated after said NHBE cells are contacted with said tobacco smoke or said tobacco smoke condensate.

More embodiments concern the method above, further comprising providing a second population of isolated human bronchial epithelial cells (NHBE cells), which are not contacted with an amount of tobacco smoke or tobacco smoke condensate; and comparing the level of expression of at least one gene of said second population of NHBE cells with the level of expression of the same gene in said first population of NHBE cells, which has been contacted with said tobacco smoke or said tobacco smoke condensate so as to identify the modulation of a gene of said first population of NHBE cells that has been contacted with said tobacco smoke or tobacco smoke condensate.

Still more embodiments concern a method to identify a predilection to acquire a tobacco-related disease in a subject comprising identifying a subject in need of a determination of a predilection to acquire a tobacco-related disease obtaining a biological sample from said subject; and measuring the level of expression in said biological sample of at least one gene selected from the group consisting of: FRHUL ferritin light chain, Ferritin, heavy polypeptide 1, Glutamate-cysteine ligase, catalytic subunit, Glutamate-cysteine ligase modifier subunit, Glutaredoxin (thioltransferase), Glutathione peroxidase 2, Glutathione reductase, Heme oxygenase 1, Jun D proto-oncogene, Microsomal glutathione S-transferase 3, NAD(P)H dehydrogenase, quinone 1, N-myc downstream regulated gene 1, Nuclear factor (erythroid-derived 2)-like 2, PDZ and LIM domain 1, Peroxiredoxin 1, S-adenosylhomocysteine hydrolase, Thioredoxin, Thioredoxin reductase 1, V-maf musculoaponeurotic fibrosarcoma oncogene homolog F, V-maf musculoaponeurotic fibrosarcoma oncogene homolog G, Amphiregulin (schwannoma-derived growth factor), Apoptosis related protein APR-3, Aurora-A kinase interacting protein, BH3 interacting domain death agonist, Calpain 1, (mu/I) large subunit, CDK4-binding protein p34SEI1, Cell death-regulatory protein GRIM19, Cysteine-rich, angiogenic inducer 61, DEAD/H (Asp-Glu-Ala-Asp/H is) box polypeptide 5, Dickkopf homolog 3, Dual specificity phosphatase 5, Dual specificity phosphatase 6, EphA2, FAT tumor suppressor homolog 1, Granulin, Growth arrest and DNA-damage-inducible alpha, Histone deacetylase 3, Immediate early response 3, Immediate early response 5, Interleukin 1-beta, Kruppel-like factor 5, Myeloid/lymphoid or mixed-lineage leukemia trithorax homolog, Placental growth factor, vascular endothelial growth factor-related protein, Plasminogen activator, urokinase, PR domain containing ZNF domain, PRKC, WT1 regulator, Protein phosphatase 1, regulatory subunit 15A, Putative lymphocyte G0/G1 switch gene, Rho GTPase activating protein 4, Serum-inducible kinase, SKB1 homolog, Suppressor of G2 allele of SKP1, homolog of Testis enhanced gene transcript (BAX inhibitor 1), V-myc myelocytomatosis viral oncogene homolog, disintegrin and metalloproteinase domain 8, BCL2-associated athanogene 3, Chaperonin containing TCP1, subunit 5 (epsilon), Chaperonin containing TCP1, subunit 7 (eta), GABA(A) receptor-associated protein, DnaJ (Hsp40) homolog, subfamily A (member 1), DnaJ (Hsp40) homolog, subfamily B (member 1), DNAJ, Heat shock 105 kD, Heat shock 10 kD protein 1 (chaperonin 10), Heat shock 70 kD protein 1A, Heat shock 70 kD protein 8, Heat shock 70 kD protein 9B (mortalin-2), Heat shock protein 75, Stress-induced-phosphoprotein 1 (Hsp70/Hsp90-organizing protein), Matrix metalloproteinase 14 (membrane-inserted), Proteasome (prosome, macropain) 26S subunit, ATPase, 1, Proteasome (prosome, macropain) 26S subunit, ATPase 6, Proteasome (prosome, macropain) 26S subunit, non-ATPase, 11, Proteasome (rosome, macropain) 26S subunit, non-ATPase 8, Proteasome (prosome, macropain) subunit, beta type 5, Proteasome (prosome, macropain) subunit beta type 7, Protein translocation complex beta, Ring-box 1, Sequestosome 1, Signal recognition particle 14 kD (homologous Alu RNA binding protein), Tetratricopeptide repeat domain 1, Thyroid hormone receptor interactor 12, Ubiquitin C, Ubiquitin carrier protein, Ubiquitin-activating enzyme E1 (A1S9T and BN75 temperature sensitivity complementing), Ubiquitin-conjugating enzyme E2 variant 1, Ubiquitin-conjugating enzyme E2M (UBC12 homolog), 3-hydroxy-3-methylglutaryl-Coenzyme A reductase, 3-hydroxy-3-methylglutaryl-Coenzyme A synthase 1 (soluble), Acetyl-Coenzyme A acetyltransferase 2 (acetoacetyl Coenzyme A thiolase), Annexin A1, Cytosolic acyl coenzyme A thioester hydrolase, Diazepam binding inhibitor (GABA receptor modulator, acyl-Coenzyme A binding protein), Enoyl Coenzyme A hydratase, short chain, 1, mitochondrial, Fatty acid synthase, Hydroxyacyl-Coenzyme A dehydrogenase/3-ketoacyl-Coenzyme A thiolase/enoyl-Coenzyme A hydratase, Insulin induced gene 1, Isopentenyl-diphosphate delta isomerase, Niemann-Pick disease, type C1, Phosphatidic acid phosphatase type 2B, Prosaposin (variant Gaucher disease and variant metachromatic leukodystrophy), Sterol regulatory element binding transcription factor 2, Sterol-C4-methyl oxidase-like, and Sterol-C5-desaturase (ERG3 delta-5-desaturase homolog)-like, whereby a level of expression of said at least one gene that differs from the level of expression of the same gene in a biological sample obtained from a second subject that has not consumed tobacco indicates that said subject has a predilection to acquire a tobacco-related disease.

BRIEF DESCRIPTION OF THE DRAWINGS

FIG. 2A shows Clusters that contain 50 or more genes in CSC-A-treated cells. FIG. 2B shows Clusters containing 50 or more genes in CSC-B-treated cells. FIG. 2C shows Clusters containing 50 or more genes in S9-treated cells.

DETAILED DESCRIPTION OF THE PREFERRED EMBODIMENT

Figure 1A:
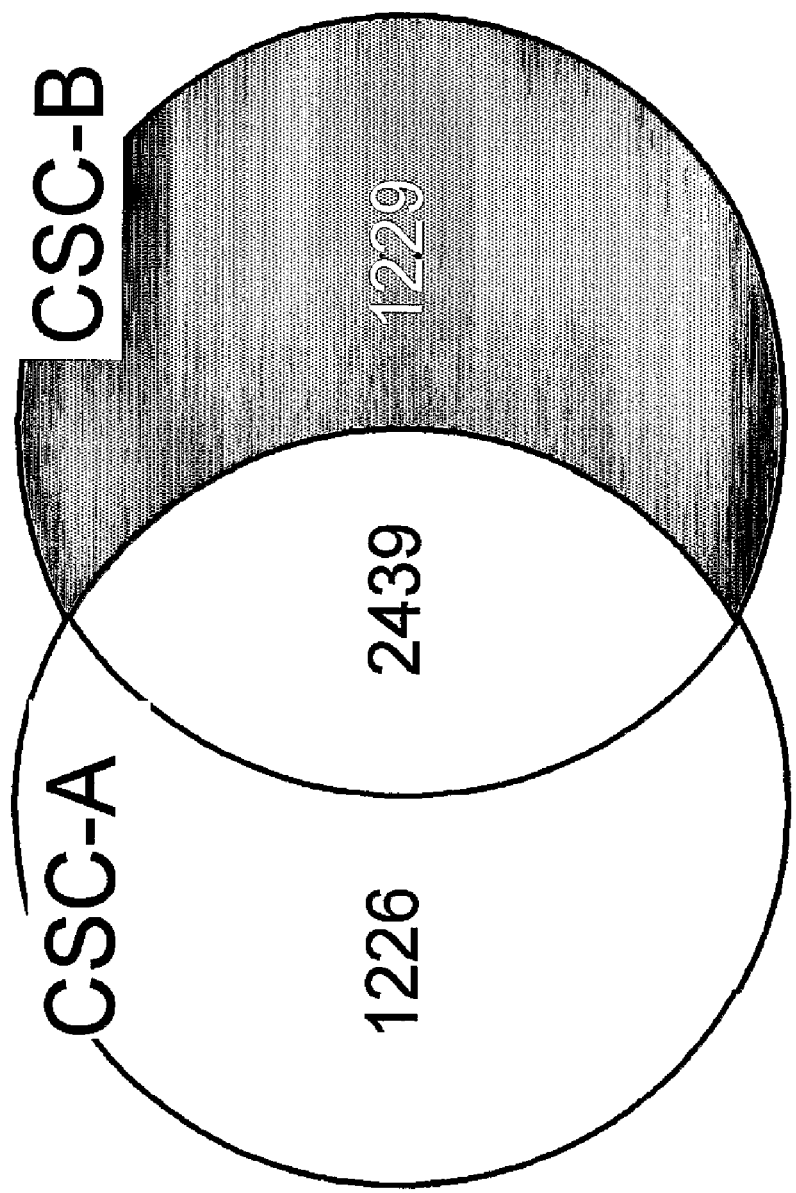
FIG. 1A is a Venn diagram comparing gene expression modulations induced by cigarette smoke condensates of two different tobacco products (e.g., cigarettes) CSC-A (3665) and CSC-B (3668). The number of genes uniquely affected by exposure to each product CSC-A (1226) and CSC-B (1229) is given in each sector. The intersections between sectors reflect the number of genes that are affected by both CSCs (2439).

Aspects of the present invention concern the discovery that high-density microarrays can be used to elucidate how cells of the oral cavity, mouth, tongue, trachea, bronchi, and lung mount a multigenic response to cigarette smoke and the major classes of smoke constituents (e.g., vapor and particulate phases). Using microarray technology and/or Reverse Transcriptase Polymerase Chain Reaction (RTPCR), gene expression patterns and levels of gene expression in short-term cultures of normal human bronchial epithelial (NHBE) cells exposed to cigarette smoke and cigarette smoke condensates were analyzed. It was found that subtle alterations to the 'homeostatic transcriptome' are useful in defining the major signaling pathways activated upon exposure to chronic, but low level, doses of carcinogenic mixtures such as that which occur daily in an individual smoker. This type of analysis is especially relevant for complex bioactive mixtures, such as cigarette smoke (CS), cigarette smoke condensate (CSC), tobacco smoke (TS), and tobacco smoke condensate (TSC), since assessing the specific effects of individual components of such mixtures does not reflect the true impact on a cell or the body due to the synergistic or antagonistic interactions that occur with the entirety of the components that are normally present. Moreover, because the contemplated methods described herein analyze human cells of the mouth, oral cavity, trachea, and lungs, either normal or immortalized cell lines (e.g., human bronchial cells (e.g., BEP2D or 16HBE140 cells), human bronchial epithelial cells (e.g., HBEC cells, 1198, or 1170-I cells), normal human bronchial epithelial cells (NHBE cells), BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226) tongue cells (e.g., CAL 27), and mouth cells (e.g., Ueda-1)), which are contacted with cigarette smoke or smoke condensates (as opposed to exposure to a single agent with a well-defined mechanism of toxicity), one can identify unique genomic responses and cellular damage over time. That is, novel genes and gene expression patterns are identified using the methods described herein because the vapor and particulate components of tobacco smoke contain numerous substances that immediately and directly damage a range of biomolecules, as well as, other substances whose toxicity is activated only after biotransformation by cellular enzymes into reactive nucleophiles that then attack various cellular elements.

Although it is known that cigarette smoke, as well as various smoke components, can cause numerous disruptions to the genome (see Chujo et al., *Lung Cancer* 38: 23-29, 2002; Wistuba, et al. *Semin Oncol* 28: 3-13, 2001), transcriptome (see Bhattacharjee, et al. *Proc Natl Acad Sci USA* 98: 13790-13795, 2001 and Garber et al., *Proc Natl Acad Sci USA* 98: 13784-13789, 2001), and proteome (see Hanash, et al. *Dis*

*Markers* 17: 295-300, 2001); relatively little is known about the effects of cigarette smoke condensates (CSC) and cigarette smoke (CS) exposure on the overall impact on steady state mRNA levels, transcriptional regulation, protein production, and protein modification in normal cells of the oral cavity, mouth, tongue, trachea, bronchi, and lung. Accordingly, experiments were conducted to identify a set of biomarkers that could be used to monitor exposure to tobacco toxins, detect pre-malignant disease, improve diagnosis and prognosis of current tobacco-related disease, develop patient-specific treatment options, test risk reduction strategies for current and former smokers, and identify and develop tobacco products that have a lower potential to contribute to a tobacco-related disease (e.g., a tobacco product that has a lower carcinogenic potential than a conventional tobacco product, a reduced risk tobacco product). More particularly, as described herein, several approaches to identify a gene expression pattern or fingerprint from cells of the oral cavity, mouth, tongue, trachea, bronchi, and lung (normal or immortal), which have been exposed to tobacco smoke or a tobacco smoke condensate have been discovered and the information generated by practicing these methods can be used in diagnostics, therapeutic and prophylactic procedures, as well as, approaches to identify and develop less harmful tobacco products. In addition, elucidating the various molecular, genetic, cellular, and systemic effects of cigarette smoke provides a detailed mechanistic understanding of how chronic tobacco exposure ultimately causes disease.

Several studies assessing the clinical usefulness of alterations in global gene and protein expression patterns in malignant and normal human lung tissues have shown that quantitative and/or qualitative changes in a small number of expressed genes and proteins, in combination with standard clinicopathological variables, have prognostic and/or diagnostic potential for patients with tobacco-related diseases. A direct cause and effect relationship between any of these documented molecular events and cell exposure to tobacco smoke is unclear, however. Thus, it was decided to examine the effects of tobacco constituents on the transcriptome of normal lung cells in a controlled in vitro environment.

Several methods described herein analyze the transcriptome of cells of the oral cavity, mouth, tongue, trachea, bronchi, and lung after exposure to a smoke or smoke condensate using high-density microarrays, RTPCR, or another conventional nucleic acid or protein detection method. The data show that exposure of such cells (e.g., normal human bronchial epithelial cells (NHBE cells)) to cigarette smoke or cigarette smoke condensates results in a modulation of a specific set of genes whose expression levels varied over the normal variability of gene expression in these cells. Accordingly, these genes can be used to monitor tobacco-induced changes to the transcriptome. By sorting these genes into biologically functional classes, dominant biochemical pathways known to be relevant to tobacco-related disease were identified. In addition, it was surprising to learn that treatment with an S9 microsomal fraction, a step common in many toxicological studies, has a broad impact on gene expression in normal lung cells that is distinctly different from the impact of tobacco exposure.

Accordingly, some embodiments concern the identification of a gene or a plurality of genes from cells of the oral cavity, mouth, tongue, trachea, bronchi, and lung (e.g., NHBE cells), which are modulated (e.g., up-regulated or down-regulated expression) in response to contact with a cigarette smoke (CS), a cigarette smoke condensate (CSC), tobacco smoke (TS), or a tobacco smoke condensate (TSC). In some embodiments, a gene expression pattern, fingerprint, or signature is obtained, which is an identification of a specific plurality of genes or set of genes that are modulated (i.e., up-regulated or down-regulated) after contact with CS, CSC, TS, or TSC. The plurality of genes that are affected can be any combination or subset of genes that are identified as being influenced by exposure to CS, CSC, TS, or TSC. In some embodiments, the plurality of affected genes are a subset of suppressor genes. In some embodiments, the plurality of genes that are affected by exposure to CS, CSC, TS, or TSC are a subset of genes affecting cholesterol regulation and production. In some embodiments, the subset of genes that are affected genes are involved in oxidative stress, cell proliferation, apoptosis, protein turn-over, heat shock, or ubiquitination.

Several approaches to conduct a gene expression analysis that involve the use of NHBE cells are provided herein, whereby said cells are contacted with a CS, CSC, TS, or TSC and a gene, pattern of gene expression or a fingerprint from said CS, CSC, TS, or TSC-treated cells is obtained. The gene expression data generated by the approaches described herein can be recorded onto a recordable media (e.g., a hard drive, memory, cache, floppy, CD-ROM, DVD-ROM) and can be analyzed using various statistical approaches to determine whether said data identifies a genetic modulation event (e.g., an up-regulation or down-regulation of expression) that is statistically relevant. Statistically relevant genetic modulation events that occur in the cells that were contacted with a CS, CSC, TS, or TSC can then be used to identify a molecular pathway that is involved in a tobacco-related disease. Accordingly, the approaches described herein can be used to identify a marker for a tobacco-related disease and to determine whether this marker is modulated (e.g., a marker gene is up-regulated or down-regulated) in response to exposure to a particular CS, CSC, TS, or TSC.

Furthermore, this data can be used to create a genetic profile for a particular tobacco product, which allows one to empirically determine the components of a given tobacco product's smoke (or tobacco per se) that contribute to a gene expression event in a human cell that is associated with a tobacco-related disease. Accordingly, by using the approaches described herein, one can identify specific tobacco products, as well as, growing, harvesting, curing, processing, and blending practices that have a reduced potential to contribute to a genetic modulation that is associated with a tobacco-related disease. That is, the approaches described herein can be used to identify and develop reduced risk cigarettes. Still further, the markers for tobacco-related disease, and the genetic profiles identified by using the approaches described herein can be used to diagnose, provide a prognosis or otherwise identify an individual at risk of acquiring a tobacco-related disease and the effect of tobacco smoke on a subject at a molecular level. The section below describes several methods that can be used to identify genes that are modulated after exposure to CS, CSC, TS, or TSC and to identify and develop tobacco products that have a reduced risk of contributing to a tobacco-related disease.

Approaches to Identify Genes that are Modulated after Contact with Tobacco Smoke condensates and tobacco smoke In a first series of experiments, the influence of cigarette smoke condensates (CSC) from two different tobacco products (cigarettes) on the gene expression of NHBE cells was examined. In a second set of experiments, the influence of cigarette smoke (CS) generated from one tobacco product (a cigarette) on the gene expression of NHBE cells was examined. Although NHBE cells are preferred for the methods described herein, other cells of the mouth, oral cavity, trachea, and lungs, either normal or immortalized cell lines (e.g., human bronchial cells (e.g., BEP2D or 16HBE140 cells), human bronchial epithelial cells (e.g., HBEC cells, 1198, or 1170-I cells), normal human bronchial epithelial cells, BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226) tongue cells (e.g., CAL 27), and mouth cells (e.g., Ueda-1)) can be used. Accordingly, several embodiments concern methods of identifying one or more genes present in human cells of the mouth, tongue, oral cavity, trachea, or lungs (e.g., NHBE cells) that are modulated by exposure to CS, CSC, TS, or TSC.

In some embodiments, the methods include providing a first population of isolated human cells of the mouth, tongue, oral cavity, or lungs (e.g., NHBE cells), contacting the cells with a CS, CSC, TS, or TSC from a first tobacco product (e.g., a cigarette) in an amount and for a time sufficient to modulate expression or modification of one or more genes or gene products, and identifying the gene that is modulated or the modified gene product (e.g., phosphorylated) or the level or amount of gene expression or modification. The identification of a gene that is modulated or modified gene product or the level or amount of gene expression or presence or absence of a modification on a gene product can be accomplished using any technique available that analyzes transcription (e.g., microarray, genechip, oligonucleotide array, an amplification technique, RTPCR, or hybridization), protein production (e.g., ELISA or other antibody detection techniques), or modifications of proteins (e.g., oxidation or phosphorylation, such as detection methods that employ anti-phospho-tyrosine antibodies). Additionally, the appearance or disappearance of metabolites associated with genes that are modulated in response to exposure to CS, CSC, TS, or TSC can also be monitored (e.g., cysteine, glutathione, fragments of proteins or lipids or fatty acids) using techniques that are available.

In some embodiments, the pattern and/or level of gene expression or gene product modification of a control population (e.g., a second population of isolated human cells of the mouth, tongue, oral cavity, or lungs (e.g., NHBE cells)), is compared to the level of expression or gene product modification in the first population of isolated cells. By this approach, preferably using the same type of cells for each of the two populations, a first population is contacted with a CS, CSC, TS, or TSC and the second population of isolated cells is not. In this manner, the second population of isolated cells is a control population, which will exhibit the baseline pattern or level or amount of gene expression or gene product modification (homeostasis). Data generated from the first or second population of isolated cells before or after exposure to CS, CSC, TS, or TSC or air (control) can be recorded on a computer readable media and databases containing this information can be used to identify a gene that is modulated in response to contact with a CS, CSC, TS, or TSC or to investigate the gene expression pathways that lead to a particular tobacco-related disease.

In some embodiments, a second tobacco product (e.g., a cigarette) is compared to a first tobacco product (e.g., a cigarette) using the analysis above. That is, for example, a first population of isolated human cells of the mouth, tongue, oral cavity, or lungs (e.g., NHBE cells), is contacted with a CS, CSC, TS, or TSC from a first tobacco product (e.g., a cigarette) in an amount and for a time sufficient to modulate expression of one or more genes or to modify a gene product, and identification of a gene that is modulated or modified gene product (e.g., phosphorylated) or the level or amount of gene expression or modification can be determined using any technique available that analyzes transcription (e.g., RTPCR or hybridization), protein production (e.g., ELISA or other antibody detection techniques), modifications of proteins (e.g., oxidation or phosphorylation), or the appearance or disappearance of metabolites associated with genes that are modulated in response to exposure to CS, CSC, TS, or TSC (e.g., cysteine, glutathione, fragments of proteins or lipids or fatty acids). A second population of isolated human cells of the mouth, tongue, oral cavity, or lungs (e.g., NHBE cells), preferably the same type of cell as used in the analysis of the first tobacco product, is also contacted with a CS, CSC, TS, or TSC from a second tobacco product (e.g., a cigarette) in an amount and for a time sufficient to modulate expression of one or more genes or to modify a gene product. Identification of a gene that is modulated or modified gene product (e.g., phosphorylated) or the level or amount of gene expression or modification can also be accomplished using any technique available that analyzes transcription (e.g., RTPCR or hybridization), protein production (e.g., ELISA or other antibody detection techniques), modifications of proteins (e.g., oxidation or phosphorylation), or the appearance or disappearance of metabolites associated with genes that are modulated in response to exposure to CS, CSC, TS, or TSC (e.g., cysteine, glutathione, fragments of proteins or lipids or fatty acids).

The data obtained from the analysis of the first tobacco product can be compared to the data obtained from the analysis of the second tobacco product so as to identify, for example, a gene(s) that is induced in response to exposure to the first tobacco product but not the second tobacco product or vice versa. Additionally, the comparison will reveal that the level of expression of one or more genes induced by both tobacco products differs with respect to the two tobacco products or that the first product has more, less, or no modification of a particular gene product (e.g., phosphorylation), as compared to the second tobacco product or vice versa. These data (e.g., the types of genes expressed, the amount of expression, and modification) allow one to develop a profile for each tobacco product analyzed (in this example only two products are being compared but a plurality of products can be compared using the same approach). These tobacco product profiles can be recorded on a computer readable media and databases containing this information can be created. Many of the genes that are expressed, the amount of expression, and/or modification can be associated with molecular events that contribute to a tobacco related disease. By analyzing the differences between the tobacco products analyzed, (e.g., the types of genes expressed, the amount of expression, and modification), one can identify a tobacco product that has less potential to contribute to a tobacco related disease or that, for example, a first tobacco product has a reduced risk to contribute to a tobacco-related disease, as compared to a second tobacco product or vice versa. Thus, reduced risk tobacco products identified by the approaches described herein are embodiments of the invention.

More embodiments concern methods to identify components of CS, CSC, TS, or TSC that modulate the expression of a gene that contributes to a tobacco-related disease. In one embodiment, the pattern or level of gene expression or modification of a gene product in cells of the mouth, oral cavity, trachea, or lung (e.g., NHBE cells) that are exposed to a first tobacco product that lacks a component associated with a tobacco-related disease (e.g., nicotine) is compared to a second tobacco product (preferably of the same type of tobacco as the first tobacco product) that contains the component (e.g., nicotine) and the impact on the types of genes expressed, the amount of expression, and modification of gene products is analyzed (e.g., microarray analysis and/or RTPCR). By this approach, the genes or modifications of a gene product, which are modulated as a result of the presence or absence of the component (e.g., nicotine), can be identified. Because many of these modulated genes or modifications of gene products will be associated with molecular events that contribute to a tobacco-related disease, one can rapidly identify whether the presence or absence of a particular component in a tobacco product elevate the risk of acquiring a particular tobacco-related disease. Once a component that contributes to a tobacco-related disease has been identified using the approaches described herein, one can use various techniques to remove this component from tobacco (e.g., genetic modification, chemical treatment, or adjustments in the harvesting, curing, or processing of the tobacco) and thereby develop reduced risk tobacco products (e.g., cigarettes). Thus, reduced risk tobacco products identified by these approaches are embodiments of the invention.

In more embodiments, cells of the mouth, oral cavity, trachea, or lung (e.g., NHBE cells) from a plurality of individuals, preferably the same cell type, are independently contacted with CS, TS, CSC, or TSC from a tobacco product (cigarette) in an amount and for a time sufficient to modulate expression of one or more genes or to modify a gene product. Identification of the genes that are modulated or modified gene products (e.g., phosphorylated) or the level or amount of gene expression or modification can then be accomplished using any technique available that analyzes transcription (e.g., RTPCR or hybridization), protein production (e.g., ELISA or other antibody detection techniques), modifications of proteins (e.g., oxidation or phosphorylation), or the appearance or disappearance of metabolites associated with genes that are modulated in response to exposure to CS, CSC, TS, or TSC (e.g., cysteine, glutathione, fragments of proteins or lipids or fatty acids). By analyzing the modulation of various genes of the same cell type from different individuals before, during, or after exposure to a tobacco product, one can identify a particular subject's predilection to acquire a tobacco-related disease. In this way, the genes or modifications of gene products identified by the approaches described herein are markers for the diagnosis or prognosis of acquiring a tobacco-related disease.

For example, primary cultures of lung cells, bronchial cells, cells of the mouth, pharynx, larynx, and tongue are generated from an individual to be tested and these cells are be contacted with CS or CSC from a tobacco product so as to elucidate the individuals proclivity to acquire a tobacco related disease. Certain patterns of gene expression (types of genes expressed, as well as, gene product modifications, such as phosphorylation) and certain ranges of levels of gene expression for a particular gene or subset of genes are associated with individuals that do not develop a tobacco related disease and a different pattern of gene expression and ranges of levels of gene expression for a particular gene or subset of genes are associated with individuals that have developed a tobacco-related disease. Analysis of the levels of gene expression of the various genes and subsets of genes of many of such individuals allows the development of databases that provide an expected range of gene expression, patterns of gene expression, or gene product modifications that are associated or not associated with a tobacco-related disease. That is, this information can be used to provide a baseline for an individual that is not likely to acquire a tobacco-related disease (e.g., a control level indicated by the pattern or average level of gene expression exemplified by non-tobacco users that do not develop a tobacco-related disease) and a baseline for an individual that is likely to acquire a tobacco related disease (e.g., a control level indicated by the pattern and average level of gene expression exemplified by tobacco users that have developed a tobacco-related disease). Accordingly, when a subject is analyzed for the predilection to develop a tobacco-related disease, the gene expression pattern, as well as, levels of gene expression of a gene or subset of genes associated with a tobacco-related disease, or modifications of particular gene products can be evaluated and, by comparing the determined values to that in one or both of the databases described above, the analyzed subject can be identified as having a predilection for developing a tobacco-related disease.

Many embodiments described herein employ normal human bronchial cells (NHBE cells) that are maintained in culture. Although NHBE cells are preferred for the methods described herein, it should be understood that many other cells that are typically contacted with tobacco or tobacco smoke during the process of smoking (e.g., lung cells, bronchial cells, cells of the mouth, pharynx, larynx, and tongue) can also be used. Additionally, many immortal cell lines can be used with the methods described herein. Preferred cells for use with the embodied approaches include, but are not limited to, human bronchial cells (e.g., BEP2D or 16HBE14o cells), human bronchial epithelial cells (e.g., HBEC cells, 1198, or 1170-I cells), normal human bronchial epithelial cells, BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226), tongue cells (e.g., CAL 27), and mouth cells (e.g., Ueda-1)). Many of such cultures are available commercially or through a public repository (e.g., ATCC). Further, several techniques exist that allow for one to generate primary cultures of said cells and these primary cultures can be used with the methods described herein.

Conventional approaches in tissue culture can be used to establish and maintain said cells in preparation for the methods described herein. That is, the cells may be grown in culture by any method known to one of skill in the art and with the appropriate media and conditions. The cells grown in culture may require feeder layers, for example. The cells may be grown to confluence or may be grown to less than confluence before, during, or after treatment. In one embodiment the cells are grown to between about 10% and about 90% confluence, including but not limited to, at least, equal to, or more than 15%, 20%, 25%, 30%, 35%, 40%, 45%, 50%, 55%, 60%, 65%, 70%, 75%, 80%, 85%, 90%, 95%, and 99% confluence before contact with CS, CSC, TS, or TSC.

The contacting of the cells with the CS, CSC, TS, or TSC can be accomplished using any method known to one of skill in the art, including but not limited to, placing said cells into a smoking machine or smoke chamber (e.g., CULTEX®) for a period of time to allow the cells to be contacted with smoke, and/or providing a CSC or TSC to the media for a designated period of time (e.g., in beeswax or other formulation). The contacting can be for any amount of time, however, preferably the cells are contacted for an amount of time that does not result in nonviability of more than 40% of the cells. In some embodiments, the amount of time can be varied and the results are compared. In a further embodiment, the cells are treated for an amount of time in which the gene expression is modulated, but the majority of cells are still viable. That is, in some embodiments, the cells are treated to a point in which the cells are at least, equal to, or more than 1% viable, including but not limited to 1%, 5%, 10%, 15%, 20%, 25%, 30%, 35%, 40%, 45%, 50%, 55%, 60%, 65%, 70%, 75%, 80%, 85%, 90%, 95%, 99%, and 100% viable.

In a another embodiment, the amount of time for contacting a cell with the CS, CSC, TS, or TSC is any amount selected from the group consisting of about at least, equal to, or more than 1 seconds to about 24 hours, including but not limited to at least, equal to, or more than 1 second, 15 seconds, 30 seconds, 45 seconds, 1 minute, 3 minutes, 5 minutes, 10 minutes, 15 minutes, 20 minutes, 25 minutes, 30 minutes, 35 minutes, 40 minutes, 45 minutes, 60 minutes, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, 20 hours, 20.5 hours, 21 hours, 22 hours 23 hours and 24 hours. In a further embodiment, the cells are contacted for less than and including about 20 minutes. In yet another embodiment, the cells are contacted for about 2 to about 20 minutes. The following example describes approaches that were used to obtain and maintain the NHBE cells and procedures that were used to contact the cells with CSCs and CS.

EXAMPLE 1

Treatment of NHBE Cells with CSCs

The tobacco smoke condensates were prepared as follows. Smoke was generated from two commercially available nationally sold brands of American cigarettes (Brand A and Brand B) using an INBIFO-Condor smoking machine under Federal Trade Commission (FTC) smoking parameters (2.0 second puff duration, 35 milliliter puff every 60 seconds). Both brands of cigarettes were non-menthol, full-flavor types of American-blended cigarettes with averaged FTC measured values of 13.2 mg tar/0.88 mg nicotine (Brand A), and 14.5 mg tar/1.04 mg nicotine (Brand B). Brand A contains tobacco that has been chemically modified to reduce carcinogens (see U.S. Pat. No. 6,789,548, herein expressly incorporated by reference in its entirety), whereas Brand B contains conventional tobacco. Smoke condensates extracted from these two cigarette brands and designated CSC-A and CSC-B, respectively, were collected from the smoke via a series of three cold traps (−10° C., −40° C., and −70° C.) onto impingers filled with glass beads. The condensates were dissolved in acetone, which was then removed by rotary evaporation at 35° C. The resulting cigarette smoke condensates (CSCs) were weighed and dissolved in dimethylsulfoxide (DMSO) to make stock solutions of each condensate at a concentration of 40 mg/mL, which were stored at −20° C. prior to use.

NHBE (Normal Human Bronchial Epithelial) cells were purchased from Cambrex Corporation, East Rutherford, N.J. The cells were cultured in complete Bronchial Epithelial Cell Growth Medium (BEGM), prepared by supplementing Bronchial Epithelial Basal Medium with retinoic acid, epidermal growth factor, epinephrine, transferrin, T3, insulin, hydrocortisone, antimicrobial agents and bovine pituitary extract by addition of SingleQuots,™ (both purchased from Cambrex Corporation, East Rutherford, N.J.). S9 metabolic fraction from Aroclor 1254-treated rats was obtained from BioReliance Corporation, Rockville, Md. A 5× concentration of S9 microsomal fraction with cofactors was prepared immediately before treating the cells, and contained 10% S9 microsomal fraction, 4 mM NADP, 5 mM glucose-6-phosphate, 50 mM phosphate buffer pH 8.0, 30 mM KCl, and 10 mM $CaCl_2$.

Twenty-eight flasks were seeded with 14.6 ml of a 2.52× $10^4$ cells/ml cell suspension and an additional 15.4 ml pre-warmed BEGM were added to each flask for a final volume of 30 mL/flask. All incubations were at 37° C. in a humidified atmosphere of 5% $CO_2$ in air. Cells were grown to 40% confluence, at which time the cultures were treated. Four flasks were used as untreated control cultures. Following medium removal in these four control flasks, the cells were re-fed with 30 ml pre-warmed BEGM and their RNA harvested at 0 h (2 flasks) and 20 hr (2 flasks). The remaining 24 experimental flasks were treated with either CSC-A in the presence of 2% S9 microsomal fraction, CSC-B in the presence of 2% S9 fraction, or 2% S9 microsomal fraction alone. Following medium removal, each flask received 9.0 ml of fresh BEGM, 15.0 mL BEGM containing CSC or vehicle (400 µg/ml of CSC-A or CSC-B and 1% DMSO for the CSC-treated groups, 15.0 mL containing 1% DMSO for the S9-only group), and 6 ml of 5× S9 fraction for a final concentration of 2% S9 and a final media volume of 30 mL. Incubation was carried out under the incubation conditions described above. Duplicate flasks were used for each treatment/time point of the experiment (i.e., 2, 4, 8, and 12 h).

The monolayer cultures of NHBE cells were treated in logarithmic phase of growth for up to 12 hours with CSC-A or CSC-B in the presence of 2% S9 microsomal fraction, or with 2% S9 fraction alone. Cell viability after 12 hours exposure was 84% and 73% for CSC-A and CSC-B treatments, respectively, when compared to untreated cells. RNA was then extracted from cells at 2, 4, 8, and 12 hours post-treatment, fluorescently labeled and hybridized to genome-scale microarrays, as described in the examples that follow.

Treatment of NHBE cells with CS

Two identical and independent smoke exposure experiments using NHBE cells were performed. In both experiments, the cells were exposed to cigarette smoke (CS) or air ("mock-exposed") for 15 min, after which the cells were re-fed with fresh media and allowed to incubate for either 4 h or 24 h (the "washout" period). In preparation for exposure, cells were seeded into 35 mm Petri dishes (Fisher Scientific, Falcon #35-3001, Pittsburgh, Pa.) at a density of $10^5$ cells/dish. This resulted in no more than 70% confluence at the time of smoke treatment 48 hours later.

Experiment 1 used cells from a 23-year-old nonsmoking, non-diabetic Caucasian male donor purchased from Cambrex Corporation (Walkersville, Md.). A total of ten Petri dishes were treated: two dishes were mock-exposed with a 4 h washout, two dishes were CS-exposed with a 4 h washout, three dishes were mock-exposed with a 24 h washout, and three dishes were CS-exposed with a 24 h washout.

Experiment 2 was performed in an essentially identical manner as Experiment 1, except for the cell donor (a 13-year-old nonsmoking, non-diabetic male, purchased from Cambrex Corporation, Walkersville, Md.), and the number of Petri dishes used for the mock- and CS-exposed samples with a 24 h washout (two instead of three). This resulted in a total of eight Petri dishes treated for Experiment 2.

Smoke was generated from a commercially available, nationally sold, non-menthol, full-flavor brand of American filter cigarettes (averaged FTC measured values of 14.5 mg tar/1.04 mg nicotine) using a KC 5 Port Smoker (KC Automation, Richmond, Va.) smoking machine under Federal Trade Commission (FTC) smoking parameters (35±0.3 cc puff volume, one puff every 60 seconds, 2-second puff duration with none of the ventilation holes blocked, using cigarettes which have been equilibrated at 23.9° C.±1.1° C. and 60%±2% relative humidity for a minimum of 24 hours and a maximum of 14 days).

Immediately prior to smoke exposure the culture medium was removed from each dish and replaced with pre-warmed Dulbecco's Phosphate Buffered Saline (PBS) containing calcium and magnesium (BioSource, Rockville, Md.). The Petri dishes were placed in a smoke exposure chamber (20.6 cm×6.7 cm×6.3 cm). Each 35 cc puff was diluted to 500 cc using compressed air containing 5% $CO_2$ and then was drawn over the cells with the aid of a vacuum pump in order to keep a constant flow of smoke over the cells with minimal accumulation in the exposure chamber. Cigarettes were smoked to a maximum of seven puffs per cigarette, within 31 mm of the filter tip. Mock exposure conditions were identical to smoke conditions without a cigarette placed in the smoking port. Immediately after exposure, the PBS was removed from each dish and replaced with fresh pre-warmed cell culture medium. The Petri dishes were transferred to a 37° C. 5% $CO_2$ incubator and incubated for 4 or 24 hours post-exposure.

Cells were cultured in complete Bronchial Epithelial Cell Growth Medium, prepared by supplementing Bronchial Epithelial Basal Medium with retinoic acid, epidermal growth factor, epinephrine, transferrin, T3, insulin, hydrocortisone, antimicrobial agents and bovine pituitary extract by addition of SingleQuots,™ (Cambrex Corporation, Walkersville, Md.). All incubations were at 37° C. in a humidified atmosphere of 5% $CO_2$ in air. All cells were used before their fifth passage, although NHBE cells can be used up to 10 passages or more in the methods described herein.

Once the cells are contacted with a CS, CSC, TS, or TSC, an approach to analyze the genes that are modulated in response to the exposure is employed. In some embodiments, the identification of at least one gene that is modulated by exposure to CS, CSC, TS, or TSC is accomplished using an array technology, an oligonucleotide array technology, a genechip technology, any type of hybridization or blot, PCR, RTPCR, another amplification technology or protein detection methodologies, such as antibody detection methods and ELISA. In some embodiments, the identification is made by observing a modulation (up-regulation or down-regulation) in the level or activity of an mRNA and/or a protein. In some embodiments, the modulation is seen as an increase in mRNA or protein production. In other embodiments, the modulation is seen as a decrease in mRNA or protein production. In some embodiments, the modulation is identified as being statistically relevant. In some embodiments, the presence or absence of a modification of a gene product (e.g., phosphorylation, acylation, or cleavage of a peptide) or the presence or absence of a metabolite (e.g., cysteine or glutathione) is analyzed. In still more embodiments the modulation, modification, metabolite or amounts thereof are recorded on a computer readable medium (e.g., disc drive, floppy, CD-ROM, DVD-ROM, zip disc, memory cache, and the like). Accordingly, specific genes or patterns of genes and modified gene products that appear in response to exposure to CS, CSC, TS, or TSC can be identified, recorded on a computer readable medium and this data can be used to generate a profile for each product tested.

In the example that follows, approaches that were used to analyze the pattern and level of expression of genes from NHBE cells exposed to a tobacco smoke condensate (CSC) from two different tobacco products are described.

EXAMPLE 2

Isolation of RNA from CSC-treated Cells and Production of cDNA

After NHBE cells were exposed to the cigarette smoke condensates (CSC-A and CSC-B), as explained in Example 1, RNA was prepared by harvesting cells for total RNA extraction after 0 (untreated), 2, 4, 8, and 12 hours of treatment. The medium was aspirated and the flasks were rinsed twice with pre-warmed 15 mL Dulbecco's Phosphate Buffered Saline. After the second rinse, 5.0 mL of cold TRIzol® (Invitrogen Corp., Carlsbad, Calif.) were added to cover the cells in each flask. Each flask was vigorously vortexed for approximately one minute. The TRIzol® was pipetted up and down over the surface of the flask at least five times to suspend the cell lysate. The resulting TRIzol®/cell lysate was allowed to remain in the flask for at least 10 minutes at room temperature after which it was transferred to microfuge tubes and extracted with 0.2 ml chloroform per 1.0 ml TRIzol/cell lysate. The tubes were capped and shaken vigorously to initiate the RNA extraction, and centrifuged at >15,000×g for two 5-minute spins. Following the second 5-minute centrifugation, the aqueous layer was collected (~500 µl) and transferred to a second set of microfuge tubes containing an equal volume of isopropyl alcohol. The samples were centrifuged for 30 minutes at >15,000×g. Following centrifugation, most (~90%) of the liquid was removed from the microfuge tube. The remaining RNA pellet was frozen and stored at <−60° C. RNA was resuspended in diethylpyrocarbonate-treated water. RNA integrity was assessed using capillary gel electrophoresis (Agilent Technologies, Palo Alto, Calif.) to determine the ratio of 28s:18s rRNA in each sample. cDNA was synthesized with a direct incorporation of Cy3-dUTP from 2 ug total RNA using Clontech Powerscript (Clontech, Palo Alto, Calif.) reverse transcriptase. Labeled cDNA was then purified using a Montage 96-well vacuum system.

Microarray Printing and Processing in CSC Experiments

The microarrays used in experiments involving CSC-treated cells were purchased from the Oklahoma Medical Research Foundation Microarray Research Facility. Slides were produced using commercially available libraries of 70 nucleotide long DNA molecules whose length and sequence specificity were optimized to reduce the cross-hybridization problems encountered with cDNA-based microarrays (Human Genome Oligo Set Version 2.0, Qiagen, Valencia, Calif.). The microarrays had 21,329 human genes represented. The oligonucleotides were derived from the UniGene and RefSeq databases. The RefSeq database is an effort by the NCBI to create a true reference database of genomic information for all genes of known function. For the genes present in this database, information on gene function, chromosomal location, and reference naming are available. All 11,000 human genes of known or suspected function are represented on these arrays. In addition, most undefined open reading frames were represented (approximately 10,000 additional genes). Oligonucleotides were resuspended at 40 µM concentrations in 3×SSC and spotted onto Corning® UltraGAPS™ aminosilane coated slides, rehydrated with water vapor, snap dried at 90° C., and then covalently fixed to the surface of the glass using 300 mJ, 254 nm wavelength ultraviolet radiation. Unbound free amines on the glass surface were blocked for 15 min with moderate agitation in a 143 mM solution of succinic anhydride dissolved in 1-methyl-2-pyrrolidinone, 20 mM sodium borate, pH 8.0. Slides were rinsed for 2 min in distilled water, immersed for 1 min in 95% ethanol, and dried with a stream of nitrogen gas.

The cDNA generated above was added to hybridization buffer containing Cot-1 DNA (0.5 mg/ml final concentration), yeast tRNA (0.2 mg/ml), and poly(dA)$_{40\text{-}60}$ (0.4 mg/ml). Hybridization was performed on a Ventana Discovery system for 6 hr at 42° C. (Ventana Medical Systems, Tucson, Ariz.). Microarrays were washed to a final stringency of 0.1×SSC. Microarrays were scanned on a dual-channel, dynamic auto focus, fluorescent scanner at 10 um resolution (Agilent Technologies, Palo Alto, Calif.). Fluorescent intensity was determined using Imagene™ software (BioDiscovery, Marina del Rey, Calif.).

Genechip Analysis in CSC Experiments

CSC-induced changes in gene expression were then determined in a comprehensive manner using hypervariable analysis, which is based on the observation that gene expression for a majority of genes is relatively stable among replicates in untreated cells. Any measurable variation in this large set of genes by micro array analysis reflects the combined effects of intrinsic normal biologic variation and extrinsic technological variation in an unmanipulated cell. Genes that were impacted by exposure to CSCs, and whose mRNA expression varied over time in a statistically significant manner, which was greater than this normal biologic and technical variation, are termed "hypervariable" (HV).

Of the 21,349 genes and open reading frames (ORFs) on the high-density array used in these experiments, a combined total of 4,894 (22.9%) were classified as HV after CSC treatment (see FIG. 1A). Individually, the expression of 3,665 genes/ORFs was modulated by CSC-A contact (i.e., 17.2% of all the genes/ORFs on the array), and the expression of 3,668 genes/ORFs was modulated by CSC-B contact (17.2%). These genes were hypervariable in at least one time point during the 12-hour exposure period to CSC-A and CSC-B respectively (see FIG. 3, Table 1). The observation that the expression of a large number of genes was altered in a significant manner during the 12 h treatment demonstrated a significant impact by CSCs on steady-state levels of mRNAs in NHBE cells. A majority of the HV genes (i.e., 2,439) were common to both CSC-treated groups, providing evidence that the two CSCs affected cells largely in a similar manner. However, unique non-overlapping sets of HV genes were also identified after treatment with CSC-A (i.e., 1226 genes) and CSC-B (i.e., 1229 genes), which demonstrate that each tobacco product has a specific quantitative and/or qualitative difference in the chemical constituents comprising the two CSCs and the cellular responses thereto.

TABLE 1

Genes Common to CSC-A and CSC-B exposed cells, which are associated with a tobacco-related disease

| GenBank accession no. | Gene Abbreviation | Gene description | Disease |
|---|---|---|---|
| NM_001613 | ACTA2 | Actin, alpha 2, smooth muscle, aorta | Lung Cancer |
| NM_005181 | CA3 | Carbonic anhydrase III, muscle specific | Lung Cancer |
| NM_005199 | CHRNG | Cholinergic receptor, nicotinic, gamma polypeptide | Lung Cancer |
| NM_002594 | PCSK2 | Proprotein convertase subtilisin/kexin type 2 (PC2) | Lung Cancer |
| NM_004624 | VIPR1 | Vasoactive intestinal peptide receptor 1 (VPAC1) | Lung Cancer |
| NM_004448 | ERBB2 (HER2/NEU) | V-erb-b2 erythroblastic leukemia viral oncogene homolog 2 | Lung Cancer |
| NM_024083 | ASPSCR1 | Alveolar soft part sarcoma chromosome region, candidate 1 | Lung Cancer |
| NM_003872 | NRP2 | Neuropilin 2 | Lung Cancer |
| U33749 | TITF1 | Thyroid transcription factor 1 | Lung Cancer |
| NM_002639 | SERPINB5 | Serine (or cysteine) proteinase inhibitor, clade B (ovalbumin), member 5, (maspin) | Lung Cancer |
| AF135794 | AKT3 | V-akt murine thymoma viral oncogene homolog 3 (protein kinase B, gamma) | Lung Cancer |
| NM_001618 | ADPRT | ADP-ribosyltransferase (NAD+; poly (ADP-ribose) polymerase) PARP1 | Lung Cancer |
| NM_016434 | TNFRSF6B | Tumor necrosis factor receptor superfamily, member 6b, decoy | Lung Cancer |
| NM_003072 | SMARCA4 (BRG1) | SWI/SNF related, matrix associated, actin dependent regulator of chromatin, subfamily a, member 4 | Lung Cancer |
| NM_004061 | CDH12 | Cadherin 12, type 2 (N-cadherin 2) | Lung Cancer |
| U28749 | HMGIC | High-mobility group (nonhistone chromosomal) protein isoform I-C | Lung Cancer |
| NM_002592 | PCNA | Proliferating cell nuclear antigen | Lung Cancer |
| NM_033215 | PPP1R3F | Protein phosphatase 1, regulatory (inhibitor) subunit 3F (PPP1R3F), mRNA | Lung Cancer |
| NM_006218 | PIK3CA | Phosphoinositide 3-kinase, catalytic, alpha polypeptide | Lung Cancer |
| NM_005506 | CD36L2 | CD36 antigen (collagen type I receptor, thrombospondin receptor)-like 2 (lysosomal integral membrane | Lung Cancer |
| NM_004994 | MMP9 | Matrix metalloproteinase 9 | Lung Cancer |
| NM_003810 | TNFSF10 | Tumor necrosis factor (ligand) superfamily, member 10 (TRAIL) | Lung Cancer |
| NM_002961 | S100A4 | S100 calcium binding protein A4 (calcium protein, calvasculin, metastasin, murine placental homolog) | Lung Cancer |

TABLE 1-continued

Genes Common to CSC-A and CSC-B exposed cells, which are associated with a tobacco-related disease

| GenBank accession no. | Gene Abbreviation | Gene description | Disease |
|---|---|---|---|
| NM_007084 | SOX21 | SRY (sex determining region Y)-box 21 | Lung Cancer |
| NM_003682 | MADD | MAP-kinase activating death domain (DENN) | Lung Cancer |
| BC002712 | MYCN | V-myc myelocytomatosis viral related oncogene, neuroblastoma derived (avian) | Lung Cancer |
| NM_004353 | SERPINH1 | Serine (or cysteine) proteinase inhibitor, clade H), member 1, HSP47 | Oral Cancer |
| NM_000640 | IL13RA2 | Interleukin 13 receptor, alpha 2 | Asthma |
| NM_002046 | GAPD | Glyceraldehyde-3-phosphate dehydrogenase | Asthma |
| NM_021804 | ACE2 | Angiotensin I converting enzyme (peptidyl-dipeptidase A) 2 | Coronary Heart Disease |
| NM_017614 | BHMT2 | Betaine-homocysteine methyltransferase 2 | Coronary Heart Disease |
| NM_020974 | CEGP1 | CEGP1 protein | Coronary Heart Disease |
| NM_018641 | C4S0 | Chondroitin 4-O-sulfotransferase 2 | Coronary Heart Disease |
| NM_006874 | ELF2 | E74-like factor 2 (ets domain transcription factor), NERF | Coronary Heart Disease |

*The sequences of the genes above are available from GenBank using the referenced Gene ID No. and said sequences are hereby expressly incorporated by reference in their entireties.

Signals from independent samples can vary on a global-basis and, preferably, are adjusted to a common standard. Adjustment of expression levels in compared samples was performed as described. (See Dozmorov, et al. Bioinformatics 19:204-211, 2003, expressly incorporated by reference in its entirety). Briefly, compared samples were first normalized using low level noise signals (commonly referred to as additive noise (AN). The parameters of the AN were calculated from non-expressed genes whose signal values exhibited a normal distribution. The mean and standard deviation (SD) of the AN signals was obtained by nonlinear curve fitting after exclusion of expressed genes from the distribution. Expression values from a given chip were then normalized such that the AN distribution had a mean of 0 and a SD of 1. Genes expressed 3 SD above the mean of AN are defined as expressed genes and used for further analysis. A second scaling step was then performed on expressed genes that were scaled to a common standard through a robust linear regression analysis.

Genes responsive to CSCs were also identified using an analysis of temporally induced gene expression changes. This procedure utilized an internal standard, denoted "the reference group" to define the levels of technologic and normal biologic variance in the experiment so that these values can be used to define stimuli-induced variation in a statistically robust manner. The majority of genes in the control group were not sensitive to temporal changes. The reference group was therefore composed of a group of genes that were statistically expressed significantly above the mean of AN in control samples, whose residuals approximate a normal distribution based on the Kolmogorov-Smirnov criterion, and that have low variability of expression over time as determined by an F-test. Variance in the reference group is due only to technical variation and normal biologic variation and therefore the distribution of expression of the reference group can be used to identify genes that vary due to experimental conditions in a manner that is statistically significantly higher than the technologic and normal biologic variance of the system using an F-test. Genes identified using these procedures are denoted "hypervariable genes" or "HV-genes".

F-means cluster analysis of HV-genes co-expression involved groupings of genes that varied in expression over time in a similar manner, based on the technologic and normal biologic variation in the system, in a given cluster. The reference group defined above is once again used as a reference to define statistically significant thresholds for clustering parameters used in an F-test. In this manner, the variance of the system is used to define the number of clusters thus removing the subjective nature of most clustering methods. The method is not without some subjective criterion as genes can belong to multiple clusters. In this method, a given gene is placed into the largest cluster such that the broadest biologic phenomena of the system, that is those involving the largest number of genes, can be distinguished. To do this, clustering is begun by defining a simple parameter for each HV-gene. This parameter, denoted connectivity, is equal to the number of genes that vary in expression in a similar manner as a given gene. Clusters are nucleated starting with genes of highest connectivity. Genes of lower connectivity will be included in a given cluster if their expression varies over time in a manner similar to the gene used to nucleate the cluster, i.e. if their deviations of expression over time do not exceed the variation of the residuals in the reference group based on an F test.

F-clustering was used to identify the kinetic behavior of genes for each stimulus. Correlation coefficient analysis was used to identify genes that behave in a similar manner among groups. In this type of analysis, a Pearson correlation coefficient is used for clustering of genes with similar time-dependent behavior among groups. A correlation threshold was established using a Monte-Carlo simulation experiment such that the chances of identifying a false positive or false negative selection is <1. Matrices of correlation coefficients are calculated for these clusters and are represented in a graphical output termed a connectivity mosaic such that patterns of correlated and non-correlated behavior of genes can be identified by visual inspection.

Discriminant function analysis (DFA) is a method that identifies a subset of genes whose expression values can be linearly combined in an equation, denoted a root, whose overall value is distinct for a given characterized group. DFA therefore, allows the genes that maximally discriminate among the distinct groups analyzed to be identified. (See Moore et al. Genet Epidemiol 23: 57-69, (2002), expressly incorporated by reference in its entirety). In the experiments described herein, a variant of the classical DFA, named the Forward Stepwise Analysis, was used for selection of the set of genes whose expression maximally discriminates among experimentally distinct groups. The Forward Stepwise Analysis was built systematically. Specifically, at each step all variables were reviewed to identify the one that most contributes to the discrimination between groups. This variable was included in the model, and the process proceeds to the next step. The statistical significance of discriminative power of each gene was also characterized by partial Wilk's Lambda coefficients (see Cho et al., Optimal approach for classification of acute leukemia subtypes based on gene expression data. *Biotechnol Prog* 18: 847-854, 2002), expressly incorporated by reference in its entirety, which are equivalent to the partial correlation coefficients generated by multiple regression analyses. The Wilk's Lambda coefficient used a ratio of within group differences and the sum of within plus between group differences. Its value ranged from 1.0 (no discriminatory power) to 0.0 (perfect discriminatory power).

The 1229 genes that were induced by exposure to CSC-B but not CSC-A were also analyzed with the commercially-available microarray data analysis software Genespring (version 7.2, Agilent Technologies), which identifies genes that are associated with a tobacco-related disease. Of the 1229 unique genes that were induced by exposure to CSC-B but not CSC-A, a total of 33 genes were identified as being associated with cancer (see Table 2).

TABLE 2

Genes modulated by contact with CSC-B but not CSC-A, which are associated with a tobacco-related disease

| GeneBank # | Name | Description |
| --- | --- | --- |
| NM_00359 | CUL4A | Cullin 4A |
| NM_00405 | CDR1 | Cerebellar degeneration-related protein (34 kD) |
| NM_00521 | CSF1R | Colony stimulating factor 1 receptor, formerly McDonough feline sarcoma viral (v-fms) oncogene homol |
| NM_00626 | TFDP2 | Transcription factor Dp-2 (E2F dimerization partner 2) |
| NM_01225 | SNW1 | SKI-interacting protein |
| NM_00482 | NTN1 | Netrin 1 |
| NM_00284 | RAP1A | RAP1A, member of RAS oncogene family |
| AF308602 | NOTCH1 | Notch homolog 1, translocation-associated (Drosophila) |
| NM_01438 | LAMP3 | Lysosomal-associated membrane protein 3 |
| NM_00371 | PPAP2A | Phosphatidic acid phosphatase type 2A |
| NM_00164 | ARHA | Ras homolog gene family, member A |
| NM_01633 | LOC51191 | Cyclin-E binding protein 1 |
| NM_01865 | ERBB2IP | Erbb2 interacting protein |
| NM_01242 | SETDB1 | SET domain, bifurcated 1 |
| AF156165 | DCTN4 | Dynactin 4 (p62) |
| NM_00205 | FOXO1A | Forkhead box O1A (rhabdomyosarcoma) |
| AF163473 | PPP2R1B | Protein phosphatase 2 (formerly 2A), regulatory subunit A (PR 65), beta isoform |
| NM_03328 | PML | Promyelocytic leukemia |
| AK024486 | GLTSCR2 | Glioma tumor suppressor candidate region gene 2 |
| NM_00343 | ZNF151 | Zinc finger protein 151 (pHZ-67) |
| U18018 | ETV4 | Ets variant gene 4 (E1A enhancer binding protein, E1AF) |
| NM_00523 | EWSR1 | Ewing sarcoma breakpoint region 1 |
| BC013971 | HOXA10 | Homeo box A10 |
| AJ420488 | EEF1A1 | Eukaryotic translation elongation factor 1 alpha 1 |
| NM_00548 | ST5 | Suppression of tumorigenicity 5 |
| NM_00578 | HNRPA3 | Heterogeneous nuclear ribonucleoprotein A3 |
| NM_00094 | RARA | Retinoic acid receptor, alpha |
| NM_00675 | N33 | Putative prostate cancer tumor suppressor |
| NM_00228 | JUN | V-jun sarcoma virus 17 oncogene homolog (avian) |
| AL110274 | ALDH1A2 | Aldehyde dehydrogenase 1 family, member A2 |
| NM_01428 | RBX1 | Ring-box 1 |
| NM_01787 | FLJ20429 | Hypothetical protein FLJ20429 |
| NM_00437 | BCR | Breakpoint cluster region |

*The sequences of the genes above are available from GenBank using the referenced Gene ID No. and these sequences are hereby expressly incorporated by reference in their entireties.

Notably, it was discovered that CSC-B induced expression of the proto/oncogenes Cullin 4A, C-jun, Hoxa10, and PPP2R1B, whereas CSC-A did not. Cullin 4A has been described in non-small cell lung cancer (see Singhal et al., *Cancer Biol. Ther.* 2(3):291-298 (2003)); C-jun has been found to be amplified or over expressed in small cell lung cancer (see Cook et al., *Curr. Probl. Cancer* 17(2):69-141 (1993)); Hoxa10 has been found to be amplified or over expressed in leukemia (see Calvo et al., *Proc. Natl. Acad. Sci. USA* 97(23):12776-12781 (2000)); and altered expression of PPP2R1B is involved in lung and colorectal carcinomas (see Calin et al., *Oncogene* 19(9):1191-1195 (2000)); all of these references are expressly incorporated by reference in their entireties). Accordingly, these results demonstrate that the tobacco product comprising chemically modified tobacco (Brand A cigarette), which was used to generate CSC-A, has a reduced potential to contribute to a tobacco-related disease as compared to the tobacco product (Brand B cigarette) used to generate CSC-B because CSC-A induces expression of fewer genes associated with a tobacco-related disease (e.g., 33 fewer genes associated with cancer). Notably, the tobacco product used to generate CSC-A (Brand A) does not induce key genes that have been associated with cancer in humans (e.g., the proto/oncogenes Cullin 4A, C-jun, Hoxa10, and PPP2R1B); whereas the tobacco product used to generate CSC-B (Brand B) induces expression of these proto/oncogenes. Further, these results demonstrate that the methods described herein can be used to effectively identify a tobacco product that is less likely or more likely to contribute to a tobacco related disease (e.g., cancer). That is, this example demonstrates that the approaches described herein can be used to identify a reduced risk tobacco product, which can be a tobacco product that is less likely to contribute to a tobacco-related disease because it modulates fewer genes associated with a tobacco-related disease (e.g., cancer) or induces fewer modifications to a gene product, which are associated with a tobacco-related to disease, as compared to a second tobacco product. To confirm these data, more experiments were conducted on the tobacco product used to generate CSC-A (Brand A) to determine whether it was in fact less likely to contribute to a tobacco-related disease (e.g., cancer), as compared to the tobacco product used to generate CSC-B (Brand B). These experiments are discussed in the following example.

EXAMPLE 3

This example describes experiments that were conducted on mice to demonstrate that the tobacco product used to generate CSC-A (Brand A) is a reduced risk tobacco product in that it was less likely to contribute to a tobacco-related disease, as compared to a conventional tobacco product of the same class (e.g., "fall flavor" cigarette), Brand B, which was used to generate CSC-B in the previous examples. In summary, the response of previously initiated SENCAR mice to repeated topical applications of Brand-A or Brand-B Cigarette Smoke Condensates (CSC-A or CSC-B), was tested over a period of 24 consecutive weeks. One week after a single initiating dose of 50 µg 7,12-dimethylbenzanthracene (7,12-DMBA), female SENCAR mice were exposed to the following three-times-per-week treatment regimen: Negative-Initiation Control (0.1 ml acetone promotion); Positive Control (1 µg TPA promotion); Test (Brand-A CSC promotion, low-dose [10 mg] and high-dose [20 mg]); or Test (Brand-B CSC promotion, low-dose [10 mg] and high-dose [20 mg]). The condensates and positive control articles were dissolved in acetone and applied three times a week to the shaved dorsal skin of female SENCAR mice. In addition, a vehicle control group was initiated and promoted with acetone only. The effects of treatment with the various articles on survival and group mean body weights did not appear to be significantly affected by the Test CSC's during the duration of the study phase.

The extent of tumor promotion by the cigarette smoke condensates was quantitated by the incidence of tumor-bearing animals per group, the multiplicity of tumors per animal, and the latency period until the appearance of tumors. All quantitative scoring was based on gross tumor detection, gross tumor numbers, and gross characterization of tumors which was shown to be accurate by histopathologic examination. The response to the Test CSCs was evident in 13-87% incidence of DMBA-initiated animals exhibiting actual tumors in the effective animals of those groups after 25 weeks compared to a 3% incidence (a single animal) exhibiting actual tumors in the Negative Control (DMBA-Initiated) group. There were no incidences of animals exhibiting actual tumors in the acetone-initiated group.

The SENCAR mouse is an acceptable short-term in vivo model for evaluating the promoting potential of a cigarette on multi-stage epidermal carcinogenesis. This assay system takes advantage of a mouse strain that is extremely sensitive to the two-stage induction of skin tumors. SENCAR mice were bred for increased sensitivity to skin tumor initiation and promotion. The strain originated from Rockland all-purpose mice which were inbred for sensitivity to skin tumor initiation by DMBA and promotion by 12-0-tetradecanoyl-phorbol-13-acetate (TPA) in 1959. In 1971, these susceptible mice were outbred with Charles River CD-1 mice to produce hybrid vigor. These mice have been bred for use in skin carcinogenesis studies of up to 12 months duration.

Accordingly, the SENCAR mouse skin painting bioassay was utilized to determine the relative promoting potential of various cigarette smoke condensate (CSC) preparations applied topically for 24 consecutive weeks. The mice in Groups, as described below, were initiated with a single application of 50 µg 7,12-dimethylbenzanthracene (DMBA). One week after initiation, the animals of each group received three topical applications per week of either acetone (Negative Controls), TPA (Positive Control), or one of two dose levels of cigarette smoke condensates (CSC) from the Test cigarettes. The mice in Group 1 were initiated with acetone vehicle rather than DMBA and received acetone promotion thereafter.

Late in the quarantine period, the animals were weighed and randomly distributed into nine study groups using a computerized randomization program. This program insured that no statistically significant differences in the group mean body weights existed between the study groups at study start. Animals with body weights that were ±20% of the mean body weight of the animal pool were assigned to the study. Following assignment to a group (as listed in TABLE 3), each animal was identified by a uniquely numbered tail tattoo. A color-coded card which listed the study number, animal number, group designation and treatment was displayed on each cage.

TABLE 3

| Group No. | Animal No. | Test Group | No. of Animals | Test Article No. |
|---|---|---|---|---|
| 1 | 1-30 | Negative-Vehicle Control, Acetone Initiation and Acetone Promotion (0.1 ml each) | 30 | Not Applicable |
| 2 | 31-60 | Negative-Initiation Control, DMBA Initiation (50 µg) Acetone Promotion (0.1 ml) | 30 | Not Applicable |

TABLE 3-continued

| Group No. | Animal No. | Test Group | No. of Animals | Test Article No. |
|---|---|---|---|---|
| 3 | 61-80 | Positive Control, DMBA Initiation (50 µg) TPA promotion (1 µg) | 20 | Not Applicable |
| 4 | 81-120 | Low Dose Brand A, DMBA Initiation (50 µg) Brand A CSC Promotion (10 mg) | 40 | AA49LY |
| 5 | 121-160 | High Dose Brand A, DMBA Initiation (50 µg) Brand A CSC Promotion (20 mg) | 40 | AA49LY |
| 8 | 241-280 | Low Dose Brand B, DMBA Initiation (50 µg) Brand B CSC Promotion (10 mg) | 40 | AA52CE |
| 9 | 281-320 | High Dose Brand B, DMBA Initiation (50 µg) Brand B CSC Promotion (20 mg) | 40 | AA52CE |

The Test cigarette smoke condensates at 100 and 200 mg total tar content/ml were collected and prepared by Arista Laboratories at a frequency of approximately every 8 weeks. Upon receipt, the CSC samples were stored at =−20° C. until further sub-aliquoted by BioReliance (5.0 ml per vial for both the low and high doses) and stored at =−20° C. The dose preparations, as received from Arista Laboratories, were divided into 26 tightly sealed amber vials, with an expiration date of approximately 13 weeks and stored at =−20° C. This allowed the use of one vial per dosing day and two backups which could be used in case of spillage. All dosing solutions were used within eight weeks of preparation. The Positive Control article (TPA) was diluted with acetone to produce the desired concentration of 10.0 µg/ml once (prior to initiation of dosing) and delivered to the animal laboratory and stored at room temperature (an extra vial was stored at =−20° C.).

The mice from Groups 2-9 received a single topical application of DMBA (50 µg/0.1 ml acetone/animal) as an initiator on Day 1 of the study. The mice from Group 1 received a single topical application of acetone vehicle (0.1 ml) as an initiator. After one week, the animals were dosed topically three times a week (Monday, Wednesday and Friday except for Holidays) for 24 consecutive weeks with the appropriate Vehicle Control, Positive Control or Test article.

The dorsal application site (approximately 2×3 cm) was shaved 3 days prior to the single application of the initiator, and at least once a week thereafter, at least one day prior to application of the appropriate dosing solution or vehicle. Shaving was performed on all animals with an Oster Model 76059 small animal electric clippers (Oster Co., Racine, Wis.) using a narrow blade.

The animals were weighed at study initiation and at weekly intervals for the next 11 weeks (12 total data collection points), and once every four weeks thereafter and at terminal sacrifice. The animals were observed twice daily (including weekends and holidays) for mortality and moribundity, once in the morning before 10:00 a.m. and once in the afternoon after 2:00 p.m. (at least six hours apart). Clinical observations performed cage-side to detect abnormalities other than skin tumor responses were made once daily for the first 5 weeks of the study (Days 1-35) and hands on once every two weeks thereafter (beginning on Day 36). Clinical signs noted at times other than the scheduled observation timepoints were recorded on the Unscheduled Observations Sheet.

On Day 1 and at weekly intervals thereafter, the mice were examined grossly for the presence of skin tumors. Pertinent information such as date of observation, lesion location, morphology, and type were recorded for each lesion at each observation time. At necropsy, all representative skin from the application site, skin from an untreated area, and other lesions taken for histopathologic evaluation were indicated on the necropsy data sheet. Lesions were identified in a manner which allowed correlation of the individual lesion-specific histopathologic findings with data collected during the in-life phase of the study.

A tissue mass (in vivo) was considered to be a tumor (papilloma) when that mass attained a 2 mm diameter and protruded from the surface of the skin. The date at which a 2 mm diameter was attained was recorded and represented the end of the "tumor latency period" for that animal and the tumor was scored as a latent papilloma. If a latent tumor remained countable for three (3) consecutive weeks, it was considered an actual tumor. Such a tumor remained in the total count of actual tumors for that animal even if it subsequently decreased in size, disappeared, or the animal died or was sacrificed early. The record of skin lesion data served to differentiate papillomas from carcinomas and latent tumors from actual tumors. In vivo differentiation of papillomas and carcinomas was made on the basis of palpation, evidence of subcutaneous invasion, and ulceration.

Group 3 (the positive control) served as a qualitative indicator of the test system's response to a known and chemically defined initiator (DMBA) and promotor (TPA). Considering the time course and magnitude of the response in SENCAR mice, treated as described above, collection of skin lesion data in the positive control was discontinued after 90-100% of the animals in the group exhibited tumors and the mean number of tumors per animal was at least 8. Since this group was not counted through the entire study, it was not included in any group comparisons noted below.

The number and location of skin papillomas (benign tissue masses having attained a diameter >2 mm and protruding from the surface) and carcinomas (malignant tissue masses with gross evidence of invasive growth and tissue necrosis due to growth outstripping vascular supply) were documented weekly. The reliability of gross diagnoses of tumors was confirmed by representative histopathologic examination of individually identified and historically tracked skin lesions. Tumor data for specific groups were calculated based on the appearance of tumors of either type. The following parameters were recorded or calculated for all groups (with the exception of Group 3, Positive Control):

1. Date of tumor appearance for all tumors on all mice.
2. Date of appearance of latent and actual tumors.
3. Date of death or sacrifice for each mouse.

4. Time interval from Day 1 of the study until the date of the appearance of; 1) latent papillomas and carcinomas and, 2) actual papillomas or carcinomas on each mouse.
5. Latency for all latent or actual tumors (i.e., this was defined as the time from Day 1 to the time a mass qualified as a latent tumor and subsequently as an actual tumor). Three methods for numerically scoring latency were used:
   a. The time elapsed until the appearance of the first tumor of a specific type in a group.
   b. The mean time elapsed until the appearance of all first tumors of a specific type from all animals in a group developing one or more such tumors.
   c. Time elapsed to attain 50% of the maximum incidence of animals in a group with one or more tumors of a specific type.
6. Percent of mice developing one or more latent and/or actual tumors (Incidence) equals:
   Number of mice with at least one latent and/or actual tumor×100
   Number of mice surviving at the time the first non-positive control group shows a tumor
7. Tumors per tumor-bearing animal=
   Number of total or specific-type tumors
   Number of animals bearing that type of tumor Group means and standard deviations were calculated for body weights and skin tumor data. A Fisher's Exact test was performed to analyze the percent of surviving animals in each group which developed latent and/or actual tumors and percent of animals started on study which developed actual tumors. Analysis of Variance tests (ANOVA) were performed in order to determine if differences in group means existed for the selected parameters. If a significant F ratio was obtained ($p<0.05$), a Dunnett's t-test was used for pair-wise comparisons of treatment test CSC groups to the Negative Control (non-Initiated DMBA) and test CSC groups with each other.

Incidence of Tumor-Bearing Animals

Statistical analysis of the incidence of animals bearing actual tumors (Fisher's Exact Test, $p<0.05$) indicated a significant increase in both the low- and high-dose groups receiving CSC-B when compared to the negative vehicle control group. Of the groups receiving the CSC-A, only the high-dose exhibited a significantly increased number of animals bearing actual tumors when compared to the negative vehicle control group. When comparing the incidence of animals bearing actual tumors in the low-dose CSC treatment groups to each other, a significant increase was noted in the groups that received CSC-B when compared to the group that received CSC-A. The same results were obtained when making the same comparisons in the groups receiving the high-dose CSC treatment. These findings are presented in TABLE 4.

TABLE 4

Statistical Results of Analysis of Percent of Animals Bearing Actual Tumors

| Group | Treatment | Percent of Animals Bearing Actual Tumors[a,b] |
|---|---|---|
| 1 | Negative Vehicle Control | 0% |
| 4 | Low-Dose Brand A | 13% |
| 5 | High-Dose Brand A | 40% |
| 8 | Low-Dose Brand B | 53% |
| 9 | High-Dose Brand B | 78% |

[a]Represents the percent of animals started on study that developed at least one actual tumor.
[b]Significantly increased when compared to the group indicated in the superscript (Fisher's exact test, $p < 0.05$).

Statistical analysis of the incidence of animals bearing actual and/or latent tumors (Fisher's Exact Test, $p<0.05$) comparing the CSC treatment groups to the negative vehicle control indicated the same results as the analyses of animals bearing actual tumors discussed above.

Tumor Multiplicity

Statistical analysis of the number of actual tumors (papillomas and carcinomas combined) per animal, after 26 weeks, revealed significant increases (ANOVA, $p \leq 0.05$) in the groups treated with the high-dose CSC-B when compared to the negative control group (acetone-initiated Group 1). The number of actual tumors per animal in the group treated with the high-dose CSC-A group was statistically comparable to the negative vehicle control group. Analysis of the number of actual tumors per animal in the low-dose CSC treatment groups indicated the group treated with the low-dose Brand B CSC exhibited a statistically significantly increased number of actual tumors when compared to the negative control group. Group means, standard deviations, and statistical results are presented in TABLE 5.

TABLE 5

Statistical Results of Analysis Number of Actual Tumors per Animal

| Group | Treatment | Mean Number of Actual Tumors per Animal[a] |
|---|---|---|
| 1 | Negative Vehicle Control | 0.00 ± 0.00 |
| 4 | Low-Dose Brand A | 1.03 ± 3.90 |
| 5 | High-Dose Brand A | 2.58 ± 8.05 |
| 8 | Low-Dose Brand B | 3.80 ± 7.22 |
| 9 | High-Dose Brand B | 7.46 ± 7.86 |

[a]Significantly increased when compared to the group indicated in the superscript.

When comparing the high-dose CSC treatment groups against each other, a statistically significantly increased number of actual tumors per animal was noted in the high-dose groups treated with the Brand B CSC when compared to the high-dose Brand A group. No statistically significant differences in the numbers of actual tumors were noted in the low dose CSC treatment groups when compared to each other. Statistical analysis of the number of actual and/or latent tumors (ANOVA, $p \leq 0.05$) indicated the same results as the analyses of the number of actual tumors per animal, as discussed above. Results are presented in the following Table.

TABLE 6

Statistical Results of Analysis Number of Latent and Actual Tumors per Animal

| Group | Treatment | Mean Number of Actual Tumors per Animal[a] |
|---|---|---|
| 1 | Negative Vehicle Control | 0.00 ± 0.00 |
| 4 | Low-Dose Brand A | 1.20 ± 4.33 |
| 5 | High-Dose Brand A | 2.75 ± 8.13 |
| 8 | Low-Dose Brand B | 4.73 ± 8.35[1] |
| 9 | High-Dose Brand B | 8.49 ± 8.70[1,5] |

[a]Significantly increased when compared to the group indicated in the superscript.

Latency Period Until Appearance of Tumors

Mean latency per group when defined as the time elapsed until the appearance of the first actual tumor per animal was 18 weeks in the low-dose of both CSC-A and CSC-B treatment groups. In the high-dose CSC treatment groups, mean actual tumor latency was 19 and 15 weeks in the groups treated with CSCs obtained from Brands A and B, respectively.

Thus, the promotional capacity of the Brand A CSC was statistically comparable to the negative vehicle control group in terms of the incidences of tumor-bearing animals (at the low-dose level) and the number of tumors per animal (both dose levels). Statistical analysis comparing the groups that received the CSCs to each other revealed significant increases in the high-dose Brand B group when compared to the high-dose Brand A group in terms of percent of animals bearing designated tumor types and the number of those tumors per animal. Also, at the high-dose level, the Brand A CSC mean latency period (until the appearance of the first tumor per animal) was longer than the latency period of the Brand B CSC treatment groups. The data provided in this example confirm that the in vitro methods described herein, which utilize cell cultures that are contacted with CS, CSC, TS, or TSC (see Examples 1, 2, and 5-10), accurately identify a tobacco product that has less potential to contribute to a tobacco-related disease than another tobacco product. The data provided in this example also confirm that the in vitro methods described herein (see Examples 1, 2, and 5-10), can be used to develop tobacco products that have a reduced potential to contribute to a tobacco-related disease and provide further evidence, in particular, that Brand A is a reduced risk tobacco product, as compared to Brand B.

Subsequent to exposure in vivo, the human body attempts to detoxify, neutralize, and eliminate cigarette smoke toxins through the action of Phase I and Phase II enzymes functioning in various metabolic pathways. During this detoxification process, however, a number of pro-carcinogenic compounds in tobacco smoke are bioactivated into reactive electrophiles that have potent carcinogenic potential in exposed cells. Thus, in order to dissect the full biological potential of complex chemical mixtures, such as a cigarette smoke condensate, it is desirable to evaluate the pattern of gene expression after tobacco smoke condensate exposure in an environment that contains a mixture of enzymes that mimic the detoxification process in mammalian cells. The S9 microsomal fraction from Aroclor 1254-treated rats, provides a set of enzymes that mimic the detoxification process in mammalian cells. Accordingly, experiments were conducted in the presence of the S9 microsomal fraction, as described in the following example, to elucidate how the genetic fingerprint of particular tobacco products shift in the presence of a mixture of enzymes that mimic the detoxification process in mammals.

EXAMPLE 4

S9 Microsomal Fraction Experiments

NHBE cells were exposed to cigarette smoke condensate (CSC) in conjunction with an S9 microsomal fraction so as to identify the effect detoxification enzymes have on the pattern or level of gene expression. As a control to discriminate the effects of the S9 microsomal fraction on gene expression, alone, some experiments were conducted on NHBE cells in the presence of the S9 microsomal fraction in the absence of contact with a tobacco condensate. As described above, an HV analysis was performed on microarray results obtained from cells treated only with the S9 microsomal fraction for 2, 4, 8, and 12 hours.

Figure 1B:
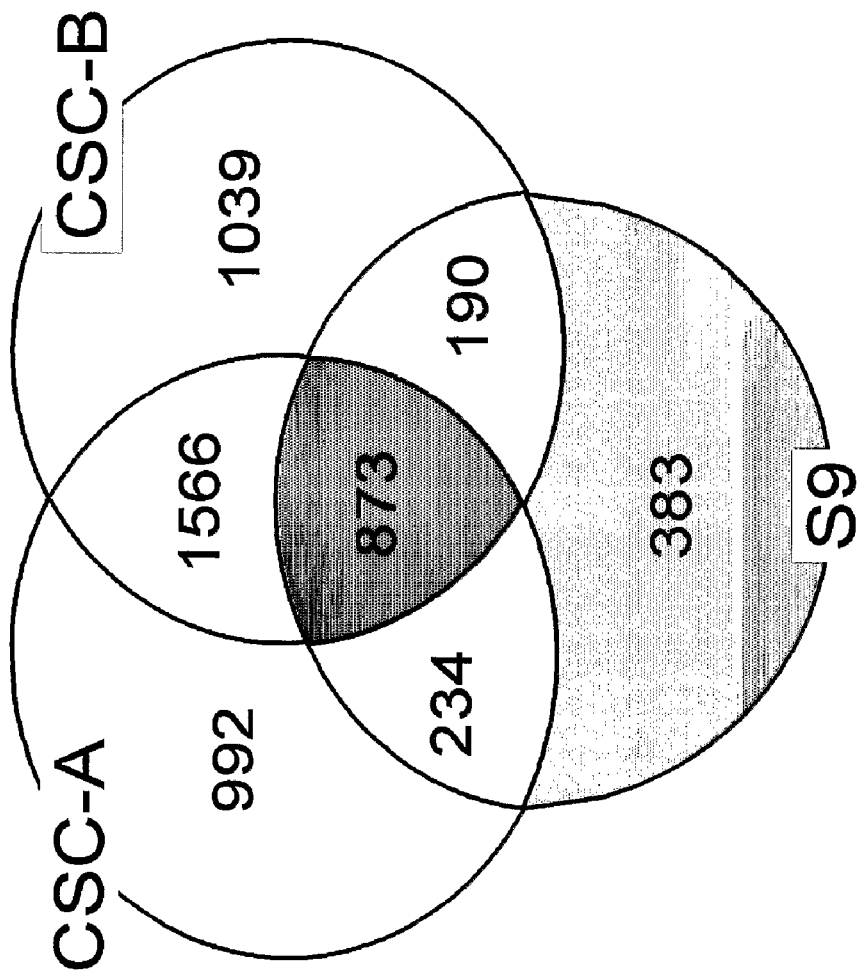
FIG. 1B is a Venn diagram comparing gene expression modulations induced by CSC-A (3665), CSC-B (3668), and S9 metabolic fraction (1680). The number of unique genes affected by each treatment is given, CSC-A (992), CSC-B (1039), and S9 (383) and the intersections between sectors reflect the number of genes that are affected by more than one treatment (e.g., a common set of 873 genes is affected by CSC-A, CSC-B and S9).

Several interesting observations emerged from this analysis. First, the expression of 1680 (7.9%) genes became HV sometime during the 12-hour exposure period with the S9 microsomal fraction (see FIG. 1B). Second, FIG. 1B also shows that 1297 of these 1680 genes were also HV in one or both CSC treatments, which is not surprising since all three treatment conditions (i.e., CSC-A, CSC-B, and S9) had the same concentration of S9 microsomal fraction. Third, even though the CSCs and the S9 microsomal fraction induce a HV state in a large common set of genes, CSCs and the S9 microsomal fraction did not affect these genes in similar ways indicating differential kinetic effects between the S9 microsomal fraction alone and the S9 microsomal fraction in conjunction with CSCs.

Subsequent to determining that the complex mixture of toxins and carcinogens in CSCs had a broad impact on the transcriptome of NHBE cells, it was contemplated that a sustained treatment to CSCs (e.g., over a 12-hour period) would also allow detection, not only of alterations such as induction and suppression, but of gene induction/suppression with transient, sustained, or periodic characteristics. Accordingly, the kinetic effects of gene expression profiles generated from cells treated with CSC-A, CSC-B, or S9 microsomal fraction from 0-12 hours using F-cluster analysis were defined, which is a statistically robust method for defining clusters of genes with similar expression patterns over time. These experiments are described in the following example.

EXAMPLE 5

Gene Expression Kinetics in CSC-Treated Cells

In this analysis, the normal variance of the system was calculated and used to identify a statistical threshold for cluster selection at which groups of genes were likely to cluster by chance. This threshold was then used for further analysis to ensure the statistical robustness of the clustering process. The biologic significance of the cluster is related to cluster size, as the largest clusters identified represent synchronous changes in the greatest number of cellular processes. (See Spellman et al., *Mol Biol Cell* 9: 3273-3297, 1998). Specifically, larger clusters represent, in a statistically robust manner, the most significant experimentally induced processes in these cells. When F-cluster analysis was applied to the total HV set of 4894 genes/ORFs, 306 clusters were defined by statistical analysis, the majority of which contained less than 50 member genes. Cluster numbers were arbitrarily assigned from –150 to 150, with the corresponding positive and negative numbers representing complementary gene expression patterns (e.g., steady increase in expression over time compared to a steady decrease in expression).

Figure 2A:
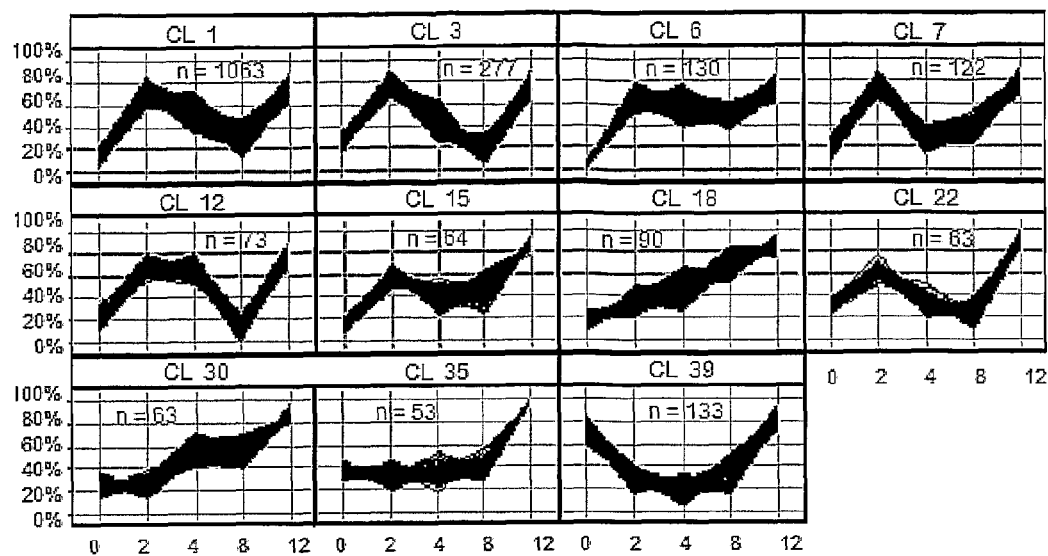
FIGS. 2A-2C illustrate gene expression profiles between 0 and 12 hours, which are expressed a percent of highest expression value for each gene. F-cluster numbers are given at the top of each cluster of profiles. The number of member genes in each cluster (n) is shown for each cluster.
Figure 2B:
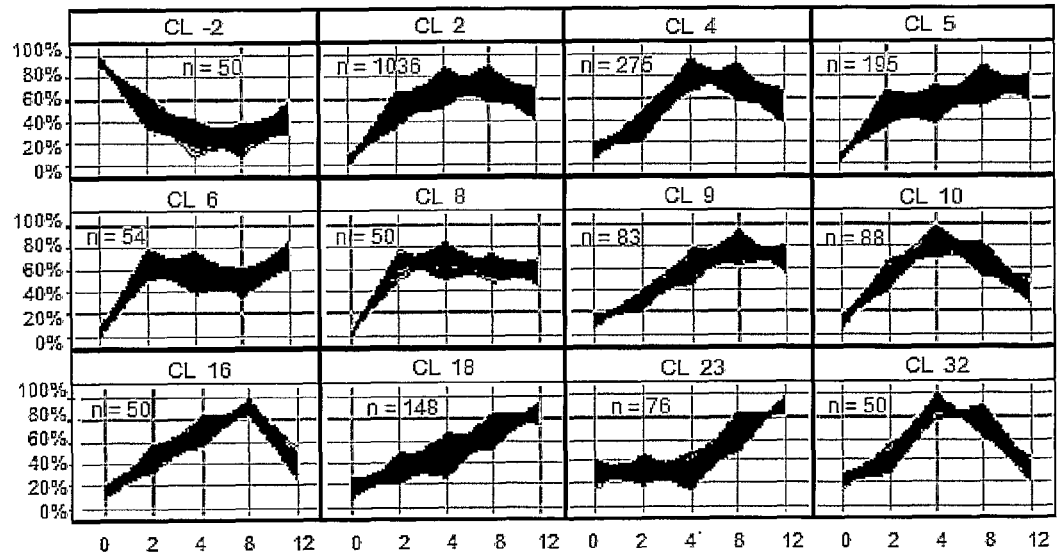
Figure 2C:
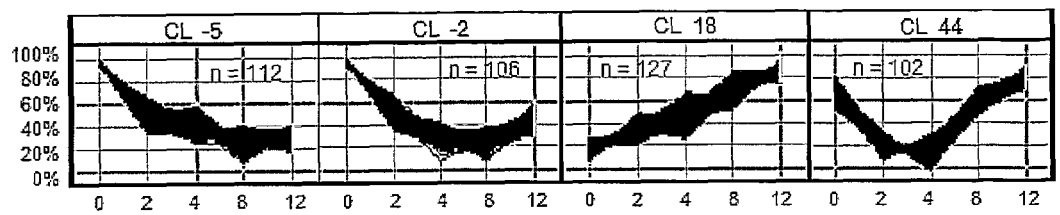

In each of the three treatment conditions, clusters containing 50 or more genes were chosen for further characterization because this cutoff generated a sufficient number of large clusters that adequately represented the major kinetic changes caused by each treatment (see FIGS. 2A-C and TABLE 7). As predicted, gene expression changes induced by CSCs were complex, with the majority of clusters in CSC-treated cells being multi-modal (see FIGS. 2A and B). For example, in CSC-A-treated cells, genes in clusters 1, 3, 7, 12, 15, and 22 were up-regulated within the first two hours, began to return to baseline, then were once again induced late in the experiment, indicating that initial treatment effected gene expression and some secondary effect (e.g., a CSC metabolite or the action of early gene expression changes, reinitiated a cellular response). (See FIG. 2A). While genes within each of these clusters showed early increases in expression (within the first 2 h of treatment), indicating that CSC-A treatment had immediate effects on cells, Clusters 18, 30, 35, and 39 showed a later increase in gene expression (i.e., =4 h). FIG.

2B shows that in CSC-B treated cells, cluster analysis revealed that gene expression peaks primarily between 4-8 hours, as opposed to a 2 hour peak in CSC-A treated cells, cluster 2, which contains 1,036 genes and whose expression peaked at 4-8 hours, indicating that some of the effects of CSC-B treatment are delayed with respect to those of CSC-A.

TABLE 7

HV Genes Specific for CSC-A and CSC-B Treatment

| GenBank accession no. | Gene abbreviation | Gene description |
| --- | --- | --- |
| AB032985 | NXPH3 | Neurexophilin 3 |
| AB046848 | KIAA1628 | KIAA1628 protein |
| AB058772 | SEMA6C | Sema domain, transmembrane domain (TM), and cytoplasmic domain, (semaphorin) 6C |
| AF178532 | BACE2 | Beta-site APP-cleaving enzyme 2 |
| BC015737 | | *Homo sapiens*, ninjurin 2, clone MGC: 22993 IMAGE: 4907813 |
| BC015929 | NR1D2 | Nuclear receptor subfamily 1, group D, member 2 |
| BC017732 | STRBP | Spermatid perinuclear RNA binding protein |
| M23326 | TRDV3 | T cell receptor delta variable 3 |
| NM_000341 | SLC3A1 | Solute carrier family 3 (cystine, dibasic and neutral amino acid transporters, activator of cystine), member 1 |
| NM_000663 | ABAT | 4-aminobutyrate aminotransferase |
| NM_000922 | PDE3B | Phosphodiesterase 3B, cGMP-inhibited |
| NM_000981 | RPL19 | Ribosomal protein L19 |
| NM_001383 | DPH2L1 | Diptheria toxin resistance protein required for diphthamide biosynthesis-like 1 (*S. cerevisiae*) |
| NM_002046 | GAPD | Glyceraldehyde-3-phosphate dehydrogenase |
| NM_002757 | MAP2K5 | Mitogen-activated protein kinase kinase 5 |
| NM_002890 | RASA1 | RAS p21 protein activator (GTPase activating protein) 1 |
| NM_003286 | TOP1 | Topoisomerase (DNA) I |
| NM_003408 | ZFP37 | Zinc finger protein 37 homolog (mouse) |
| NM_004057 | CALB3 | Calbindin 3, (vitamin D-dependent calcium binding protein) |
| NM_004066 | CETN1 | Centrin, EF-hand protein, 1 |
| NM_004083 | DDIT3 | DNA-damage-inducible transcript 3 |
| NM_004282 | BAG2 | BCL2-associated athanogene 2 |
| NM_004846 | EIF4EL3 | Eukaryotic translation initiation factor 4E-like 3 |
| NM_004939 | DDX1 | DEAD/H (Asp-Glu-Ala-Asp/His) box polypeptide 1 |
| NM_005476 | GNE | UDP-N-acetylglucosamine-2-epimerase/N-acetylmannosamine kinase |
| NM_005619 | RTN2 | Reticulon 2 |
| NM_007217 | PDCD10 | Programmed cell death 10 |
| NM_007275 | FUS1 | Lung cancer candidate |
| NM_012192 | FXC1 | Fracture callus 1 homolog (rat) |
| NM_012288 | KIAA0057 | TRAM-like protein |
| NM_013366 | APC2 | Anaphase-promoting complex subunit 2 |
| NM_013401 | RAB3IL1 | RAB3A interacting protein (rabin3)-like 1 |
| NM_014395 | DAPP1 | Dual adaptor of phosphotyrosine and 3-phosphoinositides |
| NM_015057 | KIAA0916 | KIAA0916 protein |
| NM_017491 | WDR1 | WD repeat domain 1 |
| NM_017581 | CHRNA9 | Cholinergic receptor, nicotinic, alpha polypeptide 9 |
| NM_020122 | PCMF | Potassium channel modulatory factor |
| NM_020685 | HT021 | HT021 |
| NM_021120 | DLG3 | Discs, large (*Drosophila*) homolog 3 (neuroendocrine-dlg) |
| NM_031310 | PLVAP | Plasmalemma vesicle associated protein | providing evidence that some of the effects of CSC-B treatment were delayed with respect to those of CSC-A (e.g., see clusters 4, 5, 9, 10, 16, and 32). These data are in distinct contrast to the major clusters of genes in S9-only treated cells, which displayed simple kinetics, i.e., expression decreasing or increasing continuously over time (see FIG. 2C). Although 66% of HV genes affected by CSC-A and CSC-B were identical (see FIG. 1), it is clear from FIG. 2 that the expression kinetics for these genes were nevertheless distinct for the two different CSCs. This is evidenced by the fact that the predominant coordinated behavior in CSC-A-treated cells is represented by the largest cluster (i.e., cluster 1), that contains 1063 HV genes and whose expression peaked at 2 hours post-treatment. This is in contrast to CSC-B-treated cells in which case the predominant behavior of genes is represented by Accordingly, these experiments demonstrated that not only do different tobacco products induce different genes, gene expression patterns, and kinetics of gene expression but different tobacco products have a different impact on a cell or a tobacco consumer. That is, the procedures described above can be used to obtain a genetic signature, pattern, or profile for a plurality of tobacco products and, because some of the modulated genes are associated with the induction or repression of a tobacco-related disease, this data can be compared and/or analyzed to identify a tobacco product with a reduced potential to contribute to a tobacco-related disease.

Since clusters with a large number of member genes reflect predominant biological behavior patterns that are likely to be functionally interrelated, it was contemplated that the cluster 1 set of 1063 genes from CSC-A-treated cells and the cluster 2 set of 1036 genes from CSC-B-treated cells corresponded to important biological phenomena common to the two CSCs. If this were correct, then despite the fact that CSC-A and CSC-B treatments modulate genes in a temporally distinct manner, the two clusters should contain many of the same genes. To demonstrate this point, the experiments in the following example were conducted.

EXAMPLE 6

Analysis of Cluster 1 and Cluster 2 in CSC-treated Cells

Upon analysis of cluster 1 and cluster 2 in CSC-treated cells, it was found that a set of 554 genes (approximately 50% of the genes in each cluster) were present in both cluster 1 (from CSC-A) and cluster 2 (from CSC-B). A total of 330 genes from this set of 554 genes (59.5%) have known functions while the remaining 224 are ORFs.

Functional classification of these 330 genes common to cluster 1 and cluster 2 indicates that 10% have functional roles in proliferation, 12.4% in transcription, 4.5% in apoptosis, and 5.1% in damage/repair responses. In addition, as shown in TABLE 1, 34 (10%) of the identified genes are documented as having roles in diseases that are associated with/long-term tobacco exposure (e.g., lung cancer, coronary heart disease, and asthma).

Figure 3:
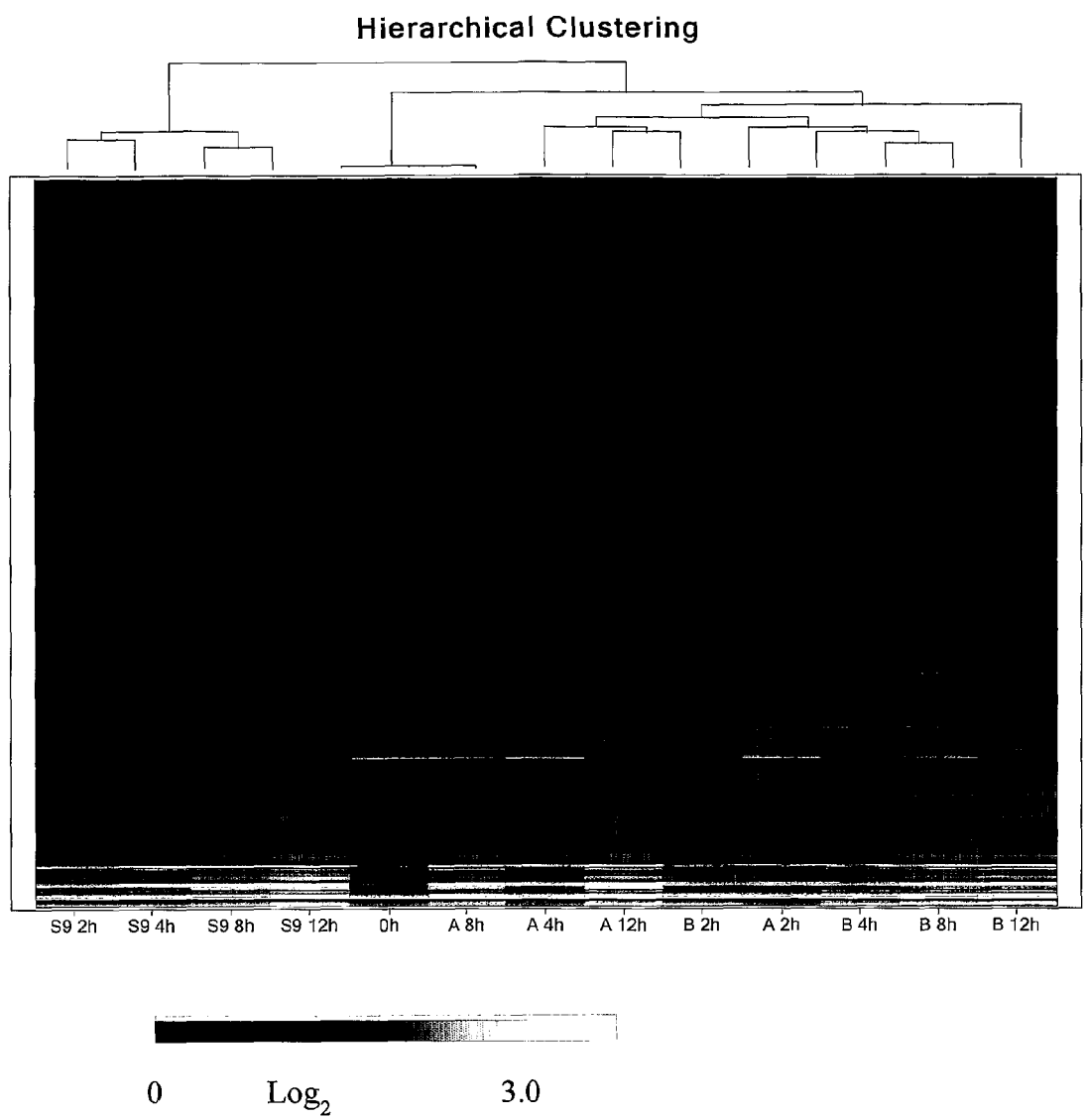
FIG. 3 illustrates a cluster analysis of genes that were hypervariable (HV) in all three treatment groups (A: CSC-A, B: CSC-B, and S9) in the form of a Dendrogram that depicts the hierarchical relationship between the three treatments based on their gene expression patterns at all time points from 0-12 hours.

In clear contrast to both CSC-A and CSC-B treated cells, the S9 microsomal fraction-treated cells show a pronounced tendency towards suppression of gene expression. An F-clustering analysis of the S9 microsomal fraction data (shown in FIG. 2C) resulted in only four clusters that contained 50 or more genes. Clusters 2, 5, and 44 all show decreases in gene expression level with a nadir at 4-8 h. Cluster 18 contains genes that show an increase in gene expression levels, but whose expression peaks at 12 h, which is notably different from the robust early gene responses elicited by treatment with both CSCs. Additional evidence that the overall effects of S9 microsomal fraction and CSC exposure on gene expression levels are quite distinct was obtained when traditional hierarchical clustering algorithms were used to compare the overall differences in HV gene expression in each treatment group over the entire 12-hour time course. FIG. 3 shows the results of this analysis for the common subset of genes that were HV in all three treatment groups (i.e., the 873 genes denoted in FIG. 1). Notably, the expression data for these 873 genes partition into two separate groups with S9-treated cells being clearly distinguishable from CSC-A and CSC-B treated cells, which are similar to each other. The data further indicate that the S9 microsomal fraction exerts a largely suppressive effect on the transcriptome of NHBE cells in contrast to a predominant inductive effect of CSC-A and CSC-B.

As discussed above, tobacco smoke condensates induce a range of temporally distinct alterations to the homeostatic transcriptome of the NHBE cells, which were unique in that they were qualitatively and quantitatively dissimilar from the effects of exposure to a S9 microsomal fraction. In an attempt to define a biological context for these data, correlation analyses was used to identify genes whose expression changes were highly correlated in CSC-A and CSC-B treated cells but not in S9-treated cells. This was achieved using a Monte Carlo analysis to establish a statistical threshold above which correlated behavior was unlikely to have occurred by chance. By this approach, gene expression levels were randomized maintaining the same mean and standard deviation. A correlation coefficient was then identified above which no genes were correlated in the randomized data sets. The probability that genes that correlate in experimental data sets above this threshold would occur by chance is <1/total number of genes analyzed. The following example describes these experiments in greater detail.

EXAMPLE 7

Defining CSC-specific Toxicological Effects

The evidence provided in FIGS. 2 and 3 indicated that the effect of exposure to CSC was significantly different than exposure to an S9 microsomal fraction. Using the Monte Carlo analysis, as shown in TABLE 7, forty HV genes were identified as having a modulation of gene expression that was correlated in CSC-A and CSC-B treated cells but not in S9-treated cells. The similarities between the two tobacco-treated sample groups can be visualized by applying a correlation coefficient analysis to the genes within a given treatment, representing this visually in a correlation mosaic, and comparing the visual pattern of the mosaic to other such mosaics generated using data from different treatments. The correlation coefficients of these genes were presented in a correlation mosaic map (see FIG. 4) in which genes with a highly correlated behavior were denoted by a grey pixel, and genes with highly negatively correlated behavior by a black pixel. This mosaic provided a way to assess the similarities of expression behavior of the correlated genes in CSC-A, CSC-B, and S9-treated cells by visual inspection.

The highly correlated expression characteristics of the CSC-impacted genes identified by this analysis indicated that these genes were likely to participate in pathways relevant to the effects specific to CSC exposure and not to exposure to the S9 microsomal fraction. These pathways were more clearly defined using PathwayAssist™ software (Stratagene, La Jolla, Calif.), a commercially available visualization engine that scans and assesses documented literature and available standardized databases in order to filter, classify, and prioritize proteins in terms of their functional relationships to known biological pathways. The results, provided in FIG. 5, highlight the fact that this set of genes encodes proteins that play key roles in pathways that are relevant to the documented pathological effects of cigarette smoke. For example, several of the genes listed in TABLE 7 are implicated in lung oncogenesis (e.g., FUS1, GAPD, & semaphorin), in various types of dysfunctions in lung cells involving apoptosis (e.g., PDE3B, PDCD10), in cell cycle control (e.g., MAP2K5, RASA1, APC2, RASA1), in DNA topology and DNA repair (e.g., TOP1, DDIT3), and in cellular stress (e.g., BAG2). In addition, several genes are involved in neurosignaling (e.g., neurexophilin, KIAA1628), neuroregeneration (e.g., semaphorin), neuropathology (e.g., BACE2, ABAT, DLG3), and inflammation (e.g., NINJ2, TRDV3, SLC3A1).

The induction of a range of neuroendocrine-related genes is interesting in light of the fact that many small cell lung cancers and some non-small cell lung cancers exhibit a variety of pathological and molecular features of pulmonary endocrine cells, and can be stimulated by an autocrine/paracrine array of neuroendocrine peptides. Accordingly, expression of neuroendocrine markers has been shown to be useful in the differential diagnosis of lung cancers. The gene set shown in TABLE 7 also includes CHRNA9, a human nicotinic acetylcholine receptor expressed in several tissues including inner ear hair cells, brain, and in activated fibrosarcoma cells and whose relevance to nicotine signaling in primary lung cells is as yet uncharacterized.

Figure 4:
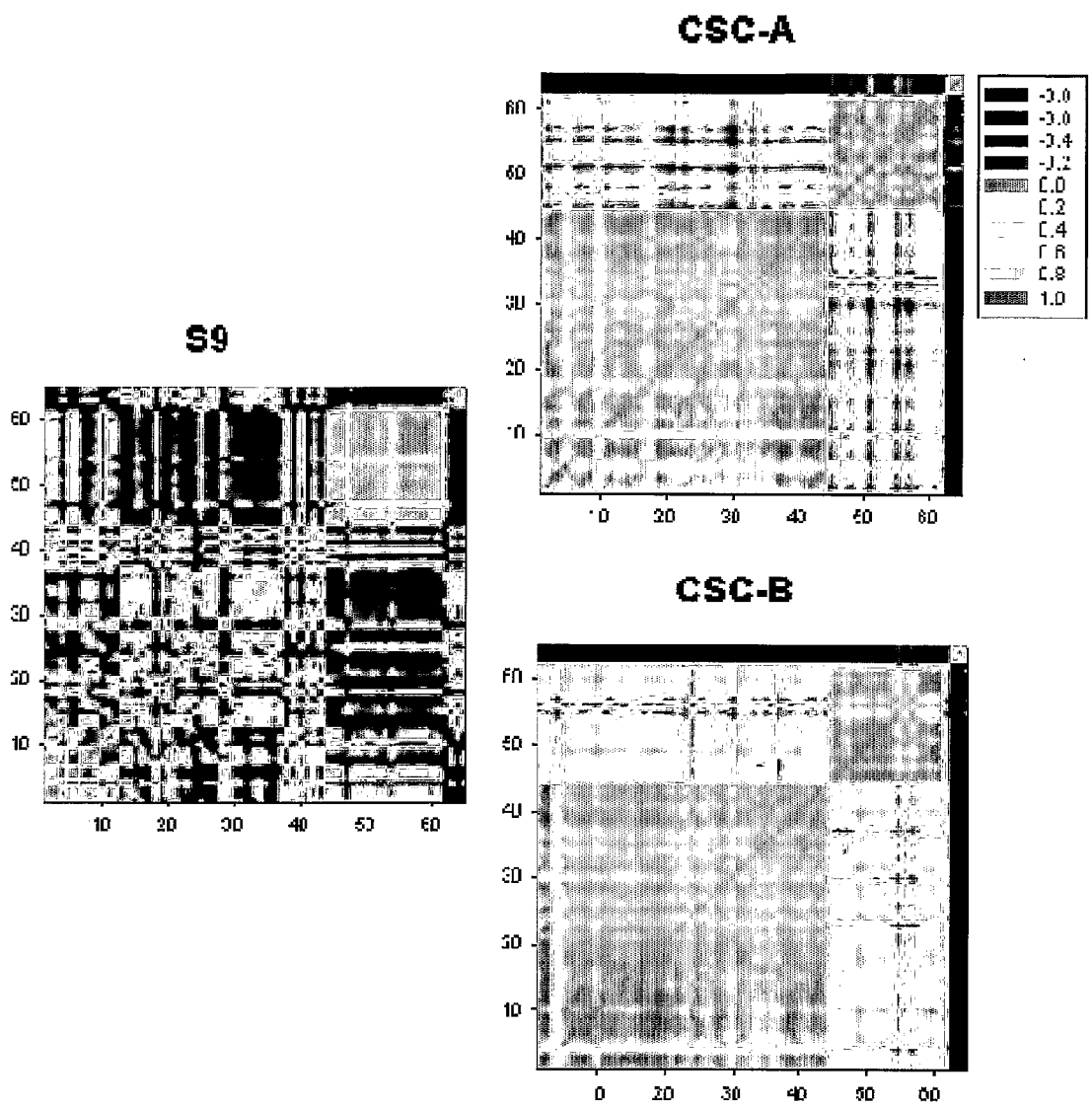
FIG. 4 shows correlation mosaics of the genes listed in Table 2. Correlation coefficients were generated for each of the 40 genes in Table 2, comparing the set to itself in each of the three conditions. The same gene order runs across the x and y axes of the mosaics. Correlation mosaics for HV genes highly correlated in response to CSC-A and CSC-B, and not correlated with responses to S9. Each pixel in the plot represents a correlation coefficient of gene expression. Genes highly positively correlated are denoted in gray and those highly negatively correlated are in black. The same order of the genes along axis is used for all three mosaics. Genes highly correlated in CSC-A and CSC-B, but not in S9-treated cells are denoted as a gray cluster in the lower left hand corner of CSC-A and the CSC-B mosaic. This cluster is disrupted in the S9 mosaic demonstrating the variance in gene regulation that occurred in S9-treated cells.

Using a similar approach, as described for the analysis of CSC exposure in TABLE 7 and FIG. 4, the global effects of the exposure to the S9 microsomal fraction were assessed by first identifying the subset of HV genes that were correlated among all three treatment groups and then assuming that the effect on these genes was due to the S9 microsomal fraction solely, since their expression characteristics did not change when the S9 microsomal fraction was combined with contact to a CSC. As described above, a Monte Carlo analysis was performed to define a statistically robust correlation coefficient unlikely to occur by chance. Using this threshold, the probability of identifying a gene correlated in all three groups by chance was <1/total number of genes analyzed, thereby confirming the high statistical specificity of this method.

Figure 6:
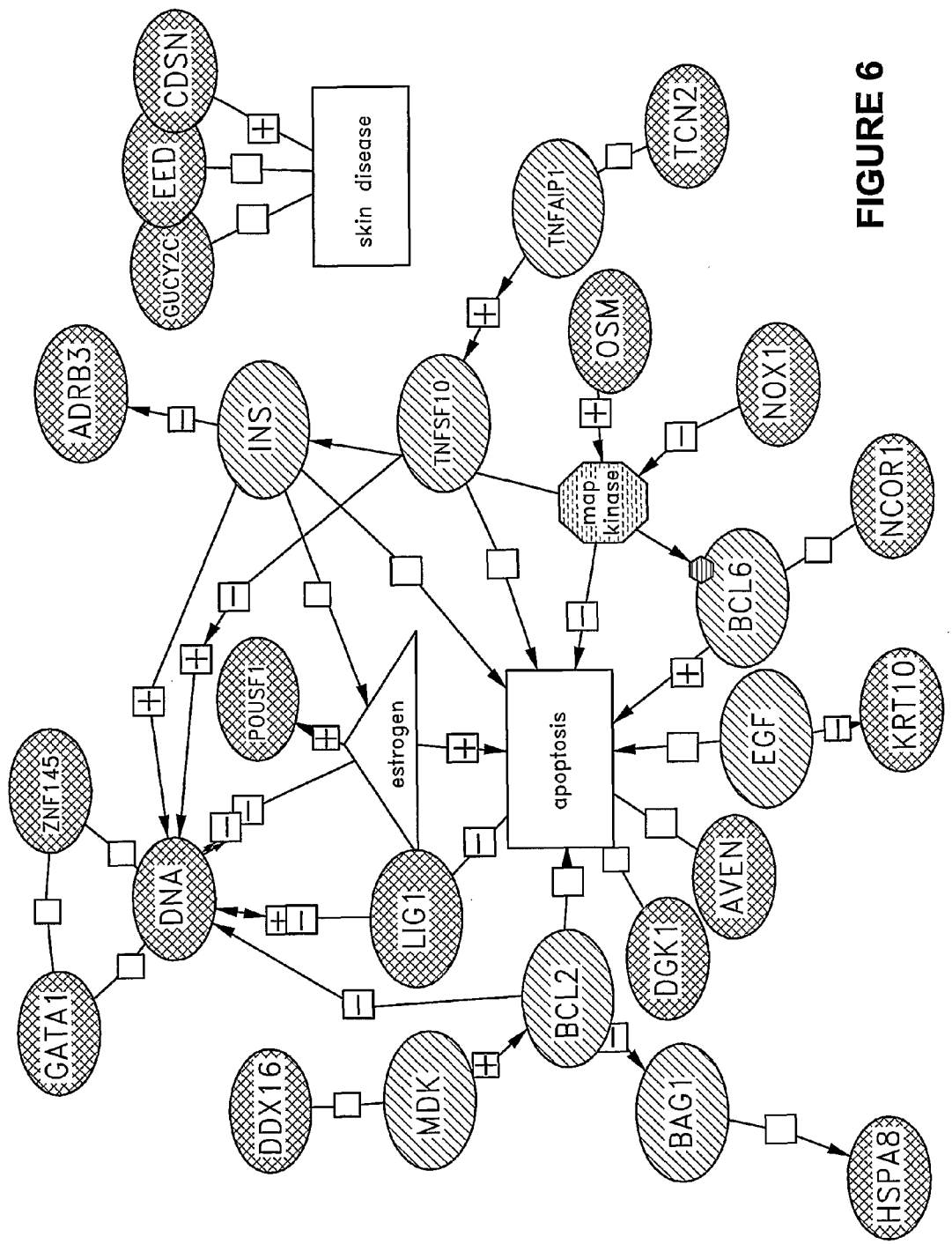
FIG. 6 shows the functional associations of genes, which are highly correlated in all three treatment groups (CSC-A, CSC-B, and S9). The genes, pathways, and functional interconnections among these elements for genes correlated in all three treatment groups are represented. Gene and pathway symbols are described in FIG. 5. Cross-hatched ovals indicate genes from Table 3 (i.e., genes specific for S9 treatment). Ovals with slanted lines (indicate additional proteins not in Table 3), cross-hatched oval (cell object—DNA) and white triangle (indicating small molecule—estrogen) were added to better define the regulatory networks of the genes identified in this analysis. Ovals with dashed lines indicate classes of functional peptides. White rectangles indicate cellular processes in which these genes participate. Each line indicates a regulatory relationship (binding, regulation, etc.) based upon a literature reference. Regulatory relationships are denoted in a box on the line with positive regulation represented as a plus sign, negative regulation as a minus sign, and unknown relationships by no sign.

As shown in TABLE 8, a set of 52 genes was identified and the probable function of these genes was assessed using PathwayAssist™ software (see FIG. 6). Many of the genes appeared to have roles in modulating apoptosis (e.g., AVEN, LIG1, PTEN, etc.) indicating that the predominant cellular response to chronic S9 microsomal fraction exposure is to activate apoptotic programs. A second group of S9-modulated genes modulates cellular surface chemistry, adhesion, and cellular differentiation (e.g., SIAT4B, KRT10, CDSN and EXT2). These results indicate that the inclusion of S9 microsomal fractions in toxicogenetic experiments significantly modulates cellular physiology, which may complicate and bias the results assessing the effects of CSCs or any other type of complex hydrocarbon mix requiring metabolic activation.

TABLE 8

Genes Specific for S9 Treatment

| GenBank accession no. | Gene abbreviation | Gene description |
|---|---|---|
| NM_001303 | COX10 | COX10 homolog, cytochrome c oxidase assembly protein |
| AK056540 | | *Homo sapiens* cDNA FLJ31978, weakly similar to Probable hexosyltransferase |
| NM_016013 | LOC51103 | CGI-65 protein |
| NM_031916 | ASP | AKAP-associated sperm protein |
| NM_000947 | PRIM2A | Primase, polypeptide 2A (58 kD) |
| NM_006927 | SIAT4B | Sialyltransferase 4B |
| NM_006441 | MTHFS | 5,10-methenyltetrahydrofolate synthetase |
| NM_002699 | POU3F1 | POU domain, class 3, transcription factor 1 |
| NM_002954 | RPS27A | Ribosomal protein S27a |
| AK055508 | FLJ11785 | Rad50-interacting protein 1 |
| NM_024636 | FLJ23153 | Likely ortholog of mouse tumor necrosis-alpha-induced adipose-related protein |
| BC011231 | | *Homo sapiens*, Similar to angiotensinogen |
| NM_007052 | NOX1 | NADPH oxidase 1 |
| NM_000234 | LIG1 | Ligase I, DNA, ATP-dependent |
| NM_032553 | FKSG79 | Putative purinergic receptor |
| NM_000025 | ADRB3 | Adrenergic, beta-3-, receptor |
| AF023203 | | *Homo sapiens* homeobox protein Og12 |
| U50536 | | Human BRCA2 region, mRNA sequence CG011 |
| NM_000421 | KRT10 | Keratin 10 (epidermolytic hyperkeratosis; keratosis palmariset plantaris) |
| NM_001264 | CDSN | Corneodesmosin |
| NM_000355 | TCN2 | Transcobalamin II; macrocytic anemia |
| NM_000401 | EXT2 | Exostoses (multiple) 2 |
| NM_014214 | IMPA2 | Inositol(myo)-1(or 4)-monophosphatase 2 |
| NM_003797 | EED | Embryonic ectoderm development |
| AF319523 | | *Homo sapiens* RT-LI mRNA, complete sequence |
| AF074331 | PAPSS2 | 3'-phosphoadenosine 5'-phosphosulfate synthase 2 |
| AF189011 | RNASE3L | Putative ribonuclease III |
| BC009752 | | *Homo sapiens*, Similar to sex comb on midleg-like 1 (*Drosophila*) |
| NM_000691 | ALDH3A1 | Aldehyde dehydrogenase 3 family, memberA1 |
| NM_006006 | ZNF145 | Zinc finger protein 145 (expressed in promyelocytic leukemia) |
| NM_005831 | NDP52 | Nuclear domain 10 protein |
| L26584 | RASGRF1 | Ras protein-specific guanine nucleotide-releasing factor 1 |
| NM_014182 | HSPC160 | HSPC160 protein |
| NM_004963 | GUCY2C | Guanylate cyclase 2C (heat stable enterotoxin receptor) |
| AB023223 | STXBP-TOM | Tomosyn |
| NM_018919 | PCDHGA6 | Protocadherin gamma subfamily A, 6 |
| NM_002968 | SALL1 | Sal-like 1 (*Drosophila*) |
| NM_003587 | DDX16 | DEAD/H (Asp-Glu-Ala-Asp/His) box polypeptide 16 |
| AK024449 | PP2135 | PP2135 protein |
| AB034205 | LUC7A | Cisplatin resistance-associated overexpressed protein |
| BC011589 | OSM | Oncostatin M |
| NM_006597 | HSPA8 | Heat shock 70 kD protein 8 |
| NM_004384 | CSNK1G3 | Casein kinase 1, gamma 3 |
| AK057672 | | *Homo sapiens* cDNA FLJ33110 fis |
| NM_016344 | PRO1900 | PRO1900 protein |
| NM_018651 | ZFP | Zinc finger protein |
| NM_004717 | DGKI | Diacylglycerol kinase, iota |
| NM_006479 | PIR51 | RAD51-interacting protein |
| AK024250 | | *Homo sapiens* cDNA FLJ14188 fis |
| NM_001382 | DPAGT1 | Dolichyl-phosphate N-acetylglucosaminephosphotransferase 1 |
| NM_020371 | AVEN | Cell death regulator aven |
| NM_006311 | NCOR1 | Nuclear receptor co-repressor 1 |

Discriminant Function Analysis (DFA) is a form of multivariate analysis that identifies subsets of dependent variables that characterize a system made up of related groups. In this kind of gene expression analysis, a linear equation is calculated, denoted a root, whose overall value is distinct for a given characterized group. Accordingly, DFA identifies genes most characteristic of a given state. DFA analysis was conducted on the genes that were correlated after CSC treatment but not correlated after S9 treatment, as described in the following example.

EXAMPLE 8

Refined Analysis of CSC-correlated Genes Using Discriminant Function Analysis (DFA)

The set of 40 genes that were correlated after CSC treatments (see TABLE 7 and FIG. 4) but not correlated after S9 microsomal fraction treatment were further analyzed using DFA. Of the 40 CSC-correlated genes, 11 were identified by DFA as being most highly distinct among CSC and S9 treated cells (TABLE 9). Interestingly, a significant number of these genes were associated with oncogenesis. For example, this gene set included 3 putative proto-oncogenes including (1) MAP2K5, the over-expression of which is associated with increased proliferative and invasive potential of metastatic prostate cancer and is reported to be a potent survival molecule in APO- MCF-7 breast carcinoma cells; (2) DDIT3, a C/EBP transcriptional regulator involved in growth arrest induced by DNA damage that is a common breakpoint in human myxoid liposarcomas; and (3) BAG2, a BCL-2-binding apoptosis suppressor that is over-expressed in human cervical, breast and lung cancer cell lines. In addition, three putative tumor suppressor genes were also identified in this gene set. These were FUS1, RASA1, and FPH2L1. FUS1 can inhibit tumor cell growth by inducing apoptosis, and was first identified in a search for potential tumor suppressors within a critical homozygous deletion region at 3p21.3 common in lung cancers. RASA1 as a key member of the GAP1 family of GTPase-activating proteins plays a key role in the Ras signaling pathway. DPH2L1 is a BRCA1-induced gene that maps within a region of 17p13.3, which is deleted in 80% of all ovarian epithelial malignancies. DPH2L1 was identified by exon trapping in this region and was implicated as a tumor suppressor as its expression is reduced or undetectable in ovarian tumors and tumor cell lines. In addition, a nicotinic cholinergic receptor, CHRNA9, and two putative neural growth factors, NxpH3, a neuropeptide-like neural signaling molecule, and NINJ2, a gene up-regulated in damaged nerve cells that upregulates neurite outgrowth, were also identified in this gene set. The impact on neural growth factors is not surprising in light of the fact that many lung cancers express neuroendocrine features and are also stimulated by an autocrine/paracrine system of neuroendocrine peptide hormones.

Figure 7:
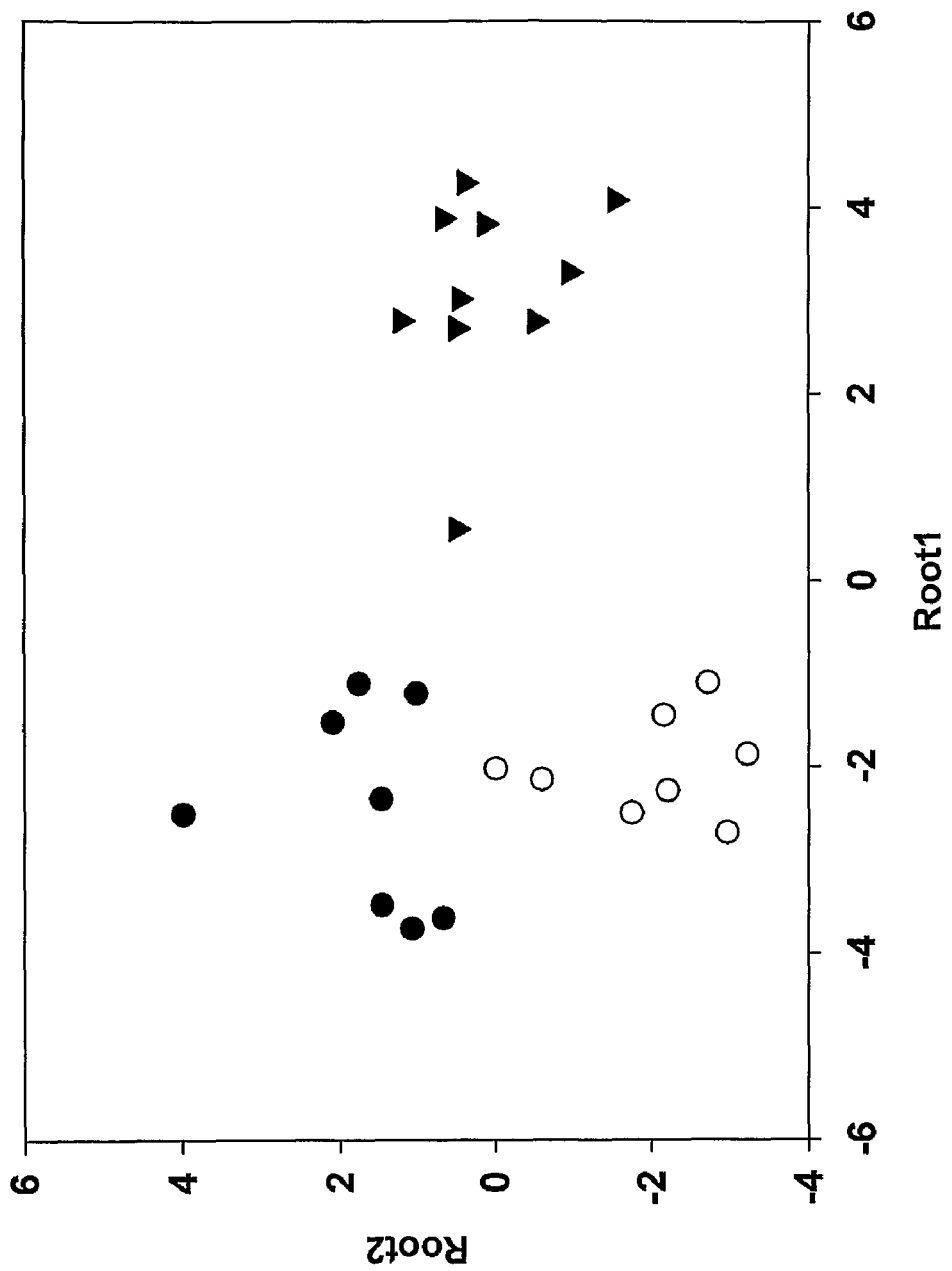
FIG. 7 shows the results of a discriminant function analysis (DFA), which identified genes having high discriminatory capabilities. Values of the roots obtained by DFA analysis were used to graphically depict the differences of the gene expression values obtained for the three treatments (CSC-A, CSC-B, and S9). Root values for the 2-12 h time points for each treatment are represented by filled circles (CSC-A), open circles (CSC-B), and filled triangles (S9).

A graphical representation of the DFA results for the three treatment conditions at all time points was generated. The spatial organization of the elements in this representation provided a measure of the overall variance among groups (see FIG. 7). The genes used for this analysis were correlated in CSC exposed cells and not correlated in S9-treated cells. A correlation coefficient of 0.8 was used as a threshold for defining similarity. The expression of these genes should therefore be similar in CSC-treated cells. Indeed the two CSC groups were more closely associated than either CSC group was to the S9 microsomal fraction-treated group. Of note, the samples from the CSC groups did not overlap, indicating that the two CSC treatments elicit somewhat distinct responses even in genes highly correlated in their behavior in each CSC group.

TABLE 9

Discriminant Function Analysis of CSC-Correlated Genes

| GenBank accession no. | Gene abbreviation | Gene description |
|---|---|---|
| M23326 | TRDV3 | T cell receptor delta variable 3 |
| NM_002757 | MAP2K5 | Mitogen-activated protein kinase kinase 5 |
| NM_004083 | DDIT3 | DNA-damage-inducible transcript 3 |
| NM_004282 | BAG2 | BCL2-associated athanogene 2 |
| NM_007275 | FUS1 | Lung cancer candidate |
| NM_003408 | ZFP37 | Zinc finger protein 37 homolog (mouse) |
| NM_002046 | GAPD | Glyceraldehyde-3-phosphate dehydrogenase |
| NM_017581 | CHRNA9 | Cholinergic receptor, nicotinic |
| BC015737 | NINJ2 | Ninjurin 2 |
| AB032985 | NXPH3 | Neurexophilin 3 |
| NM_002890 | RASA1 | RAS p21 protein activator |
| NM_001383 | DPH2L1 | Diptheria toxin resistance protein |

Figure 5:
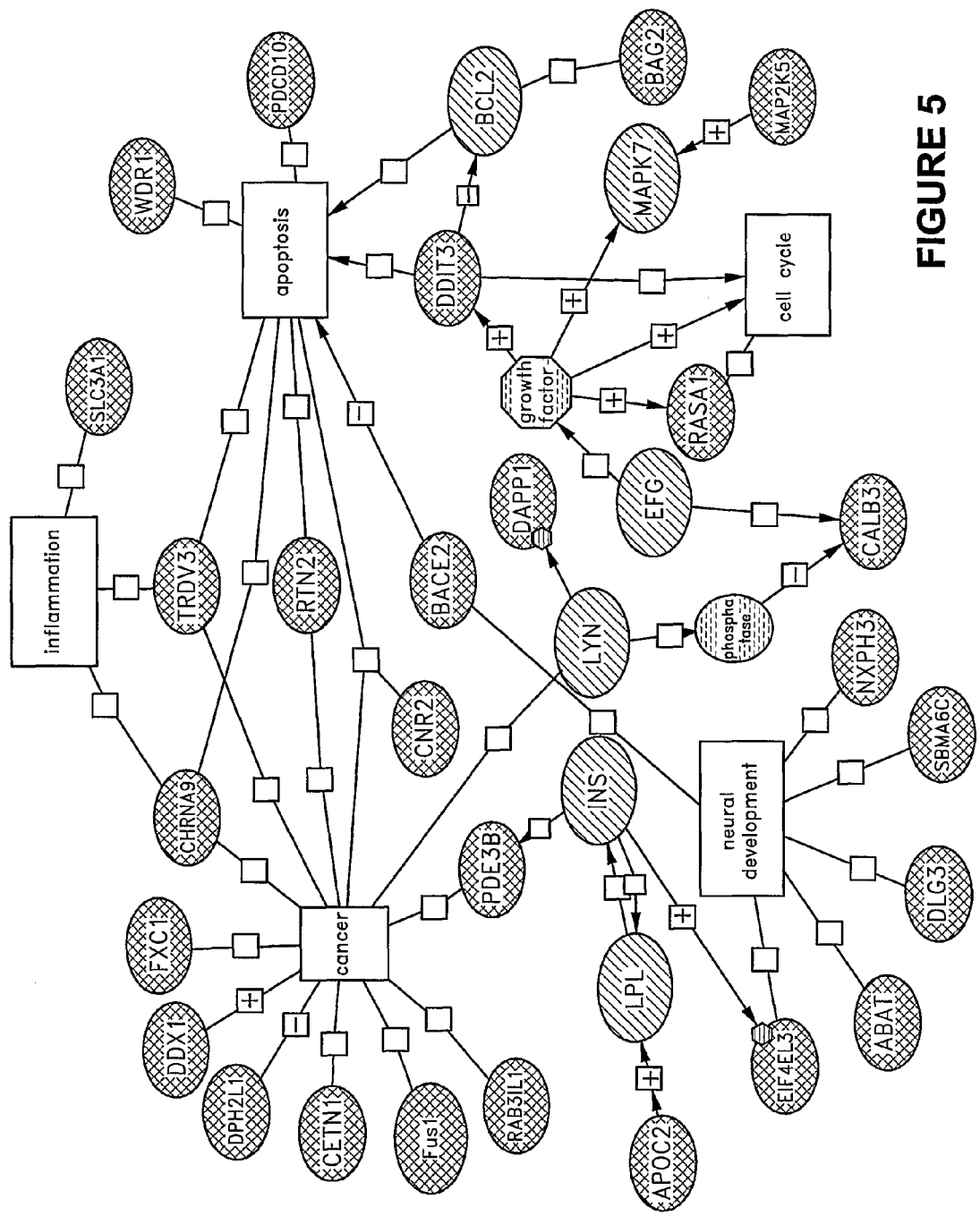
FIG. 5 shows the functional associations of HV genes specific for CSC-A and CSC-B treatment. The expression patterns of this set of genes are highly correlated in CSC-treated NHBE cells and not correlated with those seen in cells treated with S9 alone. Cross-hatched ovals indicate genes from Table 2 (i.e., HV genes specific for CSC-A and CSC-B treatment). Ovals with slanted lines (indicating additional proteins not in Table 2) were added to better define the regulatory networks of the genes identified in this analysis. Ovals with dashed lines indicate classes of functional peptides. Rectangles indicate cellular processes in which these genes participate. Each line indicates a regulatory relationship (binding, regulation, etc.) based upon a literature reference. Regulatory relationships are denoted in a box on the line with positive regulation represented as a plus sign, negative regulation as a minus sign, and unknown relationships by no sign.
Figure 8:
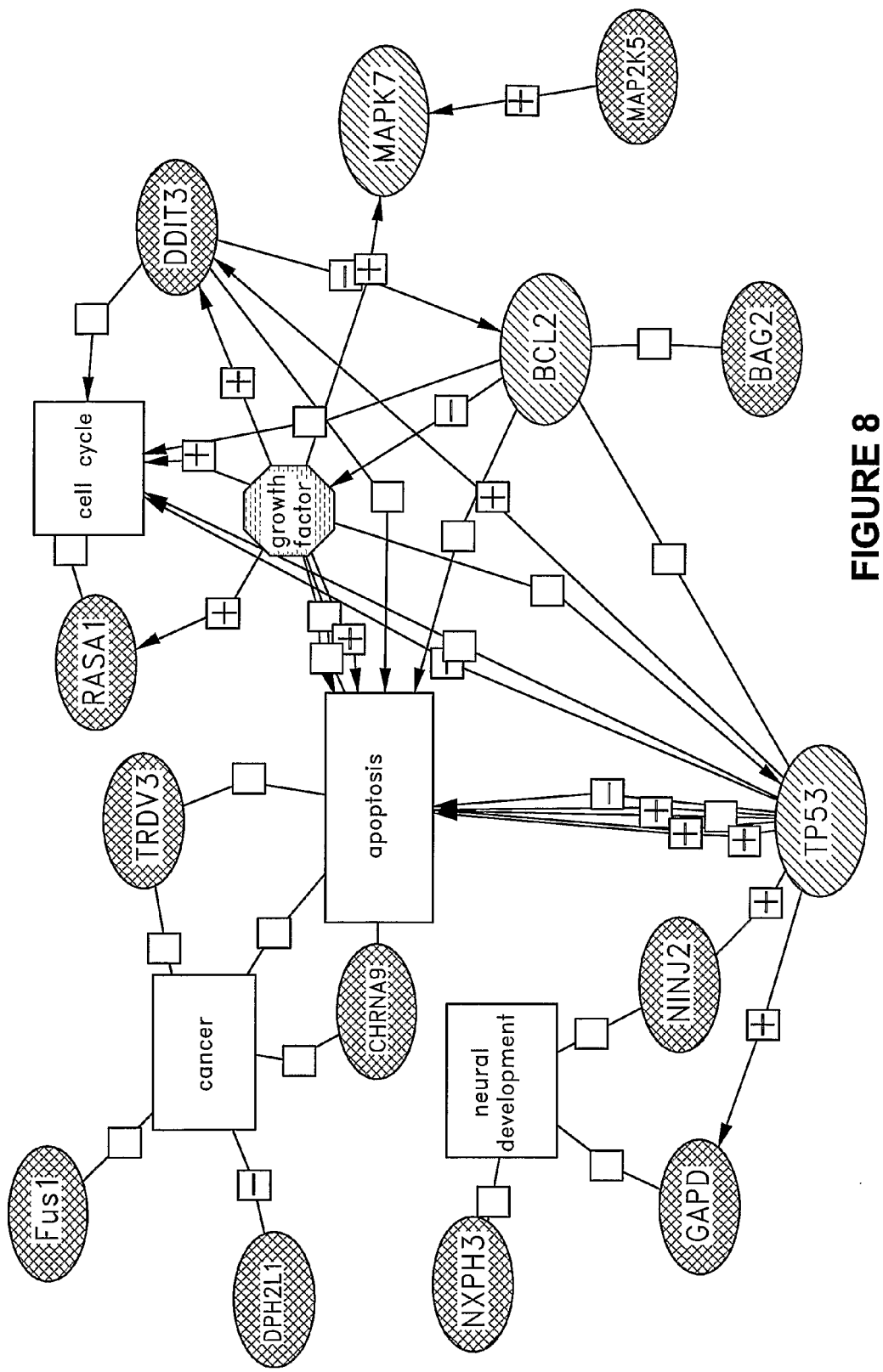
FIG. 8 shows the functional associations of genes, which are provided in Table 3. The genes, pathways, and functional interconnections among these elements for genes having the highest discriminatory potential among all three treatment groups are represented. Gene and pathway symbols are described in previous figures.

FIG. 8 shows the result of a functional analysis of the gene set in TABLE 8 using Pathway Assist. Not surprisingly, the major cellular processes affected by these genes were subset of the processes affected by the parent gene set, as illustrated in FIG. 5.

Four post-treatment expression characteristics were established for each gene on the array: (1) whether or not the gene was expressed above background at each time-point; (2) whether or not the gene showed hypervariability (i.e. change greater than normal) of expression in one, two, or all three treatment conditions over the 12 h treatment period; (3) what was the specific pattern of gene expression over the 12 h treatment period; and (4) whether or not the gene expression pattern in each condition correlated with its behavior under the two other conditions from 0-12 h. Several interesting observations emerged from this analysis. Significantly, treatment of NHBE cells with CSCs from two American brands of cigarettes altered the expression of approximately 3600 genes and ORFs (or 17% of the array) sometime during the 12-hour exposure (see FIGS. 1 and 2). These data provide evidence that due to their chemical complexity and temporal requirement for metabolic activation, CSCs should have a broad and dynamic effect on the homeostatic transcriptome of the NHBE cell. In addition to the quantitative similarities in gene alterations induced by the different CSCs, there were also qualitative similarities in that both CSCs affected a large common block of genes, which is not surprising given the relatively comparable types of blended tobaccos used in most American cigarette brands.

Several approaches were employed to discriminate and cluster genes that became hypervariable after CSC treatment so as to develop a robust and accurate statistical estimate of functional significance for these perturbations. For example, as shown in FIG. 5, CSCs affected networks of genes that intersect critical signaling pathways such as apoptosis, transcription, and cell cycle regulation, which are known to play key roles in specific diseases such as cancer, chronic inflammation, and impaired neural development, and which both epidemiological and functional studies conclude can be caused by chronic cigarette smoking. The relevance of these pathways to smoking-related diseases is further supported by a limited body of published data in which other cell types or tissues exposed to either smoke, CSC, or a specific substance in CSC (e.g., benzo[a]pyrene, nicotine, etc.) were assessed using low-density arrays (see Nadadur et al., *Chest* 121: 83S-

84S, 2002; Nordskog et al. *Cardiovasc Toxicol* 3: 101-117, 2003; Zhang et al. *Physiol Genomics* 5: 187-192, 2001; Gebel et al. *Carcinogenesis* 2003).

The sensitivity and accuracy of the methodologies used herein to identify genes impacted by CSCs was further shown by the fact that the set of HV genes in CSC-treated cells included many of the genes and/or gene families that have been identified using various global expression analyses (e.g., Serial Analysis of Gene Expression, Differential Display, and microarrays) and concluded to be of importance in the development and/or maintenance of lung cancers. These include erb-B2, matrix metalloproteinase 9 (MMP9), the heterogeneous nuclear ribonucleoprotein (hnRNP) family, the Fus1 lung cancer candidate, glutathione S-transferase pi, the β-retinoic acid receptor, chromogranin B, RAB5, death-associated protein kinase 1 (DAPK), various cancer/testis antigens [MAGE genes], and others. For the first time, however, the present disclosure demonstrates that expression of these genes is altered in normal bronchial epithelial cells exposed to CSCs for only a short period of time, which provides evidence that one or more of these genes are an early indicator of tobacco-related cellular damage. In addition, the data herein identify a large number of genes and gene families that had not yet been associated with the induction or maintenance of pulmonary neoplasms or to other tobacco-related diseases involving the cardiovascular and immune systems. Accordingly, many of the genes identified using the approaches described herein are particularly useful biomarkers of the pathogenesis of these diseases.

The highly correlated expression characteristics of the CSC-impacted genes shown in TABLE 1 and FIG. 5, for example, highlight several genes that appear to play prominent roles in tobacco-related diseases. Both DPH2L1 and Fus1 are putative tumor suppressor genes associated with ovarian and lung cancer, respectively. Fus1 is found at a homozygous deleted region of chromosome 3p21 in lung tumors, and its forced expression in lung carcinoma cells suppresses cell growth in vitro and growth and metastases of tumors in vivo by mechanisms involving G1-arrest and induction of apoptosis. The RASA1 is a component of the GAP1 family of GTPase-activating proteins, which can suppress proliferation signals by enhancing the weak intrinsic GTPase activity of normal RAS p21 protein and maintaining it in its inactive GDP-bound form. It is contemplated that Ras acts as a major nexus for multiple signaling pathways that control a diverse range of functions, but many of the subtleties of Ras functioning in individual cell types remain unclear. It is also though that Ras plays an important role in tumor cell survival. The MAP2K5 is a novel mitogen activated protein kinase implicated in the regulation of cell proliferation. Over-expression of MAP2K5 can, in cooperation with other effectors, transform rodent cells, and function as a potent survival molecule in breast cancer cells. MAP2K5 represents a potential therapeutic target in prostate cancer as over-expression of MAP2K5 can induce proliferation, motility, and invasion. Interestingly, MAP2K5 also dramatically up-regulates the expression of matrix metalloproteinase-9 (MMP-9) in prostate cancers. As shown in TABLE 1, MMP-9 was hypervariable in both CSC-treatment groups. The matrix metalloproteinases (MMPs) are a large family of extracellular matrix degrading enzymes believed to play central roles in degradation, remodeling, and repair of basement membranes. Inappropriate or over-expression of these proteins appear to a critical determinant in tumor invasion and metastasis of a number of neoplasms including those of the lung. For example, MMP9 potentiates pulmonary metastasis formation, and high serum levels of MMP-9 in patients with non-small-cell lung cancer (NSCLC) correlated with significantly shorter survival than patients with low serum levels of this protein.

In addition to a common set of affected genes, each individual CSC also altered the expression of a relatively large gene set that was unique to each CSC. That is, it was discovered that each tobacco smoke condensate was associated with a unique genetic fingerprint. The impact on these unique gene sets may be due to qualitative and/or quantitative differences in the constellation of chemical constituents in the two CSCs. It is interesting to note that despite the fact that both Brand A and Brand B are similar types of cigarettes (i.e., 'full-flavor') as determined by FTC criteria, there are measurable differences in the quantities of nicotine, tar, as well as, toxins and carcinogens between Brand-A and Brand-B cigarettes. It is contemplated that the differences in one or more of these substances directly correlates with the observed differences in gene induction and level of expression. Moreover, it is contemplated that each unique gene set affected by CSC-A and CSC-B ultimately influences different cellular pathways and results in different biological consequences.

Several basic assumptions of the emerging field of toxicogenomics are that there are reasonable similarities in gene expression patterns induced by multiple members of one specific class of toxicants, and subtle differences in these gene expression patterns may distinguish distinct chemical-specific 'gene signatures' of exposure (Afshari et al., *Cancer Res* 59: 4759-4760, 1999; Neumann et al. *Biotechnol Adv* 20: 391-419, 2002). For the first time, the approaches described herein provide one with the ability to identify a unique genetic fingerprint or signature for a plurality of tobacco products by contacting NHBE cells or another cell type of the lung, mouth or oral cavity with a tobacco smoke condensate or tobacco smoke from said plurality of tobacco products, identifying the genes expressed as a result of the contact in each individual tobacco product, as well as the level of expression of each, comparing the fingerprint or component thereof (e.g., a specific gene or set of genes or level of expression of a specific gene or set of genes) of the plurality of tobacco products that are being analyzed (or to a database containing genetic fingerprints of tobacco products), identifying differences in the fingerprint or component thereof between the products that are being analyzed, and associating the difference in the fingerprint or component thereof to an increased or decreased risk, proclivity, or potential to acquire a tobacco-related disease (e.g., lung cancer).

Another significant discovery made in the experiments described above, as shown in FIG. 2, is that the majority of CSC-affected genes do not return to baseline within the 12-hour treatment period, especially for CSC-B-affected genes. This observation is not simply due to the fact that the cells were chronically exposed to the CSCs for the entire 12-hours, as is discussed infra. It is contemplated that many of the affected genes require a significant amount of time to return to baseline even after exposure is terminated. Accordingly, a current pack-a-day smoker who averages >150 cigarette puffs/day may alter the homeostatic expression of a large number of genes that cannot return to a baseline state during a typical day. This chronically perturbed state (either increased or decreased compared to baseline) of one or more of these genes may ultimately be etiologically involved in various pathological states caused by exposure to cigarette smoke. Evidence of this is provided by the fact that in subjects who quit smoking there is both short-term improvement in the functioning of a number of affected organ systems (e.g., lung, cardiovascular structures, kidneys, etc.) and a long-term decline in incidence and mortality from various diseases affecting these systems. Presumably, this reversal of smoking-related damage at the tissue and population levels reflects a corresponding reversal at a molecular and cellular level.

For example, chronic inflammatory processes in smokers play fundamental roles in the pathogenesis of atherosclerosis, and increased plasma and tissue levels of several biomarkers associated with inflammation such as various cytokines (e.g., IL-1β, TNF-a), pro-atherogenic enzymes (e.g., lipoprotein lipase) and cell adhesion molecules (e.g., VCAM-1) are associated with future cardiovascular risk, while smoking cessation leads to decreased expression of many pro-inflammatory biomolecules and a concomitant reduction in cardiovascular risk. It is also possible that the altered expression of one or more genes in the habitual smoker becomes attenuated with time as an adaptive response to the stress of chronic activation, and this phenomenon may have unanticipated long-term biological consequences for the smoker.

Another unexpected finding of this study was that the S9 metabolic enzyme fraction significantly influenced gene expression in NHBE cells. S9-exposed cells are traditionally considered a negative control for toxicogenetic experiments performed to establish environmental and occupational exposure guidelines. The fact that gene alterations were observed as early as 2 hours post-S9 exposure has interpretive implications for standard toxicological assays that routinely measure biological and genetic effects of control and test substances after 4 hours of exposure. This observation is particularly relevant as the global shift towards advanced genomic and proteomic technologies transforms the field of toxicology from one relying on the induction of gross genetic abnormalities such as mutations and structural/numerical chromosomal abnormalities to one where altered expression of panels of genes and proteins are used to determine risk to the human population. In order to clearly establish the potential toxicity or efficacy of an environmental substance, drug, or chemopreventive agent, it is important to show that control substances or vehicles used in the methodology cause minimal disruption of the physiologically normal transcriptome. Furthermore, since S9 can induce a range of alterations in gene expression levels independent of any test substance, it is possible that one or more S9-induced effects can be synergistic or antagonistic with the test substances. For example, FIG. 3 shows that many of the same genes that are down-regulated in S9-treated cells are up-regulated in CSC-treated cells despite the fact that CSCs contain the same concentration of S9 enzymes. Alternatively, the effects of S9 can be mitigated by the test substance. Evidence for this is strongly supported by the data, which shows that a number of genes whose steady-state mRNA level were found to be altered only by S9 were not found to be altered when cells were exposed to S9 in context with either CSC-A or CSC-B. In this scenario, the direct effects of S9, which can be directly cytotoxic to cells in cultures, may be attenuated when sequestered and modified through contact with substances in CSCs.

Although the analysis of normal human bronchial epithelial cells (NHBE cells) contacted with tobacco smoke condensates, described above, provide several ways to identify the genes that are modulated in response to human exposure to tobacco smoke, another approach involves analysis of cells of the mouth, oral cavity, trachea, and lungs, either normal or immortalized cell lines (e.g., human bronchial cells (e.g., BEP2D or 16HBE14o cells), human bronchial epithelial cells (e.g., HBEC cells, 1198, or 1170-I cells), normal human bronchial epithelial cells (NHBE cells), BEAS cells (e.g., BEAS-2B), NCI-H292 cells, non-small cell lung cancer (NSCLC) cells or human alveolar cells (e.g., H460, H1792, SK-MES-1, Calu, H292, H157, H1944, H596, H522, A549, and H226) tongue cells (e.g., CAL 27), and mouth cells (e.g., Ueda-1)), which are contacted with cigarette smoke. Accordingly, as described in the following example, several experiments were conducted to evaluate the genes that were expressed, as well as the expression levels, when NHBE cells were exposed to tobacco smoke.

EXAMPLE 9

Microarray Analysis in CS Experiments

Once the NHBE cells were contacted with tobacco smoke or with air ("mock exposure"), as described in Example 1, the cDNA of NHBE cells that were either mock exposed or tobacco smoke exposed was prepared for microarray analysis as follows. Cells were harvested for total RNA extraction after either mock or smoke treatment. The RNA from each Petri dish was used for a separate microarray chip, which resulted in a total of 18 microarrays (ten from Experiment 1 and eight from Experiment 2). The medium was aspirated and the dishes were rinsed twice with 1 mL prewarmed PBS per dish. After the second rinse, 1 mL of cold TRIzol® (Invitrogen Corp., Carlsbad, Calif.) was added to each dish. NHBE cell lysates were prepared and the RNA was extracted according to the manufacturer's protocol. The RNA pellet was frozen and stored at −80° C.

Prior to cDNA synthesis, the RNA was resuspended in diethylpyrocarbonate-treated water. RNA integrity was assessed using capillary gel electrophoresis (Agilent BioAnalyzer, Agilent Technologies, Palo Alto, Calif.) to determine the ratio of 28s:18s rRNA in each sample. A threshold of 1.0 was used to define samples of sufficient quality and only these samples were used for microarray studies. The RNA quality of all samples was extremely high with no ratios less than 1.8. Fluorescently labeled cDNA was synthesized and purified as previously described. (See Jarvis et al. Arthritis Res Ther, 6: R15-R32, 2004, expressly incorporated by reference in its entirety).

A commercially available, genome-scale oligonucleotide library containing gene-specific 70-mer oligonucleotides representing 21,329 human genes was used for microarray production (QIAGEN Inc., Valencia, Calif.). Oligonucleotides were spotted onto Corning® UltraGAPS™ aminosilane coated slides, which were then rehydrated with water vapor, snap dried at 90° C. Oligonucleotide DNAs were covalently fixed to the surface of the glass using 300 mJ of ultraviolet radiation at a 254 nm wavelength. Unbound free amines on the glass surface were blocked for 15 min with moderate agitation in a solution of 143 mM succinic anhydride dissolved in 1-methyl-2-pyrrolidinone, 20 mM sodium borate, pH 8.0. Slides were rinsed for 2 min in distilled water, immersed for 1 min in 95% ethanol, and dried with a stream of nitrogen gas.

Hybridization was performed in an automated liquid delivery, air-vortexed, hybridization station for 9 hr at 58° C. under an oil-based cover slip (Ventana Medical Systems, Inc. Tucson, Ariz.). Microarrays were washed at a final stringency of 0.1×SSC. Microarrays were scanned using a simultaneous dual color, 48-slide scanner (Agilent Technologies). Fluorescent intensity was quantified using Imagene™ software (BioDiscovery, Marina del Rey, Calif.).

Adjustment of expression levels in compared samples was performed as previously described. (See Dozmorov, et al. Bioinformatics., 19: 2004-211, 2003; Knowlton, N., et al. Bioinformatics., 20: 3687-3690, 2004; and Dozmorov, et al. Bioinformatics., 5:53, 2004, each of which is incorporated by reference in its entirety). To determine differentially expressed genes, the analysis was confined to the set of genes that were expressed above background in at least one condition (i.e., 4 and/or 24 hours post-exposure, CS-treated or mock-treated). For each experiment, replicates from each condition were averaged and genes that were under- or over-expressed ("modulated") in response to tobacco smoke treatment (e.g., cigarette smoke (CS)) by 1.5-fold or more at either or both time points were identified. Genes exhibiting similar expression behavior in both experiments were determined.

Quantitative Reverse Transcriptase PCR (QRTPCR)

To determine the level of expression, RNA was reverse-transcribed using an Omniscript RT™ kit according to manufacturer's instructions (Qiagen, Valencia, Calif.) and the resultant cDNA subsequently purified using the Montage PCR 96-well cleanup plate (Millipore, Billerica, Mass., USA). The qRT-PCR amplifications were performed on an ABI®PRISM 7700 sequence detection system using SYBR®Green I dye assay chemistry. A 15 uL PCR reaction for each gene of interest was prepared consisting of 7.5 uL of 2×SYBR®Green PCR mix (Applied Biosystems Inc., Foster City, Calif.), 4.9 µl of $H_2O$, 0.6 µl (30 pmoles) of gene-specific forward and reverse primers, and 2 µt (1 ng) of cDNA template. All samples were run in triplicate with the appropriate single qRT-PCR controls (no reverse transcriptase and no template). Cycling conditions used for all amplifications were one cycle of 95° C. for 10 minutes and 40 cycles of 95° C. for 15 seconds and 60° C. for 1 minute. Following the QRTPCR, dissociation curve analysis was performed to determine if the desired single gene product was produced.

Gene Expression Alterations Induced by CS Exposure

In order to determine the broad impact of a brief transient exposure to cigarette smoke (CS) on the transcriptome of NHBE cells, monolayer cultures of NHBE cells were treated in logarithmic phase of growth for 15 minutes with whole smoke from a leading representative brand of American cigarettes, and then assessed for global alterations in their transcriptome at 4 h and 24 h post-exposure. Furthermore, in an attempt to unambiguously define a set of genes consistently impacted by CS, this experiment was performed twice and then the focus was restricted to only those individual genes whose RNA levels similarly deviated by 1.5 fold or greater in the two experiments (either overexpressed or underexpressed in response to CS treatment). By assessing global RNA changes at 4 and 24 h post-exposure, the temporal relationships of those genes whose RNA levels were altered a) by 4 hours and that returned to baseline by 24 hours; b) by 4 hours and did not return to baseline by 24 hours; and c) only by 24 hours could be observed.

Approximately 10% of the 21,329 human genes represented on the array were expressed above background in mock-treated cells. This amount of expression presumably represents the typical transcriptome of unstressed NHBE cells in vitro, and agrees well with published data on the human airway transcriptome of healthy nonsmokers. Interestingly, CS-treated NHBE cells also expressed approximately 10% of the total gene complement, suggesting that brief CS-exposure does not induce a major quantitative reorganization of the normal transcriptome of lung cells.

Of the 21,329 genes on the array, a set of 364 genes exhibited similar changes in expression level in both experiments (See TABLE 10). A subset of 298 genes that were overexpressed 1.5-fold or more in both experiments was compared to mock-treated cells. Of this set of 298 up-regulated genes, 184 were up-regulated exclusively at 4 h post cigarette smoke exposure, while 69 were up-regulated exclusively at 24 h post-exposure, and 45 were up-regulated at both time points. The number of genes that were under-expressed at least 1.5-fold in cells exposed to cigarette smoke was 66, with 35 down-regulated exclusively at 4 h post CS-exposure, 30 down-regulated exclusively at 24 h post-exposure, and one down-regulated at both time points. Further confirmation that the entire set of 364 up and down-regulated genes accurately reflect a reliable genetic response to cigarette smoke exposure is evidenced by the fact that a majority of the genes exhibited remarkably consistent expression behaviors in both experiments.

TABLE 10

Genes Upregulated by Cigarette Smoke

| Gene ID | Gene Name | Description | Fold Increase at 4 h | Fold Increase at 24 h |
| --- | --- | --- | --- | --- |
| NM_004261 | SEP 15 | 15 kDa selenoprotein | 1.71 | 1.29 |
| NM_000859 | HMGCR | 3-hydroxy-3-methylglutaryl-Coenzyme A reductase | 2.25 | 1.33 |
| AK025736 | HMGCS1 | 3-hydroxy-3-methylglutaryl-Coenzyme A synthase 1 (soluble) | 1.02 | 1.63 |
| NM_002526 | NT5 | 5' nucleotidase (CD73) | 1.45 | 1.69 |
| NM_001109 | ADAM8 | A disintegrin and metalloproteinase domain 8 | 1.17 | 2.72 |
| NM_005891 | ACAT2 | Acetyl-Coenzyme A acetyltransferase 2 (acetoacetyl Coenzyme A thiolase) | 1.44 | 1.77 |
| NM_006409 | ARPC1A | Actin related protein 2/3 complex, subunit 1A (41 kD) | 2.01 | 1.79 |
| NM_018445 | LOC55829 | AD-015 protein | 1.64 | 2.02 |
| NM_001284 | AP3S1 | Adaptor-related protein complex 3, sigma 1 subunit | 2.18 | 1.27 |
| NM_000485 | APRT | Adenine phosphoribosyltransferase | 1.56 | 1.63 |
| NM_007002 | ADRM1 | Adhesion regulating molecule 1 | 1.68 | 1.61 |
| NM_006829 | APM2 | Adipose specific 2 | 1.96 | 2.34 |
| NM_001667 | ARL2 | ADP-ribosylation factor-like 2 | 2.06 | 0.80 |
| NM_000693 | ALDH1A3 | Aldehyde dehydrogenase 1 family, member A3 | 0.82 | 2.88 |

TABLE 10-continued

| | | | | |
|---|---|---|---|---|
| NM_001635 | AMPH | Amphiphysin (Stiff-Mann syndrome with breast cancer 128 kD autoantigen) | 1.78 | 2.16 |
| NM_001657 | AREG | Amphiregulin (schwannoma-derived growth factor) | 1.96 | 0.33 |
| NM_001145 | ANG | Angiogenin, ribonuclease, RNase A family, 5 | 1.61 | 1.10 |
| NM_000700 | ANXA1 | Annexin A1 | 1.39 | 1.82 |
| NM_005139 | ANXA3 | Annexin A3 | 1.34 | 1.71 |
| NM_001154 | ANXA5 | Annexin A5 | 2.40 | 2.43 |
| NM_004034 | ANXA7 | Annexin A7 | 2.10 | 1.64 |
| NM_016476 | ANAPC11 | APC11 anaphase promoting complex subunit 11 homolog (yeast) | 1.68 | 1.30 |
| NM_016085 | APR-3 | Apoptosis related protein APR-3 | 1.44 | 0.84 |
| NM_005721 | ACTR3 | ARP3 actin-related protein 3 homolog (yeast) | 1.63 | 1.72 |
| NM_017900 | AKIP | aurora-A kinase interacting protein | 2.07 | 5.18 |
| M90355 | BTF3L2 | Basic transcription factor 3, like 2 | 1.87 | 1.47 |
| NM_004281 | BAG3 | BCL2-associated athanogene 3 | 3.85 | 1.58 |
| NM_001196 | BID | BH3 interacting domain death agonist | 1.54 | 1.05 |
| NM_003860 | BCRP1 | Breakpoint cluster region protein, uterine leiomyoma, 1-barrier to autointegration factor | 1.99 | 1.52 |
| NM_014567 | BCAR1 | Breast cancer anti-estrogen resistance 1 | 1.00 | 1.88 |
| NM_021096 | CACNA1I | Calcium channel, voltage-dependent, alpha 1I subunit | 1.68 | 2.75 |
| NM_005186 | CAPN1 | Calpain 1, (mu/l) large subunit | 1.62 | 1.11 |
| NM_001750 | CAST | Calpastatin | 1.47 | 1.76 |
| NM_013376 | SEI1 | CDK4-binding protein p34SEI1 | 2.46 | 1.87 |
| NM_015965 | GRIM19 | Cell death-regulatory protein GRIM19 | 2.16 | 2.23 |
| NM_016041 | F-LAN-1 | CGI-101 protein | 1.51 | 1.58 |
| NM_016038 | LOC51119 | CGI-97 protein | 1.78 | 2.34 |
| BC002971 | CCT5 | Chaperonin containing TCP1, subunit 5 (epsilon) | 1.81 | 1.74 |
| NM_006429 | CCT7 | Chaperonin containing TCP1, subunit 7 (eta) | 2.85 | 3.21 |
| NM_000647 | CCR2 | Chemokine (C—C motif) receptor 2 | 0.69 | 3.35 |
| NM_012111 | C14orf3 | Chromosome 14 open reading frame 3 | 1.88 | 1.15 |
| AK026450 | C20orf162 | Chromosome 20 open reading frame 162 | 1.16 | 1.49 |
| NM_007096 | CLTA | Clathrin, light polypeptide (Lca) | 1.96 | 2.01 |
| BC010039 | CLP | Coactosin-like protein | 1.54 | 1.24 |
| NM_016451 | COPB | Coatomer protein complex, subunit beta | 1.82 | 1.79 |
| NM_007263 | COPE | Coatomer protein complex, subunit epsilon | 2.58 | 2.98 |
| NM_004645 | COIL | Coilin | 1.21 | 1.79 |
| AL162070 | CORO1C | Coronin, actin binding protein, 1C | 2.00 | 1.59 |
| NM_000389 | CDKN1A | Cyclin-dependent kinase inhibitor 1A (p21, Cip1) | 4.69 | 1.38 |
| NM_000099 | CST3 | Cystatin C (amyloid angiopathy and cerebral hemorrhage) | 2.11 | 1.54 |
| NM_001554 | CYR61 | Cysteine-rich, angiogenic inducer, 61 | 2.44 | 0.67 |
| NM_007274 | HBACH | Cytosolic acyl coenzyme A thioester hydrolase | 1.61 | 2.28 |
| NM_020189 | DC6 | DC6 protein | 1.64 | 1.73 |
| NM_004396 | DDX5 | DEAD/H (Asp-Glu-Ala-Asp/His) box polypeptide 5 (RNA helicase, 68 kD) | 2.01 | 4.10 |
| NM_001357 | DDX9 | DEAD/H (Asp-Glu-Ala-Asp/His) box polypeptide 9 (RNA helicase A, nuclear DNA helicase II-leukophysin | 1.44 | 1.53 |
| AB040961 | DTX2 | Deltex homolog 2 (*Drosophila*) | 1.76 | 1.62 |
| NM_007326 | DIA1 | Diaphorase (NADH) (cytochrome b-5 reductase) | 1.84 | 2.06 |
| NM_020548 | DBI | Diazepam binding inhibitor (GABA receptor modulator, acyl-Coenzyme A binding protein) | 1.69 | 1.84 |
| NM_013253 | DKK3 | Dickkopf homolog 3 (*Xenopus laevis*) | 1.64 | 0.84 |
| NM_004405 | DLX2 | Distal-less homeo box 2 | 29.27 | 2.13 |
| AL080156 | DKFZP434J214 | DKFZP434J214 protein | 2.97 | 1.43 |
| NM_014045 | DKFZP564C1940 | DKFZP564C1940 protein | 1.79 | 1.73 |
| NM_001539 | DNAJA1 | DnaJ (Hsp40) homolog, subfamily A, member 1 | 2.11 | 1.85 |
| NM_006145 | DNAJB1 | DnaJ (Hsp40) homolog, subfmaily B, member 1 | 4.99 | 1.57 |
| NM_004419 | DUSP5 | Dual specificity phosphatase 5 | 1.97 | 0.47 |
| NM_001946 | DUSP6 | Dual specificity phosphatase 6 | 2.08 | 2.29 |
| NM_014390 | p100 | EBNA-2 co-activator (100 kD) | 2.00 | 1.02 |

TABLE 10-continued

| | | | | |
|---|---|---|---|---|
| NM_005451 | ENIGMA | Enigma (LIM domain protein) | 1.21 | 2.34 |
| NM_004092 | ECHS1 | Enoyl Coenzyme A hydratase, short chain, 1, mitochondrial | 1.60 | 1.23 |
| NM_004431 | EPHA2 | EphA2 | 2.37 | 1.93 |
| NM_016357 | EPLIN | Epithelial protein lost in neoplasm beta | 1.74 | 1.63 |
| BF541376 | | ESTs, Weakly similar to FRHUL ferritin light chain [*H. sapiens*] | 2.71 | 4.50 |
| NM_003757 | EIF3S2 | Eukaryotic translation initiation factor 3, subunit 2 (beta, 36 kD) | 1.83 | 1.47 |
| NM_003755 | EIF3S4 | Eukaryotic translation initiation factor 3, subunit 4 (delta, 44 kD) | 2.12 | 2.40 |
| NM_001417 | EIF4B | Eukaryotic translation initiation factor 4B | 2.33 | 2.41 |
| NM_004095 | EIF4EBP1 | Eukaryotic translation initiation factor 4E binding protein 1 | 1.69 | 1.26 |
| NM_005243 | EWSR1 | Ewing sarcoma breakpoint region 1 | 2.02 | 1.33 |
| NM_005245 | FAT | FAT tumor suppressor homolog 1 (*Drosophila*) | 1.87 | 0.77 |
| NM_004104 | FASN | Fatty acid synthase | 1.24 | 1.60 |
| AK054816 | FTH1 | Ferritin, heavy polypeptide 1 | 2.07 | 3.32 |
| NM_001457 | FLNB | Filamin B, beta (actin binding protein 278) | 1.05 | 1.90 |
| NM_014164 | FXYD5 | FXYD domain-containing ion transport regulator 5 | 1.24 | 1.67 |
| AL365404 | GPR108 | G protein-coupled receptor 108 | 2.00 | 1.17 |
| NM_007278 | GABARAP | GABA(A) receptor-associated protein | 1.55 | 1.75 |
| NM_001520 | GTF3C1 | General transcription factor IIIC, polypeptide 1 (alpha subunit, 220 kD) | 8.72 | 0.41 |
| AK024486 | GLTSCR2 | Glioma tumor suppressor candidate region gene 2 | 2.63 | 1.85 |
| NM_001498 | GCLC | Glutamate-cysteine ligase, catalytic subunit | 8.96 | 1.40 |
| NM_002061 | GCLM | Glutamate-cysteine ligase, modifier subunit | 2.85 | 1.56 |
| NM_004446 | EPRS | Glutamyl-prolyl-tRNA synthetase | 1.76 | 0.73 |
| NM_002064 | GLRX | Glutaredoxin (thioltransferase) | 3.12 | 2.31 |
| NM_002083 | GPX2 | Glutathione peroxidase 2 (gastrointestinal) | 3.71 | 9.99 |
| NM_000637 | GSR | Glutathione reductase | 1.57 | 1.54 |
| NM_002087 | GRN | Granulin | 1.36 | 1.58 |
| L24498 | GADD45A | Growth arrest and DNA-damage-inducible, alpha | 2.81 | 0.61 |
| NM_006644 | HSP105B | Heat shock 105 kD | 2.83 | 1.02 |
| NM_002157 | HSPE1 | Heat shock 10 kD protein 1 (chaperonin 10) | 1.92 | 1.34 |
| NM_005345 | HSPA1A | Heat shock 70 kD protein 1A | 5.77 | 1.30 |
| NM_006597 | HSPA8 | Heat shock 70 kD protein 8 | 1.48 | 4.56 |
| NM_004134 | HSPA9B | Heat shock 70 kD protein 9B (mortalin-2) | 2.23 | 1.39 |
| NM_016292 | TRAP1 | Heat shock protein 75 | 1.57 | 1.05 |
| NM_002133 | HMOX1 | Heme oxygenase (decycling) 1 | 55.83 | 2.81 |
| NM_004712 | HGS | Hepatocyte growth factor-regulated tyrosine kinase substrate | 1.21 | 1.64 |
| NM_001533 | HNRPL | Heterogeneous nuclear ribonucleoprotein L | 1.50 | 0.89 |
| AK057120 | HMG1 | High-mobility group (nonhistone chromosomal) protein 1 | 1.72 | 0.79 |
| AF130111 | HDAC3 | Histone deacetylase 3 | 1.92 | 1.38 |
| NM_001536 | HRMT1L2 | HMT1 hnRNP methyltransferase-like 2 (*S. cerevisiae*) | 1.83 | 1.16 |
| AK023395 | | *Homo sapiens* cDNA FLJ13333 fis, clone OVARC1001828 | 1.82 | 1.39 |
| AK054711 | | *Homo sapiens* cDNA FLJ30149 fis, clone BRACE2000280, weakly similar to MNN4 PROTEIN | 1.57 | 0.76 |
| AK055071 | | *Homo sapiens* cDNA FLJ30509 fis, clone BRAWH2000595 | 1.36 | 1.64 |
| AK056736 | | *Homo sapiens* cDNA FLJ32174 fis, clone PLACE6001064 | 1.18 | 4.26 |
| AK024927 | | *Homo sapiens* cDNA: FLJ21274 fis, clone COL01781 | 1.83 | 0.89 |
| AK055564 | | *Homo sapiens* cDNA: FLJ22182 fis, clone HRC00953 | 1.00 | 1.50 |
| AK026181 | | *Homo sapiens* cDNA: FLJ22528 fis, clone HRC12825 | 4.30 | 1.72 |
| AK026902 | | *Homo sapiens* cDNA: FLJ23249 fis, clone COL04196 | 1.76 | 1.09 |

TABLE 10-continued

| | | | | |
|---|---|---|---|---|
| AL512727 | | Homo sapiens mRNA-cDNA DKFZp547P042 (from clone DKFZp547P042) | 2.01 | 2.48 |
| AL117595 | | Homo sapiens mRNA-cDNA DKFZp564C2063 (from clone DKFZp564C2063) | 2.71 | 1.30 |
| AL050378 | | Homo sapiens mRNA-cDNA DKFZp586I1420 (from clone DKFZp586I1420)-partial cds | 1.37 | 1.70 |
| AF041429 | | Homo sapiens pRGR1 mRNA, partial cds | 1.37 | 1.86 |
| AF118072 | | Homo sapiens PRO1716 mRNA, complete cds | 5.32 | 19.31 |
| AF065241 | | Homo sapiens thioredoxin delta 3 (TXN delta 3) mRNA, partial cds | 1.20 | 1.80 |
| BC010009 | | Homo sapiens, clone IMAGE: 3355383, mRNA, partial cds | 1.49 | 1.93 |
| BC011880 | | Homo sapiens, Similar to hypothetical protein, MGC: 7764, clone MGC: 20548 IMAGE: 3607345, mRNA, comple | 1.07 | 1.65 |
| BC017001 | | Homo sapiens, Similar to RIKEN cDNA 1700127B04 gene, clone IMAGE: 4425440, mRNA, partial cds | 26.36 | 5.69 |
| BC007307 | | Homo sapiens, Similar to zinc finger protein 268, clone IMAGE: 3352268, mRNA, partial cds | 1.89 | 1.59 |
| NM_014029 | HSPC022 | HSPC022 protein | 1.33 | 3.77 |
| NM_014047 | HSPC023 | HSPC023 protein | 1.64 | 1.98 |
| AF161415 | HSPC030 | HSPC030 protein | 4.27 | 1.52 |
| NM_016099 | LOC51125 | HSPC041 protein | 1.46 | 1.08 |
| NM_014168 | HSPC133 | HSPC133 protein | 1.58 | 1.41 |
| NM_014182 | HSPC160 | HSPC160 protein | 1.28 | 2.58 |
| AL139112 | | Human DNA sequence from clone GS1-103B18 on chromosome Xq27.1-27.3 Contains ESTs, STSs and GSSs. Con | 1.88 | 2.68 |
| AL354915 | | Human DNA sequence from clone RP11-392A19 on chromosome 13. Contains ESTs, STSs and GSSs. Contains a | 1.38 | 2.01 |
| NM_000182 | HADHA | Hydroxyacyl-Coenzyme A dehydrogenase/3-ketoacyl-Coenzyme A thiolase/enoyl-Coenzyme A hydratase (trif | 2.39 | 1.22 |
| NM_016404 | HSPC152 | Hypothetical protein | 1.59 | 1.30 |
| NM_016623 | BM-009 | Hypothetical protein | 1.53 | 1.08 |
| NM_015932 | HSPC014 | Hypothetical protein | 1.31 | 1.56 |
| NM_015343 | HSA011916 | Hypothetical protein | 1.79 | 1.22 |
| AF103803 | H41 | Hypothetical protein | 1.63 | 2.00 |
| NM_014886 | YR-29 | Hypothetical protein | 1.53 | 1.44 |
| NM_018437 | EDAG-1 | Hypothetical protein EDAG-1 | 1.46 | 1.94 |
| NM_018306 | FLJ11036 | Hypothetical protein FLJ11036 | 2.07 | 2.12 |
| NM_032813 | FLJ14624 | Hypothetical protein FLJ14624 | 1.80 | 2.88 |
| NM_022842 | FLJ22969 | Hypothetical protein FLJ22969 | 3.39 | 31.88 |
| NM_031207 | HT036 | Hypothetical protein HT036 | 1.26 | 2.55 |
| NM_024508 | MGC10796 | Hypothetical protein MGC10796 | 1.46 | 1.84 |
| AK027859 | MGC11266 | Hypothetical protein MGC11266 | 2.46 | 2.14 |
| NM_032771 | MGC12217 | Hypothetical protein MGC12217 | 1.56 | 1.02 |
| BC014850 | MGC13071 | Hypothetical protein MGC13071 | 1.74 | 1.98 |
| NM_032899 | MGC14128 | Hypothetical protein MGC14128 | 1.15 | 6.78 |
| NM_024040 | MGC2491 | Hypothetical protein MGC2491 | 2.69 | 2.86 |
| NM_024038 | MGC2803 | Hypothetical protein MGC2803 | 1.59 | 1.48 |
| NM_031943 | IFP38 | IFP38 | 2.11 | 1.95 |
| NM_052815 | IER3 | Immediate early response 3 | 2.94 | 1.54 |
| NM_016545 | IER5 | Immediate early response 5 | 9.20 | 1.18 |
| NM_005542 | INSIG1 | Insulin induced gene 1 | 2.02 | 2.62 |
| NM_021999 | ITM2B | Integral membrane protein 2B | 1.84 | 1.06 |
| NM_006147 | IRF6 | Interferon regulatory factor 6 | 2.30 | 1.09 |
| NM_000576 | IL1B | Interleukin 1, beta | 0.98 | 3.03 |
| Z17227 | IL10RB | Interleukin 10 receptor, beta | 1.74 | 1.68 |
| NM_004508 | IDI1 | Isopentenyl-diphosphate delta isomerase | 1.89 | 2.68 |
| NM_005354 | JUND | Jun D proto-oncogene | 1.67 | 1.25 |
| NM_006854 | KDELR2 | KDEL (Lys-Asp-Glu-Leu) endoplasmic reticulum protein retention receptor 2 | 2.03 | 1.42 |

TABLE 10-continued

| | | | | |
|---|---|---|---|---|
| NM_000421 | KRT10 | Keratin 10 (epidermolytic hyperkeratosis-keratosis palmaris et plantaris) | 1.87 | 1.68 |
| NM_000224 | KRT18 | Keratin 18 | 1.22 | 1.81 |
| NM_005555 | KRT6B | Keratin 6B | 1.44 | 2.26 |
| NM_014815 | KIAA0130 | KIAA0130 gene product | 1.31 | 4.73 |
| NM_000899 | KITLG | KIT ligand | 1.35 | 2.21 |
| NM_001730 | KLF5 | Kruppel-like factor 5 (intestinal) | 2.34 | 1.01 |
| NM_003937 | KYNU | Kynureninase (L-kynurenine hydrolase) | 3.31 | 3.29 |
| NM_005558 | LAD1 | Ladinin 1 | 1.44 | 2.29 |
| NM_016201 | LCCP | Leman coiled-coil protein | 1.89 | 1.09 |
| NM_015925 | LISCH7 | Liver-specific bHLH-Zip transcription factor | 1.29 | 1.64 |
| NM_014463 | LSM3 | Lsm3 protein | 1.85 | 1.98 |
| NM_004995 | MMP14 | Matrix metalloproteinase 14 (membrane-inserted) | 2.20 | 2.57 |
| NM_005916 | MCM7 | MCM7 minichromosome maintenance deficient 7 (*S. cerevisiae*) | 1.60 | 1.07 |
| NM_006428 | MAAT1 | Melanoma-associated antigen recognised by cytotoxic T lymphocytes | 1.99 | 1.43 |
| NM_006636 | MTHFD2 | Methylene tetrahydrofolate dehydrogenase (NAD+ dependent), methenyltetrahydrofolate cyclohydrolase | 1.81 | 0.68 |
| NM_004528 | MGST3 | Microsomal glutathione S-transferase 3 | 1.73 | 1.76 |
| NM_022818 | MAP1A/1BLC3 | Microtubule-associated proteins 1A/1B light chain 3 | 2.18 | 0.95 |
| NM_014341 | MTCH1 | Mitochondrial carrier homolog 1 | 1.81 | 1.69 |
| NM_014161 | MRPL18 | Mitochondrial ribosomal protein L18 | 3.58 | 1.63 |
| NM_021134 | MRPL23 | Mitochondrial ribosomal protein L23 | 1.58 | 1.23 |
| NM_017446 | MRPL39 | Mitochondrial ribosomal protein L39 | 1.74 | 1.13 |
| NM_021210 | MUM2 | MUM2 protein | 1.20 | 1.61 |
| NM_004529 | MLLT3 | Myeloid/lymphoid or mixed-lineage leukemia (trithorax homolog, *Drosophila*)-translocated to, 3 | 1.15 | 2.41 |
| NM_033546 | MLC-B | Myosin regulatory light chain | 1.95 | 1.89 |
| AB032945 | MYO5B | Myosin VB | 1.50 | 1.74 |
| NM_017534 | MYH2 | Myosin, heavy polypeptide 2, skeletal muscle, adult | 1.66 | 0.90 |
| NM_002473 | MYH9 | Myosin, heavy polypeptide 9, non-muscle | 1.82 | 2.60 |
| NM_002356 | MARCKS | Myristoylated alanine-rich protein kinase C substrate | 0.22 | 2.70 |
| NM_000903 | NQO1 | NAD(P)H dehydrogenase, quinone 1 | 2.64 | 2.77 |
| NM_004541 | NDUFA1 | NADH dehydrogenase (ubiquinone) 1 alpha subcomplex, 1 (7.5 kD, MWFE) | 1.27 | 1.88 |
| NM_004548 | NDUFB10 | NADH dehydrogenase (ubiquinone) 1 beta subcomplex, 10 (22 kD, PDSW) | 1.63 | 1.29 |
| NM_004547 | NDUFB4 | NADH dehydrogenase (ubiquinone) 1 beta subcomplex, 4 (15 kD, B15) | 1.63 | 2.11 |
| NM_002494 | NDUFC1 | NADH dehydrogenase (ubiquinone) 1, subcomplex unknown, 1 (6 kD, KFYI) | 1.70 | 1.17 |
| NM_014328 | NESCA | Nesca protein | 1.52 | 1.23 |
| BC010285 | NET1 | Neuroepithelial cell transforming gene 1 | 0.78 | 2.28 |
| NM_000271 | NPC1 | Niemann-Pick disease, type C1 | 2.31 | 1.39 |
| NM_006096 | NDRG1 | N-myc downstream regulated gene 1 | 1.50 | 1.95 |
| NM_006164 | NFE2L2 | Nuclear factor (erythroid-derived 2)-like 2 | 3.80 | 1.23 |
| NM_003489 | NRIP1 | Nuclear receptor interacting protein 1 | 0.94 | 1.63 |
| NM_017838 | NOLA2 | Nucleolar protein family A, member 2 (H/ACA small nucleolar RNPs) | 1.83 | 1.94 |
| NM_002820 | PTHLH | Parathyroid hormone-like hormone | 1.66 | 2.59 |
| NM_020992 | PDLIM1 | PDZ and LIM domain 1 (elfin) | 1.56 | 1.60 |
| NM_002574 | PRDX1 | Peroxiredoxin 1 | 1.68 | 1.80 |
| NM_003713 | PPAP2B | Phosphatidic acid phosphatase type 2B | 1.22 | 1.84 |
| NM_002631 | PGD | Phosphogluconate dehydrogenase | 4.37 | 23.25 |
| NM_002632 | PGF | Placental growth factor, vascular endothelial growth factor-related protein | 3.61 | 1.79 |
| NM_002658 | PLAU | Plasminogen activator, urokinase | 1.69 | 1.78 |
| NM_014287 | PM5 | PM5 protein | 1.55 | 1.54 |
| NM_003819 | PABPC4 | Poly(A) binding protein, cytoplasmic 4 (inducible form) | 1.62 | 1.25 |
| NM_000937 | POLR2A | Polymerase (RNA) II (DNA directed) polypeptide A (220 kD) | 1.23 | 1.65 |

TABLE 10-continued

| | | | | |
|---|---|---|---|---|
| NM_001198 | PRDM1 | PR domain containing 1, with ZNF domain | 7.04 | 3.20 |
| NM_002583 | PAWR | PRKC, apoptosis, WT1, regulator | 1.96 | 1.50 |
| NM_000917 | P4HA1 | Procollagen-proline, 2-oxoglutarate 4-dioxygenase (proline 4-hydroxylase), alpha polypeptide I | 1.08 | 1.51 |
| NM_053024 | PFN2 | Profilin 2 | 1.73 | 1.17 |
| AB051437 | ProSAP2 | Proline rich synapse associated protein 2 (rat) | 2.30 | 1.25 |
| NM_002778 | PSAP | Prosaposin (variant Gaucher disease and variant metachromatic leukodystrophy) | 1.70 | 2.72 |
| NM_000963 | PTGS2 | Prostaglandin-endoperoxide synthase 2 (prostaglandin G/H synthase and cyclooxygenase) | 6.51 | 0.98 |
| BC013908 | PSMC1 | Proteasome (prosome, macropain) 26S subunit, ATPase, 1 | 1.68 | 1.13 |
| NM_002806 | PSMC6 | Proteasome (prosome, macropain) 26S subunit, ATPase, 6 | 1.64 | 1.25 |
| NM_002815 | PSMD11 | Proteasome (prosome, macropain) 26S subunit, non-ATPase, 11 | 1.77 | 1.35 |
| NM_002812 | PSMD8 | Proteasome (prosome, macropain) 26S subunit, non-ATPase, 8 | 2.17 | 3.03 |
| NM_002797 | PSMB5 | Proteasome (prosome, macropain) subunit, beta type, 5 | 2.82 | 3.28 |
| NM_002799 | PSMB7 | Proteasome (prosome, macropain) subunit, beta type, 7 | 1.36 | 1.74 |
| NM_014330 | PPP1R15A | Protein phosphatase 1, regulatory (inhibitor) subunit 15A | 7.10 | 0.88 |
| NM_004156 | PPP2CB | Protein phosphatase 2 (formerly 2A), catalytic subunit, beta isoform | 1.67 | 1.11 |
| NM_006808 | SEC61B | Protein translocation complex beta | 1.44 | 1.57 |
| NM_015714 | G0S2 | Putative lymphocyte G0/G1 switch gene | 0.90 | 6.31 |
| BC012513 | ARHE | Ras homolog gene family, member E | 2.39 | 0.99 |
| NM_003979 | RAI3 | Retinoic acid induced 3 | 1.05 | 3.46 |
| NM_001666 | ARHGAP4 | Rho GTPase activating protein 4 | 2.49 | 1.96 |
| NM_001033 | RRM1 | Ribonucleotide reductase M1 polypeptide | 1.54 | 0.87 |
| NM_002950 | RPN1 | Ribophorin I | 2.08 | 1.10 |
| NM_001029 | RPS26 | Ribosomal protein S26 | 1.31 | 1.70 |
| NM_002953 | RPS6KA1 | Ribosomal protein S6 kinase, 90 kD, polypeptide 1 | 1.65 | 2.00 |
| AB037819 | RRBP1 | Ribosome binding protein 1 homolog 180 kD (dog) | 3.68 | 2.68 |
| NM_014248 | RBX1 | Ring-box 1 | 1.30 | 2.13 |
| NM_006743 | RBM3 | RNA binding motif protein 3 | 2.01 | 1.74 |
| NM_004902 | RNPC2 | RNA-binding region (RNP1, RRM) containing 2 | 1.61 | 0.75 |
| NM_000687 | AHCY | S-adenosylhomocysteine hydrolase | 1.74 | 1.82 |
| AB051532 | SEMA4B | Sema domain, immunoglobulin domain (Ig), transmembrane domain (TM) and short cytoplasmic domain, (se | 1.11 | 1.77 |
| NM_003900 | SQSTM1 | Sequestosome 1 | 3.34 | 2.82 |
| NM_001085 | SERPINA3 | Serine (or cysteine) proteinase inhibitor, clade A (alpha-1 antiproteinase, antitrypsin), member 3 | 2.74 | #DIV/0! |
| NM_030666 | SERPINB1 | Serine (or cysteine) proteinase inhibitor, clade B (ovalbumin), member 1 | 3.11 | 2.58 |
| NM_000602 | SERPINE1 | Serine (or cysteine) proteinase inhibitor, clade E (nexin, plasminogen activator inhibitor type 1), | 2.32 | 2.38 |
| NM_015966 | SDBCAG84 | Serologically defined breast cancer antigen 84 | 1.86 | 1.45 |
| NM_006622 | SNK | Serum-inducible kinase | 3.02 | 1.13 |
| AB000462 | SH3BP2 | SH3-domain binding protein 2 | 4.63 | 2.02 |
| NM_003134 | SRP14 | Signal recognition particle 14 kD (homologous Alu RNA binding protein) | 1.58 | 1.45 |
| NM_003145 | SSR2 | Signal sequence receptor, beta (translocon-associated protein beta) | 1.64 | 1.79 |
| NM_007107 | SSR3 | Signal sequence receptor, gamma (translocon-associated protein gamma) | 1.74 | 1.26 |
| AF395440 | HEJ1 | Similar to DNAJ | 2.50 | 1.94 |
| NM_005870 | SAP18 | Sin3-associated polypeptide, 18 kD | 1.50 | 1.21 |
| NM_006109 | SKB1 | SKB1 homolog (S. pombe) | 1.55 | 2.52 |

TABLE 10-continued

| Gene ID | Gene Name | Description | M4/S4 | M24/S24 |
|---|---|---|---|---|
| NM_015523 | DKFZP566E144 | Small fragment nuclease | 2.04 | 1.55 |
| NM_030981 | RAB1B | Small GTP-binding protein | 1.53 | 1.16 |
| NM_006518 | SPRR2C | Small proline-rich protein 2C | 1.41 | 4.09 |
| NM_005628 | SLC1A5 | Solute carrier family 1 (neutral amino acid transporter), member 5 | 1.87 | 0.82 |
| NM_004207 | SLC16A3 | Solute carrier family 16 (monocarboxylic acid transporters), member 3 | 1.56 | 2.65 |
| NM_018976 | SLC38A2 | Solute carrier family 38, member 2 | 2.48 | 0.85 |
| NM_014331 | SLC7A11 | Solute carrier family 7, (cationic amino acid transporter, y+ system) member 11 | 2.40 | 0.73 |
| NM_003130 | SRI | Sorcin | 0.92 | 1.80 |
| NM_004599 | SREBF2 | Sterol regulatory element binding transcription factor 2 | 1.47 | 1.03 |
| NM_006745 | SC4MOL | Sterol-C4-methyl oxidase-like | 1.68 | 1.82 |
| NM_006918 | SC5DL | Sterol-C5-desaturase (ERG3 delta-5-desaturase homolog, fungal)-like | 1.59 | 1.11 |
| NM_006819 | STIP1 | Stress-induced-phosphoprotein 1 (Hsp70/Hsp90-organizing protein) | 2.88 | 2.34 |
| NM_006704 | SGT1 | Suppressor of G2 allele of SKP1, S. cerevisiae, homolog of | 1.81 | 1.32 |
| NM_002999 | SDC4 | Syndecan 4 (amphiglycan, ryudocan) | 1.21 | 1.71 |
| NM_006289 | TLN1 | Talin 1 | 1.53 | 1.59 |
| NM_015641 | TES | Testis derived transcript (3 LIM domains) | 2.10 | 0.95 |
| NM_003217 | TEGT | Testis enhanced gene transcript (BAX inhibitor 1) | 1.71 | 1.28 |
| NM_003314 | TTC1 | Tetratricopeptide repeat domain 1 | 1.68 | 2.06 |
| NM_003329 | TXN | Thioredoxin | 1.39 | 2.24 |
| NM_003330 | TXNRD1 | Thioredoxin reductase 1 | 7.66 | 2.72 |
| NM_004238 | TRIP12 | Thyroid hormone receptor interactor 12 | 1.73 | 1.43 |
| NM_006755 | TALDO1 | Transaldolase 1 | 1.96 | 1.72 |
| NM_003234 | TFRC | Transferrin receptor (p90, CD71) | 1.51 | 3.15 |
| NM_001064 | TKT | Transketolase (Wernicke-Korsakoff syndrome) | 1.60 | 1.44 |
| NM_012459 | TIMM8B | Translocase of inner mitochondrial membrane 8 homolog B (yeast) | 1.32 | 1.57 |
| NM_006470 | TRIM16 | Tripartite motif-containing 16 | 1.57 | 1.53 |
| NM_003449 | TRIM26 | Tripartite motif-containing 26 | 1.39 | 2.55 |
| NM_003289 | TPM2 | Tropomyosin 2 (beta) | 2.13 | 1.79 |
| NM_003404 | YWHAB | Tyrosine 3-monooxygenase/tryptophan 5-monooxygenase activation protein, beta polypeptide | 2.06 | 3.12 |
| NM_012321 | LSM4 | U6 snRNA-associated Sm-like protein | 1.61 | 0.95 |
| M26880 | UBC | Ubiquitin C | 1.73 | 1.07 |
| NM_014501 | E2-EPF | Ubiquitin carrier protein | 1.83 | 1.41 |
| NM_003334 | UBE1 | Ubiquitin-activating enzyme E1 (A1S9T and BN75 temperature sensitivity complementing) | 1.91 | 1.67 |
| AL110132 | UBE2V1 | Ubiquitin-conjugating enzyme E2 variant 1 | 1.80 | 1.66 |
| BC007657 | UBE2M | Ubiquitin-conjugating enzyme E2M (UBC12 homolog, yeast) | 1.58 | 1.80 |
| NM_003364 | UP | Uridine phosphorylase | 2.48 | 1.13 |
| NM_003574 | VAPA | VAMP (vesicle-associated membrane protein)-associated protein A (33 kD) | 1.85 | 1.71 |
| NM_012323 | MAFF | V-maf musculoaponeurotic fibrosarcoma oncogene homolog F (avian) | 1.71 | 0.72 |
| NM_002359 | MAFG | V-maf musculoaponeurotic fibrosarcoma oncogene homolog G (avian) | 1.85 | 1.41 |
| NM_002467 | MYC | V-myc myelocytomatosis viral oncogene homolog (avian) | 2.75 | 1.98 |
| NM_006007 | ZNF216 | Zinc finger protein 216 | 2.01 | 1.29 |
| NM_013360 | ZNF222 | Zinc finger protein 222 | 2.26 | 1.86 |
| NM_004234 | ZFP93 | Zinc finger protein 93 homolog (mouse) | 0.75 | 1.64 |

| Genes Downregulated by Cigarette Smoke | | | | |
|---|---|---|---|---|
| Gene ID | Gene Name | Description | M4/S4 | M24/S24 |
| NM_006856 | ATF7 | activating transcription factor 7 | 0.81 | 2.32 |
| NM_001143 | AMELY | amelogenin, Y-linked | 1.61 | 1.03 |

TABLE 10-continued

| | | | | |
|---|---|---|---|---|
| NM_001657 | AREG | amphiregulin (schwannoma-derived growth factor) | 0.50 | 2.95 |
| AB053314 | ALS2CR12 | amyotrophic lateral sclerosis 2 (juvenile) chromosome region, candidate 12 | 2.01 | 1.12 |
| AK023086 | | CDNA FLJ13024 fis, clone NT2RP3000865 | 1.56 | 1.05 |
| BI820294 | | CDNA FLJ26296 fis, clone DMC07192, highly similar to Ig kappa chain V-III region HAH precursor | 1.69 | 0.89 |
| AK025253 | | CDNA FLJ42432 fis, clone BLADE2006412 | 2.15 | 1.70 |
| NM_001271 | CHD2 | chromodomain helicase DNA binding protein 2 | 1.10 | 1.62 |
| NM_006589 | C1orf2 | chromosome 1 open reading frame 2 | 1.56 | 0.87 |
| AK000796 | C14orf129 | chromosome 14 open reading frame 129 | 0.79 | 1.80 |
| NM_001934 | DLX4 | distal-less homeobox 4 | 1.29 | 2.08 |
| NM_005509 | DMXL1 | Dmx-like 1 | 2.05 | 1.22 |
| NM_004419 | DUSP5 | dual specificity phosphatase 5 | 0.45 | 2.37 |
| NM_003494 | DYSF | dysferlin, limb girdle muscular dystrophy 2B (autosomal recessive) | 1.19 | 2.31 |
| NM_000145 | FSHR | follicle stimulating hormone receptor | 1.58 | 1.29 |
| NM_005708 | GPC6 | glypican 6 | 1.78 | 1.51 |
| NM_002053 | GBP1 | guanylate binding protein 1, interferon-inducible, 67 kDa | 1.31 | 1.58 |
| AB033063 | HEG | HEG homolog | 0.88 | 1.97 |
| NM_002129 | HMGB2 | high-mobility group box 2 | 0.69 | 2.78 |
| NM_003542 | HIST1H4F | histone 1, H4f | 1.57 | 1.92 |
| NM_024598 | FLJ13154 | hypothetical protein FLJ13154 | 0.81 | 1.67 |
| NM_017933 | FLJ20701 | hypothetical protein FLJ20701 | 1.37 | 2.03 |
| NM_024037 | MGC2603 | hypothetical protein MGC2603 | 1.59 | 0.74 |
| BC016840 | MGC34695 | hypothetical protein MGC34695 | 0.99 | 2.33 |
| AK027858 | MGC4248 | hypothetical protein MGC4248 | 1.53 | 0.92 |
| NM_006903 | PPA2 | inorganic pyrophosphatase 2 | 0.63 | 1.64 |
| NM_000526 | KRT14 | keratin 14 (epidermolysis bullosa simplex, Dowling-Meara, Koebner) | 1.09 | 2.13 |
| NM_000424 | KRT5 | keratin 5 (epidermolysis bullosa simplex, Dowling-Meara/Kobner/Weber-Cockayne types) | 1.48 | 1.86 |
| NM_005554 | KRT6A | keratin 6A | 1.53 | 1.17 |
| NM_005556 | KRT7 | keratin 7 | 1.54 | 1.06 |
| AK024583 | | LOC400078 (LOC387888), mRNA | 1.60 | 1.19 |
| NM_005583 | LYL1 | lymphoblastic leukemia derived sequence 1 | 1.73 | 1.17 |
| AL137524 | | MRNA* cDNA DKFZp434H2218 (from clone DKFZp434H2218) | 1.03 | 1.67 |
| AL117623 | | MRNA* cDNA DKFZp564O2364 (from clone DKFZp564O2364) | 1.72 | 1.02 |
| NM_012334 | MYO10 | myosin X | 2.08 | 1.13 |
| AB007959 | NHLH2 | nescient helix loop helix 2 | 1.08 | 1.53 |
| NM_002520 | NPM1 | nucleophosmin (nucleolar phosphoprotein B23, numatrin) | 1.62 | 1.67 |
| NM_033014 | OGN | osteoglycin (osteoinductive factor, mimecan) | 1.21 | 1.62 |
| NM_024594 | PANK3 | pantothenate kinase 3 | 1.88 | 1.42 |
| AB029015 | PLCL2 | Phospholipase C-like 2 | 5.45 | 2.99 |
| NM_018049 | PLEKHJ1 | pleckstrin homology domain containing, family J member 1 | 2.48 | 1.68 |
| BC015542 | PVR | poliovirus receptor | 1.54 | 0.98 |
| NM_018936 | PCDHB2 | protocadherin beta 2 | 1.64 | 1.02 |
| NM_000320 | QDPR | quinoid dihydropteridine reductase | 1.24 | 1.81 |
| NM_000456 | RAB5B | RAB5B, member RAS oncogene family | 2.56 | 2.22 |
| NM_007273 | REA | repressor of estrogen receptor activity | 0.83 | 1.51 |
| NM_005978 | S100A2 | S100 calcium binding protein A2 | 1.89 | 1.55 |
| NM_016372 | TPRA40 | seven transmembrane domain orphan receptor | 1.57 | 0.84 |
| NM_006456 | SIAT7B | sialyltransferase 7 ((alpha-N-acetylneuraminyl-2,3-beta-galactosyl-1,3)-N-acetyl galactosaminide alpha-2,6-sialyltransferase) B | 0.77 | 2.21 |
| NM_024624 | SMC6L1 | SMC6 structural maintenance of chromosomes 6-like 1 (yeast) | 1.74 | 1.71 |
| AL353933 | SLC22A15 | solute carrier family 22 (organic cation transporter), member 15 | 1.85 | 1.07 |

TABLE 10-continued

| | | | | |
|---|---|---|---|---|
| AK027663 | STC2 | stanniocalcin 2 | 0.77 | 1.74 |
| AK024451 | DKFZp762C186 | Tangerine | 1.56 | 1.30 |
| NM_005480 | TROAP | trophinin associated protein (tastin) | 1.77 | 1.12 |
| NM_002466 | MYBL2 | v-myb myeloblastosis viral oncogene homolog (avian)-like 2 | 1.01 | 1.63 |
| NM_006385 | ZNF211 | zinc finger protein 211 | 1.96 | 1.22 |
| NM_005096 | ZNF261 | zinc finger protein 261 | 1.68 | 1.53 |
| NM_003430 | ZNF91 | zinc finger protein 91 (HPF7, HTF10) | 1.47 | 1.53 |
| AC006033 | | | 1.52 | 1.21 |
| AF111848 | | | 1.68 | 1.27 |
| AK025272 | | | 8.36 | 4.55 |
| AL137077 | | | 2.59 | 1.28 |
| L24498 | | | 0.31 | 1.58 |
| NM_003590 | | | 2.06 | 1.03 |
| NM_005774 | | | 1.72 | 1.29 |
| NM_014111 | | | 1.53 | 2.49 |

Figure 9A:
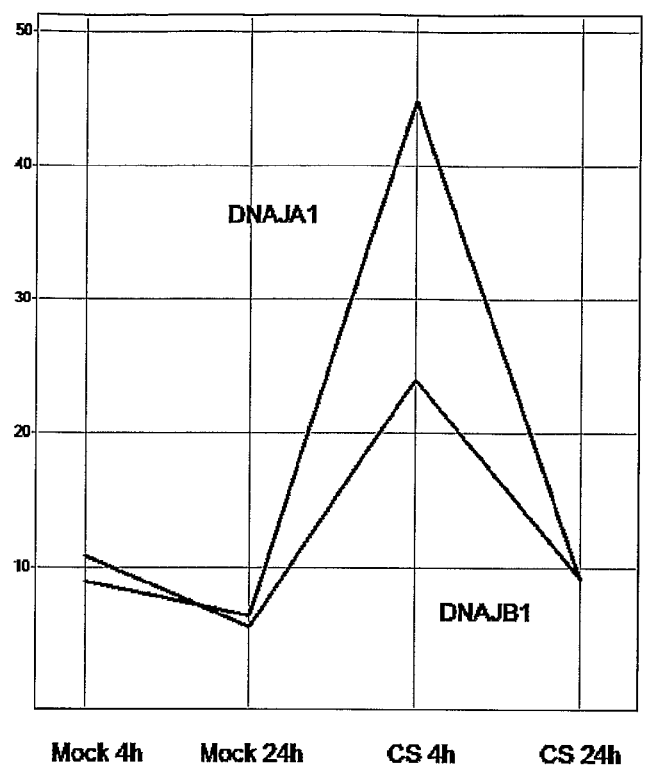
FIGS. 9A and 9B show a comparison of expression behavior of heat shock protein family members DNAJA1 and DNAJB1 in Experiment 1 (FIG. 9A) and 2 (FIG. 9B). Each time point represents the average of 2 or 3 replicates per condition.
Figure 9B:
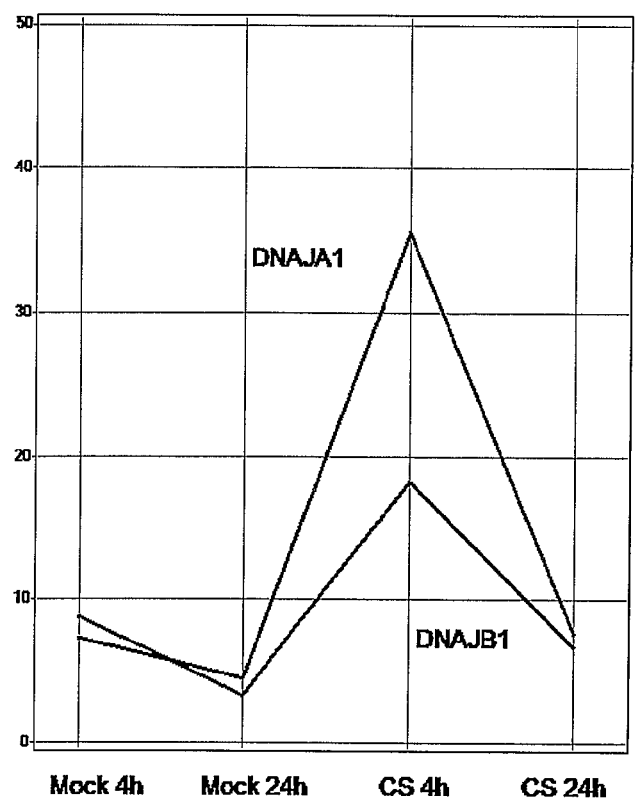

A typical example is shown in FIG. 9, which compares the expression of the heat shock genes DnaJ (HSP40) A1/B1 at 4 and 24 h in mock-treated and CS-treated cells in both experiments. The figure shows not only a consistent temporal relationship in the two experiments with both genes being up-regulated by 4 hrs and then returning to baseline by 24 hrs, but also that there is a consistent relative level of expression between the two genes (i.e., 4 hr expression levels of B1 exceed that of A1 in both experiments).

Confirmation of Differential Expression by QRTPCR

The relative expression levels of 6 genes that were determined by microarray analysis to be up-regulated in CS-treated NHBE cells were reassessed by quantitative PCR using RNA from samples taken at both 4 and 24 hr. This gene set included: ferritin heavy polypeptide, heat shock protein 70, heme oxygenase, thioredoxin reductase, cyclooxygenase 2, and sequestosome 1. It was determined that beta-actin expression levels in the normalized microarray data were nearly identical among all the CS and mock-treated samples, so this gene was used as an internal normalization standard in these experiments. Quantitative PCR results were in strong qualitative agreement with the microarray results, as all 6 genes were also up-regulated by CS when assessed by QRT-PCR. Moreover, the QRTPCR results recapitulated the general trends of expression at both 4 and 24 hr that were observed by microarray (TABLE 11).

TABLE 11

| | Microarray data | | | |
|---|---|---|---|---|
| Gene I | microarray 4 hr/fold change | Qpcr 4 hr/fold change | microarray 24 hr/fold change | qPCR 24 hr/fold change |
| FTH1 | 2.3 | 2.6 | 3.4 | 3.5 |
| HSPA1A | 16.1 | 25.1 | 2.4 | 5.0 |
| TXNRD1 | 11.4 | 16.0 | 3.2 | 2.0 |
| HMOX1 | 42.5 | 77.6 | 1.7 | 4.7 |
| PTGS2 | 5.4 | 17.0 | 0 | 0 |
| SQSTM1 | 3.9 | 7.7 | 2.6 | 3.3 |

Since the wide range of gases, toxins, free radicals, and carcinogens present in tobacco smoke are believed to cause multiple types of structural and chemical damage, the NHBE cells that are exposed to tobacco smoke would presumably have to mount an integrated biological and genetic response in an attempt to prioritize and attenuate this damage. In an effort to understand the type of response mounted by the NHBE cells after cigarette smoke exposure, several databases were analyzed and genes that were identified as being over-expressed or under-expressed in response to exposure to cigarette smoke were grouped according to functional similarities. The following example describes this effort in greater detail.

EXAMPLE 10

Functional Grouping of Genes Modulated in Response to CS Exposure

Information from the Gene Ontology (GO) Consortium and from the scientific literature was used to categorize the genes identified as being modulated (i.e., over-expressed or under-expressed) in response to cigarette smoke exposure. Of the genes up-regulated by CS exposure that have known functions (235 out of 298 genes), four major groups of functionally related genes were identified (Table 5). These four groups collectively represent a large proportion (45%; 105 out of 235 genes) of the differentially expressed genes with known function, indicating that these genes are involved in biological pathways that are highly responsive to CS-induced damage. In contrast, although 42 of the 66 genes that were under-expressed in response to CS have known functions, they reflected multiple biological processes without a clear dominance of specific function. As can be seen in Table 5, the predominant pathways highlighted by the over-expressed gene set indicate that the cell is responding to a sudden increase in oxidative stress and the concentration of misfolded or damaged proteins, while simultaneously attempting to modulate its cell cycle and apoptotic controls. Unexpectedly, it was also observed that a proportionally large group of CS-responsive genes are related to the metabolism and cellular trafficking of cholesterol.

TABLE 12

| Gene ID | Symbol | Description | Fold Increase at 4 h | Fold Increase at 24 h |
|---|---|---|---|---|
| | | RESPONSE TO OXIDATIVE STRESS | | |
| BF541376 | FTL | ESTs, Weakly similar to FRHUL ferritin light chain [*H. sapiens*] | 2.71 | 4.50 |
| AK054816 | FTH1 | Ferritin, heavy polypeptide 1 | 2.07 | 3.32 |
| NM_001498 | GCLC | Glutamate-cysteine ligase, catalytic subunit | 8.96 | 1.40 |
| NM_002061 | GCLM | Glutamate-cysteine ligase, modifier subunit | 2.85 | 1.56 |
| NM_002064 | GLRX | Glutaredoxin (thioltransferase) | 3.12 | 2.31 |
| NM_002083 | GPX2 | Glutathione peroxidase 2 (gastrointestinal) | 3.71 | 9.99 |
| NM_000637 | GSR | Glutathione reductase | 1.57 | 1.54 |
| NM_002133 | HMOX1 | Heme oxygenase (decycling) 1 | 55.83 | 2.81 |
| NM_005354 | JUND | Jun D proto-oncogene | 1.67 | 1.25 |
| NM_004528 | MGST3 | Microsomal glutathione S-transferase 3 | 1.73 | 1.76 |
| NM_000903 | NQO1 | NAD(P)H dehydrogenase, quinone 1 | 2.64 | 2.77 |
| NM_006096 | NDRG1 | N-myc downstream regulated gene 1 | 1.50 | 1.95 |
| NM_006164 | NFE2L2 | Nuclear factor (erythroid-derived 2)-like 2 | 3.80 | 1.23 |
| NM_020992 | PDLIM1 | PDZ and LIM domain 1 (elfin) | 1.56 | 1.60 |
| NM_002574 | PRDX1 | Peroxiredoxin 1 | 1.68 | 1.80 |
| NM_000687 | AHCY | S-adenosylhomocysteine hydrolase | 1.74 | 1.82 |
| NM_003329 | TXN | Thioredoxin | 1.39 | 2.24 |
| NM_003330 | TXNRD1 | Thioredoxin reductase 1 | 7.66 | 2.72 |
| NM_012323 | MAFF | V-maf musculoaponeurotic fibrosarcoma oncogene homolog F (avian) | 1.71 | 0.72 |
| NM_002359 | MAFG | V-maf musculoaponeurotic fibrosarcoma oncogene homolog G (avian) | 1.85 | 1.41 |
| | | CELL GROWTH/PROLIFERATION/APOPTOSIS | | |
| NM_001657 | AREG | Amphiregulin (schwannoma-derived growth factor) | 1.96 | 0.33 |
| NM_016085 | APR-3 | Apoptosis related protein APR-3 | 1.44 | 0.84 |
| NM_017900 | AKIP | aurora-A kinase interacting protein | 2.07 | 5.18 |
| NM_001196 | BID | BH3 interacting domain death agonist | 1.54 | 1.05 |
| NM_005186 | CAPN1 | Calpain 1, (mu/l) large subunit | 1.62 | 1.11 |
| NM_013376 | SEI1 | CDK4-binding protein p34SEI1 | 2.46 | 1.87 |
| NM_015965 | GRIM19 | Cell death-regulatory protein GRIM19 | 2.16 | 2.23 |
| NM_001554 | CYR61 | Cysteine-rich, angiogenic inducer, 61 | 2.44 | 0.67 |
| NM_004396 | DDX5 | DEAD/H (Asp-Glu-Ala-Asp/His) box polypeptide 5 (RNA helicase, 68 kD) | 2.01 | 4.10 |
| NM_013253 | DKK3 | Dickkopf homolog 3 (*Xenopus laevis*) | 1.64 | 0.84 |
| NM_004419 | DUSP5 | Dual specificity phosphatase 5 | 1.97 | 0.47 |
| NM_001946 | DUSP6 | Dual specificity phosphatase 6 | 2.08 | 2.29 |
| NM_004431 | EPHA2 | EphA2 | 2.37 | 1.93 |
| NM_005245 | FAT | FAT tumor suppressor homolog 1 (*Drosophila*) | 1.87 | 0.77 |
| NM_002087 | GRN | Granulin | 1.36 | 1.58 |
| L24498 | GADD45A | Growth arrest and DNA-damage-inducible, alpha | 2.81 | 0.61 |
| AF130111 | HDAC3 | Histone deacetylase 3 | 1.92 | 1.38 |
| AF103803 | H41 | Hypothetical protein | 1.63 | 2.00 |
| NM_052815 | IER3 | Immediate early response 3 | 2.94 | 1.54 |
| NM_016545 | IER5 | Immediate early response 5 | 9.20 | 1.18 |
| NM_000576 | IL1B | Interleukin 1, beta | 0.98 | 3.03 |
| NM_001730 | KLF5 | Kruppel-like factor 5 (intestinal) | 2.34 | 1.01 |
| NM_004529 | MLLT3 | Myeloid/lymphoid or mixed-lineage leukemia (trithorax homolog, *Drosophila*)-translocated to, 3 | 1.15 | 2.41 |
| NM_002632 | PGF | Placental growth factor, vascular endothelial growth factor-related protein | 3.61 | 1.79 |
| NM_002658 | PLAU | Plasminogen activator, urokinase | 1.69 | 1.78 |
| NM_001198 | PRDM1 | PR domain containing 1, with ZNF domain | 7.04 | 3.20 |
| NM_002583 | PAWR | PRKC, apoptosis, WT1, regulator | 1.96 | 1.50 |
| NM_014330 | PPP1R15A | Protein phosphatase 1, regulatory (inhibitor) subunit 15A | 7.10 | 0.88 |
| NM_015714 | G0S2 | Putative lymphocyte G0/G1 switch gene | 0.90 | 6.31 |
| NM_001666 | ARHGAP4 | Rho GTPase activating protein 4 | 2.49 | 1.96 |
| NM_006622 | SNK | Serum-inducible kinase | 3.02 | 1.13 |
| NM_006109 | SKB1 | SKB1 homolog (*S. pombe*) | 1.55 | 2.52 |
| NM_006704 | SGT1 | Suppressor of G2 allele of SKP1, *S. cerevisiae*, homolog of | 1.81 | 1.32 |

TABLE 12-continued

| Gene ID | Symbol | Description | Fold Increase at 4 h | Fold Increase at 24 h |
|---|---|---|---|---|
| NM_003217 | TEGT | Testis enhanced gene transcript (BAX inhibitor 1) | 1.71 | 1.28 |
| NM_002467 | MYC | V-myc myelocytomatosis viral oncogene homolog (avian) | 2.75 | 1.98 |
| UBIQUITINATION/PROTEIN TURNOVER/HEAT SHOCK | | | | |
| NM_001109 | ADAM8 | A disintegrin and metalloproteinase domain 8 | 1.17 | 2.72 |
| NM_004281 | BAG3 | BCL2-associated athanogene 3 | 3.85 | 1.58 |
| BC002971 | CCT5 | Chaperonin containing TCP1, subunit 5 (epsilon) | 1.81 | 1.74 |
| NM_006429 | CCT7 | Chaperonin containing TCP1, subunit 7 (eta) | 2.85 | 3.21 |
| NM_007278 | GABARAP | GABA(A) receptor-associated protein | 1.55 | 1.75 |
| NM_001539 | DNAJA1 | DnaJ (Hsp40) homolog, subfamily A, member 1 | 2.11 | 1.85 |
| NM_006145 | DNAJB1 | DnaJ (Hsp40) homolog, subfmaily B, member 1 | 4.99 | 1.57 |
| AF395440 | HEJ1 | Similar to DNAJ | 2.50 | 1.94 |
| NM_006644 | HSP105B | Heat shock 105 kD | 2.83 | 1.02 |
| NM_002157 | HSPE1 | Heat shock 10 kD protein 1 (chaperonin 10) | 1.92 | 1.34 |
| NM_005345 | HSPA1A | Heat shock 70 kD protein 1A | 5.77 | 1.30 |
| NM_006597 | HSPA8 | Heat shock 70 kD protein 8 | 1.48 | 4.56 |
| NM_004134 | HSPA9B | Heat shock 70 kD protein 9B (mortalin-2) | 2.23 | 1.39 |
| NM_016292 | TRAP1 | Heat shock protein 75 | 1.57 | 1.05 |
| NM_006819 | STIP1 | Stress-induced-phosphoprotein 1 (Hsp70/Hsp90-organizing protein) | 2.88 | 2.34 |
| NM_004995 | MMP14 | Matrix metalloproteinase 14 (membrane-inserted) | 2.20 | 2.57 |
| BC013908 | PSMC1 | Proteasome (prosome, macropain) 26S subunit, ATPase, 1 | 1.68 | 1.13 |
| NM_002806 | PSMC6 | Proteasome (prosome, macropain) 26S subunit, ATPase, 6 | 1.64 | 1.25 |
| NM_002815 | PSMD11 | Proteasome (prosome, macropain) 26S subunit, non-ATPase, 11 | 1.77 | 1.35 |
| NM_002812 | PSMD8 | Proteasome (prosome, macropain) 26S subunit, non-ATPase, 8 | 2.17 | 3.03 |
| NM_002797 | PSMB5 | Proteasome (prosome, macropain) subunit, beta type, 5 | 2.82 | 3.28 |
| NM_002799 | PSMB7 | Proteasome (prosome, macropain) subunit, beta type, 7 | 1.36 | 1.74 |
| NM_006808 | SEC61B | Protein translocation complex beta | 1.44 | 1.57 |
| NM_014248 | RBX1 | Ring-box 1 | 1.30 | 2.13 |
| NM_003900 | SQSTM1 | Sequestosome 1 | 3.34 | 2.82 |
| NM_003134 | SRP14 | Signal recognition particle 14 kD (homologous Alu RNA binding protein) | 1.58 | 1.45 |
| NM_003314 | TTC1 | Tetratricopeptide repeat domain 1 | 1.68 | 2.06 |
| NM_004238 | TRIP12 | Thyroid hormone receptor interactor 12 | 1.73 | 1.43 |
| M26880 | UBC | Ubiquitin C | 1.73 | 1.07 |
| NM_014501 | E2-EPF | Ubiquitin carrier protein | 1.83 | 1.41 |
| NM_003334 | UBE1 | Ubiquitin-activating enzyme E1 (A1S9T and BN75 temperature sensitivity complementing) | 1.91 | 1.67 |
| AL110132 | UBE2V1 | Ubiquitin-conjugating enzyme E2 variant 1 | 1.80 | 1.66 |
| BC007657 | UBE2M | Ubiquitin-conjugating enzyme E2M (UBC12 homolog, yeast) | 1.58 | 1.80 |
| NM_000859 | HMGCR | 3-hydroxy-3-methylglutaryl-Coenzyme A reductase | 2.25 | 1.33 |
| AK025736 | HMGCS1 | 3-hydroxy-3-methylglutaryl-Coenzyme A synthase 1 (soluble) | 1.02 | 1.63 |
| CHOLESTEROL/LIPID METABOLISM | | | | |
| NM_005891 | ACAT2 | Acetyl-Coenzyme A acetyltransferase 2 (acetoacetyl Coenzyme A thiolase) | 1.44 | 1.77 |
| NM_000700 | ANXA1 | Annexin A1 | 1.39 | 1.82 |
| NM_007274 | HBACH | Cytosolic acyl coenzyme A thioester hydrolase | 1.61 | 2.28 |
| NM_020548 | DBI | Diazepam binding inhibitor (GABA receptor modulator, acyl-Coenzyme A binding protein) | 1.69 | 1.84 |
| NM_004092 | ECHS1 | Enoyl Coenzyme A hydratase, short chain, 1, mitochondrial | 1.60 | 1.23 |

TABLE 12-continued

| Gene ID | Symbol | Description | Fold Increase at 4 h | Fold Increase at 24 h |
|---|---|---|---|---|
| NM_004104 | FASN | Fatty acid synthase | 1.24 | 1.60 |
| NM_000182 | HADHA | Hydroxyacyl-Coenzyme A dehydrogenase/3-ketoacyl-Coenzyme A thiolase/enoyl-Coenzyme A hydratase | 2.39 | 1.22 |
| NM_005542 | INSIG1 | Insulin induced gene 1 | 2.02 | 2.62 |
| NM_004508 | IDI1 | Isopentenyl-diphosphate delta isomerase | 1.89 | 2.68 |
| NM_000271 | NPC1 | Niemann-Pick disease, type C1 | 2.31 | 1.39 |
| NM_003713 | PPAP2B | Phosphatidic acid phosphatase type 2B | 1.22 | 1.84 |
| NM_002778 | PSAP | Prosaposin (variant Gaucher disease and variant metachromatic leukodystrophy) | 1.70 | 2.72 |
| NM_004599 | SREBF2 | Sterol regulatory element binding transcription factor 2 | 1.47 | 1.03 |
| NM_006745 | SC4MOL | Sterol-C4-methyl oxidase-like | 1.68 | 1.82 |
| NM_006918 | SC5DL | Sterol-C5-desaturase (ERG3 delta-5-desaturase homolog, fungal)-like | 1.59 | 1.11 |

Figure 10:
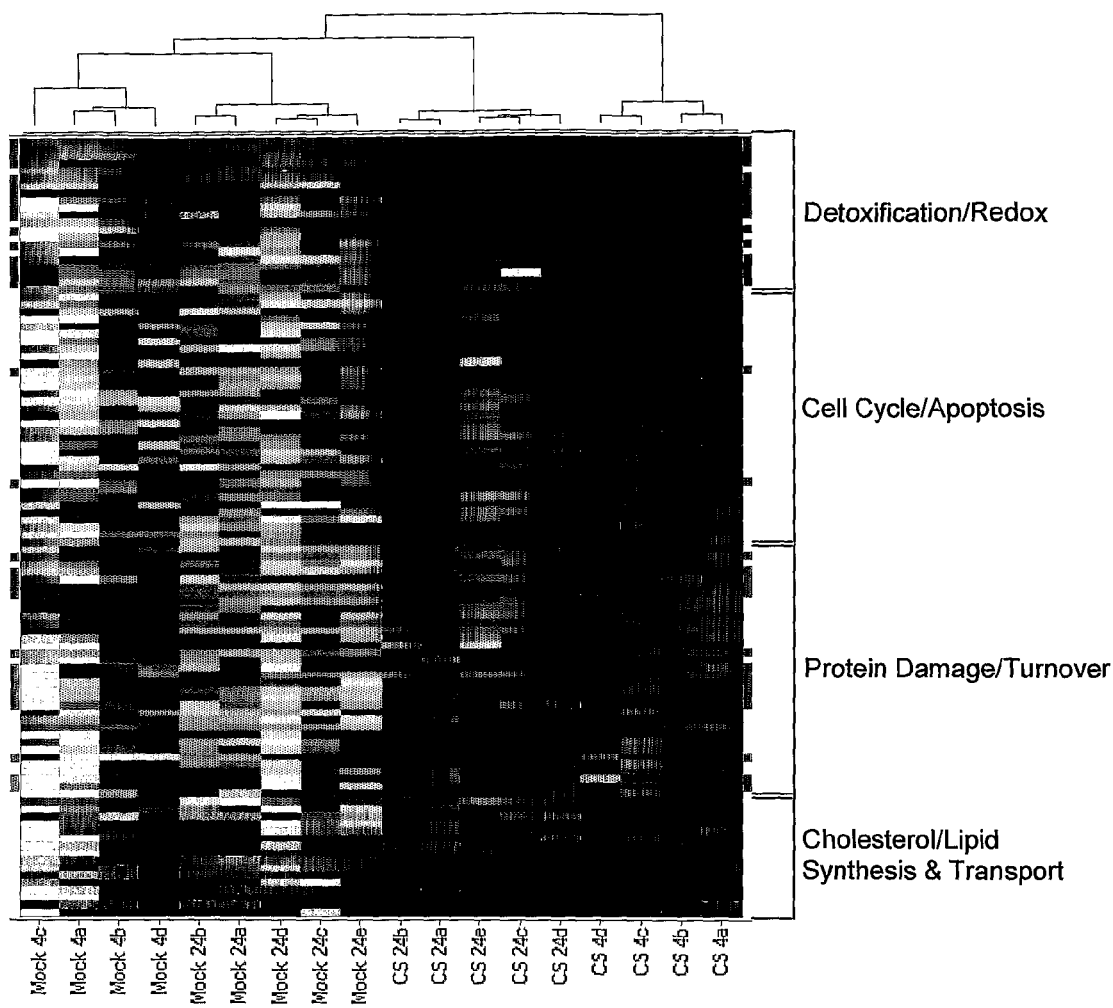
FIG. 10 is a hierarchical clustering of samples using 105 genes that were both over-expressed upon treatment of NHBE cells with CS in two separate experiments, and encoded protein products that modulate one of the 4 major CS-affected GO-defined cellular functions identified. Samples a-b are from Experiment 1, samples c-e are from Experiment 2. A bar indicates heat shock and heat shock-associated genes showing greatly increased expression exclusively at 4 h. Markings indicate genes whose expression is known to be regulated by transcription factor NRF2.

In order to visualize any underlying temporal expression patterns among these four functional classes a hierarchical clustering of the genes was made (see FIG. 10). This cluster analysis of the expression data shows two important points: 1) that the four conditions (4 & 24 h mock-treated and 4 & 24 h CS-treated) are clearly distinguishable by these functional groups of genes; and 2) that the expression of the specific genes in the four functional groups do not have strong temporal relationships (i.e. they do not overwhelmingly cluster within either the 0-4 hours or 4-24 hour time frame). However, it is clear from FIG. 10 that the majority of the CS-responsive genes in these functional groups exhibit a higher expression at 4 h post-exposure than at 24 h. Since the cells were treated for only 15 minutes and then analyzed for a change in gene expression after 4 and 24 hrs, the decrease in expression for many of these genes by 24 hrs indicates that the cell is attempting to "reset" its transcriptome to pre-exposure levels, which would not be an unexpected response to a transient insult. However, the fact that the expression of many of these genes remains increased over pre-exposure levels for up to 24 hrs also indicates that the biological ramifications of CS-exposure can affect the cell for a long period of time after exposure to tobacco smoke is terminated. Accordingly, it is plausible that many of these genes may not return to homeostatic baseline in a habitual smoker, which may have unforeseen pathological consequences.

A notable exception to most of the genes shown in FIG. 10 and TABLE 12, whose expression remain elevated up to 24 hrs post-exposure, is a large block of genes in the protein damage/turnover group, and which encode primarily heat shock and heat shock-associated proteins. The expression of these heat shock related genes is dramatically elevated at 4 hrs but returns to baseline by 24 hrs, indicating that the processes that engage and clear a buildup of CS-induced damaged and dysfunctional proteins are rapid. Finally, there are a small subset of genes whose expression levels are higher at 24 h than at 4 h, including ferritin, NADH dehydrogenase, peroxiredoxin 1, and glutathione peroxidase. Since each of these genes is involved in redox reactions, it could signify that oxidative stress caused by CS induces long-lived perturbations to redox homeostasis.

The four major functional groups of genes listed in TABLE 12 and shown in FIG. 10 show a well-organized attempt by the NHBE cell to attenuate the damage caused by exposure to tobacco smoke. This type of coordinated response provides evidence that functionally related blocks of genes are transcriptionally regulated by the same or similar transcriptional activators. In the full set of 298 genes up-regulated by CS (see TABLE 10), there are 21 genes with gene products that function as transcriptional regulators, including v-myc, interferon regulatory factor 6, eukaryotic translation initiation factor 4B, Kruppel-like factor 5, sterol regulatory element binding transcription factor 2 (SREB2), and Nuclear factor (erythroid-derived 2)-like 2 (NRF2). NRF2 is of particular interest in this regard since studies of NRF2-knockout mice show that this transcription factor activates over 200 genes in several functional classes with the two most predominant being oxidative stress response and protein turnover. As shown in TABLE 12, both of these classes of genes are disproportionately activated by exposure of NHBE cells to tobacco smoke. Specifically, of the 105 genes presented in TABLE 12, 33 are known to be under transcriptional control of NRF2, or to act as cofactors for NRF2-regulated transcription (see FIG. 10).

In addition, it has been shown that the short-term exposure of mice to cigarette smoke results in the induction of a set of 46 protective genes, all of which are under the control of NRF2. In concordance with this observation, the data show that despite only brief exposure cells to CS in vitro, the RNA levels of 19 human homologues of these 46 mouse genes (41%) are similarly induced, indicating that the CS-related molecular events occurring in vitro are very similar to those observed in vivo. This set of CS-induced genes in both the mouse and NHBE cells includes those responsive to oxidative stress (heme oxygenase, phosphogluconate dehydrogenase, thioredoxin reductase, glutathione pathway genes, NADPH:quinone reductase), protein damage (HSP40, mortalin, GADD45), and protein turnover (ubiquitin C, proteasome subunits, sequestosome).

The fact that cigarette smoke, as well as various constituents of cigarette smoke, can cause disruptions to the genome, transcriptome, and proteome, allows one to develop a set of relevant biomarkers that are useful for monitoring exposure to tobacco toxins, detecting pre-malignant disease, improving diagnosis and prognosis of current disease, developing new treatment options, and testing risk reduction strategies for current and former smokers. A number of studies assessing the clinical usefulness of alterations in global gene and protein expression patterns in malignant and normal human lung tissues have recently shown that quantitative and/or qualitative changes in a small number of expressed genes and proteins, in combination with standard clinicopathological variables, may have prognostic and/or diagnostic potential in patients with tobacco-related diseases. Thus, elucidating the various molecular, genetic, and cellular dysfunctions induced by tobacco smoke may not only reveal a useful set of tobacco-specific biomarkers, but also result in a detailed mechanistic understanding of how chronic tobacco exposure causes disease.

One relevant strategy that addresses these goals is to examine the effects of tobacco smoke on the transcriptome of lung cells in an in vitro environment where important variables such as dose, smoke complexity, and exposure time can be precisely controlled. The data herein show that exposing NHBE cells to cigarette smoke or cigarette smoke condensates from commercial brands of American cigarettes affects a specific set of genes whose expression levels vary in a consistent manner and, therefore, may be direct indicators of CS-damage. Further, by sorting these genes into biologically functional classes, both expected and unexpected biochemical pathways were found to be responsive to tobacco smoke and the components therein. Finally, a number of genes in these pathways appear to have direct relevance to human pulmonary diseases caused by chronic use of tobacco products.

In addition to simply listing the genes whose regulation was altered by tobacco smoke exposure (see TABLE 10), the impacted genes were placed in biological context by developing a functional model indicating their potential roles in relation to the probable effects of cigarette smoke (CS). In the development of this model, the primary focus was on pathways in which more than one gene member was altered by CS exposure. The rationale was that since the proteins encoded by many genes can have multiple, sometimes opposing, functions depending on a specific cellular and molecular context, the activation of several genes in a specific circuit increases the confidence that these genes are working in concert and have integrated functions in response to CS exposure. In contrast, it is more difficult to predict the most probable function if only a single gene, rather than an integrated circuit, was affected by a particular treatment.

For example, the array data provided herein indicate that after a 15 min exposure to CS, a number of pathways in NHBE cells are activated, which attempt to modulate the adverse effects of oxidative stress. It is well documented that increased oxidative stress is a major mechanism by which CS causes airway damage that can lead to a host of pathogenic conditions including asthma, pulmonary fibrosis, chronic obstructive pulmonary disease, and lung cancer. However, a detailed understanding of the specific molecular mechanisms that link oxidative stress with CS-induced pathologies is still lacking. It is assumed that despite efficient antioxidant defense mechanisms in the respiratory tract, the large amounts of free radicals (on the order of $10^{13}$) generated in tobacco smoke from reactive oxygen and nitrogen species (ROS and RNS respectively) transiently overwhelm its steady-state antioxidant capacity. One predicted result of this damage and disruption to the respiratory tract's redox state is the activation of a wide array of stress-responsive genes. TABLE 12 and FIG. 10 support this by indicating that after CS exposure, the cell launches a coordinated and multi-faceted response (at least at the RNA level) that attempts to attenuate the sudden increase in oxidative stress. This response includes activation of a) heme oxygenase I (HO-1), a stress inducible enzyme that catabolizes heme containing proteins with the subsequent production of free iron, CO, and bilirubin; b) ferritin, which sequesters highly reactive iron molecules; c) thioredoxin and thioredoxin reductase 1, components of a ubiquitous thiol oxidoreductase system that protects the cell from oxidative stress; and d) peroxiredoxin 1, a peroxidase that has high antioxidant capacity. The transcription of each of these genes is controlled by Antioxidant Response Element (ARE) cis-acting regulatory elements, which allows their coordinated regulation in a cell exposed to many different types of oxidizing substances including tobacco smoke.

An important master regulator of this battery of ARE-responsive genes, as well as others whose encoded proteins prevent oxidative stress and detoxify a wide range of electrophiles, is the basic leucine zipper transcription factor Nrf2, which was found herein to be up-regulated in NHBE cells by CS exposure. Nrf2 activity is controlled at multiple levels. For example, in the absence of oxidative stress, Nrf2 is kept inactive by sequestration in the cytoplasm and by undergoing ubiquitination and rapid proteasomal degradation. A protein critical to both these functions is the cytoskeletal anchoring protein, Keap1 protein, which not only retains Nrf2 in the cytoplasm, but also acts as an adaptor protein that bridges Nrf2 to a third protein, cullin-3, a subunit of the E3 ligase complex. Inhibition or alterations of either Keap1 or cullin-3 increases Nrf2 nuclear accumulation and subsequent gene transcription. Oxidants may disrupt the Nrf2-Keap1-Cullin3 complex in several ways, e.g., by modifying cysteine residues in the Keap1 protein thereby releasing Nrf2 and allowing it to translocate to the nucleus, or by down-regulating the levels of cullin-3.

It is noteworthy that in the experiments described herein, cullin-3 was one of the few genes whose expression was down-regulated in CS-exposed cells (see TABLE 10). In addition, the small Maf proteins, MafF, and MafG, which form functional homodimer and heterodimer complexes with Nrf2 that modulate its transcriptional specificity, were also up-regulated by CS exposure. Thus, tobacco smoke may promote the functional activation of Nrf2 by several mechanisms resulting in the rapid induction of Nrf2-responsive genes as part of an overall effort to protect the cell from oxidative damage.

Recent studies have shown that genetic ablation of Nrf2 in mice enhances susceptibility to CS-induced emphysema and bleomycin-induced pulmonary fibrosis. Other data shows that the Nrf2-Keap1 provides a major defense mechanism against a wide range of pathological conditions, including chronic inflammation, cancer, and genetic instability. Accordingly, it appears that acute exposure to tobacco smoke and similar xenobiotics, rapidly induces the Nrf2 defense system in order to protect cells from the damaging effects of these substances. Many of the CS-responsive genes whose expression are directly affected by Nrf2 (i.e., heme oxygenase 1, peroxiredoxin, thioredoxin reductase, thioredoxin, and ferritin) are frequently up-regulated in a range of cancers including carcinomas of the lung. Moreover, there is accumulating data that these proteins may aid malignant cells by promoting angiogenesis, preventing apoptosis, or inducing proliferation. Finally, it is contemplated that functional polymorphisms in one or more Nrf2-induced genes impart an increased or decreased risk to the smoker.

The data herein also show that tobacco smoke impacts a number of other genes that are pivotal to redox homeostasis and modulation of oxidative stress. For example, tobacco smoke increases the expression of several genes involved in the synthesis and functioning of glutathione, including gamma glutamylcysteine synthase, glutaredoxin, glutathione peroxidase 2, glutathione reductase, and microsomal glutathione S-transferase 3. This major antioxidant system plays important roles, not only in antioxidant defense, but also in a range of cellular events such as gene expression, cell proliferation, apoptosis, and signal transduction. Chronic depletion in the activity of one or more of the proteins in this class of glutathione related antioxidant enzymes (e.g., by cigarette smoking) can lead to lung damage and disease. Moreover, gamma glutamylcysteine synthase, glutathione peroxidase 2, glutathione reductase, and microsomal glutathione S-transferase 3 have ARE response elements and are also activated by the Nrf2 transcription factor. These data further highlight the importance of the Nrf2-signaling pathway as a mediator of CS-induced damage and indicate that manipulation of Nrf2 or one of the downstream genes that it transcriptionally regulates can be exploited for novel treatment opportunities for smoking-related diseases.

To date, the most prominent transcription factor studied in relation to smoking related diseases is the nuclear factor kappa B (NF-kappaB), which appears to play key roles in a range of molecular events (for example, inflammation, proliferation, and angiogenesis) that are central to a number of pathogenic conditions in smokers. While there is little published data concerning the relationship between global gene expression alterations and NF-kappaB induction in CS-treated lung cells, some of the genes affected in the experiments described herein are also known to be activated by NF-kappaB [e.g., HSP70, GADD45, and COX2].

Another result from the data presented herein is that oxidative stress is among the most prominent effects of tobacco smoke exposure (e.g., the increased expression of a battery of highly conserved heat shock (HSPs; HSP40, HSP70, and HSP-105B) and related chaperone proteins (i.e., sequestosome 1 and BAG-3)). These proteins play critical roles in maintaining homeostasis and cell survival by promoting the correct folding of nascent proteins, the functional restoration of damaged and misfolded proteins caused by various types of stress including tobacco smoke exposure, or the elimination of irreversibly damaged proteins by the ubiquitin-proteasome system.

HSP70 is a key chaperone protein that responds to oxidative stress. A majority of adenocarcinomas of the lung show high expression of HSP70, which have also been correlated with lymph node involvement. These data indicate that HSP70 may be a survival factor for lung cancer cells, a finding supported by the observation that its down-regulation induced apoptosis in lung cancer but not in normal lung cells. In addition, antibodies to HSP70 were found to be at a significantly greater level in patients with NSCLCs than in matched controls, providing evidence that HSP70 may be idiopathically released from stressed malignant lung cells. Hsp40 is a chaperone adaptor protein that plays an essential regulatory function by targeting unfolded proteins to HSP70 and stimulating its ATPase activity, which aids HSP70 in its protein folding functions. Interestingly, it has been reported that HSP40 may play a chaperone role in cilia regeneration, which may be of significance in CS-exposed subjects since many components in tobacco smoke are ciliatoxic. HSP40 is not only over-expressed in lung tumor tissues and cells, but patients with lung cancer had significantly higher levels of autoantibodies to Hsp40 than healthy control subjects, indicating that high levels of HSP40, possibly induced by chronic CS exposure, results in an immunological response (and possibly attack) by the host with unknown consequences. Hsp105beta, a chaperone protein that co-regulates the constitutive form of HSP70, suppresses protein aggregation in cells under severe stress, especially when cellular ATP levels are significantly depleted. Hsp105 is also a marker for survival in patients with adenocarcinoma of the lung. The BAG family proteins are regulatory co-chaperones for Hsp70 and may be involved in signal transduction. BAG-3 inhibits HSP70-mediated proteasomal degradation after protein ubiquitination, thus protecting client proteins of HSP70 from destruction, including important signaling molecules such as Akt, cdk4, raf-1, and EGFR. Bag-3 also may interact with and enhance the anti-apoptotic functions of Bcl-2. Sequestosome 1 is a multifunctional protein that binds and sequesters poly-ubiquitinated protein aggregates and plays a critical role in the survival of stressed cells by promoting proteasomal degradation of these aggregates.

Additional evidence that tobacco smoke significantly impacts protein damage control mechanisms is the observed increase in the levels of genes involved in ubiquitination conjugation and transport processes (e.g., ubiquitin-activating enzyme E1 and E2, F-lan-1, Ring-Box 1, ubiquitin carrier protein, etc.). These data indicate a cooperative linkage between oxidative stress and the chaperone and ubiquitination pathways in CS-exposed cells. It is also worth noting that most subunits that assemble to form the 26S proteasome are also induced by Nrf2.

It should also be understood that CS-induced oxidative stress can cause various types of damage in membranes and lipoproteins that lead to an accumulation of oxidized low-density cholesterol, an important risk factor for the development of atherosclerosis and myocardial infarction in smokers. However, little is known about the direct membrane effects of CS-exposure in lung cells. The data provided herein show that tobacco smoke alters the RNA transcripts for a number of genes involved in cholesterol metabolism, synthesis, and transport. It is likely that the goal of these processes is to repair CS-induced damage, such as cholesterol oxidation and lipid peroxidation to cell membranes and other lipid containing structures. The up-regulated genes involved in lipid breakdown include a) prosaposin, a sphingolipid activator protein that helps degrade glycosphingolipids delivered to the lysosomes; b) cytosolic acyl coenzyme A thioester hydrolase, a member of the acyl coenzyme family that catalyze the hydrolysis of acyl-CoA thioesters to free fatty acids; and c) acetyl-coenzyme A acetyltransferase 2, another enzyme involved in lipid metabolism. Up-regulated genes involved in lipid synthesis include (a) phosphatidic acid phosphatase type 2B, which functions in de novo glycolipid synthesis by converting phosphatidic acid to diacylglycerol; (b) isopentenyl-diphosphate isomerase-1, which generates substrate molecules necessary for the synthesis of cholesterol; (c) 3-hydroxy-3-methylglutaryl-coenzyme A redutase (HMG-CoA Reductase), a rate-limiting enzyme for cholesterol synthesis, whose inhibition results in increased catabolism of plasma LDL and a reduced risk of cardiovascular disease.

HMG-CoA Reductase is a potential therapeutic target for head and neck squamous cell carcinomas since its suppression can lead to apoptosis; (d) 3-hydroxy-3-methylglutaryl-Coenzyme A synthase (HMG-COA Synthase) catalyzes the formation of HMG-CoA, the substrate for HMG-CoA reductase and is usually coordinately regulated with this enzyme; (e) sterol-C5 desaturase, an integral membrane protein involved in cholesterol synthesis; (f) sterol regulatory element binding transcription factor 2, a member of a family of transcription factors [the Sterol Regulatory Element Binding Proteins (SREBPs)] that regulate genes involved in lipid synthesis and cholesterol homeostasis; and (g) fatty acid synthase (FAS), an enzyme responsible for de novo synthesis of fatty acids. Of relevance is the fact that fatty acid synthesis in tumor tissues occurs at very high rates and almost all fatty acids in tumor cells derive from de novo synthesis despite adequate nutritional supply. In addition, tumors that over-express FAS display aggressive biologic behavior compared to those tumors with normal FAS levels, indicating that FAS over-expression confers a selective growth advantage. The frequent over-expression of FAS in many epithelial cancers indicates that this enzyme may be a potential therapeutic target. FAS is also regulated by an SREBP.

Additional evidence that tobacco smoke influences cholesterol homeostasis is the observed increase in the insulin-induced gene 1 (insig-1) transcripts. Insig-1 plays a critical role in blocking lipid synthesis and regulating the levels of cholesterol in the cell. Upon rising levels of cholesterols, such as induced by CS-mediated lipid damage, insig-1, downregulates cholesterol synthesis by various mechanisms, including binding to HMG CoA) reductase, which promotes its ubiquitination and proteasomal degradation. Furthermore, even though lipogenesis is regulated primarily by sterols & by insulin induction through expression of SREBPs, cells can uncouple sterol and insulin regulation by overexpressing INSIG-1, which makes lipogenesis more sensitive to cholesterol & less sensitive to insulin.

Once cholesterol is synthesized in the endosomes it is transported to the cell membrane by the NPC1 (Niemann-Pick type C) protein (among others). Up-regulation of NPC1 increases the rate of transport trafficking of LDL cholesterol to the PM. The data provided herein also show that tobacco smoke up-regulates NPC1. Diazepam binding inhibitor/Acyl-CoA binding protein (DBI), another gene whose RNA levels are increased by CS exposure, contains a functional sterol regulatory element that allows it to be co-regulated with other genes that are stimulated by conditions that promote lipogenesis. Of additional interest is the fact that DBI indirectly modulates gamma-aminobutyric acid (GABA)-mediated inhibitory neurotransmission. Consequently, DBI may have a role in specific psychotropic effects such as anxiety, mood & psychiatric disorders, all conditions known to be affected by chronic cigarette smoking. While it remains to be determined how cholesterol perturbations affect smoking-related diseases, the evidence presented herein indicates that manipulation of the cholesterol biosynthetic pathway may provide novel therapeutic modalities for multiple CS-induced pathologies. For example, it has been observed that the growth of lung cancer cells can be inhibited by the station class of cholesterol lowering drugs. Moreover, lipid oxidation products may be useful biomarkers of acute exposure to CS.

The data discussed herein demonstrate that a brief exposure of NHBE cells to cigarette smoke alters the expression of a number of genes in specific functional pathways that are associated with many pathological conditions found in long-term smokers. Since the expression of these genes remained altered for up to 24 hours, it is contemplated that in the current pack-a-day smoker who averages >150 cigarette puffs/day, the function of pathways in which these genes participate may not return to a homeostatic baseline during a typical day. One contemplated outcome of this chronically perturbed state is that one or more of the genes observed in the experiments described herein are either permanently activated, attenuated, or disabled over time in a habitual smoker and that the failure to reach homeostasis contributes to the adverse biological consequences that are observed in long-term smokers.

For example, DUSP5/6 was up-regulated in the NHBE cells that were exposed to cigarette smoke. DUSP5/6 is a dual-specificity phosphatase that negatively regulates stress activated protein kinases ERK1/2, which are up-regulated in advanced NSCLCs. Whether DUSP5/6 was deranged or lost in lung cancers is unknown, but lack of expression of DUSP5/6 may promote constitutive activation of ERK and abnormal cell growth. CS was also shown to up-regulate DKK3. DKK3 is an antagonist of the Wnt oncogenic signaling pathway whose expression is significantly down-regulated in non-small cell lung cancer. Disruption of these genes and/or biological pathways in which they function may contribute specific steps in the pathogenesis or progression of a tobacco-related disease.

The data presented here are instrumental in developing a new generation of candidate target genes for which functional models of CS-affected pathways, gene interactions, and clinical relationships can be constructed and tested. This is particularly important since, as yet, there is no single lung cancer biomarker that has achieved sufficient diagnostic significance to be of primary use in the clinic.

Using the data herein with CS, as well as that with CSCs, the identification of tobacco-affected gene sets or gene signatures, as well as the biological phenomena in which these genes participate, will allow the development of a detailed atlas of molecular events caused by exposure to tobacco smoke constituents. This atlas will be invaluable for clarifying the relationship between altered gene expression and cellular dysfunction, which is an important step toward developing a highly accurate model of disease risk for current and former users of tobacco products. This can also be used for diagnostic and prognostic methods for analyzing patient outcome, risk and disease.

Accordingly, some preferred embodiments concern providing a first population of isolated human cells of the mouth, tongue, oral cavity, or lungs (e.g., NHBE cells), contacting said cells with cigarette smoke from a first tobacco product (e.g., a cigarette smoke generated from a smoking chamber or CULTEX®) in an amount and for a time sufficient to modulate expression or modification of one or more genes or gene products (e.g., at least or equal to 1, 5, 10, 15, 20, 25, 30, 45, 60, or more minutes), and identifying the gene that is modulated or the modified gene product (e.g., phosphorylated) or the level or amount of gene expression or modification. The identification of a gene that is modulated or modified gene product or the level or amount of gene expression or presence or absence of a modification on a gene product can be accomplished using any technique available that analyzes transcription (e.g., microarray technology, genechip technology, an amplification technique, RTPCR, or hybridization), protein production (e.g., ELISA or other antibody detection techniques), or modifications of proteins (e.g., oxidation or phosphorylation). Additionally, the appearance or disappearance of metabolites associated with genes that are modulated in response to exposure to CS, CSC, TS, or TSC can also be monitored (e.g., cysteine, glutathione, fragments of proteins or lipids or fatty acids) using techniques that are available. Once a gene is identified, it can be analyzed using PathwayAssist™ software (Stratagene, La Jolla, Calif.), a commercially available visualization engine that scans and assesses documented literature and available standardized databases in order to filter, classify, and prioritize proteins in terms of their functional relationships to known biological pathways. Identified genes can also be analyzed with Genespring software (version 7.2, Agilent Technologies) so as to determine whether the gene is associated with a tobacco-related disease, such as cancer. Using these approaches, it was discovered that a "full flavor" cigarette modulates the expression of several genes that are involved in tobacco-related disease. (See Examples 1, 9 and 10). Accordingly, these genes are biomarkers that can be used to monitor the presence or absence of a tobacco related disease or the predilection for an individual to acquire a tobacco-related disease.

Optionally, the pattern and/or level of gene expression or gene product modification of a control population (e.g., a second population of isolated human cells of the mouth, tongue, oral cavity, or lungs (e.g., NHBE cells)), is compared to the level of expression or gene product modification in the first population of isolated cells. By this approach, preferably using the same type of cells for each of the two populations, a first population is contacted with a CS and the second population of isolated cells is not. In this manner, the second population of isolated cells is a control population, which exhibits the baseline pattern or level or amount of gene expression or gene product modification (homeostasis). Data generated from the first or second population of isolated cells before or after exposure to CS or air (control) can be compared so as to identify a gene that is statistically modulated in response to contact with a CS.

In more embodiments, a second tobacco product (e.g., a cigarette) is compared to a first tobacco product (e.g., a cigarette) using the methods above so as to identify which of the two tobacco products is less likely to contribute to a tobacco-related disease. For example, a first population of isolated human cells of the mouth, tongue, oral cavity, or lungs (e.g., NHBE cells), is contacted with a CS from a first tobacco product (e.g., a "reduced risk full flavor" cigarette) in an amount and for a time sufficient to modulate expression of one or more genes or to modify a gene product, and identification of the genes that are modulated or modified gene product (e.g., phosphorylated) or the level or amount of gene expression or modification can be determined using any technique available that analyzes transcription (e.g., microarray, genechip, RTPCR or hybridization), protein production (e.g., ELISA or other antibody detection techniques), modifications of proteins (e.g., oxidation or phosphorylation), or the appearance or disappearance of metabolites associated with genes that are modulated in response to exposure to CS (e.g., cysteine, glutathione, fragments of proteins or lipids or fatty acids). A second population of isolated human cells of the mouth, tongue, oral cavity, or lungs (e.g., NHBE cells), preferably the same type of cell as used in the analysis of the first tobacco product, is also contacted with a CS from a second tobacco product (e.g., a cigarette) in an amount and for a time sufficient to modulate expression of one or more genes or to modify a gene product. Identification of a gene that is modulated or modified gene product (e.g., phosphorylated) or the level or amount of gene expression or modification can be accomplished using any technique available that analyzes transcription (e.g., microarray, genechip, RTPCR or hybridization), protein production (e.g., ELISA or other antibody detection techniques), modifications of proteins (e.g., oxidation or phosphorylation), or the appearance or disappearance of metabolites associated with genes that are modulated in response to exposure to CS (e.g., cysteine, glutathione, fragments of proteins or lipids or fatty acids).

The data obtained from the analysis of the first tobacco product can be compared to the data obtained from the analysis of the second tobacco product so as to identify, for example, a gene(s) that are induced in response to exposure to the first tobacco product but not the second tobacco product or vice versa. Additionally, the comparison will reveal that the level of expression of one or more genes induced by both tobacco products differs with respect to the two tobacco products or that the first product has more, less, or no modification of a particular gene product (e.g., phosphorylation), as compared to the second tobacco product or vice versa. These data (e.g., the types of genes expressed, the amount of expression, and modification) allow one to develop a profile for each tobacco product analyzed (in this example only two products are being compared but a plurality of products can be compared using the same approach). These tobacco product profiles can be recorded on a computer readable media and databases containing this information can be created. Once a gene is identified, it can be analyzed using PathwayAssist™ software (Stratagene, La Jolla, Calif.), Genespring (version 7.2, Agilent Technologies), or other similar software so as to determine whether the gene contributes to a tobacco-related disease.

By analyzing the differences between the tobacco products analyzed, (e.g., the types of genes expressed, the amount of expression, and modifications), one can identify a tobacco product that has less potential to contribute to a tobacco related disease or that, for example, a first tobacco product has a reduced risk to contribute to a tobacco-related disease, as compared to a second tobacco product or vice versa. By one technique, for example, a tobacco product that is less likely to contribute to a tobacco-related disease is identified because it induces fewer genes associated with a tobacco-related disease. A related approach (using CSC) was employed to identify a tobacco product as having a reduced potential to contribute to a tobacco-related disease, as compared to a second tobacco product. (See Examples 1-3).

The methods provided herein can be used not only to identify a tobacco product that has a reduced potential to contribute to a tobacco-related disease, as compared to a second tobacco product, but also to develop tobacco products that have a reduced potential to contribute to a tobacco-related disease, as compared to a second tobacco product. That is, by coordinating techniques (e.g., chemical or genetic modification) to modulate expression of genes that produce various components in tobacco with the analytical methods disclosed herein, one can rapidly determine whether the modulation of a particular gene that produces a particular component in tobacco results in a modulation of a gene in human cells (e.g., NHBE cells) that results in a reduced potential to contribute to a tobacco-related disease, as compared to the tobacco prior to modulation of component-producing gene. The section below describes these embodiments in greater detail.

Tobacco Products that have a Reduced Potential to Contribute to a Tobacco-related Disease More embodiments concern methods to identify components of a tobacco product that contribute to a tobacco-related disease, the selective removal or inhibition of production of these components, and the determination that the removal of the component(s) modulates expression of a gene that is associated with a tobacco-related disease in a manner that reduces the potential for the tobacco product to contribute to a tobacco related disease. It is contemplated that particular components of tobacco products are the factors that modulate expression of genes in human cells that contribute to tobacco-related disease. It is further contemplated that modification of genes that contribute to the production of these toxic components in tobacco (e.g., genetic engineering or chemical treatment) will, concomitantly, result in a modulation of gene expression in human cells that come in contact with the smoke from said modified tobacco, which is less likely to contribute to a tobacco-related disease than the tobacco prior to modification of the component-producing gene. Accordingly, by selectively removing the components that induce the genetic events that contribute to tobacco-related disease in a human, one can develop tobacco products that are less likely to contribute to a tobacco-related disease.

By one approach, for example, CS is generated using a smoking machine from a first tobacco product that has been genetically modified to have a reduced amount of a compound. A first population of NHBE cells is contacted with said CS obtained from the modified tobacco, as described in Examples 1, 9, and 10. As described in these examples, the RNA is isolated and analyzed by microarray or RTPCR or both and a pattern of gene expression and gene product modification events are obtained. Programs such as PathwayAssist™ software (Stratagene, La Jolla, Calif.) and/or Genespring (version 7.2, Agilent Technologies) can be used to determine the identity of the genes that are modulated and their relationship to a tobacco-related disease.

A second population of NHBE cells is then contacted with CS generated from the parental variety of tobacco. That is, the parental variety of tobacco is the un-modified tobacco variety used to generate the modified tobacco variety, wherein the unmodified tobacco retains the component that was removed or inhibited in the modified tobacco. As above, the RNA is isolated and analyzed by microarray or RTPCR or both and a pattern of gene expression and gene product modification events are obtained. Programs such as PathwayAssist™ (Stratagene, La Jolla, Calif.) and/or Genespring (version 7.2, Agilent Technologies) can be used to determine the identity of the genes that are modulated and their relationship to a tobacco-related disease.

A comparison of the data obtained from the analysis of the first and second tobacco products will reveal that the modified tobacco modulates fewer genes associated with a tobacco-related disease than the parental, unmodified tobacco. The data will also show that the modified tobacco product induces expression of fewer proto/oncogenes. By this approach, one can effectively identify the contribution of individual components of a tobacco product to a tobacco-related disease. This combinatorial approach can be used to develop tobacco products that are less likely to contribute to a tobacco-related disease and reduced risk tobacco products identified by these methods are aspects of the invention. Further, tobacco products prepared by these approaches can be prepared according to good manufacturing processes (GMP) (e.g., suitable for or accepted by a governmental regulatory body, such as the Federal Drug Administration (FDA), and containers that house said tobacco products can comprise a label or other indicia, with or without structure-function indicia, which reflects approval of said tobacco product from said regulatory body. The example below describes this approach in greater detail.

EXAMPLE 11

This example provides several approaches that can be used to obtain tobacco and tobacco products that have a reduced potential to contribute to a tobacco-related disease. Generally, these methods involve a two-tiered analysis involving first, an analysis of a parent strain of tobacco that has a component or compound that contributes to a tobacco related disease and second, an analysis of a progeny of the parent strain of tobacco that has been modified to modulate (i.e., up-regulate or down-regulate) expression of a gene that induces a cascade that contributes to a tobacco-related disease.

Accordingly, by one approach, a first tobacco (e.g., Burley 21 LA) that comprises a compound that contributes to a tobacco-related disease (e.g., nicotine) is provided. Next, preferably, smoke is obtained from said first tobacco (e.g., CS), however a smoke condensate from the first tobacco can also be obtained. Once the smoke or smoke condensate has been prepared from the first tobacco, a first isolated population of cells, preferably human cells of the mouth, tongue, trachea, bronchi, or lungs (e.g., NHBE cells) is contacted with said smoke or smoke condensate from said first tobacco. The contact can be made in a smoking chamber, for example, for less than, equal to, or more than, 5 seconds, 20, seconds, 45 seconds, 1 minute, 5 minutes, 10 minutes, 15 minutes, 20 minutes, 30 minutes, 45 minutes, 1 hour, two hours, three hours. Subsequent to the contact with the smoke or smoke condensate, a first gene that is modulated (up-regulated or down-regulated) in said first population of cells in response to said contact with said smoke or smoke condensate from said first tobacco is identified (e.g., an proto/oncogene). The identification of the first gene can be accomplished using an oligonucleotide array, micro array, RTPCR, nucleic acid detection (e.g., hybridization), protein detection (e.g., antibody detection or ELISA), or detection of a metabolite (e.g., protein fragment or cysteine) or a modified gene product (e.g., oxidized or phosphorylated protein or amino acid). The first gene identified as being modulated (e.g., up-regulated or down-regulated) in response to contact with the smoke or smoke condensate of the first tobacco is then analyzed for its contribution to a tobacco-related disease. The correlation of many of the genes that are identified by the approach above to a tobacco-related disease can be accomplished by simply reviewing available literature or by employing commercially available software that identifies the association of a particular gene with a tobacco-related disease (e.g., PathwayAssist™, available from Stratagene, La Jolla, Calif. and/or Genespring (version 7.2, available from Agilent Technologies).

Next, a second tobacco that is, preferably, the same variety and grown under the same conditions as the first tobacco is provided. The second tobacco has been modified to reduce expression of a second gene, a gene that contributes to the production of a compound or component present in the first tobacco (e.g., a gene involved in nicotine synthesis, such as QPTase or PMTase). The modification of the second gene can be accomplished by genetic engineering or chemical treatment. Several approaches to modify tobacco to reduce the amount of nicotine are known. (See e.g., U.S. patent application Ser. No. 10/729,121, WO0067558A1, WO9428142A1, WO05000352A1, WO05018307A1, WO03086076A1, and WO0218607A2, all of which are hereby expressly incorporated by reference in their entireties).

By one approach, the second tobacco is genetically modified to reduce expression of QPTase, as follows. Tobacco of the variety Burley 21 LA is transformed with the binary *Agrobacterium* vector pYTY32 to produce the low nicotine tobacco variety, Vector 21-41. The binary vector pYTY32 carries the 2.0 kb NtQPT1 root-cortex-specific promoter driving antisense expression of the NtQPT1 cDNA and the nopaline synthase (nos) 3' termination sequences from *Agrobacterium tumefaciens* T-DNA. The selectable marker for this construct is neomycin phosphotransferase (nptII) from *E. coli* Tn5, which confers resistance to kanamycin; the expression of nptII was directed by the nos promoter from *Agrobacterium tumefaciens* T-DNA. Transformed cells, tissues and seedlings are selected by their ability to grow on Murashige-Skoog (MS) medium containing 300 ug/ml kanamycin.

Independent pYTY32 transformants of Burley 21 LA ($T_0$) are allowed to self. Progeny of the selfed plants ($T_1$) are germinated on medium containing kanamycin and the segregation of kanamycin resistance is scored. $T_1$ progeny segregating 3:1 result from transformation at a single locus and are subjected to further analysis. Nicotine levels of said $T_1$ progeny are measured qualitatively using a micro-assay technique, wherein approximately 200 mg fresh tobacco leaves are collected and ground in 1 ml extraction solution (extraction solution: 1 ml Acetic acid in 100 ml water). Homogenate is centrifuged for 5 min at 14,000×g and the supernatant is removed to a clean tube, to which the following reagents are added: 100 uL NH$_4$OAC (5 g/100 ml water +50 uL Brij 35); 500 uL Cyanogen Bromide (Sigma C-6388, 0.5 g/100 ml water+50 uL Brij 35); 400 uL Aniline (0.3 ml buffered Aniline in 100 ml NH$_4$OAC+50 uL Brij 35). A nicotine standard stock solution of 10 mg/ml in extraction solution is prepared and diluted to create a standard series for calibration. Absorbance at 460 nm is read and a reduction in nicotine content of Vector 21-41 test samples is verified using a standard calibration curve.

Vector 21-41 has been made and has been found to be similar to Burley 21 LA in all assessed characteristics, with the exception of alkaloid content and total reducing sugars (e.g., nicotine and nor-nicotine). Vector 21-41 may be distinguished from the parent Burley 21 LA by its substantially reduced content of nicotine, nor-nicotine and total alkaloids.

RNAi constructs that comprise fragments of a gene involved in nicotine synthesis have also been used to reduce the amount of nicotine and TSNA in tobacco. By one approach, for example, the RNAi construct provided in FIG. 11 was used to generate a reduced nicotine and TSNA tobacco. By another approach, the RNAi construct provided in FIG. 12 was used to generate a reduced nicotine and TSNA tobacco. More details on the preparation of these RNAi constructs and the methods used to create transgenic tobacco having a reduced amount of nicotine and TSNAs is provided in the section that follows and Example 12.

Once the modified second tobacco is obtained, preferably a genetically modified second tobacco (e.g., a second tobacco that has been genetically modified to reduce the amount of nicotine), smoke or a smoke condensate is obtained from said second tobacco. Then, a second isolated population of cells, preferably the same cell type as analyzed above (e.g., NHBE cells) is contacted with the smoke or smoke condensate from the second tobacco, preferably for the same amount of time as the cells that were contacted with the first tobacco. Subsequent to the exposure of the second population of cells to the second tobacco, an approach to identify the modulation of gene expression in said second population of cells is employed, preferably the same approach that was used to analyze the first population of cells after exposure to the smoke or smoke condensate of the first tobacco product (e.g., an oligonucleotide array, microarray, RTPCR, nucleic acid detection (e.g., hybridization), protein detection (e.g., antibody detection or ELISA), or detection of a metabolite (e.g., protein fragment or cysteine) or a modified gene product (e.g., oxidized or phosphorylated protein or amino acid).

A modulation (up-regulation or down-regulation) in expression of a first gene that contributes to a tobacco-related disease in said second population of cells, as compared to the amount of expression of the same gene induced by the first tobacco, will be observed. This difference in expression of a gene that is related to a tobacco-related disease provides strong evidence that the modification in the second tobacco has resulted in a tobacco that has a reduced potential to contribute to a tobacco-related disease. That is, said (modified) second tobacco has a reduced risk to contribute to a tobacco-related disease, as compared to the first (unmodified) tobacco.

Conventional techniques in cultivation of said second tobacco, harvesting, curing, blending, and processing are then employed so as to generate a tobacco product (e.g., snuff, chew, tobacco leaf, cigarette, pipe tobacco, cigar, or lozenge) and said tobacco product can be identified as a product that has a reduced potential to contribute to a tobacco-related disease as compared to a tobacco product comprising said first tobacco. The section below provides more detail on the preparation of RNAi constructs that inhibit nicotine synthesis in tobacco, the generation of modified tobacco using these constructs, and the preparation of tobacco products from this tobacco.

Rna Interference (RNAi) and Gene Silencing

Several approaches to create tobacco and tobacco products that have a reduced amount of nicotine and/or TSNAs using RNAi have been discovered. Some aspects of the technology described herein are also described in PCT/US98/11893, which is hereby expressly incorporated by reference in its entirety. By one approach, transgenic or genetically modified tobacco plants that have reduced nicotine and TSNA levels are created and tobacco harvested from said transgenic tobacco plants is used to prepare a variety of tobacco products. One such genetically modified tobacco plant comprises an interfering RNA that comprises an RNA strand that is complementary to at least a portion of the coding strand of a gene, which encodes a gene product involved in nicotine biosynthesis. In some embodiments, the gene involved in nicotine biosynthesis is the quinolate phosphoribosyl transferase (QPTase) gene. In other embodiments, the gene involved in nicotine biosynthesis is putrescene N-methyltransferase. In such embodiments, interfering RNA reduces expression of the endogenous nicotine biosynthesis, which, in turn, reduces the amount of nicotine and, concomitantly, the amount of TSNA in the tobacco plant. Thus, one inventive concept concerns the reduction of nicotine and TSNAs in a tobacco plant using interfering RNA (RNAi).

The term nitrosamine generally refers to any of a class of organic compounds with the general formula R$_2$NNO or RNHNO (where R denotes an amine-containing group). Nitrosamines are present in numerous foods and have been found to be carcinogenic in laboratory animals. These compounds are formed by nitrosation reactions of amines such as amino acids and alkaloids with nitrites and/or nitrous oxides. By themselves, nitrosamines are not carcinogenic substances, but in mammals nitrosamines undergo decomposition by enzymatic activation to form alkylating metabolites which appear to react with biopolymers to initiate their tumorogenic effect. Thus, by reducing the amount of nitrosamine intake, one has effectively reduced the carcinogenic potential in humans.

Nitrosamines have been identified in tobacco, tobacco products, and tobacco smoke by the use of techniques such as gas chromatography-thermal energy analysis (GC-TEA). Some of these nitrosamines have been identified as tobacco-specific nitrosamines (TSNAs). TSNAs are primarily formed by reactions between the two most abundant alkaloids, nicotine and nornicotine, with nitrous oxides (NOx), and they account proportionately for the highest concentration of nitrosamines in both tobacco products and in mainstream smoke. Of the TSNAs identified, and the subset that have been found to be present in cigarette smoke, the most characterized is N-nitrosamine, 4-(methylnitrosamino)-1-(3-pyridyl)-1-butanone (N-nitrosamine-ketone), or NNK. When injected at relatively high doses, NNK is carcinogenic in rodents. Minimal amounts of TSNAs are found in green tobacco, indicating that TSNA formation may occur during processing steps such as curing, drying, fermentation, burning or storage of tobacco.

TSNA formation is attributed to chemical, enzymatic and bacterial influences during tobacco processing, particularly during curing, fermentation and aging. Nitrosation of nornicotine, anatabine, and anabasine gives the corresponding nitrosamines: N'-nitrosonornicotine (NNN), N'-nitrosoanatabine (NAT) and N'-nitrosoanabasine (NAB). Nitrosation of nicotine in aqueous solution affords a mixture of 4-(N-nitrosomethylamino)-1-(3-pyridyl)-1-butanone (NNK), NNN, and 4-(N-nitrosomethylamino)-4-(3-pyridyl)-1-butanal (NNA). Less commonly encountered TSNAs include NNAL (4-N-nitrosomethylamino)-1-(3-pyridyl)-1-butanol), iso-NNAL (4-N-nitrosomethylamino)-4-(3-pyridyl)-1-butanol, 11) and iso-NNAC (4-(N-nitrosomethylamino)-4-(3-pyridyl)-butanoic acid, 12). See, U.S. Pat. No. 6,135,121, the entire disclosure of which is hereby expressly incorporated by reference in its entirety.

TSNA levels are particularly high in chewing tobaccos and snuff. The partially anaerobic processes that occur during fermentation promote the formation of TSNAs from tobacco alkaloids by promoting increased nitrite levels; in particular, over-fermentation can increase TSNA levels in snuff by its effects on nitrate levels and microbial enzymatic activity. The reduction of the nitrosamine level in snuff in recent years has been achieved by maintaining a better control over the bacterial content in these products.

Since the nitrate level of tobacco is important for nitrosamine formation in cigarette smoke, a significant reduction of nitrosamines in smoke can be achieved by low-nitrate leaf and stem blends. However, these methods may negatively impact the smokability or the taste of the tobacco. The nitrosamine content of mainstream smoke can be reduced by as much as 80% by cellulose acetate filters, and it can be reduced still further by filter ventilation.

Air-cured tobaccos such as burley and dark-fired may have higher levels of TSNAs than certain types of flue-cured bright, burley, or dark tobaccos apparently because the high temperatures associated with flue-curing can kill the microorganisms that transform the alkaloids into TSNAs. In air-cured types, nitrate ($N-NO_3$) is more abundant in the leaf (particularly in the leaf and stems) than in flue-cured tobacco and the alkaloid content is also much higher. This $N-NO_3$ is reduced to nitrite ($NO_2^-$) by microbes during curing and the $NO_2^-$ can be further reduced to NOx or react directly with alkaloids to form TSNAs.

It is contemplated that, in addition to the techniques described above, nitrate levels in tobacco (especially in the leaf) can be reduced by limiting exposure to nitrosating agents or conditions. Air-curing experiments at a higher temperature have shown that considerably higher levels of N-nitrosamines are formed at a curing temperature of 32° C. than at 16° C., which is associated with a rise of the nitrite level in the tobacco, and may also be associated with a rise in microbial enzymatic activity. Modified curing that involves faster drying from wider spacing or from more open curing structures has been shown to reduce TSNA levels in burley tobacco. The climatic conditions prevailing during curing exert a major influence on N-nitrosamine formation, and the relative humidity during air-curing can be of importance. Stalk curing results in higher TSNA levels in the smoke than primed-leaf curing. Sun-cured Oriental tobaccos have lower TSNA levels than Flue and air-cured dark tobaccos. Accelerated curing of crude tobaccos such as homogenized leaf curing limits the ability of bacteria to carry out the nitrosation reactions. However, many of the methods described above for reducing TSNAs in Burley tobacco can have undesirable effects on tobacco taste.

TSNA formation in flue-cured tobacco also results from exposure of the tobacco to combustion gases during curing, where nearly all of the TSNAs in flue-cured tobacco (e.g., Virginia Flue) result from a reaction involving NOx and nicotine. The predominant source of NOx is the mixture of combustion gases in direct-fired barns. At present, flue-cured tobacco is predominantly cured in commercial bulk barns. As a result of energy pressures in the U.S. during the 1960's, farmer-built "stick barns" with heat-exchanged flue systems were gradually replaced with more energy efficient bulk barns using direct-fired liquid propane gas (LPG) burners. These LPG direct-fired burner systems exhaust combustion gases and combustion by-products directly into the barn where contact is made with the curing tobacco. Studies indicate that LPG combustion by-products react with naturally occurring tobacco alkaloids to form TSNA.

In contrast to direct-fired curing, heat-exchange burner configurations completely vent combustion gases and combustion by-products to the external atmosphere rather than into the barn. The heat-exchange process precludes exposure of the tobacco to LPG combustion by-products, thereby eliminating an important source of nitrosating agent for TSNA formation, without degrading leaf quality or smoking quality. The use of heat exchangers reduces TSNA levels by about 90%. Steps are being taken to reduce TSNA levels in US tobacco by converting barns to indirect heat through the use of a heat exchanger, but these methods are very expensive. Although many of the approaches described in this section have significant drawbacks, it should be understood that any or all of these techniques can be used with other techniques, as described herein, to make tobacco and tobacco products having reduced nitrosamines.

Nicotine is formed primarily in the roots of the tobacco plant and is subsequently transported to the leaves, where it is stored (Tso, Physiology and Biochemistry of Tobacco Plants, pp. 233-34, Dowden, Hutchinson & Ross, Stroudsburg, Pa. (1972)). Classical crop breeding techniques have produced tobacco with lower levels of nicotine, including varieties with as low as 8% of the amount of nicotine found in wild-type tobacco. The many methods described herein can be used with virtually any tobacco variety but are preferably used with Burley, Oriental or Flue (e.g., Virginia Flue) varieties.

Nicotine is produced in tobacco plants by the condensation of nicotinic acid and 4-methylaminobutanal. Two regulatory loci (Nic1 and Nic2) act as co-dominant regulators of nicotine production. Enzyme analyses of root tissue from single and double Nic mutants show that the activities of two enzymes, quinolate phosphoribosyl transferase ("QPTase") and putrescence methyl transferase (PMTase), are directly proportional to levels of nicotine biosynthesis. An obligatory step in nicotine biosynthesis is the formation of nicotinic acid from quinolinic acid, a step that is catalyzed by QPTase. QPTase appears to be a rate-limiting enzyme in the pathway supplying nicotinic acid for nicotine synthesis in tobacco. (See, e.g., Feth et al., *Planta*, 168, pp. 402-07 (1986) and Wagner et al., *Physiol. Plant.*, 68, pp. 667-72 (1986), herein expressly incorporated by reference in its entirety). A comparison of enzyme activity in tobacco tissues (root and callus) with different capacities for nicotine synthesis shows that QPTase activity is strictly correlated with nicotine content (Wagner and Wagner, Planta 165:532 (1985), herein expressly incorporated by reference in its entirety). In fact, Saunders and Bush (Plant Physiol 64:236 (1979), herein expressly incorporated by reference in its entirety), showed that the level of QPTase in the roots of low nicotine mutants is proportional to the level of nicotine in the leaves.

The modification of nicotine levels in tobacco plants by antisense regulation of putrescence methyl transferase (PMTase) expression has been proposed in U.S. Pat. Nos. 5,369,023 and 5,260,205, to Nakatani and Malik, and in PCT application WO 94/28142 to Wahad and Malik, which describe DNA encoding PMT and the use of sense and antisense PMT constructs, the entire disclosures of each of which are hereby expressly incorporated by reference in their entireties. Other genetic modifications proposed to reduce nicotine levels are described in PCT application WO 00/67558, to Timko, and WO 93/05646, to Davis and Marcum; the entire contents of each are hereby expressly incorporated by reference in their entireties. Although many of the approaches described in this section have significant drawbacks, it should be understood that any or all of these techniques can be used with other techniques, as described herein, to make tobacco and tobacco products having reduced nicotine.

As discussed above, TSNAs and nicotine contribute significantly to the carcinogenic potential and addictive properties of tobacco and tobacco products. Thus, the need for tobacco and tobacco products that have reduced amounts of TSNAs and nicotine is manifest. Without wishing to be bound by any particular theory, it is contemplated that the creation of tobacco plants, tobacco and tobacco products that have a reduced amount of nicotine will also have reduced amounts of TSNAs. That is, by removing nicotine from tobacco plants, tobacco and tobacco products, one effectively removes the alkaloid substrate for TSNA formation. It was found that the reduction of nicotine in tobacco was directly related to the reduction of TSNAs. Unexpectedly, the methods described herein not only produce tobacco with a reduced addictive potential but, concomitantly, produce a tobacco that has a lower carcinogenic potential (e.g., a reduced amount of carcinogens in tobacco or mainstream or side-stream smoke).

It should be emphasized that the phrase "a reduced amount" in this context is intended to refer to an amount of nicotine and/or TSNAs in a treated or transgenic tobacco plant, tobacco or a tobacco product that is less than what would be found in a tobacco plant, tobacco or a tobacco product from the same variety of tobacco, processed in the same manner, which has not been treated or was not made transgenic for reduced nicotine and/or TSNAs. Thus, in some contexts, wild-type tobacco of the same variety that has been grown and processed in the same manner is used as a control by which to measure whether a reduction in nicotine and/or TSNAs has been obtained by the inventive methods described herein.

The amount of TSNAs (e.g., collective content of NNN, NAT, NAB, and NNK) and nicotine in wild-type tobacco varies significantly depending on the variety and the manner it is grown, harvested and cured. For example, a cured Burley tobacco leaf can have approximately 30,000 parts per million (ppm) nicotine and 8,000 parts per billion (ppb) TSNA (e.g., collective content of NNN, NAT, NAB, and NNK); a Flue-Cured leaf can have approximately 20,000 ppm nicotine and 300 ppb TSNA (e.g., collective content of NNN, NAT, NAB, and NNK); and an Oriental cured leaf can have approximately 10,000 ppm nicotine and 100 ppb TSNA (e.g., collective content of NNN, NAT, NAB, and NNK). Tobacco having a reduced amount of nicotine and/or TSNA, can have no detectable nicotine and/or TSNA (e.g., collective content of NNN, NAT, NAB, and NNK), or may contain some detectable amounts of one or more of the TSNAs and/or nicotine, so long as the amount of nicotine and/or TSNA is less than that found in tobacco of the same variety, grown under similar conditions, and cured and/or processed in the same manner. That is, cured Burley tobacco, as described herein, having a reduced amount of nicotine can have between 0 and 30,000 ppm nicotine and 0 and 8,000 ppb TSNA, desirably between 0 and 20,000 ppm nicotine and 0 and 6,000 ppb TSNA, more desirably between 0 and 10,000 ppm nicotine and 0 and 5,000 ppb TSNA, preferably between 0 and 5,000 ppm nicotine and 0 and 4,000 ppb TSNA, more preferably between 0 and 2,500 ppm nicotine and 0 and 2,000 ppb TSNA and most preferably between 0 and 1,000 ppm nicotine and 0 and 1,000 ppb TSNA. Embodiments of cured Burley leaf prepared by the methods described herein can also have between 0 and 1000 ppm nicotine and 0 and 500 ppb TSNA, 0 and 500 ppm nicotine and 0 and 250 ppb TSNA, 0 and 250 ppm nicotine and 0 and 100 ppb TSNA, 0 and 100 ppm nicotine and 0 and 50 ppb TSNA, 0 and 50 ppm nicotine and 0 and 5 ppb TSNA and some embodiments of cured Burley leaf described herein have virtually no detectable amount of nicotine or TSNA. In some embodiments above, the amount of TSNA refers to the collective content of NNN, NAT, NAB, and NNK.

Similarly, a cured Flue tobacco embodiment of the invention having a reduced amount of nicotine can have between 0 and 20,000 ppm nicotine and 0 and 300 ppb TSNA, desirably between 0 and 15,000 ppm nicotine and 0 and 250 ppb TSNA, more desirably between 0 and 10,000 ppm nicotine and 0 and 200 ppb TSNA, preferably between 0 and 5,000 ppm nicotine and 0 and 150 ppb TSNA, more preferably between 0 and 2,500 ppm nicotine and 0 and 100 ppb TSNA and most preferably between 0 and 1,000 ppm nicotine and 0 and 50 ppb TSNA. Embodiments of cured Flue tobacco, as described herein, can also have between 0 and 500 ppm nicotine and 0 and 25 ppb TSNA, 0 and 200 ppm nicotine and 0 and 10 ppb TSNA, 0 and 100 ppm nicotine and 0 and 5 ppb TSNA and some embodiments of cure Flue tobacco have virtually no detectable amount of nicotine or TSNA. In some embodiments above, the amount of TSNA refers to the collective content of NNN, NAT, NAB, and NNK.

Further, a cured Oriental tobacco embodiment having a reduced amount of nicotine can have between 0 and 10,000 ppm nicotine and 0 and 100 ppb TSNA, desirably between 0 and 7,000 ppm nicotine and 0 and 75 ppb TSNA, more desirably between 0 and 5,000 ppm nicotine and 0 and 50 ppb TSNA, preferably between 0 and 3,000 ppm nicotine and 0 and 25 ppb TSNA, more preferably between 0 and 1,500 ppm nicotine and 0 and 10 ppb TSNA and most preferably between 0 and 500 ppm nicotine and no detectable TSNA. Embodiments of cured Oriental tobacco can also have between 0 and 250 ppm nicotine and no detectable TSNA and some embodiments of cured Oriental tobacco have virtually no detectable amount of nicotine or TSNA. In some embodiments above, the amount of TSNA refers to the collective content of NNN, NAT, NAB, and NNK.

Some embodiments comprise cured tobaccos (e.g., Burley, Flue, or Oriental) with reduced amounts of nicotine as compared to control varieties, wherein the amount of nicotine is less than about 2 mg/g, 1 mg/g, 0.75 mg/g, 0.6 mg/g, 0.5 mg/g or desirably less than about 0.1 mg/g, and preferably less than 0.08 mg/g, 0.07 mg/g, 0.06 mg/g, 0.05 mg/g, 0.04 mg/g, 0.03 mg/g, 0.02 mg/g, 0.01 mg/g. Tobacco products made from these reduced nicotine and TSNA tobaccos are also embodiments. The term "tobacco products" include, but are not limited to, smoking materials (e.g., cigarettes, cigars, pipe tobacco), snuff, chewing tobacco, gum, and lozenges.

In some contexts, the phrase "reduced amount of nicotine and/or TSNAs" refers to the tobacco plants, cured tobacco, and tobacco products, as described herein, which have less nicotine and/or TSNAs (e.g., the collective content of NNN, NAT, NAB, and NNK) by weight than the same variety of tobacco grown, processed, and cured in the same way. For example, wild type cured tobacco can have has approximately 1-4% dry weight nicotine and approximately 0.2%-0.8% dry weight TSNA depending on the manner it was grown, harvested and cured. A typical cigarette has between 2-11 mg of nicotine and approximately 5.0 µg of TSNAs. Thus, the tobacco plants, tobacco and tobacco products of the invention can have, in dry weight for example, less than 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% nicotine and less than 0.01%, 0.015%, 0.02%, 0.025%, 0.03%, 0.035%, 0.04%, 0.045%, 0.05%, 0.055%, 0.06%, 0.065%, 0.07%, 0.075%, and 0.08% TSNA (e.g., collective content of NNN, NAT, NAB, and NNK).

Alternatively, a cigarette of the invention can have, for example, less than 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, 1.0 mg, 1.1 mg, 1.15 mg, 1.2 mg, 1.25 mg, 1.3 mg, 1.35 mg, 1.4 mg, 1.45 mg, 1.5 mg, 1.55 mg, 1.6 mg, 1.65 mg, 1.7 mg, 1.75 mg, 1.8 mg, 1.85 mg, 1.9 mg, 1.95 mg, 2.0 mg, 2.1 mg, 2.15 mg, 2.2 mg, 2.25 mg, 2.3 mg, 2.35 mg, 2.4 mg, 2.45 mg, 2.5 mg, 2.55 mg, 2.6 mg, 2.65 mg, 2.7 mg, 2.75 mg, 2.8 mg, 2.85 mg, 2.9 mg, 2.95 mg, 3.0 mg, 3.1 mg, 3.15 mg, 3.2 mg, 3.25 mg, 3.3 mg, 3.35 mg, 3.4 mg, 3.45 mg, 3.5 mg, 3.55 mg, 3.6 mg, 3.65 mg, 3.7 mg, 3.75 mg, 3.8 mg, 3.85 mg, 3.9 mg, 3.95 mg, 4.0 mg, 4.1 mg, 4.15 mg, 4.2 mg, 4.25 mg, 4.3 mg, 4.35 mg, 4.4 mg, 4.45 mg, 4.4 mg, 4.45 mg, 4.5 mg, 4.55 mg, 4.6 mg, 4.65 mg, 4.7 mg, 4.75 mg, 4.8 mg, 4.85 mg, 4.9 mg, 4.95 mg, 5.0 mg, 5.5 mg, 5.7 mg, 6.0 mg, 6.5 mgmg, 6.7 mg, 7.0 mg, 7.5 mg, 7.7 mg, 8.0 mg, 8.5 mg, 8.7 mg, 9.0 mg, 9.5 mg, 9.7 mg, 10.0 mg, 10.5 mg, 10.7 mg, and 11.0 mg nicotine and less than 0.001 ug, 0.002 ug, 0.003 ug, 0.004 ug, 0.005 ug, 0.006 ug, 0.007 ug, 0.008 ug, 0.009 ug, 0.01 ug, 0.02 ug, 0.03 ug, 0.04 ug, 0.05 ug, 0.06 ug, 0.07 ug, 0.08 ug, 0.09 ug, 0.1 ug, 0.15 ug, 0.2 ug, 0.25 ug, 0.3 ug, 0.336 ug, 0.339 ug, 0.345 ug, 0.35 ug, 0.375 ug, 0.4 ug, 0.414 ug, 0.45 ug, 0.5 ug, 0.515 ug, 0.55 ug, 0.555 ug, 0.56 ug, 0.578 ug, 0.58 ug, 0.6 ug, 0.611 ug, 0.624 ug, 0.65 ug, 0.7 ug, 0.75 ug, 0.8 ug, 0.85 ug, 0.9 ug, 0.95 ug, 1.0 ug, 1.1 ug, 1.114 ug, 1.15 ug, 1.2 ug, 1.25 ug, 1.3 ug, 1.35 ug, 1.4 ug, 1.45 ug, 1.5 ug, 1.55 ug, 1.6 ug, 1.65 ug, 1.7 ug, 1.75 ug, 1.8 ug, 1.85 ug, 1.9 ug, 1.95 ug, 2.0 ug, 2.1 ug, 2.15 ug, 2.2 ug TSNA (e.g., collective content of NNN, NAT, NAB, and NNK).

Unexpectedly, it was discovered that several methods for reducing endogenous levels of nicotine in a plant are suitable for producing tobacco that is substantially free of nitrosamines, especially TSNAs. Any method that reduces levels of other alkaloids, including norniticotine, is likewise suitable for producing tobacco substantially free of nitrosamines, especially TSNAs. As described this invention comprises a method of reducing the carcinogenic potential of a tobacco product comprising providing a cured tobacco as described herein and preparing a tobacco product from said cured tobacco, whereby the carcinogenic potential of said tobacco product is thereby reduced. Other embodiments of the invention include the use of the cured tobacco described herein for the preparation of a tobacco product that contains reduced amounts of carcinogens as compared to control varieties and/or that reduces the amount of a TSNA or TSNA metobolite in a human that uses tobacco.

In some embodiments, for example, the tobacco smoking products described herein reduce the carcinogenic potential of side stream or main stream tobacco smoke in humans exposed to said side stream or main stream tobacco smoke. By providing the genetically modified cured tobacco described herein in a product that undergoes pyrolysis, for example, the side stream and/or main stream smoke produced by said product comprises a reduced amount of TSNAs and/or nicotine. Thus, the cured tobacco described herein can be used to prepare a tobacco smoking product that comprises a reduced amount of TSNAs in side stream and/or mainstream smoke.

In some embodiments, for example, the collective content of NNN, NAT, NAB, and NNK in the mainstream or side stream smoke from a tobacco product comprising the genetically modified tobacco described herein is between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g. That is, some embodiments are genetically modified Burley tobacco, wherein the side stream or mainstream smoke produced from a tobacco product comprising said Burley tobacco has a collective content of NNN, NAT, NAB, and NNK in the mainstream or side stream smoke between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g.

Other embodiments concern genetically modified Flue tobacco, wherein the sidestream or mainstream smoke produced from a tobacco product comprising said Flue tobacco has a collective content of NNN, NAT, NAB, and NNK in the mainstream or side stream smoke between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g.

More embodiments concern genetically modified Oriental tobacco, wherein the sidestream or mainstream smoke produced from a tobacco product comprising said Oriental tobacco has a collective content of NNN, NAT, NAB, and NNK in the mainstream or side stream smoke between about 0-5.0 µg/g, 0-4.0 µg/g, 0-3.0 µg/g, 0-2.0 µg/g, 0-1.5 µg/g, 0-1.0 µg/g, 0-0.75 µg/g, 0-0.5 µg/g, 0-0.25 µg/g, 0-0.15 µg/g, 0-0.1 µg/g, 0-0.05 µg/g, 0-0.02 µg/g, 0-0.015 µg/g, 0-0.01 µg/g, 0-0.005 µg/g, 0-0.002 µg/g, or 0-0.001 µg/g.

A preferred method of producing tobacco having a reduced amount of nicotine and TSNAs, involves RNA interference (RNAi) directed at reducing the levels of nicotine and/or nornicotine or other alkaloids. Any enzyme involved in the nicotine synthesis pathway can be a suitable target for genetic engineering to reduce levels of nicotine and, optionally, levels of other alkaloids including nornicotine. Suitable targets for genetic engineering to produce tobacco having a reduced amount of nicotine and/or nitrosamines, especially TSNAs, include but are not limited to putrescene N-methyltransferase, N-methylputrescene oxidase, ornithine decarboxylase, S-adenosylmethionine synthetase, NADH dehydrogenase, phosphoribosylanthranilate isomerase, quinolate phosphoribosyl transferase (QPTase) or a combination of any of the above targets. Additionally, enzymes that regulate the flow of precursors into the nicotine synthesis pathway are suitable targets for genetic engineering to produce tobacco with a reduced amount of nicotine and nitrosamines, especially TSNAs. Suitable methods of genetic engineering are known in the art and include, for example, the use of antisense and sense suppression technology to reduce or eliminate the production of enzymes, the use of interfering RNA molecules (gene silencing) as described herein to reduce or eliminate the expression of gene products, and the use of random or targeted mutagenesis to disrupt gene function, for example, using T-DNA insertion or EMS mutagenesis.

Inhibition of gene expression refers to the absence or reduction in the level of polypeptide and/or mRNA gene product. Some embodiments relate to approaches to inhibit the expression of one or more genes involved in the biosynthesis of nicotine by genetically modifying a plant cell, such as a tobacco cell, by providing the cell with an inhibitory nucleic acid that reduces or eliminates the production of a gene product involved in nicotine biosynthesis. Preferred inhibitory nucleic acids include, but are not limited to, interfering RNAs, antisense nucleic acids and catalytic RNAs.

RNA interference and gene silencing are terms that are used to describe a process by which the expression of a gene product is inhibited by an interfering RNA molecule. Interfering RNA molecules are double-stranded RNAs (dsRNA) that are expressed in or otherwise introduced into a cell. The dsRNA molecules may by of any length, however, short dsRNA constructs are commonly used. Such constructs are known as small interfering RNAs (siRNA), and can be as small as 21-23 bp in length.

RNA interference is exhibited by nearly every eukaryote and is thought to function by a highly conserved mechanism (Dillin, A. PNAS, 100:6289-91). As with antisense inhibition of gene expression, inhibition mediated by RNA interference is gene specific. However, in contrast to antisense-mediated inhibition, inhibition mediated by interfering RNA appears to be inherited (Dillin, A. PNAS, 100:6289-91). Without being bound by theory, it is believed that specificity is achieved through nucleotide sequence interaction between complementary portions of a target mRNA and the interfering RNA. The target mRNA is selected based on the specific gene to be silenced. In particular, the target mRNA, corresponds to the sense strand of the gene to be silenced. An interfering RNA, such as a dsRNA or an siRNA, comprises an RNA duplex, which includes a first strand that is substantially similar or identical to at least a portion of the nucleotide sequence of the target mRNA, and a second strand having a nucleotide sequence that is complementary or substantially complementary to the first strand.

When used herein with reference to an RNA duplex of the interfering RNA, it will be appreciated that the terms "first strand" and "second strand" are used in a relative sense. For example, the first strand of an RNA duplex can be selected to comprise either a nucleotide sequence substantially similar or identical to at least a portion of the nucleotide sequence of the target mRNA or a nucleotide sequence that is complementary or substantially complementary to at least a portion of the nucleotide sequence of the target mRNA. If the first strand is selected to be substantially similar or identical to at least a portion of the nucleotide sequence of the target mRNA, then the second strand will be complementary to at least a portion of the target mRNA because it is complementary to the first strand. If the first strand is selected to be complementary or substantially complementary to at least a portion of the target mRNA, then the second strand will be substantially similar or identical to at least a portion of the nucleotide sequence of the target mRNA because it is complementary to the first strand.

As used herein with reference to nucleic acids, "portion" means at least or equal to 5 consecutive nucleotides, at least 6 consecutive nucleotides, at least 7 consecutive nucleotides, at least 8 consecutive nucleotides, at least 9 consecutive nucleotides, at least 10 consecutive nucleotides, at least 11 consecutive nucleotides, at least 12 consecutive nucleotides, at least 13 consecutive nucleotides, at least 14 consecutive nucleotides, at least 15 consecutive nucleotides, at least 16 consecutive nucleotides, at least 17 consecutive nucleotides, at least 18 consecutive nucleotides, at least 19 consecutive nucleotides, at least 20 consecutive nucleotides, at least 21 consecutive nucleotides, at least 22 consecutive nucleotides, at least 23 consecutive nucleotides, at least 24 consecutive nucleotides, at least 25 consecutive nucleotides, at least 30 consecutive nucleotides, at least 35 consecutive nucleotides, at least 40 consecutive nucleotides, at least 45 consecutive nucleotides, at least 50 consecutive nucleotides, at least 60 consecutive nucleotides, at least 70 consecutive nucleotides, at least 80 consecutive nucleotides, at least 90 consecutive nucleotides, at least 100 consecutive nucleotides, at least 125 consecutive nucleotides, at least 150 consecutive nucleotides, at least 175 consecutive nucleotides, at least 200 consecutive nucleotides, at least 250 consecutive nucleotides, at least 300 consecutive nucleotides, at least 350 consecutive nucleotides, at least 400 consecutive nucleotides, at least 450 consecutive nucleotides, at least 500 consecutive nucleotides, at least 600 consecutive nucleotides, at least 700 consecutive nucleotides, at least 800 consecutive nucleotides, at least 900 consecutive nucleotides, at least 1000 consecutive nucleotides, at least 1200 consecutive nucleotides, at least 1400 consecutive nucleotides, at least 1600 consecutive nucleotides, at least 1800 consecutive nucleotides, at least 2000 consecutive nucleotides, at least 2500 consecutive nucleotides, at least 3000 consecutive nucleotides, at least 4000 consecutive nucleotides, at least 5000 consecutive nucleotides or greater than at least 5000 consecutive nucleotides. In some preferred embodiments, a portion of a nucleotide sequence is between 20 and 25 consecutive nucleotides. In other preferred embodiments, a portion of a nucleotide sequence is between 21 and 23 consecutive nucleotides. In some embodiments of the present invention, a portion of a nucleotide sequence includes the full-length coding sequence of the gene or the target mRNA.

Some preferred interfering RNAs that are described herein comprise an RNA duplex, which comprises a nucleotide sequence that is substantially similar or identical to at least a portion of the coding strand of a gene involved in nicotine biosynthesis. Although nucleic acid sequences that are substantially similar or identical to at least a portion of the coding strand of the target gene involved in nicotine biosynthesis are preferred, it will be appreciated that nucleotide sequences with insertions, deletions, and single point mutations relative to the target sequence are also effective for inhibition of gene expression. Sequence identity may determined by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the interfering RNA and a portion of the target gene is preferred. In especially preferred embodiments, at least about 21 to about 23 contiguous nucleotides in the target gene are greater than 90% identical to a sequence present in the interfering RNA.

In other embodiments, the duplex region of the RNA may be defined functionally as including a nucleotide sequence that is capable of hybridizing with a portion of the target gene transcript. Exemplary hybridization conditions are 400 mM NaCl, 40 mM PIPES pH 6.4, 1 mM EDTA, 50° C. or 70° C. hybridization for 12-16 hours; followed by washing in 2×SSC 0.1% SDS at 37° C., 50° C., or 65° C.

As described above, interfering RNAs disclosed herein comprise a sequence that is complementary to at least a portion of the sense strand of a gene encoding a target mRNA, which produces a polypeptide that is involved in nicotine biosynthesis. Two preferred targets are the products of the quinolate phosphoribosyltransferase (QTPase) gene and the putrescene N-methyltransferase (PMTase) gene. However, it will be appreciated that interfering RNAs specific for other gene products or combinations or gene products involved in nicotine biosynthesis or the synthesis of other components in tobacco are contemplated. For example, additional gene products involved in nicotine biosynthesis include, but are not limited to, N-methylputrescene oxidase, ornithine decarboxylase, S-adenosylmethionine synthetase, NADH dehydrogenase, and phosphoribosylanthranilate isomerase. Additionally, the interfering RNAs described herein can comprise a plurality nucleotide sequences that are each complementary to different portions of the sense strand of a gene involved in nicotine biosynthesis. Alternatively, the interfering RNAs described herein can comprise a plurality nucleotide sequences that are each complementary to at least a portion of the sense strands of different genes involved in nicotine biosynthesis.

In preferred embodiments, the interfering RNAs described herein comprise at least one region of double-stranded RNA (duplex RNA). This duplex RNA can range from about 10 bp in length to about 10,000 bp in length. In some embodiments, the duplex RNA ranges from about 15 bp in length to about 1500 bp in length. In other embodiments, the duplex RNA ranges from about 20 bp in length to about 1200 bp in length. In still other embodiments, the duplex RNA ranges from about 21 bp in length to about 23 bp in length. In a preferred embodiment, the duplex RNA has a length of 22 bps. Short regions of duplex RNA are often designated siRNA, whereas longer regions of RNA duplex are often termed dsRNA. In some embodiments of the present invention, the interfering RNA duplex region is a dsRNA. In other embodiments, the interfering RNA duplex region is an siRNA. In a preferred embodiment, the duplex region about the length of the coding sequence of a target mRNA encoding a polypeptide involved in nicotine biosynthesis.

Interfering RNAs described herein can be generated using a variety of techniques. For example, an interfering RNA can be generated in a host cell in vivo by providing the cell with one or more a nucleic acid constructs that comprise the nucleic acids necessary to encode the strands of a double-stranded RNA. Such constructs can be included in various types of vectors. Exemplary vectors contemplated herein include, but are not limited to, plasmids, viral vectors, viroids, replicable and nonreplicable linear DNA molecules, replicable and nonreplicable linear RNA molecules, replicable and nonreplicable circular DNA molecules and replicable and nonreplicable circular RNA molecules. Preferred vectors include plasmid vectors, especially vector systems derived from the *Agrobacterium* Ti plasmid.

In some embodiments, both strands of the double-stranded region of the interfering RNA can be encoded by a single vector. In such cases, the vector comprises a first promoter operably linked to a first nucleic acid which is substantially similar or identical to at least a portion of the target mRNA. The vector also comprises a second promoter operably linked to a second nucleic acid, which is complementary or substantially to the first nucleic acid.

Another type of single vector construct, which can be used to generate interfering RNA, encodes a double-stranded RNA hairpin. In such embodiments, the vector comprises a promoter operably linked to a nucleic acid that encodes both strands of the duplex RNA. The first nucleotide sequence, which encodes the strand that is substantially similar or identical to at least a portion of the target mRNA, is separated from the second nucleotide sequence, which encodes a strand complementary or substantially complementary to the first strand, by a region of nucleotide sequence that does not substantially hybridize with either of the strands. This nonhybridizing region permits the RNA sequence transcribed from the vector promoter to fold back on itself, thereby permitting the complementary RNA sequences to hybridize so as to produce an RNA hairpin. Vectors comprising a plurality of nucleic acids, each of which encode both strands of the duplex RNA are also contemplated.

Other embodiments of the present invention relate to multiple vector systems for the production of interfering RNA. In one example, a multiple vector system is used to produce a single interfering RNA that is specific for a single gene product involved in nicotine biosynthesis. In such embodiments, at least two vectors are used. The first vector comprises a promoter operably linked to a first nucleic acid that encodes a first strand of the RNA duplex that is present in the interfering RNA. The second vector comprises a promoter operably linked to a second nucleic acid that encodes the second strand of the RNA duplex, which is complementary to the first strand.

Other multiple vector systems are combinations of vectors, wherein each vector in the system encodes a different interfering RNA. Each of the interfering RNAs are specific for different gene products involved in nicotine biosynthesis. In some embodiments, the vectors in a multiple vector system can encode different interfering RNAs that are specific to different portions of a single gene product involved in nicotine biosynthesis.

It will be appreciated that the promoters used in the above-described vectors can either be constitutive or regulatable. Constitutive promoters are promoters that are always expressed. The constitutive promoters selected for use in the above-described vectors can range from weak promoters to strong promoters depending on the desired amount of interfering RNA to be produced. Regulatable promoters are promoters for which the desired level of expression can be controlled. Ali example of a regulatable promoter is an inducible promoter. Using an inducible promoter in the above-described vector constructs permits expression of a wide range of concentrations of interfering RNA inside a cell.

It will also be appreciated that there is no requirement that the same or same types of promoters be used in vectors or multiple vector systems that comprise a plurality of promoters. For example, in some vectors or vector systems, a first promoter, which controls the expression of the first interfering RNA strand, can be an inducible promoter, whereas the second promoter, which controls the expression of the second RNA strand, can be a constitutive promoter. This same principal can also be illustrated in a multiple vector system. For example, a multiple vector system may have three vectors each of which includes one or more different types of promoters. Such a system can include, for example, a first vector having repressible promoter that controls the expression of an interfering RNA specific for a first gene product involved in nicotine biosynthesis, a second vector having a constitutive promoter that controls the expression of an interfering RNA specific for a second gene product involved in nicotine biosynthesis and a third vector having an inducible promoter that controls the expression of an interfering RNA specific for a third gene product involved in nicotine biosynthesis.

In other embodiments, interfering RNAs can be produced synthetically and introduced into a cell by methods known in the art. Synthetic interfering RNAs can include a variety of RNA molecules, which include, but are not limited to, nucleic acids having at least one region of duplex RNA. The duplex RNA in such molecules can comprise, for example, two antiparallel RNA strands that form a double-stranded RNA having flush ends, two antiparallel RNA strands that form a double-stranded RNA having at least one end that forms a hair pin structure, or two antiparallel RNA strands that form a double-stranded RNA, wherein both ends form a hair pin structure. In some embodiments, synthetic interfering RNAs comprise a plurality of RNA duplexes.

The regions of RNA duplex in synthetic interfering RNAs can range from about 10 bp in length to about 10,000 bp in length. In some embodiments, the duplex RNA ranges from about 15 bp in length to about 1500 bp in length. In other embodiments, the duplex RNA ranges from about 20 bp in length to about 1200 bp in length. In still other embodiments, the duplex RNA ranges from about 21 bp in length to about 23 bp in length. In a preferred embodiment, the duplex RNA has a length of 22 bps. In preferred embodiments, synthetic interfering RNAs are siRNAs. In another preferred embodiment, the synthetic interfering RNA is an siRNA specific for the coding sequence of a target mRNA encoding a polypeptide involved in nicotine biosynthesis.

Also contemplated herein are micro ribonucleic acids (miRNAs), and derivatives thereof (See U.S. Patent Application Publication No. 20050059005, herein expressly incorporated by reference in its entirety). miRNAs can be any of a variety of sizes known in the art, including single-stranded nucleic acids 10-40 nucleotides in length, 15-30 nucleotides in length, or 19-23 nucleotides in length. miRNAs also can be larger, such as single-stranded nucleic acids 50-300 nucleotides in length, 60-200 nucleotides in length, or 70-100 nucleotides in length; typically larger miRNAs can form a hairpin structure and can serve as substrates for cleavage by double-stranded ribonuclease. Also contemplated herein are double stranded nucleic acids similar in molecular mass to the aforementioned miRNAs that can form hairpin structures and can be cleaved by double-stranded ribonuclease. Further provided herein are large nucleic acids, at least 300, 500 or 700 nucleotides in length, and up to 700, 1000, 1500, 2000, or more nucleotides in length; typically, these large nucleic acids can be cleaved by double-stranded specific ribonucleases, including nuclear ribonucleases, to form on or more single-stranded nucleic acids that can form hairpin structures and can be cleaved by double-stranded ribonuclease.

In some embodiments, larger RNAs can be processed, for example in the cell nucleus, into hairpin RNAs of 70-100 nt by a dsRNA-specific ribonuclease such as Drosha. Hairpin RNAs can be transported to the cytoplasm via cellular mechanisms, for example a transportin-5 dependent mechanism, where the miRNA can be digested by a second, double-strand specific ribonuclease, such as Dicer, to produce a resulting 19-23 mer miRNA. This 19-23 mer miRNA can be bound by a complex that is similar to the RNA-Induced Silencing Complex (RISC) that participates in RNA interference (RNAi). In some embodiments, the complex-bound, single-stranded can miRNA bind specific mRNAs through sequences that are significantly, though not completely, complementary to the mRNA. Typically, the miRNA is at least 75%, at least 80%, at least 85%, at least 90%, at least 95% complementary to the targeted mRNA nucleotide sequence). In other embodiments, the miRNA is fully complementary or nearly fully complementary to the targeted mRNA sequence. For example, the miRNA can be at least 96%, at least 97%, at least 98% or at least 99% complementary to the targeted mRNA nucleotide sequence In some instances, the miRNA-bound mRNA remains untranslated, resulting in reduced expression of the corresponding gene. In other instances, the miRNA can cause degradation of the bound mRNA Accordingly, mrRNAs as contemplated herein, can be used in regulation of gene expression, most typically regulation of the production of polypeptide from the mRNA.

Some aspects of the present invention relate to interfering nucleic acids that are not comprised entirely of RNA. Still other aspects relate to interfering nucleic acids that do not comprise any RNA. Such interfering nucleic acids are synthetic interfering RNA analogs. These analogs substantially mimic the specificity and activity of interfering RNA from which they are modeled; however, they typically include additional properties which make their use desirable. For example, one or both strands of the interfering nucleic acid may contain one or more nonnatural nucleotide bases that improve the stability of the molecule, enhance that affinity of the molecule for the target mRNA and/or enhance cellular uptake of the molecule. Other modifications are also contemplated. For example, an interfering nucleic acid can include one or more nucleic acid strands composed of naturally-occurring nucleobases, sugars and covalent internucleoside (backbone) linkages as well as non-naturally-occurring nucleobases, sugars and covalent internucleoside linkages.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming nucleic acids, the phosphate groups covalently link adjacent nucleosides to one another to form a linear polymeric compound. In turn the respective ends of this linear polymeric structure can be further joined to form a circular structure. Within the nucleic acid structure, the phosphate groups are commonly referred to as forming the internucleoside backbone of the oligonucleotide. The normal linkage or backbone of RNA and DNA is a 3' to 5' phosphodiester linkage.

Specific examples of interfering nucleic acids useful in certain embodiments include one or more nucleic acid strands containing modified backbones or non-natural internucleoside linkages. As used herein, nucleic acids having modified backbones include those that retain a phosphorus atom in the backbone and those that do not have a phosphorus atom in the backbone.

In some embodiments, modified nucleic acid backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain nucleic acids having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

In some embodiments, modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other embodiments, the interfering nucleic acid can comprise one or more mimetic regions, wherein both the sugar and the internucleoside linkage, i.e., the backbone, of the nucleotide units are replaced with novel groups. In such embodiments, the base units are maintained for hybridization with an appropriate nucleic acid target compound. One such compound, a mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., Science, 1991, 254, 1497-1500.

In still other embodiments, interfering nucleic acids may include nucleic acid strands having phosphorothioate backbones and/or heteroatom backbones. Modified interfering nucleic acids may also contain one or more substituted sugar moieties. In some embodiments, the interfering nucleic acids comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m CH_3$, $O(CH_2)_nOCH_3$, $O(CH_2)_nNH_2$, $O(CH_2)_nCH_3$, $O(CH_2)_n ONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower allyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy (2' $OCH_2CH_2OCH_3$, also known as 2'-O-(2-methoxyethyl) or 2'-MOE) (Martin et al., Helv. Chim. Acta, 1995, 78, 486-504).

An embodiment of the present invention also includes the use of Locked Nucleic Acids (LNAs) to generate interfering nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne (—$CH_2$—)n group bridging the 2' oxygen atom and the 4' carbon atom wherein n is 1 or 2. LNAs and preparation thereof are described in WO 98/39352 and WO 99/14226, the disclosures of which are incorporated herein by reference in their entireties.

Other modifications include 2'-methoxy (2'-O—$CH_3$), 2'-aminopropoxy (2'-$OCH_2CH_2CH_2NH_2$), 2'-allyl (2'-$CH_2$—$CH=CH_2$), 2'-O-allyl (2'-O—$CH_2$—$CH=CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Interfering nucleic acids may also have sugar mimetics such as cyclobutyl moieties in place of the pentofuranosyl sugar.

The interfering nucleic acids contemplated herein may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993, the disclosures of which are incorporated herein by reference in their entireties. Certain of these nucleobases are particularly useful for increasing the binding affinity of the interfering nucleic acids described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Another modification of the interfering nucleic acids described herein involves chemically linking to at least one of the nucleic acid strands one or more moieties or conjugates which enhance the activity, cellular distribution or cellular uptake of the of the interfering nucleic acid. The interfering nucleic acids can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of nucleic acids, and groups that enhance the pharmacokinetic properties of such molecules. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve interfering nucleic acid uptake, enhance its resistance to degradation, and/or strengthen sequence-specific hybridization with target molecules. Groups that enhance the pharmacokinetic properties, in the context of this invention, include groups that improve the uptake, distribution, metabolism or excretion of the interfering nucleic acid. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyloxycholesterol moiety (Crooke et al., J. Pharmacol. Exp. Ther., 1996, 277, 923-937).

As described above, it is not necessary for all positions in a given compound to be uniformly modified, and in fact, more than one of the aforementioned modifications may be incorporated in a single compound or even at a single nucleoside within an nucleic acid. The methods described herein also contemplate the use of interfering nucleic acids which are chimeric compounds. "Chimeric" interfering nucleic acid compounds or "chimeras," as used herein, are interfering nucleic acid compounds, which contain two or more chemically distinct regions, each made up of at least one monomer unit, i.e., a nucleotide in the case of a nucleic acid compound. These interfering nucleic acids typically contain at least one region wherein the nucleic acid is modified so as to confer upon the interfering nucleic acid increased resistance to nuclease degradation, increased cellular uptake, and/or increased binding affinity for the target nucleic acid. An additional region of the nucleic acid may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby contributes further to the inhibition of gene expression by the interfering nucleic acid.

The above-described interfering nucleic acids may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives. The interfering nucleic acid compounds for use with the methods described herein encompass any pharmaceutically acceptable salts, esters, or salts of such esters, or any other compound. Although terms, such as interfering RNA, RNAi, dsRNA and siRNA, are used throughout the specification, it will be appreciated that in the context of synthetically produced interfering nucleic acids, that such terms are meant to include interfering nucleic acids of all types, including those which incorporate modifications, such as those described above.

Some embodiments of the present invention relate to methods of reducing or eliminating the expression of one or more target genes involved in nicotine biosynthesis. Target genes that are involved in nicotine biosynthesis are expressed through the transcription a first gene product, the target mRNA, which is then translated to produce a second gene product, the target polypeptide. Thus, reduction or elimination of the expression of one or more target genes results in the reduction or elimination of one or more target mRNAs and/or target polpypeptides. Target polypeptides involved in nicotine biosynthesis include, for example, putrescene N-methyltransferase, N-methylputrescene oxidase, ornithine decarboxylase, S-adenosylmethionine synthetase, NADH dehydrogenase, phosphoribosylanthranilate isomerase, and quinolate phosphoribosyl transferase (QPTase). In a preferred embodiment, the expression of the QPTase enzyme is inhibited.

Reduction of the expression of one or more target genes and/or target gene products that are involved in nicotine biosynthesis leads to a reduction in the amount of nicotine produced in tobacco. In certain embodiments, the expression of one or more target gene products involved in nicotine biosynthesis is eliminated. Elimination of such target gene products can result in the elimination of nicotine biosynthesis, thereby reducing the amount of nicotine present in tobacco to levels below the detection limit of methods commonly used to detect nicotine. Reduction of the amount of nicotine present in tobacco can lead to a reduction in the amount of TSNAs produced in the tobacco. In some embodiments, the amount of TSNA present in tobacco is reduced to levels below the detection limit of methods commonly used to detect TSNAs.

The reduction in or elimination of the expression of target genes or target gene products involved in nicotine biosynthesis is achieved by providing an interfering RNA specific to one or more such target genes to a tobacco cell, thereby producing a genetically modified tobacco cell. The interfering RNA can be provided as a synthetic double-stranded RNA, or alternatively, as a nucleic acid construct capable of encoding the interfering RNA. Synthetic double-stranded interfering RNAs are taken up by the cell directly whereas interfering RNAs encoded by a nucleic acid construct are expressed from the construct subsequent to the entry of the construct inside the cell. The reduction in or elimination of the expression of the target genes and/or the target gene products is mediated by the presence of the interfering RNA inside the cell.

In general, the interfering RNAs that are produced inside the cell, whether expressed from a nucleic acid construct or provided as synthetic double-stranded RNA molecules, include an RNA duplex having a first and second strand. At least a portion the first strand of the duplex is substantially similar or identical to at least a portion of a target mRNA or a target gene involved in nicotine biosynthesis. Correspondingly, at least a portion of the second strand of the duplex is complementary or substantially complementary to the first strand, and thus, at least a portion of the second strand is complementary or substantially complementary to at least a portion of the mRNA encoded by the target gene. In some embodiments of the present invention, the interfering RNA can comprise a first strand that is substantially similar or identical to the entire coding sequence of the target gene or target mRNA involved in nicotine biosynthesis and a second strand complementary or substantially complementary to the first strand.

The reduction in or elimination of the expression of genes and/or gene products involved in nicotine biosynthesis can be characterized by comparing the amount of nicotine produced genetically modified cells, with the amount of nicotine produced in cells that have not been genetically modified. Alternatively, such reduction in or elimination of gene expression can be characterized by genetically analyzing plant cells so as to determine the level of mRNA present in the genetically modified plant cell as compared to a non-modified plant cell. Depending on the assay, quantitation of the amount of gene expression allows one to determine a degree of reduction in gene expression, which can be greater than 10%, 33%, 50%, 90%, 95% or 99% as compared to an untreated cell. As with nicotine, the reduction in or elimination of TSNA production in tobacco can be characterized by comparing the amount of TSNAs produced genetically modified cells, with the amount of TSNAs produced in cells that have not been genetically modified.

By way of example, tobacco having reduced amounts of nicotine and TSNAs is generated from a tobacco plant that is created by exposing at least one tobacco cell of a selected tobacco variety, such as LA Burley 21, to a nucleic acid construct comprising a promoter that is operable in a plant cell, wherein the promoter controls the expression of a RNA comprising both strands of a duplex interfering RNA. For example, the RNA that is expressed comprises a first nucleotide sequence that is substantially similar or identical to at least a portion of an mRNA or at least a portion of the coding strand of a gene that is involved in nicotine biosynthesis. This first nucleotide sequence is followed by a non-complementary sequence that is involved in hairpin formation, and then, a second nucleotide sequence that is complementary or substantially complementary to at least a portion of the first nucleotide sequence. The exposed tobacco cell is then transformed with the nucleic acid construct. Cells that are successfully transformed are selected using either negative selection or positive selection techniques and at least one tobacco plant is regenerated from transformed cells. The regenerated tobacco plant or portion thereof is preferably analyzed to determine the amount of nicotine and/or TSNAs present and these values can be compared to the amount of nicotine and/or TSNAs present in a control tobacco plant or portion thereof. Preferably the transformed and control tobacco plants are of the same variety.

In some embodiments, a cDNA sequence encoding a plant quinolate phosphoribosyl transferase (QPTase) is used (See Example 12). As QPTase activity is strictly correlated with nicotine content, construction of transgenic tobacco plants in which QPTase levels are lowered in the plant roots (compared to levels in wild-type plants) result in plants having reduced levels of nicotine in the leaves. Embodiments of the invention provide methods and nucleic acid constructs for producing such transgenic plants, as well as, the transgenic plants themselves. Such methods include the expression of an interfering RNA, which lowers the amount of QPTase in tobacco roots. Other embodiments include the expression of an interfering RNA, which lowers the amount of any QPTase that may be present in tobacco leaves, stems and/or other tobacco tissues.

Some embodiments also concern transgenic plant cells comprising one or more interfering RNAs that are capable of reducing or eliminating the expression of one or more target genes and/or target gene products involved in nicotine biosynthesis. As described above, an appropriate interfering RNA comprises a duplex RNA that comprises a first strand that is substantially similar or identical to at least a portion of a target gene or target mRNA, which encodes a gene product involved in nicotine biosynthesis. The RNA duplex also comprises a second strand that is complementary or substantially complementary to the first strand.

The interfering RNA or nucleic acid construct comprising the interfering RNA can be introduced into the plant cell in any suitable manner. Plant cells possessing stable interfering RNA activity, for example, by having a nucleic acid construct stably integrated into a chromosome, can be used to regenerate whole plants using methods known in the art. As such, some aspects of the present invention relate to plants, such as tobacco plants, transformed with one or more nucleic acid constructs and/or vectors which encode at least one interfering RNA that is capable of reducing or eliminating the expression of a gene product involved in nicotine biosynthesis. Transgenic tobacco cells and the plants described herein are characterized in that they have a reduced amount of nicotine and/or TSNA as compared to unmodified or control tobacco cells and plants.

The tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the low nicotine and/or TSNA tobacco described herein can be processed and blended with conventional tobacco so as to create a wide-range of tobacco products with varying amounts of nicotine and/or nitrosamines. These blended tobacco products can be used in tobacco product cessation programs so as to slowly move a consumer from a high nicotine and TSNA product to a low nicotine and TSNA product. Some embodiments of the invention comprise a tobacco use cessation kit, comprising two or more tobacco products with different levels of nicotine and/or nitrosamines. For example, a smoker can begin the program smoking blended cigarettes having 1-2 mg of nicotine and 0.2 µg of nitrosamine, gradually move to smoking cigarettes with 0.75 mg of nicotine and 0.1 µg of nitrosamine, followed by cigarettes having 0.5 mg nicotine and 0.1 µg nitrosamine, followed by cigarettes having 0.1 mg nicotine and 0.05 µg nitrosamine, followed by cigarettes having 0.05 mg nicotine and no detectable TSNA until the consumer decides to smoke only the cigarettes having virtually no nicotine and nitrosamines or quitting smoking altogether. Accordingly, the blended cigarettes described herein provide the basis for an approach to reduce the carcinogenic potential in a human in a step-wise fashion. The components of the tobacco use cessation kit described herein may include other tobacco products, including but not limited to, smoking materials (e.g., cigarettes, cigars, pipe tobacco), snuff, chewing tobacco, gum, and lozenges.

Gene silencing has been employed in several laboratories to create transgenic plants characterized by lower than normal amounts of specific gene products. As used herein, "exogenous" or "heterologous" nucleic acids, including DNAs and/or RNAs, refer to nucleic acids that have been introduced into a cell (or the cell's ancestor) through the efforts of humans. Such heterologous nucleic acids can be copies of a sequence which is naturally found in the cell being transformed, or fragments thereof. To produce a tobacco plant having decreased QPTase levels, and a reduced amount of nicotine and TSNAs, as compared to an untransformed or control tobacco plant or portion thereof, a tobacco cell can be transformed with an exogenous nucleic acid construct which encodes an interfering RNA having an RNA duplex comprising a first strand that is substantially similar or identical to at least a portion of the coding strand of the full-length QPT cDNA sequence, a partial QPT chromosomal sequence, a full-length QPT chromosomal sequence, or an mRNA produced from the QPT gene. Alternatively, the tobacco cell can be transformed with a synthetic or an in vitro transcribed interfering RNA. In Some embodiments of the present invention, the interfering RNA and/or nucleic acid encoding the interfering RNA are stably transformed. In certain embodiments, the nucleic acid encoding the interfering RNA can be integrated in the cell genome. In other embodiments, the interfering RNA and/or nucleic acid encoding the interfering RNA are transiently transformed.

The nucleic acid constructs that are used with the transgenic plants and the methods for producing the transgenic plants described herein encode one or more interfering RNA constructs comprising regulatory sequences, which include, but are not limited to, a transcription initiation sequence ("promoter") operable in the plant being transformed, and a polyadenylation/transcription termination sequence. Typically, the promoter is located upstream of the 5'-end of the nucleotide sequence to be expressed. The transcription termination sequence is generally located just downstream of the 3'-end of the nucleotide sequence to be transcribed.

In some preferred embodiments, the nucleic acid encoding the exogenous interfering RNA, which is transformed into a tobacco cell, comprises a first RNA strand that is identical to the an endogenous coding sequence of a gene encoding a gene product involved in nicotine biosynthesis. However, minor variations between the exogenous and endogenous sequences can be tolerated. It is preferred, but not necessarily required, that the exogenously-produced interfering RNA sequence, which is substantially similar to the endogenous gene coding sequence, be of sufficient similarity to the endogenous gene coding sequence, such that the complementary interfering RNA strand is capable of binding to the endogenous sequence in the cell to be regulated under stringent conditions as described below.

In some embodiments, the heterologous sequence utilized in the methods of the present invention may be selected so as to produce an interfering RNA product comprising a first strand that is substantially similar or identical to the entire QTPase mRNA sequence, or to a portion thereof, and a second strand that is complementary to the entire QPTase mRNA sequence, or to a portion thereof. The interfering RNA may be complementary to any contiguous sequence of the natural messenger RNA. For example, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the C-terminus of the coding region, or complementary to the 3'-uitranslated region of the mRNA.

Interfering RNAs employed in carrying out the present invention include those comprising a first strand having sequence similarity to the QPTase gene or a fragment thereof at least or equal to 50, 100, 150, 200, 250, 300, 350, 400, 450, 500, 550, 600, 650, 700, 750, 800 or more consecutive nucleotides of the QTPase. (See U.S. Pat. No. 6,586,661, which provides the sequence of the QPTase gene and protein, herein expressly incorporated by reference in its entirety). This definition is intended to encompass natural allelic variations in QPTase proteins. Thus, nucleic acid sequences that hybridize to nucleic acids of the QPTase gene under the conditions provided supra may also be employed in carrying out aspects of the invention. Multiple forms of the tobacco QPT enzyme may exist. Multiple forms of an enzyme may be due to post-translational modification of a single gene product, or to multiple forms of the NtQPT1 gene.

Conditions that permit other nucleic acid sequences, which code for expression of a protein having QPTase activity, to hybridize to a QPTase gene or to other nucleic acid sequences encoding a QPTase protein can be determined in a routine manner. For example, hybridization of such sequences to nucleic acids encoding the QPTase protein may be carried out under conditions of reduced stringency or even stringent conditions (e.g., conditions represented by a wash stringency of 0.3 M NaCl, 0.03 M sodium citrate, 0.1% SDS at 60° C. or even 70° C.) herein in a standard in situ hybridization assay. See J. Sambrook et al., Molecular Cloning, A Laboratory Manual (2d Ed. 1989)(Cold Spring Harbor Laboratory)). In general, such sequences will be at least 65% similar, 75% similar, 80% similar, 85% similar, 90% similar, or even 95% similar or more, with the tobacco QPTase gene, or nucleic sequences encoding the QPTase protein. Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.

Differential hybridization procedures are available which allow for the isolation of cDNA clones whose mRNA levels are as low as about 0.05% of poly(A)RNA. (See M. Conkling et al., Plant Physiol. 93, 1203-1211 (1990)). In brief, cDNA libraries are screened using single-stranded cDNA probes of reverse transcribed mRNA from plant tissue (e.g., roots and/or leaves). For differential screening, a nitrocellulose or nylon membrane is soaked in 5×SSC and placed in a 96 well suction manifold; 150 μL of stationary overnight culture is transferred from a master plate to each well and vacuum applied until all liquid has passed through the filter. Approximately, 150 μL of denaturing solution (0.5M NaOH, 1.5 M NaCl) is placed in each well using a multiple pipetter and allowed to sit about 3 minutes. Suction is applied as above and the filter removed and neutralized in 0.5 M Tris-HCl (pH 8.0), 1.5 M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

As used herein, the term "gene" refers to a DNA sequence that incorporates (1) upstream (5') regulatory signals including the promoter, (2) a coding region specifying the product, protein or RNA of the gene, (3) downstream regions including transcription termination and polyadenylation signals and (4) associated sequences required for efficient and specific expression. The DNA sequences of the present invention may encode RNAs that complement regions of or the complete coding sequence of the QPTase gene, or equivalent nucleotide sequences representing alleles or polymorphic variants of these genes, or coding regions thereof. Use of the phrase "substantial sequence similarity" or "substantially similar" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

As used herein, a "native nucleotide sequence" or "natural nucleotide sequence" means a nucleotide sequence that can be isolated from non-transgenic cells or tissue. Native nucleotide sequences are those which have not been artificially altered, such as by site-directed mutagenesis. Once native nucleotide sequences are identified, nucleic acid molecules having native nucleotide sequences may be chemically synthesized or produced using recombinant nucleic acid procedures as are known in the art. As used herein, a "native plant nucleotide sequence" is that which can be isolated from non-transgenic plant cells or tissue. As used herein, a "native tobacco nucleotide sequence" is that which can be isolated from non-transgenic tobacco cells or tissue. Use of the phrase "isolated" or "substantially pure" in the present specification and claims as a modifier of nucleic acids, polypeptides or proteins means that the nucleic acids, polypeptides or proteins so designated have been separated from their in vivo cellular environments through the efforts of human beings.

The nucleotide sequences provided herein, such as interfering RNAs or nucleic acids encoding interfering RNAs, can be transformed into a variety of host cells. As used herein, "transformation" refers to the introduction of exogenous nucleic acid into cells so as to produce transgenic cells stably transformed with the exogenous nucleic acid. A variety of suitable host cells, having desirable growth and handling properties, are readily available in the art.

Standard techniques, such as restriction mapping, Southern blot hybridization, polymerase chain reaction (PCR) and/or nucleotide sequence analysis are employed to identify clones expressing the desired interfering RNA construct. Following the introduction and verification of the desired interfering RNA or nucleic acid construct encoding the desired interfering RNA, whole plants are regenerated from successfully transformed cells using conventional techniques.

Nucleic acid constructs, or "transcription cassettes," encoding the interfering RNAs that are used to produce the transgenic cells and plants of the present invention include, 5' to 3' in the direction of transcription, a promoter as described herein, a nucleotide sequence as described herein operatively associated with the promoter, and, optionally, a termination sequence including stop signal for RNA polymerase and a polyadenylation signal. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator or native termination signals, derived from the same gene as the transcriptional initiation region or derived from a different gene. See, e.g., Rezian et al. (1988) supra, and Rodermel et al. (1988), supra.

The term "operatively associated," as used herein, refers to nucleotide sequences on a single nucleic acid molecule that are associated so that the function of one sequence is affected by the other. Thus, a promoter is operatively associated with a nucleotide sequence when it is capable of affecting the transcription of that sequence (i.e., the nucleic acid is under the transcriptional control of the promoter). The promoter is said to be "upstream" from the transcribed nucleotide sequence, which is in turn said to be "downstream" from the promoter.

In some embodiments, the transcription cassette may be provided in a DNA construct that also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide (such as antibiotics, toxins, heavy metals or the like), provide complementation by imparting prototrophy to an auxotrophic host and/or provide a visible phenotype through the production of a novel compound in the plant.

The various fragments comprising the various constructs, transcription cassettes, markers and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature as demonstrated by J. Sambrook et al., Molecular Cloning, A Laboratory Manual (2d Ed. 1989)(Cold Spring Harbor Laboratory).

Vectors that may be used to transform plant tissue with nucleic acid constructs of the present invention include both *Agrobacterium* vectors and ballistic vectors, as well as vectors suitable for DNA-mediated transformation. In this particular embodiment, the promoter is a region of a DNA sequence that incorporates the necessary signals for the efficient expression of the coding sequence. This region may include sequences to which an RNA polymerase binds, but is not limited to such sequences, and may include sequences to which other regulatory proteins bind along with sequences involved in the control of protein translation. Such regions may also include coding sequences.

Promoters employed in carrying out the invention may be constitutively active promoters. Numerous constitutively active promoters that are operable in plants are available. A preferred example is the Cauliflower Mosaic Virus (CaMV) 35S promoter, which is expressed constitutively in most plant tissues. As an alternative, the promoter may be a root-specific promoter or root cortex specific promoter, as explained in greater detail below.

Nucleic acid sequences have been expressed in transgenic tobacco plants utilizing the Cauliflower Mosaic Virus (CaMV) 35S promoter. See, e.g., Cornelissen et al., "Both RNA Level and Translation Efficiency are Reduced by Anti-Sense RNA in Transgenic Tobacco", Nucleic Acids Res. 17, pp. 833-43 (1989); Rezaian et al., "Anti-Sense RNAs of Cucumber Mosaic Virus in Transgenic Plants Assessed for Control of the Virus", Plant Molecular Biology 11, pp. 463-71 (1988); Rodermel et al., "Nuclear-Organelle Interactions: Nuclear Antisense Gene Inhibits Ribulose Bisphosphate Carboxylase Enzyme Levels in Transformed Tobacco Plants", Cell 55, pp. 673-81 (1988); Smith et al., "Antisense RNA Inhibition of Polygalacturonase Gene Expression in Transgenic Tomatoes", Nature 334, pp. 724-26 (1988); Van der Krol et al., "An Anti-Sense Chalcone Synthase Gene in Transgenic Plants Inhibits Flower Pigmentation", Nature 333, pp. 866-69 (1988).

Use of the CaMV 35S promoter for expression of interfering RNAs in the transformed tobacco cells and plants of this invention is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", Proc. Nat. Acad. Sci. USA 86, pp. 7890-94 (1989); Poulsen et al. "Dissection of 5' Upstream Sequences for Selective Expression of the Nicotiana plumbaginifolia rbcS-8B Gene", Mol. Gen. Genet. 214, pp. 16-23 (1988)).

Other promoters that are active only in root tissues (root specific promoters) are also particularly suited to the methods of the present invention. (See, e.g., U.S. Pat. No. 5,459,252 to Conkling et al.; Yamamoto et al., The Plant Cell, 3:371 (1991)). The TobRD2 root-cortex specific promoter may also be utilized. (See, eg., U.S. patent application Ser. No. 08/508,786, now allowed, to Conkling et al; PCT WO 9705261). All patents cited herein are intended to be incorporated herein by reference in their entirety.

The recombinant interfering nucleic acid molecules and vectors used to produce the transformed tobacco cells and plants described herein may further comprise a dominant selectable marker gene. Suitable dominant selectable markers for use in tobacco include, inter alia, antibiotic resistance genes encoding neomycin phosphotransferase (NPTII) and hygromycin phosphotransferase (HPT). Other well-known selectable markers that are suitable for use in tobacco include a mutant dihydrofolate reductase gene that encodes methotrexate-resistant dihydrofolate reductase. DNA vectors containing suitable antibiotic resistance genes, and the corresponding antibiotics, are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply. Additionally, the positive selection techniques described by Jefferson (e.g., WO 00055333; WO 09913085; U.S. Pat. Nos. 5,599,670; 5,432,081; and 5,268,463, hereby expressly incorporated by reference in their entireties) can be used.

Methods of making the recombinant plants described herein, in general, involve first providing a plant cell capable of regeneration (the plant cell typically residing in a tissue capable of regeneration). The plant cell is then transformed with an interfering RNA or a nucleic acid construct encoding an interfering RNA comprising a transcription cassette of the present invention (as described above) and a recombinant plant is regenerated from the transformed plant cell. As explained below, the transforming step is carried out by techniques as are known in the art, including but not limited to bombarding the plant cell with microparticles carrying the transcription cassette, infecting the cell with an Agrobacterium tumefaciens containing a Ti plasmid carrying the transcription cassette or any other technique suitable for the production of a transgenic plant.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles suitable for the ballistic transformation of a plant cell, carrying a nucleic acid construct of the present invention, are also useful for making the transformed plants described herein. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 μm gold spheres. The nucleic acid construct may be deposited on the microparticle by any suitable technique, such as by precipitation.

Plant species may be transformed with the interfering RNA or nucleic acid construct encoding an interfering RNA by the nucleic acid-mediated transformation of plant cell protoplasts. Plants may be subsequently regenerated from the transformed protoplasts in accordance with procedures well known in the art. Fusion of tobacco protoplasts with nucleic acid-containing liposomes or with nucleic acid constructs via electroporation is known in the art. (Shillito et al., "Direct Gene Transfer to Protoplasts of Dicotyledonous and Monocotyledonous Plants by a Number of Methods, Including Electroporation", Methods in Enzymology 153, pp. 313-36 (1987)).

Transformed cells are induced to regenerate intact tobacco plants through application of tobacco cell and tissue culture techniques that are well known in the art. The method of plant regeneration is chosen so as to be compatible with the method of transformation. The stable presence of an interfering RNA or a nucleic acid encoding an interfering RNA in transgenic tobacco plants can be verified by Mendelian inheritance of the interfering RNA or a nucleic acid encoding an interfering RNA sequence, as revealed by standard methods of nucleic acid analysis applied to progeny resulting from controlled crosses. After regeneration of transgenic tobacco plants from transformed cells, the introduced nucleic acid sequence is readily transferred to other tobacco varieties through conventional plant breeding practices and without undue experimentation.

For example, to analyze the segregation of the transgene, regenerated transformed plants (RO) may be grown to maturity, tested for nicotine and/or TSNA levels, and selfed to produce $R_1$ plants. A percentage of $R_1$ plants carrying the transgene are homozygous for the transgene. To identify homozygous $R_1$ plants, transgenic $R_1$ plants are grown to maturity and selfed. Homozygous $R_1$ plants will produce $R_2$ progeny where each progeny plant carries the transgene; progeny of heterozygous $R_1$, plants will segregate 3:1.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems) and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or $T_1$) transformed plants may be selfed to give homozygous second generation (or $T_2$) transformed plants and the $T_2$ plants further propagated through classical breeding techniques. A dominant selectable marker (such as nptII) can be associated with the transcription cassette to assist in breeding.

As used herein, a crop comprises a plurality of plants of the present invention, and of the same genus, planted together in an agricultural field. By "agricultural field" is meant a common plot of soil or a greenhouse. Thus, the present invention provides a method of producing a crop of plants having lowered QPTase activity and thus having decreased nicotine and/or TSNA levels, as compared to a similar crop of non-transformed plants of the same species and variety. The example that follows illustrates some of the embodiments of the present invention, and are not to be construed as limiting thereof.

EXAMPLE 12

Figure 11:
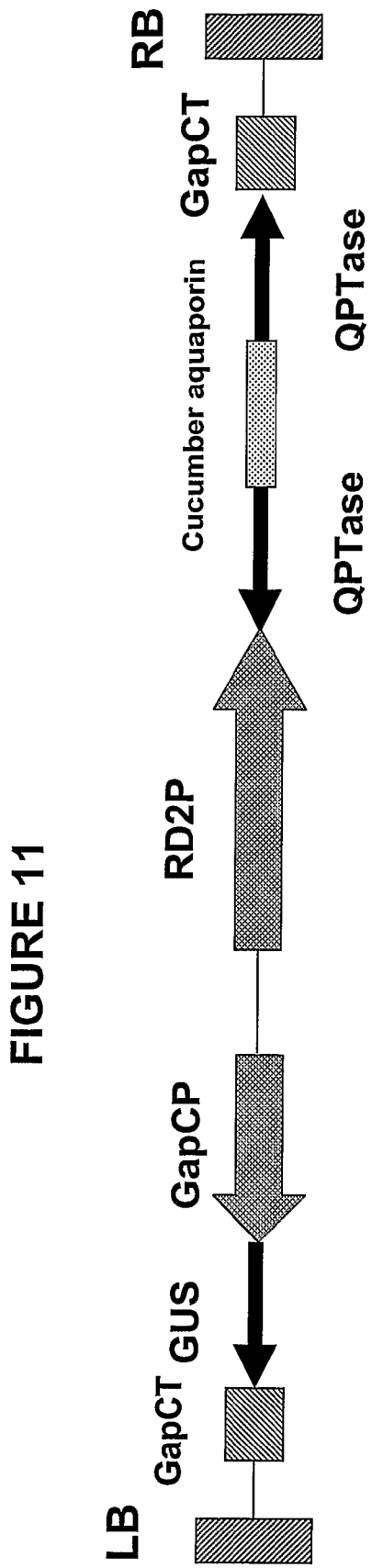
FIG. 11 illustrates a first RNAi construct that was used to create a reduced nicotine and tobacco-specific nitrosamine (TSNA) tobacco, wherein the root-specific promoter RD2 (bp1-2010) was used to drive expression of an RNAi cassette comprising an antisense full-length QPTase cDNA (bp2011-3409) linked to a 382 bp fragment of the cucumber aquaporin gene (bp3410-3792), which is linked to a sense full-length QPTase cDNA (bp3793-5191) and the GapC terminator (bp5192-5688) (see SEQ. ID. No. 1). This first RNAi construct also comprises a GUS-selection cassette comprising the GapC promoter (1-1291), which drives expression of the GUS gene (bp1292-3103), linked to the GapC terminator (bp3104-3600) (see SEQ. ID. No. 2).

FIG. 11 illustrates an RNAi construct that was used to create a reduced nicotine tobacco, wherein the root-specific promoter RD2 (bp1-2010) was used to drive expression of an RNAi cassette comprising an antisense full-length QPTase cDNA (bp2011-3409) linked to a 382 bp fragment of the cucumber aquaporin gene (bp3410-3792), which is linked to a sense full-length QPTase cDNA (bp3793-5191) and the GapC terminator (bp5192-5685) (see SEQ. ID. No. 1). This first RNAi construct also comprises a GUS-selection cassette comprising the GapC promoter (1-1291), which drives expression of the GUS gene (bp1292-3103), linked to the GapC terminator (bp3104-3600) (see SEQ. ID. No. 2). This first RNAi construct was ligated into a binary vector, pBin19 which was then introduced into *Agrobacterium tumefaciens*. Leaf disks from flue-cured variety K326 were then transformed with *Agrobacterium* that contained the RNAi construct comprising the RNAi cassette and the GUS selection cassette. GUS-based selection was then employed to select positively transformed plantlets (buds), which were then regenerated to plants. Leaf samples were then harvested and the alkaloid content was then determined. The alkaloid content of samples obtained from some of the transgenic lines created with this first RNAi construct was 6000 ppm. Accordingly, tobacco products (e.g., cigarettes), tobacco, tobacco plants, tobacco cells, and tobacco seeds, in burley, flue, or oriental comprising said RNAi construct are embodiments and preferred embodiments include K326 tobacco cells, plants, or tobacco products that comprise the aforementioned RNAi construct.

Figure 12:
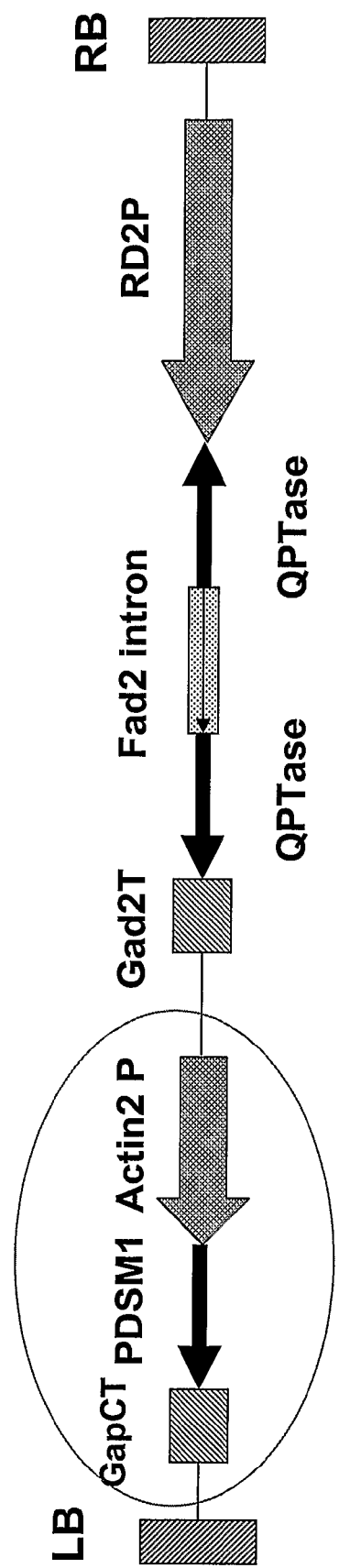
FIG. 12 illustrates a second RNAi construct that was used to create a reduced nicotine and tobacco-specific nitrosamine (TSNA) tobacco, wherein the root-specific promoter RD2 (bp 1-2010) was used to drive expression of an RNAi cassette comprising a 360 bp antisense fragment of the QPTase gene (bp 2011-2370) linked to a 1130 bp FAD2 intron (bp 2371-3501), linked to 360 bp sense QPTase fragment (bp 3502-3861), linked to a Gad2 terminator (bp 3862-4134) (see SEQ. ID. No. 3). This second RNAi construct also comprises a norflurazone-selection cassette comprising the Actin 2 promoter (bp1-1161), which drives expression of a norflurazone-resistance gene (e.g., mutated Arabadopsis phytoene desaturase gene (PDSM1) containing a T to G mutation at position 1478, resulting in a Valine to Glycine change at amino acid residue 493) (bp1162-2890), linked to gapC terminator (bp2891-3387) (see SEQ. ID. No. 4).

FIG. 12 illustrates a second RNAi construct that was used to create a reduced nicotine tobacco, wherein the root-specific promoter RD2 (bp 1-2010) was used to drive expression of an RNAi cassette comprising a 360 bp antisense fragment of the QPTase gene (bp 2011-2370) linked to a 1130 bp FAD2 intron (bp 2371-3501), linked to 360 bp sense QPTase fragment (bp 3502-3861), linked to a Gad2 terminator (bp 3862-4134) (see SEQ. ID. No. 3). This second RNAi construct also comprises a norflurazone-selection cassette comprising the Actin 2 promoter (bp1-1161), which drives expression of a norflurazone-resistance gene (e.g., mutated *Arabadopsis* phytoene desaturase gene (PDSM1) containing a T to G mutation at position 1478, resulting in a Valine to Glycine change at amino acid residue 493) (bp1162-2890), linked to gapC terminator (bp2891-3387) (see SEQ. ID. No. 4).

To generate the norflurazone resistance gene, the open reading frame of the *Arabidopsis* phytoene desaturase gene was amplified and cloned into the TOPO vector (Invitrogen). A single base pair change from T-G at nucleotide position 1478, leading to a Valine to Glycine change at amino acid residue 493, was introduced using QuickChange Site-directed Mutagenisis Kit (Stratgene). The point mutation was verified by sequencing and the resultant mutant was named PDSM1. The 1.729 Kb PDSM1 sequence was then amplified and ligated into the binary vector pWJ001, a pCambia derivative that contained the RNAi cassette above, which was then introduced into *Agrobacterium tumefaciens*.

Leaf disks from flue-cured variety K326 were then transformed with *Agrobacterium* that contained the RNAi construct comprising the RNAi cassette and the norflurazone selection cassette in the presence of the herbicide norflurazone. Accordingly, norflurazone-based selection was then employed to isolate positively transformed plantlets (buds), which were then regenerated to plants three to four weeks after transformation. 1,140 independent lines were produced and 1,097 plants were harvested and tested for alkaloid content. 608 lines were confirmed to have low levels of alkaloid (below 1,000 ppm) and of this number 139 lines were found to have less than 500 ppm total alkaloid content. Accordingly, tobacco products (e.g., cigarettes), tobacco, tobacco plants, tobacco cells, and tobacco seeds, in burley, flue, or oriental comprising said RNAi construct are embodiments and preferred embodiments include K326 tobacco cells, plants, or tobacco products that comprise the aforementioned RNAi construct.

The RNAi construct containing the norflurazone selection cassette was also introduced into burley tobacco using the approaches described above and 385 independent lines carrying the construct were produced. Of the 385 lines, 350 lines were harvested and tested for alkaloid content. Of the tested lines, it was determined that 142 lines had alkaloid content below 1,000 ppm and 10 lines were isolated that contained less than 500 ppm total alkaloid content, thus establishing that the aforementioned RNAi construct efficiently reduces nicotine in multiple varieties of tobacco.

This example demonstrates that RNAi constructs containing either full-length QPTase nucleic acids or fragments of these nucleic acids effectively reduce the levels of nicotine in tobacco. Additionally, this example demonstrates that the PDSM1 gene is resistant to the herbicide norflurazone and that the presence of this gene can be used in a general sense (e.g., in plants other than tobacco) to efficiently select positively transformed plant cells from plant cells that do not contain a construct comprising the norflurazone resistance gene. Thus, the norflurazone selection cassette or the norflurazone resistance gene described herein can be used to confer resistance to norflurazone in plants including, but not limited to, corn (*Zea mays*), canola (*Brassica napus, Brassica rapa* ssp.), alfalfa (*Medicago saliva*), rice (*Orya sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lenma*), oats, barley, vegetables, ornamentals, conifers, and turfgrasses (e.g., for ornamental, recreational or forage purposes). Vegetables include Solanaceous species (e.g., tomatoes; *Lycopersicon esculentum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschtata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*). Ornamental plants include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Turfgrass include but are not limited to zoysiagrasses, bentgrasses, fescue grasses, bluegrasses, St. Augustinegrasses, bermudagrasses, buffalograsses, ryegrasses, and orchardgrasses. Also included are plants that serve primarily as laboratory models, e.g., *Arabidopsis*. Preferred plants for use in the present methods include (but are not limited to) legumes, *solanaceous* species (e.g., tomatoes), leafy vegetables such as lettuce and cabbage, turfgrasses, and crop plants (e.g., tobacco, wheat, sorghum, barley, rye, rice, corn, cotton, cassava, and the like), and laboratory plants (e.g., *Arabidopsis*). While any plant may be used to carry out this aspect of the invention, tobacco plants are particularly preferred.

Further, aspects of the invention concern the production of norflurazone-resistant or tolerant plants, which can be sprayed with herbicide in the field. In this manner, weeds and non-transformed plants will die after contact with the herbicide but plants containing the construct harboring the norflurazone resistance gene will survive. In one embodiment, for example, a norflurazone-containing herbicide is applied to the plant comprising the DNA constructs of the present invention, and the plants are evaluated for tolerance to the herbicide. Any formulation of norflurazone can be used for testing plants comprising the DNA constructs of the present invention. The testing parameters for an evaluation of the norflurazone tolerance of the plant will vary depending on a number of factors. Factors would include, but are not limited to the type of norflurazone formulation, the concentration and amount of norflurazone used in the formulation, the type of plant, the plant developmental stage during the time of the application, environmental conditions, the application method, and the number of times a particular formulation is applied. For example, plants can be tested in a greenhouse environment using a spray application method. The testing range using norflurazone. can include, but is not limited to 0.5 oz/acre to 500 oz/acre. The preferred commercially effective range can be from 25 oz/acre to 100 oz/acre of norflurazone, depending on the crop and stage of plant development. A crop can be sprayed with at least one application of a norflurazone. For testing in cotton an application of 32 oz/acre at the 3-leaf stage may be followed by additional applications at later stages in development. For wheat, corn, soybean, and tobacco an application of 32 oz/acre of norflurazone. at the 3-5 leaf stage can be used. The test parameters can be optimized for each crop in order to find the particular plant comprising the constructs of the present invention that confers the desired commercially effective norflurazone tolerance level.

In still more embodiments, cells of the mouth, oral cavity, trachea, or lung (e.g., NHBE cells) from a plurality of individuals, preferably the same cell type, are independently contacted with CS from a tobacco product (cigarette) in an amount and for a time sufficient to modulate expression of one or more genes or to modify a gene product. Identification of the genes that are modulated or modified gene products (e.g., phosphorylated) or the level or amount of gene expression or modification can then be accomplished using any technique available that analyzes transcription (e.g., RTPCR or hybridization), protein production (e.g., ELISA or other antibody detection techniques), modifications of proteins (e.g., oxidation or phosphorylation), or the appearance or disappearance of metabolites associated with genes that are modulated in response to exposure to CS (e.g., cysteine, glutathione, fragments of proteins or lipids or fatty acids). By analyzing the modulation of various genes of the same cell type from different individuals before, during, or after exposure to a tobacco product, one can identify a particular subject's predilection to acquire a tobacco-related disease. Thus, the genes or modifications of gene products identified by the approaches described herein are markers for the diagnosis or prognosis of acquiring a tobacco-related disease.

For example, primary cultures of lung cells, bronchial cells, cells of the mouth, pharynx, larynx, and tongue are generated from an individual to be tested and these cells are be contacted with CS from a tobacco product so as to elucidate the individuals proclivity to acquire a tobacco related disease. Certain patterns of gene expression (types of genes expressed, as well as, gene product modifications, such as phosphorylation) and certain ranges of levels of gene expression for a particular gene or subset of genes are associated with individuals that do not develop a tobacco related disease and a different pattern of gene expression and ranges of levels of gene expression for a particular gene or subset of genes are associated with individuals that have developed a tobacco-related disease. Analysis of the levels of gene expression of the various genes and subsets of genes of many of such individuals allows the development of databases that provide an expected range of gene expression, patterns of gene expression, or gene product modifications that are associated or not associated with a tobacco-related disease.

That is, this information can be used to provide a baseline for an individual that is not likely to acquire a tobacco-related disease (e.g., a control level indicated by the pattern or average level of gene expression exemplified by non-tobacco users that do not develop a tobacco-related disease) and a baseline for an individual that is likely to acquire a tobacco related disease (e.g., a control level indicated by the pattern and average level of gene expression exemplified by tobacco users that have developed a tobacco-related disease). Accordingly, when a subject is analyzed for the predilection to develop a tobacco-related disease, the gene expression pattern, as well as, levels of gene expression of a gene or subset of genes associated with a tobacco-related disease, or modifications of particular gene products can be evaluated and, by comparing the determined values to that in one or both of the databases described above, the analyzed subject can be identified as having a predilection for developing a tobacco-related disease.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein. Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein. Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto. All references cited herein are hereby expressly incorporated by reference.

What is claimed is:

1. A method of selecting a tobacco that produces a reduced expression of Sequestosome 1 in human cells comprising:
   (a) providing a first tobacco;
   (b) obtaining smoke from said first tobacco;
   (c) contacting a first isolated population of human cells with said smoke from said first tobacco;
   (d) measuring the level of expression of Sequestosome 1 in said first isolated population of human cells in response to said contact, with said smoke from said first tobacco;
   (e) providing a second tobacco;
   (f) obtaining smoke from said second tobacco;
   (g) contacting a second isolated population of human cells with said smoke from said second tobacco;
   (h) measuring the level of expression of Sequestosome 1 in said second isolated population of human cells in response to said contact with said smoke from said second tobacco;
   (i) comparing the level of expression of Sequestosome 1 in said first isolated population of human cells measured in step (d) with the level of expression of Sequestosome 1 in said second isolated population of human cells measured in step (h); and (j) identifying the tobacco that produced a reduced expression of Sequestosome 1 in an isolated population of human cells in response to contact with smoke from said tobacco.

2. The method of claim 1, wherein said first tobacco and said second tobacco comprise a burley tobacco.

3. The method of claim 1, wherein said first tobacco and said second tobacco comprise a flue tobacco.

4. The method of claim 1, wherein said second tobacco comprises a modified tobacco.

5. The method of claim 1, wherein said first tobacco is provided in a first cigarette and said second tobacco is provided in a second cigarette.

6. The method of claim 5, wherein said first cigarette and said second cigarette comprise a filter.

7. The method of claim 1, wherein said first and second isolated populations of human cells are normal human cells of the lung, mouth, or tongue.

8. The method of claim 1, wherein said first and second isolated populations of human cells are normal human bronchial epithelial (NHBE) cells.

9. The method of claim 1, further comprising measuring the level of expression of a second gene in said first and second isolated populations of human cells after contacting said first and second isolated populations of human cells with said smoke.

10. The method of claim 9, wherein said second gene is selected from the group consisting of: Ferritin heavy polypeptide, Heat Shock 70 kD protein 1A, Thioredoxin reductase 1, Heme oxygenase (decycling) 1, and Prostaglandin-endoperoxide synthase 2.

11. The method of claim 1, further comprising incorporating the tobacco identified in step (j) into a tobacco product.

12. The method of claim 11, wherein said tobacco product is a cigarette.

* * * * *